United States Patent [19]
Arai et al.

[11] Patent Number: 5,981,558
[45] Date of Patent: Nov. 9, 1999

[54] DC107 DERIVATIVES

[75] Inventors: Hitoshi Arai, Shizuoka; Yutaka Kanda; Hiroyuki Yamaguchi, both of Tokyo; Tadashi Ashizawa; Chikara Murakata, both of Shizuoka; Shun-ichi Ikeda, Osaka; Tatsuya Tamaoki, Shizuoka, all of Japan

[73] Assignee: Kyowa Hakko Kogyo Co., Ltd., Tokyo, Japan

[21] Appl. No.: 09/133,614

[22] Filed: Aug. 13, 1998

Related U.S. Application Data

[63] Continuation-in-part of application No. PCT/JP97/04583, Dec. 12, 1997.

[30] Foreign Application Priority Data

Dec. 13, 1996 [JP] Japan .................................. 8-334320
Jan. 24, 1997 [JP] Japan .................................. 9-011597

[51] Int. Cl.$^6$ ....................... C07D 513/08; A61K 31/425
[52] U.S. Cl. .......................................... 514/366; 540/469
[58] Field of Search .............................. 540/469; 514/366

[56] References Cited

U.S. PATENT DOCUMENTS

| 4,999,196 | 3/1991 | Nakano et al. ........................ 424/116 |
| 5,733,924 | 3/1998 | Kanda et al. ........................ 514/431 |

FOREIGN PATENT DOCUMENTS 786 462   7/1997   European Pat. Off. .

OTHER PUBLICATIONS

Yamada, et al., Heterocycles, vol. 43, No. 2, (1996) 267–270.
Kanda, et al., Bioorganic & Medicinal Chemistry Letters 8, (1998) 909–912.

*Primary Examiner*—Robert Gerstl
*Attorney, Agent, or Firm*—Fitzpatrick, Cella, Harper & Scinto

[57] ABSTRACT

DC107 derivatives represented by formula (I) or pharmaceutically acceptable salts thereof which have antimicrobial activity and antitumor activity are provided:

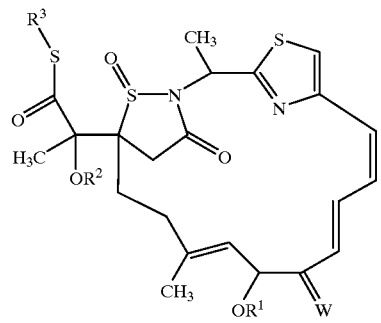

(I)

wherein $R^1$ represents hydrogen, lower alkoxyalkyl, aralkyloxyalkyl, lower alkoxyalkoxyalkyl, lower alkoxyalkoxyalkoxyalkyl, aralkyl, tetrahydropyranyl, $COR^4$, or the like; $R^2$ represents hydrogen or $COR^6$; $R^3$ represents —$CH_2OCOR^7$, phthalimidomethyl, or the like; and W represents oxygen or $NR^8$ (wherein $R^8$ represents hydroxy, lower alkoxy, lower alkenyloxy, aralkyloxy, substituted or unsubstituted arylsulfonylamino, or lower alkoxycarbonylamino).

5 Claims, No Drawings

DC107 DERIVATIVES

CROSS-REFERENCE TO RELATED APPLICATION

This is a continuation-in-part application of PCT/JP97/04583 filed on Dec. 12, 1997.

BACKGROUND OF THE INVENTION

1. Field of the Invention

The present invention relates to novel DC107 derivatives and pharmaceutically acceptable salts thereof which have antimicrobial activity and antitumor activity.

2. Brief Description of the Background

DC107 (leinamycin), which is disclosed in Japanese Published Unexamined Patent Application No. 112988/89, is a compound produced by microorganisms belonging to the genus Streptomyces. It shows not only antimicrobial activity against various bacteria but also antitumor activity, and has the following structure:

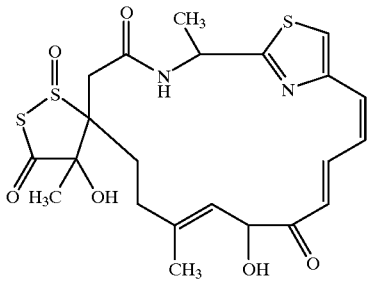

SUMMARY OF THE INVENTION

An object of the present invention is to provide novel DC107 derivatives and pharmaceutically acceptable salts thereof which have excellent antimicrobial and antitumor activities.

The present invention provides DC107 derivatives represented by formula (I) or pharmaceutically acceptable salts thereof:

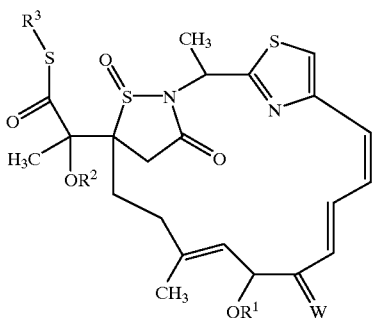

(I)

wherein $R^1$ represents:
  hydrogen;
  lower alkoxyalkyl;
  aralkyloxyalkyl;
  lower alkoxyalkoxyalkyl;
  lower alkoxyalkoxyalkoxyalkyl;
  aralkyl;
  tetrahydropyranyl;

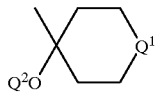

{wherein $Q^1$ represents $CH_2$, O, S, SO, $SO_2$, or N-$Q^3$ (wherein $Q^3$ represents substituted or unsubstituted aryl, or lower alkoxycarbonyl); and $Q^2$ represents a lower alkyl};

$COR^4$ (wherein $R^4$ represents alkyl, alicyclic alkyl, aralkyl, substituted or unsubstituted aryl, a substituted or unsubstituted heterocyclic group, lower alkoxy, alicyclic alkoxy, 9-fluorenylmethoxy, aralkyloxy, substituted or unsubstituted aryloxy, —$(CH_2)_{n1}R^{4A}$ <wherein n1 represents an integer of 1 to 3; and $R^{4A}$ represents hydroxy, lower alkoxy, carboxy, lower alkoxycarbonyl, lower dialkylamino, substituted or unsubstituted aryl, a substituted or unsubstituted heterocyclic group, substituted or unsubstituted aralkyloxy, or $NR^{4B}COR^{4C}$ {wherein $R^{4B}$ represents hydrogen or lower alkyl; and $R^{4C}$ represents lower alkyl, lower alkoxy, aralkyloxy, aryl, aryloxy, 9-fluorenylmethoxy, —$(CH_2)_{n2}NHCOR^{4D}$ (wherein n2 represents an integer of 1 to 3; and $R^{4D}$ represents alkyl, lower alkoxy, aralkyloxy, aryl, aryloxy, or 9-fluorenylmethoxy), or —$CHR^{4E}NHCOR^{4F}$ (wherein $R^{4E}$ represents lower alkyl or hydroxy(lower alkyl); and $R^{4F}$ has the same meaning as $R^{4D}$)}>, or —$CHR^{4G}NHCOR^{4H}$ (wherein $R^{4G}$ has the same meaning as $R^{4E}$; and $R^{4H}$ has the same meaning as $R^{4C}$)); or —$CH_2OCOR^5$ <wherein $R^5$ represents —$(CH_2)_{n3}R^{5A}$ {wherein n3 represents an integer of 1 to 5; and $R^{5A}$ represents lower alkoxy, lower alkanoyloxy, —$OSiR^{5B}_3$ (wherein $R^{5B}$s are the same or different, and represent lower alkyl or aryl), lower alkanoyl, lower alkoxycarbonyl, lower alkoxycarbonylamino, lower alkoxycarbonyloxy, lower dialkylaminocarbonyloxy, halogen, or nitro}, or —$CH_2(OCH_2CH_2)_{n4}OCH_3$ (wherein n4 represents an integer of 1 to 10)>;

$R^2$ represents:
hydrogen; or
$COR^6$ (wherein $R^6$ represents lower alkyl, aralkyl, substituted or unsubstituted aryl, or a substituted or unsubstituted heterocyclic group);

$R^3$ represents:
—$CH_2OCOR^7$ (wherein $R^7$ represents —$(CH_2)_{n5}R^{7A}$ (wherein n5 represents an integer of 1 to 5; and $R^{7A}$ represents hydroxy, lower alkoxy, substituted or unsubstituted aralkyloxy, lower alkanoyloxy, —$OPO(OH)_2$, —$OSO_3H$, —$OSiR^{7B}_3$ (wherein $R^{7B}$ has the same meaning as $R^{5B}$), lower alkanoyl, carboxy, lower alkoxycarbonyl, lower alkoxycarbonylamino, aralkyloxycarbonylamino, lower alkoxycarbonyloxy, lower dialkylaminocarbonyloxy, halogen, nitro, maleimido, 2-pyrrolidinon-1-yl, or —$NHCOR^{7C}$ (wherein $R^{7C}$ represents substituted or unsubstituted lower alkyl, substituted or unsubstituted alicyclic alkyl, substituted or unsubstituted aryl, substituted or unsubstituted aralkyl, a substituted or unsubstituted heterocyclic group,

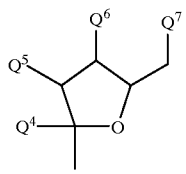

{wherein $Q^4$ to $Q^7$ are the same or different, and each represents hydrogen, hydroxy, lower alkanoyloxy, or —$OSiQ^8_3$ (wherein $Q^8$ has the same meaning as $R^{5B}$), or $Q^4$ and $Q^5$, or $Q^6$ and $Q^7$ are combined with each other to represent —$OC(CH_3)_2O$—}, or

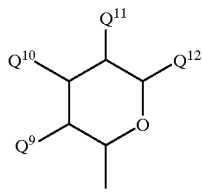

(wherein $Q^9$ to $Q^{12}$ have the same meanings as $Q^4$ to $Q^7$, respectively))), —$C(CH_3)_2R^{7D}$ {wherein $R^{7D}$ represents lower alkoxycarbonylamino, aralkyloxycarbonylamino, or —$NHCOR^{7E}$ (wherein $R^{7E}$ has the same meaning as $R^{7C}$)}, —$(CH_2)_{n6}CHR^{7F}R^{7G}$ (wherein n6 represents an integer of 0 to 3; $R^{7F}$ represents lower alkanoyl, carboxy, lower alkoxycarbonyl, substituted or unsubstituted aryl, substituted or unsubstituted lower alkyl, or substituted or unsubstituted aralkyl; and $R^{7G}$ has the same meaning as 7D $R^{7D}$), alicyclic alkyl having a substituent, substituted or unsubstituted aryl, substituted or unsubstituted aralkyl, —$CH_2(OCH_2CH_2)_{n7}OR^{7H}$ (wherein $R^{7H}$ represents hydrogen, lower alkyl, substituted or unsubstituted aryl, or substituted or unsubstituted aralkyl; and n7 represents an integer of 1 to 10), —$(OCH_2CH_2)_{n8}OCH_3$ (wherein n8 represents an integer of 1 to 10), or —$OCH_2CH_2$ (2-pyrrolidinon-1-yl));

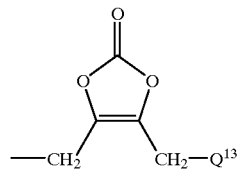

(wherein $Q^{13}$ represents halogen, hydroxy, lower alkoxyalkyl, —$OSiR^{7I}_3$ (wherein $R^{7I}$ has the same meaning as $R^{5B}$), —$OCOQ^{14}$ {wherein $Q^{14}$ represents hydrogen, alkyl, alicyclic alkyl, aralkyl, substituted or unsubstituted aryl, a substituted or unsubstituted heterocyclic group, lower alkoxy, alicyclic alkoxy, 9-fluorenylmethoxy, aralkyloxy, substituted or unsubstituted aryloxy, alkylamino, (hydroxyalkyl)amino, —$(CH_2)_{n9}Q^{14A}$ (wherein n9 represents an integer of 1 to 3; and $Q^{14A}$ represents carboxy or lower dialkylamino), $CQ^{14B}_2NQ^{14C}COQ^{14D}$ (wherein $Q^{14B}$ represents hydrogen or lower alkyl; $Q^{14C}$ represents hydrogen or lower alkyl; and $Q^{14}D$ represents lower alkyl, lower alkoxy, aralkyloxy, aryl, aryloxy, or 9-fluorenylmethoxy), or —$CH_2(OCH_2CH_2)_{n10}OCH_3$ (wherein $n_{10}$ represents an integer of 1 to 10)}, or

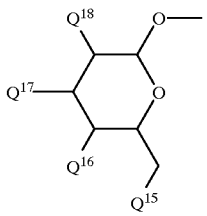

{wherein $Q^{15}$ represents hydrogen, hydroxy, —$OSiR^{7J}_3$ (wherein $R^{7J}$ has the same meaning as $R^{5B}$), or lower alkanoyloxy; and $Q^{16}$ to $Q^{18}$ are the same or different, and each represents hydroxy, —$OSiR^{7J}_3$ (wherein $R^{7J}$ has the same meaning as $R^{5B}$), or lower alkanoyloxy; and $Q^{17}$ and $Q^{18}$ may be combined with each other to represent a bond});

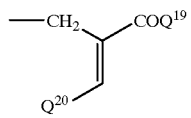

(wherein $Q^{19}$ represents hydroxy, lower alkoxy, or a substituted or unsubstituted heterocyclic group; and $Q^{20}$ represents hydrogen, lower alkyl, or aryl);

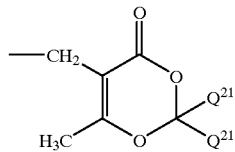

(wherein $Q^{21}$ represents alkyl);

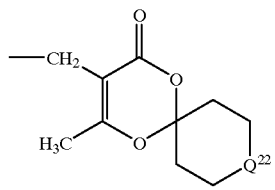

{wherein $Q^{22}$ represents $CH_2$, O, or N—$CO_2Q^{23}$ (wherein $Q^{23}$ represents lower alkyl)};
lower alkoxyalkyl;
aralkyloxyalkyl;
lower alkoxyalkoxyalkyl;
lower alkoxyalkoxyalkoxyalkyl; or
phthalimidomethyl; and
W represents:
oxygen; or
$NR^8$ (wherein $R^8$ represents hydroxy, lower alkoxy, lower alkenyloxy, aralkyloxy, substituted or unsubstituted arylsulfonylamino, or lower alkoxycarbonylamino).

Furthermore, the present invention provides a method for preventing or treating a patient exhibiting symptoms of microbial or tumor activity comprising administering an effective amount of the above DC107 derivative or a pharmaceutically acceptable salt thereof.

DETAILED DESCRIPTION OF THE INVENTION

This application is based on Japanese applications No. 8-334320 filed on Dec. 13, 1996 and No. 9-11597 filed on Jan. 24, 1997, and PCT/JP97/04583 filed on Dec. 12, 1997, the entire contents of which are incorporated hereinto by reference.

Hereinafter, the compound represented by formula (I) will be called Compound (I). Compounds of other formula numbers with also be called in the same manner.

In the definitions of each group in formula (I), examples of the alkyl include linear or branched alkyl groups having 1 to 20 carbon atoms. Specific examples include methyl, ethyl, propyl, isopropyl, butyl, isobutyl, sec-butyl, tert-butyl, pentyl, isopentyl, hexyl, heptyl, octyl, nonyl, decyl, undecyl, dodecyl, pentadecyl, and the like. The alkyl moieties in the lower alkoxyalkyl, aralkyloxyalkyl, lower alkoxyalkoxyalkyl, lower alkoxyalkoxyalkoxyalkyl, alkylamino, and hydroxyalkylamino have the same meaning as the alkyl described above. Examples of the alicyclic alkyl include those having 3 to 8 carbon atoms. Specific examples include cyclopropyl, cyclobutyl, cyclopentyl, cyclohexyl, cycloheptyl, cyclooctyl, and the like. The alicyclic alkyl moiety in the alicyclic alkoxy has the same meaning as the alicyclic alkyl described above.

The lower alkyl represents the above-described alkyls having 1 to 8 carbon atoms. The lower alkyl moieties in the hydroxy(lower alkyl), lower alkoxy, lower alkoxyalkyl, lower alkoxyalkoxyalkyl, lower alkoxyalkoxyalkoxyalkyl, lower alkanoyl, lower alkanoyloxy, lower alkoxycarbonyl, lower alkoxycarbonylamino, lower alkoxycarbonyloxy, lower dialkylamino, and lower dialkylaminocarbonyloxy have the same meaning as the lower alkyl described above.

Examples of the lower alkenyl moiety in the lower alkenyloxy include linear or branched alkenyls having 2 to 6 carbon atoms. Specific examples include vinyl, allyl, crotyl, prenyl, and the like.

Examples of the aralkyl moieties in the aralkyl, aralkyloxy, aralkyloxyalkyl, and aralkyloxycarbonylamino include those having 7 to 15 carbon atoms. Specific examples include benzyl, phenethyl, phenylpropyl, benzhydryl, naphthylmethyl, and the like.

Examples of the aryl moieties in the aryl, aryloxy, and arylsulfonylamino include phenyl and naphthyl, and the like. The heterocyclic group is a fused or nonfused 3- to 8-membered heterocyclic group containing at least one hetero atom. Specific examples of the hetero atom include oxygen, sulfur, nitrogen, and the like. Specific examples of the heterocyclic group include 5- or 6-membered monocyclic nitrogen-containing aromatic heterocyclic groups and bicyclic nitrogen-containing aromatic heterocyclic groups in which 5-membered and 6-membered or two 6-membered rings are fused (for example, imidazolyl, pyridyl, indolyl, quinolyl, isoquinolyl, quinoxalinyl, quinazolinyl, and the like), and 5- or 6-membered nitrogen-containing alicyclic heterocyclic groups (for example, pyrrolidinyl, oxopyrrolidinyl, piperidyl, piperidino, piperazinyl, morpholino, thiomorpholino, homopiperidyl, homopiperazinyl, tetrahydropyridyl, and the like). Furthermore, 1,3-dioxolan-4-yl, 1,3-dioxan-4-yl, 1,3-dioxan-5-yl, and the like are preferred oxygen-containing alicyclic heterocyclic groups.

Examples of the substituent on the lower alkyl, alicyclic alkyl, aralkyl, aralkyloxy, aryl, aryloxy, arylsulfonylamino, or heterocycle include 1 to 3 substituents, which are the same or different, such as halogen (e.g., fluorine, chlorine, bromine, iodine), nitro, hydroxy, lower alkanoyl, lower alkanoyloxy, lower alkyl, lower alkoxy, aroyl, aroyloxy, lower alkoxycarbonyl, lower alkoxycarbonylamino, lower alkoxycarbonyloxy, lower dialkylcarbamoyloxy, lower alkoxyaralkyloxycarbonyl, substituted or unsubstituted aralkyloxycarbonyl, substituted or unsubstituted aryloxycarbonyl, —OPO(OH)$_2$, —OSO$_3$H, —OSiR$^{5B}_3$, carboxy, and the like. The halogen represents fluorine, chlorine, bromine, or iodine. The lower alkanoyl, lower alkanoyloxy, lower alkyl, lower alkoxy, lower alkoxycarbonyl, lower alkoxycarbonylamino, lower alkoxycarbonyloxy, and R$^{5B}$ have the same meaning as defined above, respectively. The aryl moieties in the aralkyloxycarbonyl, aryloxycarbonyl, aroyl, and aroyloxy and the lower alkyl moiety in the lower dialkylcarbamoyloxy have the same meaning as defined above. The lower alkyl moiety and aralkyl moiety in the lower alkoxyaralkyloxycarbonyl have the same meaning as defined above.

Examples of the substituent on the substituted alkyloxycarbonyl or the substituted aryloxycarbonyl, include 1 to 3 substituents, which are the same or different, such as lower alkyl, lower alkoxy, halogen, nitro, hydroxy, lower alkanoyl, lower alkoxycarbonyl, and the like. The alkyl moieties in the lower alkyl, lower alkoxy, lower alkanoyl, and lower alkoxycarbonyl have the same meaning as defined above.

Preferred examples of compounds (I) include those in which R$^3$ is —CH$_2$OCOR$^7$ (wherein R$^7$ has the same meaning as defined above). Among these, preferred are compounds in which R$^7$ is —(CH$_2$)$_{n6}$CHR$^{7F}$R$^{7G}$ wherein n6, R$^{7F}$, and R$^{7G}$ have the same meaning as defined above).

Pharmaceutically acceptable salts of compounds (I) include pharmaceutically acceptable acid addition salts, metal salts, ammonium salts, organic-amine addition salts, and amino-acid addition salts. Examples of the acid addition salts include inorganic acid salts (for example, hydrochlorides, hydrobromides, sulfates, phosphates, and the like), and organic acid salts (for example, formates, acetates, benzoates, maleates, fumarates, succinates, tartarates, citrates, oxalates, methanesulfonates, p-toluenesulfonates, and the like). Examples of the metal salts include alkali metal salts (for example, lithium salts, sodium salts, potassium salts, and the like), alkaline earth metal salts (for example, magnesium salts and calcium salts, and the like), aluminum salts, zinc salts, and the like. Examples of the ammonium salts include ammonium salts, tetramethylammonium salts, and the like. Examples of the organic-amine addition salts include addition salts with morpholine, piperidine, and the like. Examples of the amino-acid addition salts include addition salts with glycine, phenylalanine, asparagine, glutamic acid, lysine, and the like.

Processes for producing compounds (I) are described below.

In the processes shown below, if a group defined changes under the conditions used in a process employed or is unsuitable for carrying out the process, the group can be subjected to a method ordinarily used in organic synthesis chemistry, for example, protection of a functional group, leaving of a protecting group, or a method such as oxidation, reduction, hydrolysis, or the like, whereby the process can be easily carried out.

Process 1

Among compounds (I), those in which R$^1$ and R$^2$ are hydrogen and W is oxygen are referred to as compounds (Ia); those in which R$^1$ is a substituent other than hydrogen, R$^2$ is hydrogen, and W is oxygen are referred to as compounds (Ib); and those in which R$^1$ and R$^2$ are substituents other than hydrogen, and W is oxygen are referred to as compounds (Ic). These compounds (I) can be produced, for example, through the following synthesis routes using DC107 (described in Japanese Published Unexamined Patent Application 112988/89) as a starting material.

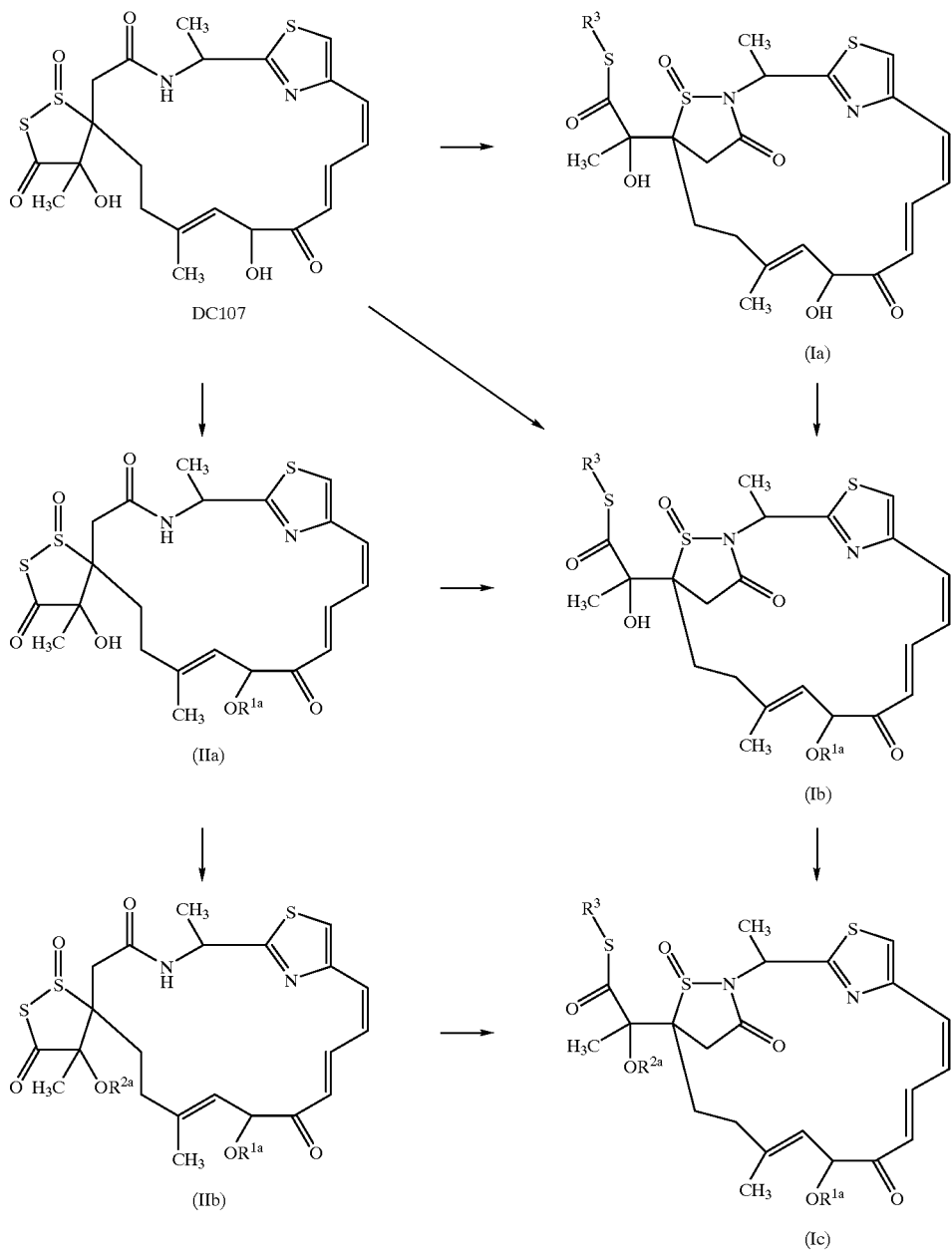

{In the above formulae, $R^{1a}$ represents a group according to the definition of $R^1$ except that hydrogen and —$CH_2OCOR^5$ (wherein $R^5$ has the same meaning as defined above) are excluded therefrom; $R^{2a}$ represents a group according to the definition of $R^2$ except that hydrogen is excluded therefrom; and $R^3$ has the same meaning as defined above.}

Compounds (Ia), (Ib), and (Ic) can be produced, for example, by the steps shown below based on the above synthesis routes according to the kinds of $R^{1a}$, $R^{2a}$, and $R^3$.

(Step 1)

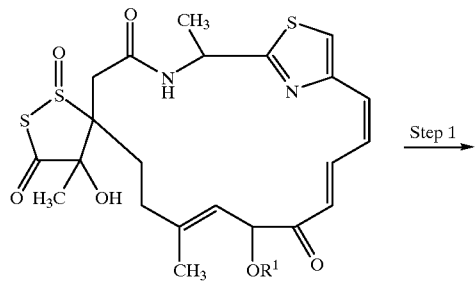

DC107; $R^1 = H$
(IIa); $R^1 = R^{1a}$

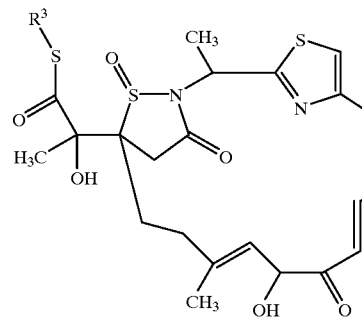

(Ia); $R^1 = H$
(Ib1); $R^1 = R^{1a}$
(Ib2); $R^1 = R^3 = CH_2OCOR^5$ (In the formulae, $R^{1a}$ and $R^3$ have the same meaning as defined above.)

Compound (Ia) or (Ib1) can be obtained by reacting DC107 or compound (IIa) with compound (III) represented by the following formula:

$$R^3X \qquad (III)$$

(wherein $R^3$ has the same meaning as defined above; and X represents chlorine, bromine, or iodine) in the presence of a base in a solvent inert to the reaction.

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. The base includes amines (for example, pyridine, imidazole, triethylamine, diisopropylethylamine, and the like), and carbonates or bicarbonates of an alkali metal or alkaline earth metal, (for example, sodium carbonate, potassium carbonate, calcium carbonate, sodium hydrogen carbonate, and the like). Dimethylaminopyridine or the like can be also used as a catalyst. It is also possible to accelerate the reaction by adding potassium iodide, sodium iodide, tetrabutylammonium iodide, or the like, in an amount of 1 to 100 equivalents. Compound (III) is generally used in an amount of at least 1 equivalent, preferably 1 to 100 equivalents, to DC107 or compound (IIa). The base is generally used in an amount of at least 1 equivalent, preferably 1 to 200 equivalents, to DC107 or compound (IIa). The reaction terminates usually in 10 minutes to 24 hours at 0 to 50° C. If DC107 is allowed to react under the above conditions with compound (IIIa), among compounds (III), in which $R^3$ is $-CH_2OCOR^5$ (wherein $R^5$ has the same meaning as defined above), compound (Ib2) in which $R^1$ and $R^3$ are the same substituent ($R^1=R^3=CH_2OCOR^5$) can be obtained together with compound (Ia). In this case, the yields of compound (Ia) and compound (Ib2) vary depending on conditions, such as the kind and equivalent amount of compound (IIIa), the solvent, and the like.

(Step 2)

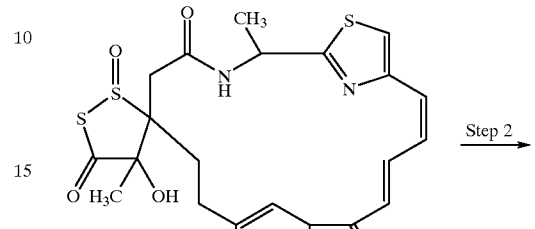

DC107

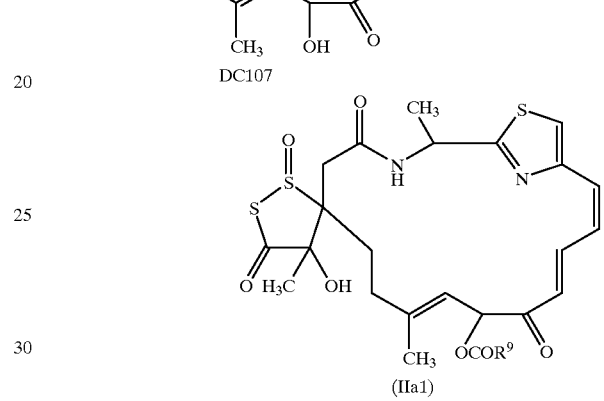

(IIa1)

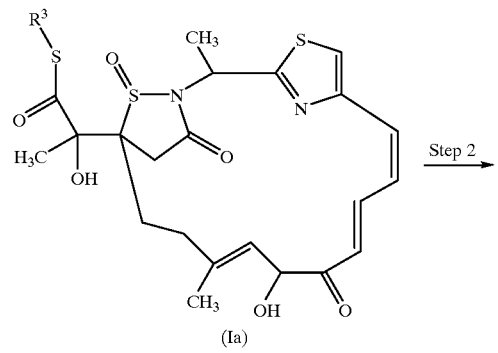

(Ia)

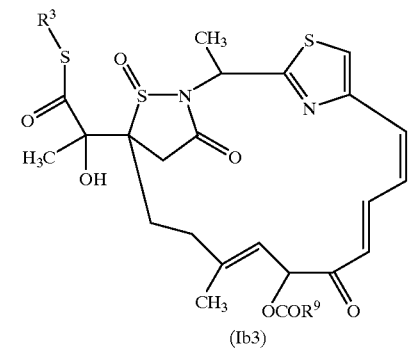

(Ib3)

(In the formulae, $R^3$ has the same meaning as defined above; and $R^9$ has the same meaning as $R^4$) Among compounds (IIa) and (Ib), compound (IIa1) or (Ib3) in which $R^1$ is $COR^9$ (wherein $R^9$ has the same meaning as $R^4$) can be obtained by reacting DC107 or compound (Ia) with compound (IV) represented by the following formula:

$$(R^4CO)_2O \qquad (IV)$$

(wherein R⁴ has the same meaning as defined above) or with compound (V) represented by the following formula:

$$R^4COX \quad (V)$$

(wherein R⁴ has the same meaning as defined above; and X represents chlorine, bromine, or iodine) in the presence of a base in a solvent inert to the reaction. Use of DC107 gives compound (IIa1), while use of compound (Ia) gives compound (Ib3). Compound (IV) or (V) is generally used in an amount of at least 1 equivalent, preferably 1 to 100 equivalents, to DC107 or compound (Ia).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the base include pyridine, triethylamine, diisopropylethylamine, and the like. These bases may be used alone or as a mixture thereof. It is possible to accelerate the reaction by adding dimethylaminopyridine or the like in an amount of 0.1 to 2 equivalents. The base is generally used in an amount of at least 1 equivalent, preferably 1 to 200 equivalents, to DC107 or compound (Ia). The reaction terminates usually in 5 minutes to 24 hours at −20 to 50° C.

(Step 3)

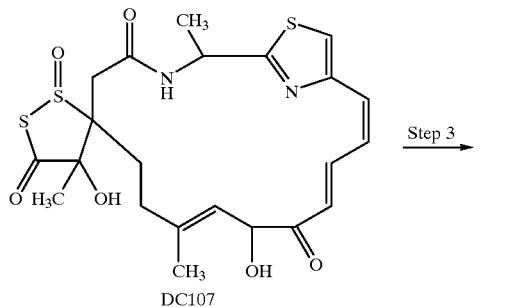

DC107

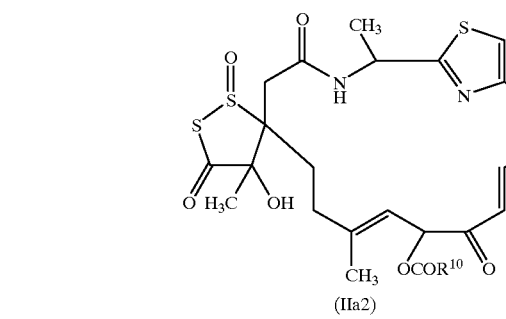

(IIa2)

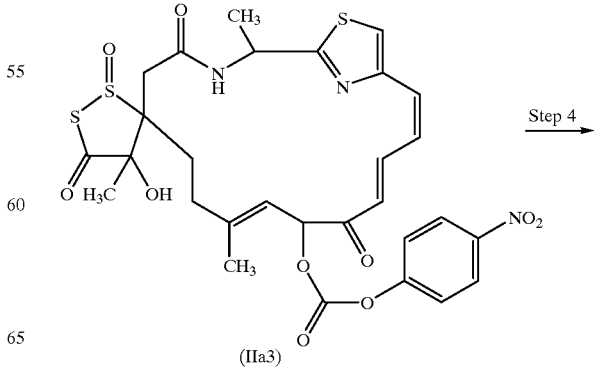

(Ia)

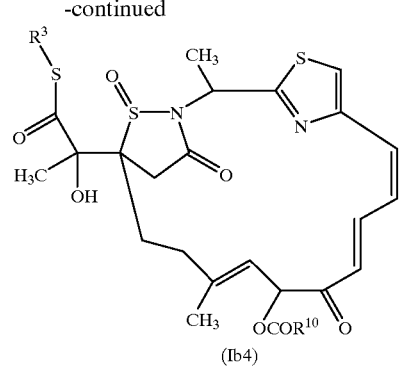

(Ib4)

(In the formulae, R³ has the same meaning as defined above; and R¹⁰ represents a group according to the definition of R⁴ except that the lower alkoxy, alicyclic alkoxy, 9-fluorenylmethoxy, aralkyloxy, and substituted or unsubstituted aryloxy are excluded therefrom.)

Among compounds (IIa) and (Ib), compound (IIa2) or (Ib4) in which $R^{1a}$ is $COR^{10}$ (wherein R¹⁰ has the same meaning as defined above) can be obtained by reacting DC107 or compound (Ia) with compound (VI) represented by the following formula:

$$R^{10}CO_2H \quad (VI)$$

(wherein R¹⁰ has the same meaning as defined above) in an inert solvent in the presence of a condensing agent. The solvent used for this reaction may be any of the above-described inert solvents. However, chloroform and dichloromethane are preferred. Any condensing agent may be used so long as it is used for the ordinary condensation of carboxylic acids with alcohols. For example, dicyclohexylcarbodiimide, 1-ethyl-3-(3-dimethylaminopropyl)carbodiimide hydrochloride, or the like is used. It is possible to further add dimethylaminopyridine or the like in an amount of 0.1 to 10 equivalents. Compound (VI) and the condensing agent are generally used in an amount of 1 to 100 equivalents to DC107 or compound (Ia). The reaction terminates usually in 10 minutes to 24 hours at 0 to 30° C.

(Step 4)

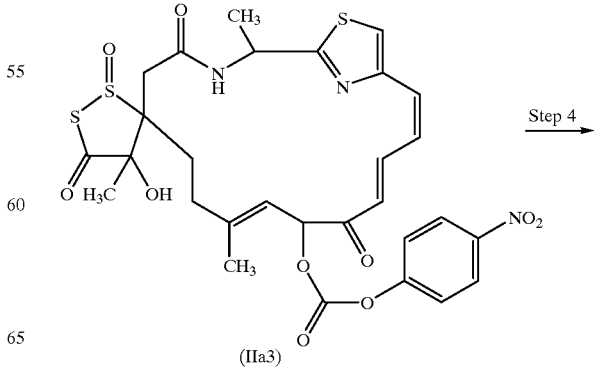

(IIa3)

-continued

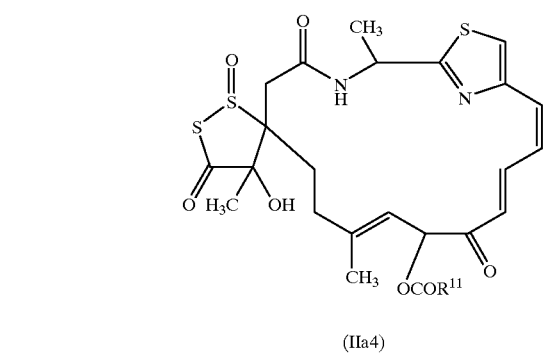

(IIa4)

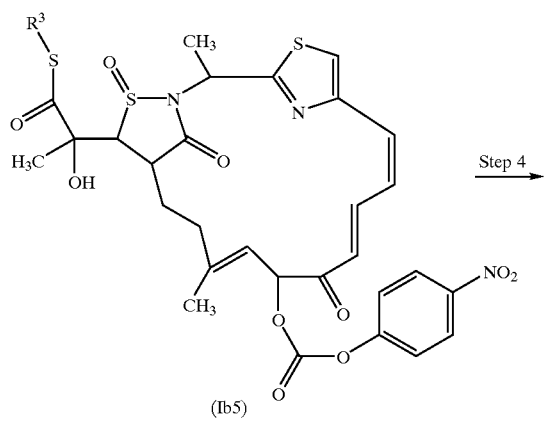

(Ib5)

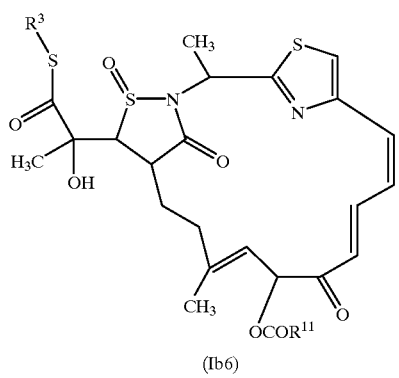

(Ib6)

(In the formulae, $R^3$ has the same meaning as defined above; and $R^{11}$ represents a nitrogen-containing alicyclic heterocyclic group.)

Among compounds (IIa) or (Ib), compound (IIa4) or (Ib6) in which $R^{1a}$ is $COR^{11}$ (wherein $R^{11}$ has the same meaning as defined above) can be produced by reacting compound (IIa3) or (Ib5) in which $R^{1a}$ is p-nitrophenyloxycarbonyl with a nitrogen-containing alicyclic heterocyclic compound in an inert solvent. Although any of the above-described inert solvents may be used for this reaction, chloroform and dichloromethane are preferred. The nitrogen-containing alicyclic heterocyclic compound is generally used in an amount of 1 to 10 equivalents. The reaction terminates usually in 10 minutes to 24 hours at 0 to 30° C.

(Step 5-1)

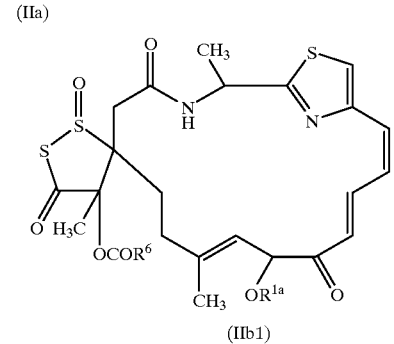

(IIa)

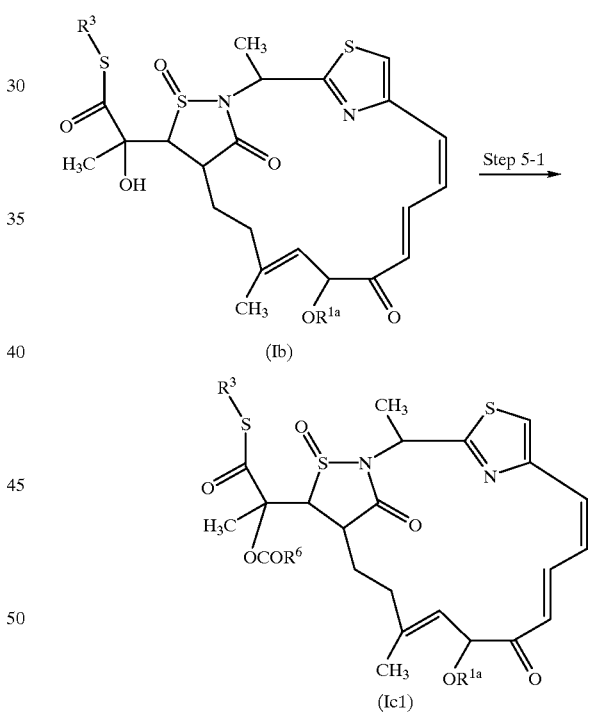

(In the formulae, $R^{1a}$, $R^3$, and $R^6$ have the same meaning as defined above.)

Compound (IIb1) or (Ic1) can be obtained by reacting compound (IIa) or (Ib) with compound (VII) represented by the following formula:

$$(R^6CO)_2O \qquad (VII)$$

(wherein $R^6$ has the same meaning as defined above) or with compound (VIII) represented by the following formula:

$$R^6COX \qquad (VIII)$$

(wherein $R^6$ and X have the same meaning as defined above) in the presence of a base in a solvent inert to the reaction. Use of compound (IIa) gives compound (IIb1), while use of compound (Ib) gives compound (Ic1).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the base include pyridine, triethylamine, diisopropylethylamine, and the like. These bases may be used alone or as a mixture

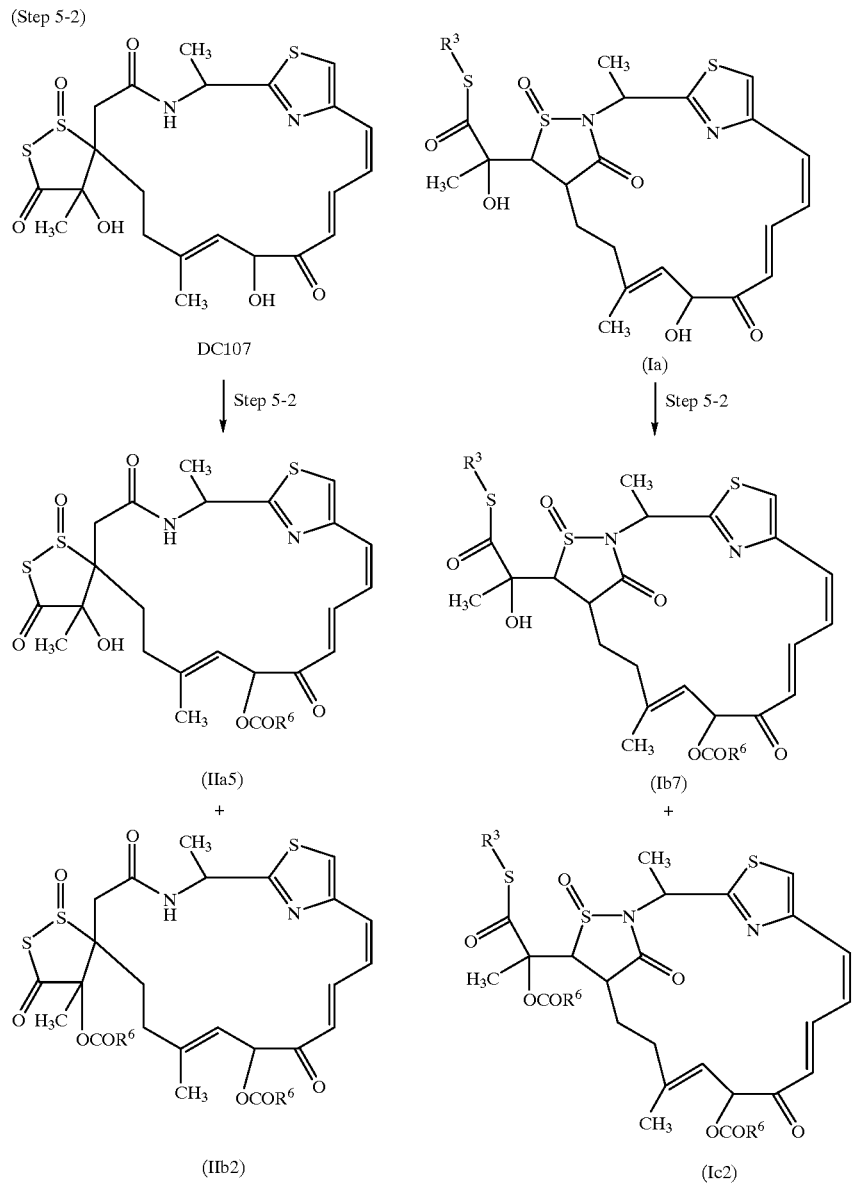

thereof. It is possible to further add dimethylaminopyridine or the like in an amount of 0.1 to 10 equivalents.

Compound (VII) or (VIII) is generally used in an amount of at least 1 equivalent, preferably 1 to 100 equivalents, to compound (IIa) or (Ib). The base is generally used in an amount of at least 1 equivalent, preferably 1 to 500 equivalents, to compound (IIa) or (Ib). The reaction terminates usually in 5 minutes to 20 hours at −20 to 50° C.

(In the formulae, $R^3$ and $R^6$ have the same meaning as defined above).

If step 5-1 is conducted using DC107 or compound (Ia) as a starting material (step 5-2), compound (IIb2) or (Ic2) in which $R^{2a}$ and $R^{1a}$ are the same substituent ($R^{1a}=R^{2a}=COR^6$) can be obtained together with compound (IIa5) or (Ib7). In this case, the yields of (IIa5) and (IIb2) or (Ib7) and (Ic2) vary depending on conditions, such as the kind and equivalent amount of compound (VII) or (VIII), the solvent, and the like.

(Step 6-1)

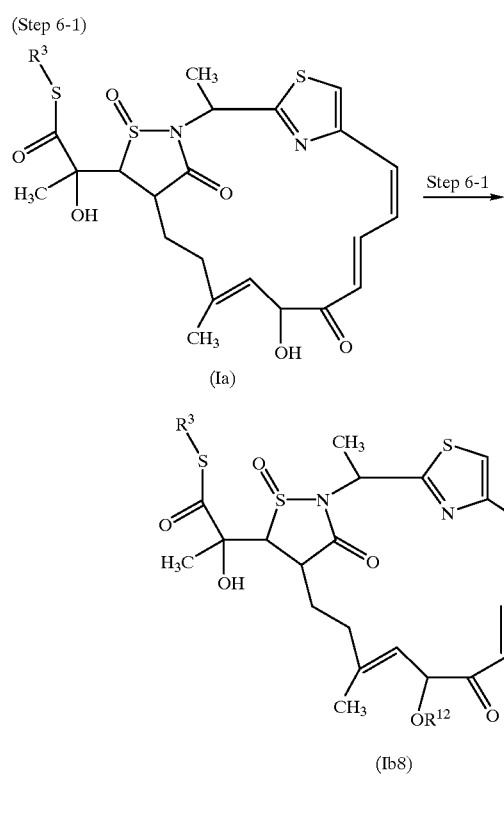

(In the formulae, $R^3$ has the same meaning as defined above; and $R^{12}$ represents lower alkoxyalkyl, aralkyloxyalkyl, lower alkoxyalkoxyalkyl, or lower alkoxyalkoxyalkoxyalkyl.)

Among compounds (Ib), compound (Ib8) in which $R^{1a}$ is lower alkoxyalkyl, aralkyloxyalkyl, lower alkoxyalkoxyalkyl, or lower alkoxyalkoxyalkoxyalkyl can be synthesized by reacting compound (Ia) with compound (IX) represented by the following formula:

$$R^{12}X \quad \text{(IX)}$$

(wherein $R^{12}$ and X have the same meaning as defined above) in a solvent inert to the reaction (for example, chloroform, dichloromethane, dimethylformamide, acetonitrile, ether, tetrahydrofuran, or the like) in the presence of a tertiary amine (for example, triethylamine, diisopropylethylamine, N-methylpiperidine, or the like). Compound (IX) and the tertiary amine are generally used in amounts of 1 to 100 equivalents and 1 to 200 equivalents, respectively. The reaction terminates usually in 1 to 24 hours at 0 to 50° C.

(Step 6-2)

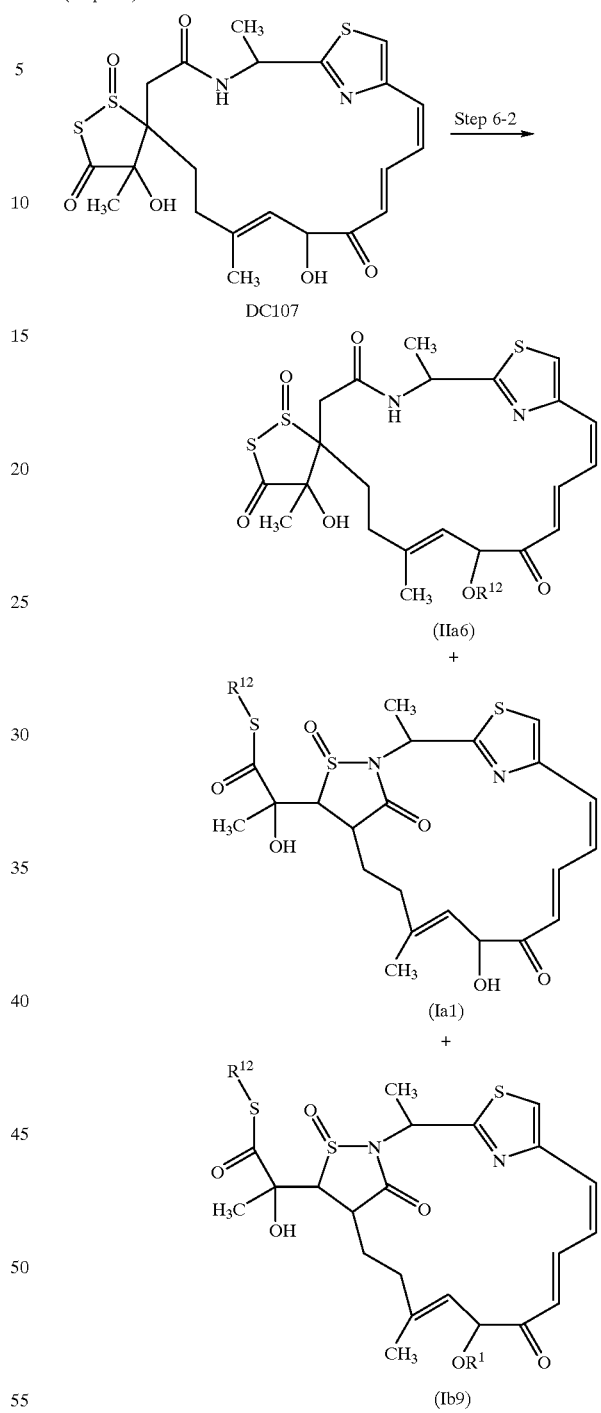

(In the formulae, $R^{12}$ has the same meaning as defined above.)

If step 6-1 is conducted using DC107 as a starting material, the reaction may yield compound (IIa6) or (Ia1) in which one of $R^{1a}$ and $R^3$ is lower alkoxyalkyl, aralkyloxyalkyl, lower alkoxyalkoxyalkyl, or lower alkoxyalkoxyalkoxyalkyl, and compound (Ib9) in which $R^{1a}$ and $R^3$ are lower alkoxyalkyl, aralkyloxyalkyl, lower alkoxyalkoxyalkyl, or lower alkoxyalkoxyalkoxyalkyl. The yields of compounds (IIa6), (Ia1), and (Ib9) vary depending on conditions, such as the kind and equivalent amount of compound (IX) or base, the solvent, reaction temperature, and the like.

(Step 7)

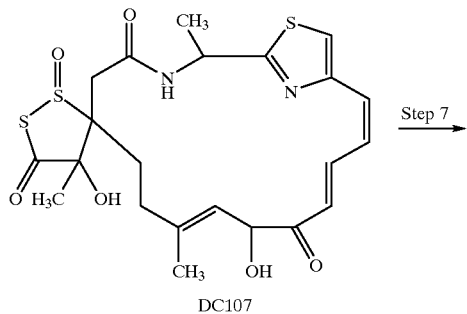

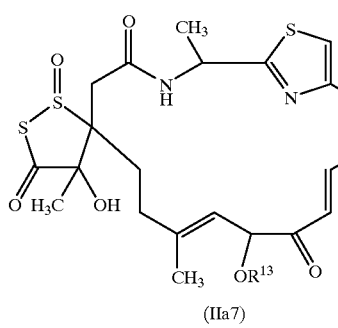

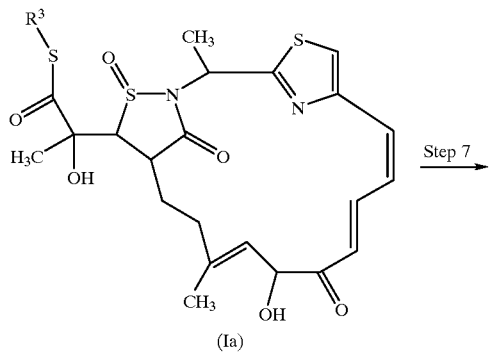

{In the formulae, $R^3$ has the same meaning as defined above; and $R^{13}$ represents tetrahydropyranyl, lower alkoxyalkyl, aralkyl, or

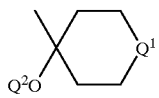

(wherein $Q^1$ and $Q^2$ have the same meaning as defined above).}

Compound (IIa7) or (Ib$_{10}$) can be produced by reacting DC107 or compound (Ia) with 3,4-dihydro-2H-pyran when $R^{13}$ is tetrahydropyranyl, or with aralkyl 2-trichloroacetimidate when $R^{13}$ is aralkyl, or with lower alkoxyalkene when $R^{13}$ is lower alkoxyalkyl, or with

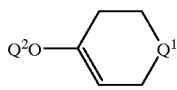

(wherein $Q^1$ and $Q^2$ have the same meaning as defined above) when $R^{13}$ is

(wherein $Q^1$ and $Q^2$ have the same meaning as defined above), in the presence of an acid in a solvent inert to the reaction. Each of these compounds is used in an amount of 1 to 300 equivalents to DC107 or compound (Ia).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the acid include organic acid (for example, p-toluenesulfonic acid, camphorsulfonic acid, pyridinium p-toluenesulfonate, trifluoroacetic acid, trifluoromethanesulfonic acid, and the like), inorganic acids (for example, hydrochloric acid, sulfuric acid, and the like), and Lewis acids (for example, titanium tetrachloride, a boron trifluoride/diethyl ether complex, and the like). The acid is generally used in an amount of 0.1 to 5 equivalents to DC107 or compound (Ia). The reaction terminates usually in 5 minutes to 24 hours at −30 to 30° C.

Process 2

Among compounds (I), those in which $R^1$ is hydrogen, $R^2$ is represented by COR (wherein $R^6$ has the same meaning as defined above), and W is oxygen are referred to as compounds (Id) or compounds (Ie). Compound (Id) or (Ie) can be produced, for example, by the following step:

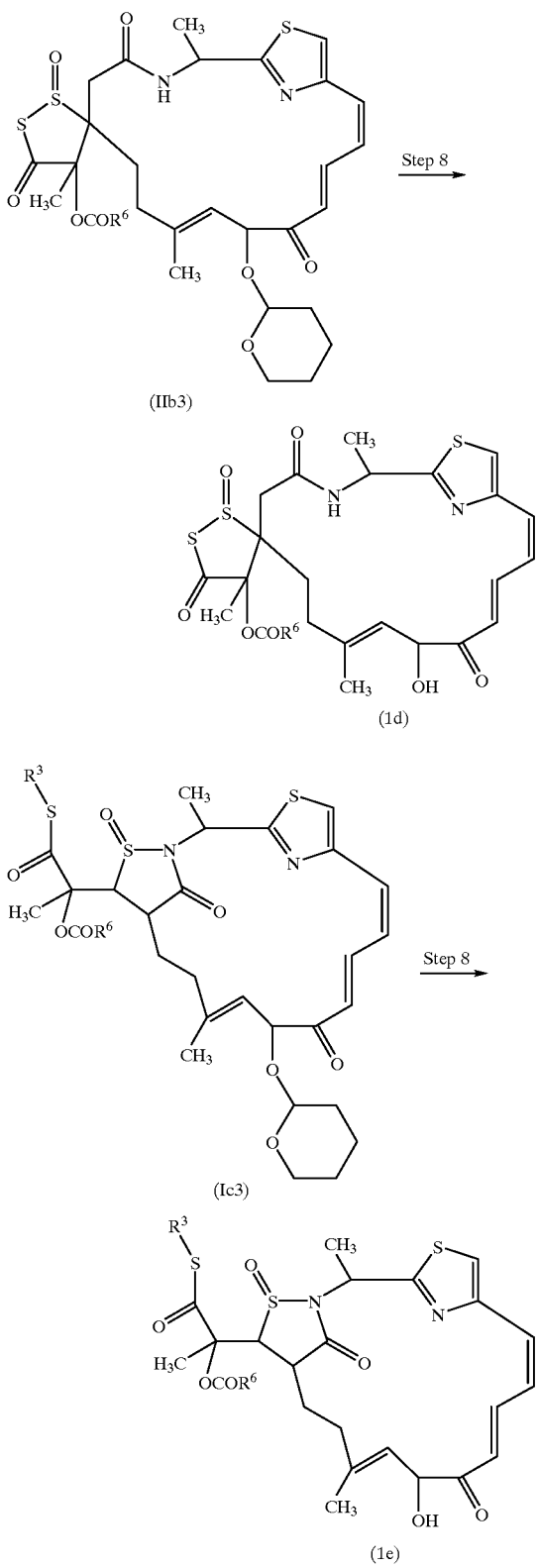

(In the formulae, $R^3$ and $R^6$ have the same meaning as defined above.)

Compound (Id) or (Ie) can be produced by treating compound (IIb3) or (Ic3) with 0.1 to 100 equivalents of an organic acid (for example, p-toluenesulfonic acid, camphorsulfonic acid, or the like) or an inorganic acid (for example, hydrochloric acid, sulfuric acid, or the like) in a solvent (for example, methanol, ethanol, or the like). The reaction terminates usually in 5 minutes to 24 hours at −30 to 30° C.

Process 3

Among compounds (I), those in which W is oxygen or $NR^8$ (wherein $R^8$ has the same meaning as defined above) are referred to as compounds (If) or compounds (Ig) respectively. Compound (Ig) can be produced from compound (If), for example, by the following step:

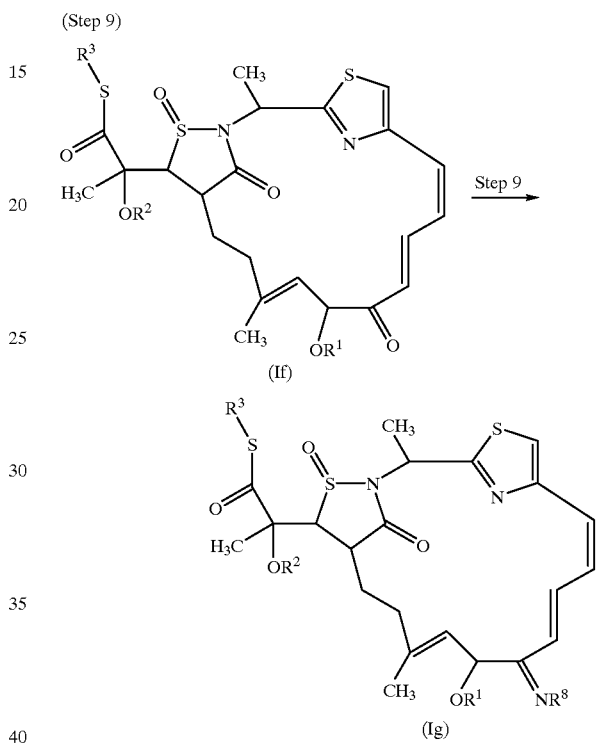

(In the formulae, $R^1$, $R^2$, $R^3$, and $R^8$ have the same meaning as defined above.)

Compound (Ig) can be obtained by reacting compound (If) with compound (X) represented by the following formula:

$$R^8NH_2 \qquad (X)$$

(wherein $R^3$ has the same meaning as defined above) or with a hydrochloride thereof in a solvent inert to the reaction.

Examples of the solvent for use in the reaction include methanol, ethanol, dichloromethane, chloroform, tetrahydrofuran, dimethylformamide, acetonitrile, and the like. These may be used alone or as a mixture thereof. This reaction can be accelerated by adding pyridine or an acid. The acid is preferably an organic acid (for example, p-toluenesulfonic acid, camphorsulfonic acid, pyridinium p-toluenesulfonate, or the like). An inorganic acid (for example, hydrochloric acid, sulfuric acid, or the like) can be also used.

Compound (X) is generally used in an amount of 1 to 50 equivalents to compound (If). Pyridine or an acid may be used in an amount of 1 to 100 equivalents. The reaction terminates usually in 5 minutes to 24 hours at 0 to 30° C.

Process 4

Among compounds (I), those in which $R^3$ is $CH_2OCOR^7$ (wherein $R^7$ has the same meaning as defined above), $R^1$ is hydrogen or $R^{1a}$, and W is oxygen are referred to as compounds (Ih) or compounds (Ii), respectively. Compound (Ih) or (Ii) can be produced, for example, by the following step according to the kind of $R^3$.

(Step 10)

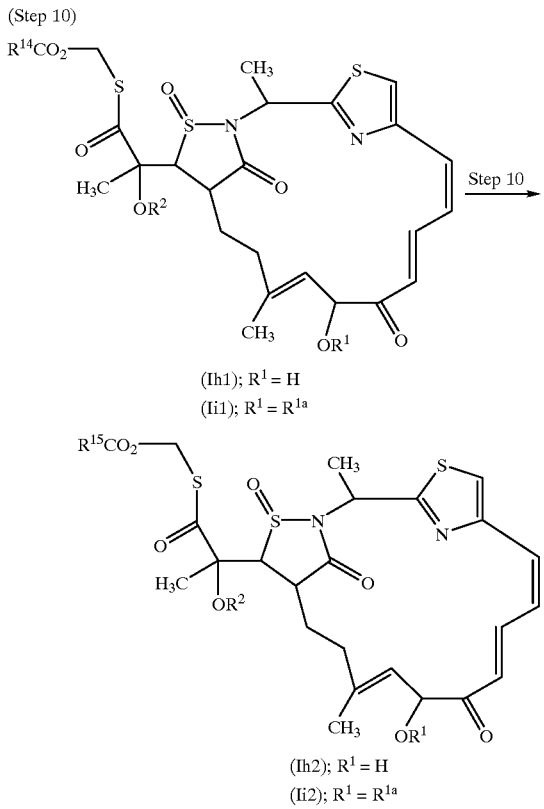

(Ih1); $R^1 = H$
(Ii1); $R^1 = R^{1a}$ (Ih2); $R^1 = H$
(Ii2); $R^1 = R^{1a}$ (In the formulae, $R^1$, $R^{1a}$, and $R^2$ have the same meaning as defined above; $R^{14}$ represents a substituent represented by $R^7$ and containing a phenyl group substituted with lower alkanoyloxy; and $R^{15}$ represents a substituent represented by $R^7$ and containing a hydroxyphenyl group corresponding to the $R^{14}$.)

Among compounds (Ih) or (Ii), compound (Ih2) or (Ii2) in which $R^3$ is $CH_2OCOR^{15}$ (wherein $R^{15}$ has the same meaning as defined above), and $R^1$ is hydrogen or $R^{1a}$ can be produced from compound (Ih1) or (Ii1), among compounds (Ii), in which $R^3$ is $CH_2OCOR^{14}$ (wherein $R^{14}$ has the same meaning as defined above), and $R^1$ is hydrogen or $R^{1a}$ by treating compound (Ih1) or (Ii1) in a solvent (for example, tetrahydrofuran, methanol, ethanol, or the like) with 0.1 to 100 equivalents of an organic acid (for example, p-toluenesulfonic acid, camphorsulfonic acid, or the like) or an inorganic acid (for example, hydrochloric acid, sulfuric acid, or the like) or with 0.1 to 100 equivalents of an aqueous solution of in inorganic base (for example, sodium bicarbonate, sodium carbonate, sodium hydroxide, or the like) to thereby convert the alkanoyloxy group to a hydroxy group. The reaction terminates usually in 5 minutes to 72 hours at −30 to 30° C. If compound (Ii1) is allowed to react under the above conditions, compound (Ih2) in which $R^1$ is hydrogen can be also obtained together with compound (Ii2). In this case, the yields of compounds (Ih2) and (Ii2) vary depending on conditions, such as the kind and equivalent amount of the acid or base used, the solvent, reaction temperature, and the like.

(Step 11)

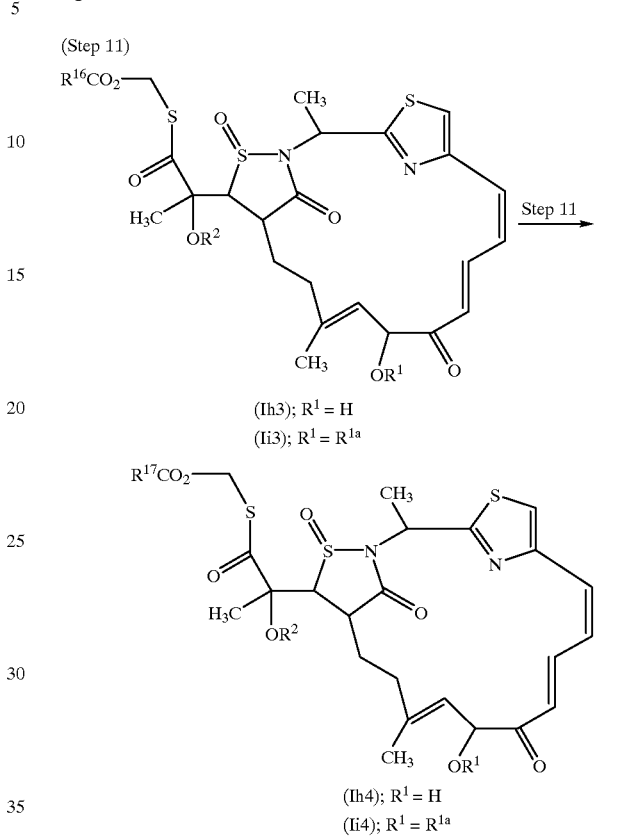

(Ih3); $R^1 = H$
(Ii3); $R^1 = R^{1a}$ (Ih4); $R^1 = H$
(Ii4); $R^1 = R^{1a}$ (In the formulae, $R^1$, $R^{1a}$, and $R^2$ have the same meaning as defined above; $R^{16}$ represents a substituent represented by $R^7$ and containing a 5- or 6-membered ring 17 structure containing —$OC(CH_3)_2O$—; and $R^{17}$ represents a substituent represented by $R^7$ and containing 1,2- or 1,3-diol resulting from leaving of the acetonide of $R^{16}$.)

Among compounds (Ih) or (Ii), compound (Ih4) or (Ii4) in which $R^3$ is $CH_2OCOR^{17}$ (wherein $R^{17}$ has the same meaning as defined above), and $R^1$ is hydrogen or $R^{1a}$ can be produced from compound (Ih3) or (Ii3), among compounds (Ii), in which $R^3$ is $CH_2OCOR^{16}$ (wherein $R^{16}$ has the same meaning as defined above), and $R^1$ is hydrogen or Ria by treating compound (Ih3) or (Ii3) in a solvent (for example, tetrahydrofuran, methanol, ethanol, or the like) with 0.1 to 100 equivalents of an organic acid (for example, p-toluenesulfonic acid, camphorsulfonic acid, or the like) or an inorganic acid (for example, hydrochloric acid, sulfuric acid, or the like) to thereby convert —$OC(CH_3)_2O$— to a diol. The reaction terminates usually in 5 minutes to 72 hours at 0 to 50° C. If compound (Ii3) is allowed to react under the above conditions, compound (Ih4) in which $R^1$ is hydrogen can be also obtained together with compound (Ii4). In this case, the yields of compounds (Ih4) and (Ii4) vary depending on conditions, such as the kind and equivalent amount of the acid or base used, the solvent, reaction temperature, and the like.

(Step 12)

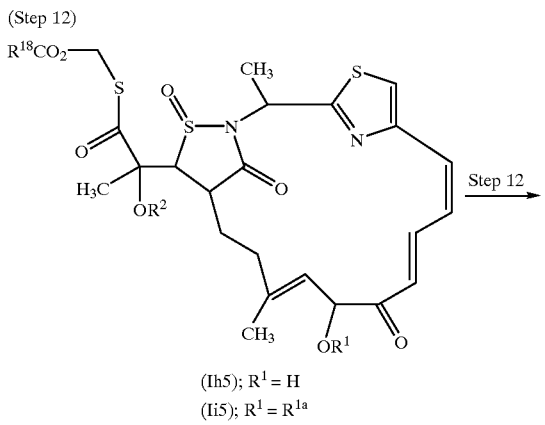

(Ih5); $R^1$ = H
(Ii5); $R^1$ = $R^{1a}$

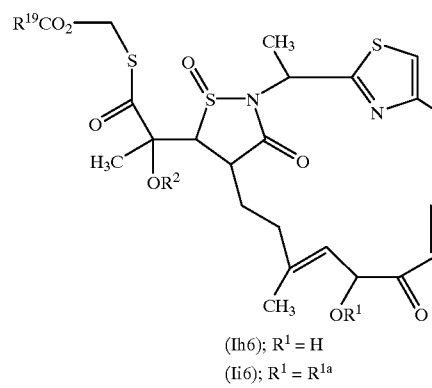

(Ih6); $R^1$ = H
(Ii6); $R^1$ = $R^{1a}$

{In the formulae, $R^1$, $R^{1a}$, and $R^2$ have the same meaning as defined above; $R^{18}$ represents a substituent represented by $R^7$ and containing —$OSiR^{7B}_3$ (wherein $R^{7B}$ has the same meaning as defined above); and $R^{19}$ represents a substituent represented by $R^7$ and containing a hydroxy group corresponding to the $R^{18}$.}

Among compounds (Ih) or (Ii), compound (Ih6) or (Ii6) in which $R^3$ is $CH_2OCOR^{19}$ (wherein $R^{19}$ has the same meaning as defined above), and $R^1$ is hydrogen or $R^{1a}$ can be produced by reacting compound (Ih5) or (Ii5), among compounds (Ii), in which $R^3$ is $CH_2OCOR^{18}$ (wherein $R^{18}$ has the same meaning as defined above), and $R^1$ is hydrogen or $R^{1a}$ with 0.1 to 100 equivalents of the anion of a fluoride (for example, tetrabutylammonium fluoride, hydrogen fluoride, or the like) in a solvent (for example, methanol, ethanol, tetrahydrofuran, acetonitrile, or the like) to convert —$OSiR^{7B}_3$ to a hydroxy group. There are cases where the yield is improved by adding an organic acid (for example, acetic acid, or the like) to the reaction system in an amount of 0.1 to 100 equivalents. The reaction terminates usually in 5 minutes to 100 hours at −30 to 50° C.

(Step 13)

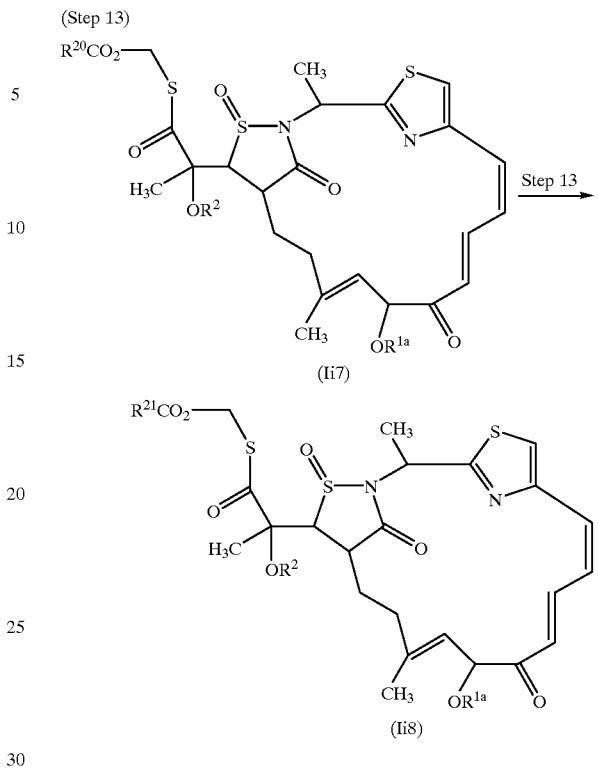

(Ii7)

(Ii8)

(In the formulae, $R^1$ and $R^2$ have the same meaning as defined above; $R^{20}$ represents a substituent represented by $R^7$ and containing a hydroxy group; and $R^{21}$ represents a substituent represented by $R^7$ and containing —$OPO(OH)_2$ or —$OSO_3H$ both corresponding to $R^{20}$.)

Among compounds (Ii), compound (Ii8) in which $R^3$ is $CH_2OCOR^{21}$ (wherein $R^{21}$ has the same meaning as defined above), and $R^1$ is $R^{1a}$ can be produced from compound (Ii7), among compound (Ii), in which $R^3$ is $CH_2OCOR^{20}$ (wherein $R^{20}$ has the same meaning as defined above) and $R^1$ is $R^{1a}$ by reacting compound (Ii7) with a phosphorylation agent (for example, phosphorus oxychloride, or the like) in the presence of a base in a solvent inert to the reaction and then adding an excess of water, a buffer solution, saturated common-salt solution, or the like, to thereby convert the hydroxy group to a phosphate group, or by reacting compound (Ii7) with a sulfonating agent (for example, chlorosulfuric acid, sulfur trioxide, or the like) in the presence of a base to thereby sulfonate the hydroxy group. The reaction terminates usually in 5 minutes to 24 hours at 0 to 50° C. Although any solvent inert to the reaction may be used for the reaction, it is preferred to use tetrahydrofuran, dimethylformamide, chloroform, or the like. The base for use in the reaction is usually an inorganic base (for example, sodium bicarbonate, potassium carbonate, sodium hydroxide, or the like) or an organic base (for example, pyridine, triethylamine, or the like). The base is used preferably in an amount of 1 to 100 equivalents.

Process 5

Although compounds (Ij), among compounds (I), in which $R^3$ is represented by

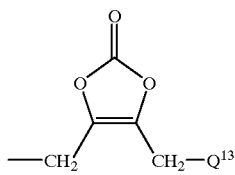

(wherein $Q^{13}$ has the same meaning as defined above), and W is oxygen can be synthesized by the steps described above, they can be also produced by the following steps 14 to 16.

(Step 14)

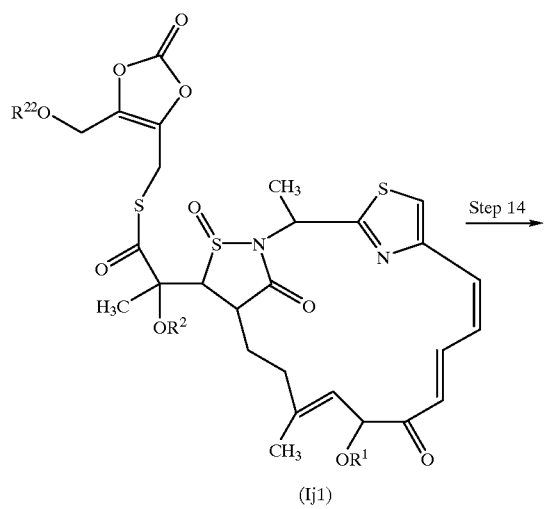

(Ij1)

$\xrightarrow{\text{Step 14}}$

-continued

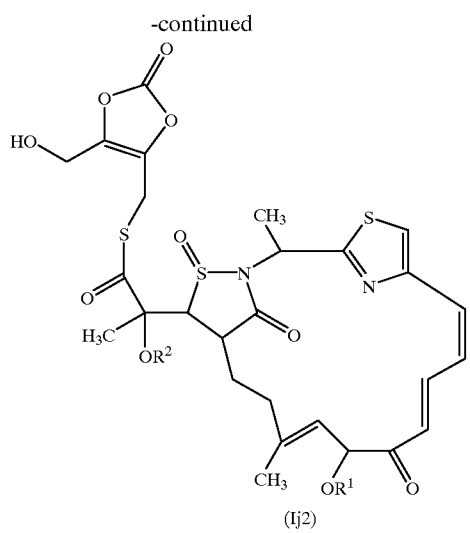

(Ij2)

(In the formulae, $R^{22}$ represents $-SiR^{71}_3$ or formyl; and $R^1$, $R^2$, and $R^{71}$ have the same meaning as defined above.)

Compound (Ij2) in which $Q^{13}$ is a hydroxy group can be produced from compound (Ij1) in which $R^{22}$ is $-SiR^{71}_3$ or formyl by a method ordinarily used in organic synthesis chemistry.

Compound (Ij1) in which $R^{22}$ is $-SiR^{71}_3$ is treated in a solvent (for example, methanol, ethanol, tetrahydrofuran, acetonitrile, or the like) with 0.1 to 100 equivalents of the anion of a fluoride (e.g., tetrabutylammonium fluoride, hydrogen fluoride, or the like), whereby the starting compound can be converted to compound (Ij2) in which $-OSiR^{71}_3$ has been converted to a hydroxy group. There are cases where the yield is improved by adding an organic acid (for example, acetic acid, or the like) to the reaction system in an amount of 0.1 to 100 equivalents. The reaction terminates usually in 5 minutes to 100 hours at $-30$ to $50°$ C. Compound (Ij1) in which $R^{22}$ is formyl is heated in a solvent (for example, water, methanol, ethanol, or the like), whereby the starting compound can be converted to compound (Ij2) in which the formyloxy has been converted to a hydroxy group. This reaction terminates usually in 5 minutes to 24 hours at 30 to 150° C. It is also possible to convert the starting compound to compound (Ij2) by treatment with 0.1 to 100 equivalents of an organic acid (for example, p-toluenesulfonic acid, camphorsulfonic acid, or the like) or an inorganic acid (for example, hydrochloric acid, sulfuric acid, or the like). This reaction terminates usually in 5 minutes to 24 hours at $-30$ to 30° C.

Compound (Ij4) having a hydroxy group as substituent of $Q^{13}$ ($Q^{13}$ has the same meaning as defined above) in $R^3$ of compound (Ij) can be produced by step 14 described above from compound (Ij3) having corresponding $-OSiR^{7J}_3$.
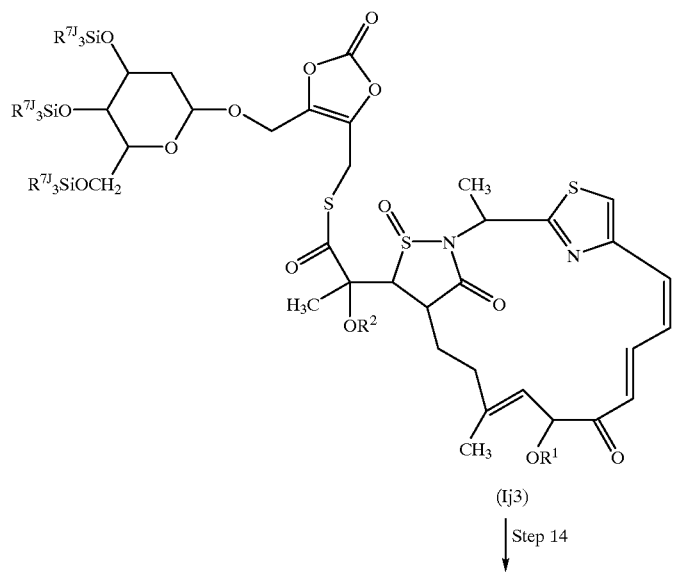
(Ij3)
Step 14
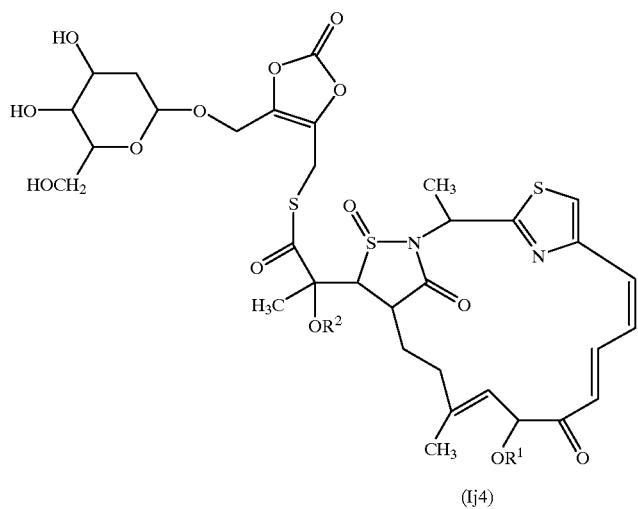
(Ij4)
(In the formulae, $R^1$, $R^2$ and $R^{7J}$ have the same meaning as defined above.)

(Step 15)

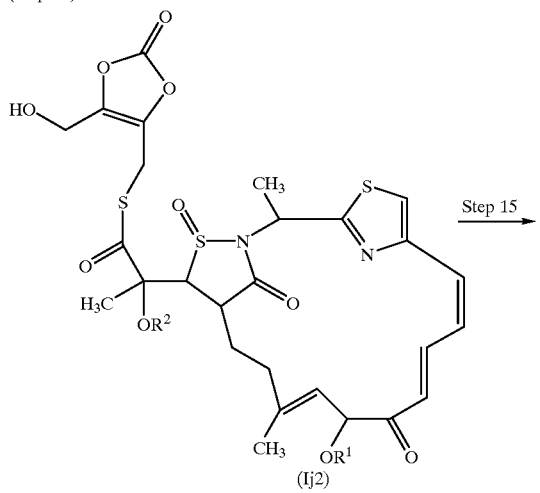

(Ij2)

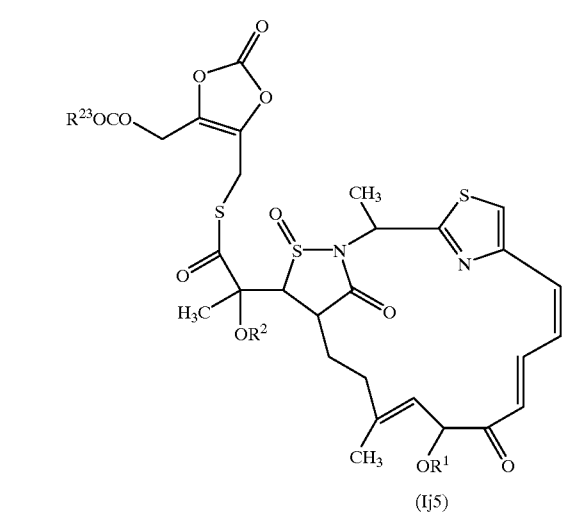

(Ij5)

(In the formulae, $R^{23}$ has the same meaning as $Q^{14}$; and R and $R^2$ have the same meaning as defined above.)

Compound (Ij5) can be obtained by reacting compound (Ij2) with compound (XI) represented by the following formula:

$$(R^{23}CO)_2O \qquad (XI)$$

(wherein $R^{23}$ has the same meaning as defined above) or with compound (XII) represented by the following formula:

$$R^{23} COX \qquad (XII)$$

(wherein $R^{23}$ and X have the same meaning as defined above) in the presence of a base in a solvent inert to the reaction. Compound (XI) or (XII) is generally used in an amount of at least 1 equivalent, preferably from 1 to 100 equivalents, to compound (Ij2).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the base include pyridine, triethylamine, diisopropylethylamine, and the like. These bases may be used alone or as a mixture thereof. It is possible to accelerate the reaction by further adding dimethylaminopyridine, or the like, in an amount of 0.1 to 2 equivalents. The base is generally used in an amount of at least 1 equivalent, preferably from 1 to 200 equivalents, to compound (Ij2). The reaction terminates usually in 5 minutes to 24 hours at −20 to 50° C.

Compound (Ij5) can be also obtained by reacting compound (Ij2) with compound (XIII) represented by the following formula:

$$R^{23} CO_2H \qquad (XIII)$$

(wherein $R^{23}$ has the same meaning as defined above) in an inert solvent in the presence of a condensing agent. Although any of the above-described inert solvents may be used for the reaction, chloroform and dichloromethane are preferred. Any condensing agent may be used so long as it is used for the ordinary condensation of carboxylic acids with alcohols. For example, dicyclohexylcarbodiimide, 1-ethyl-3-(3-dimethyl-aminopropyl)carbodiimide hydrochloride, or the like is used. It is possible to further add dimethylaminopyridine, or the like, in an amount of 0.1 to 10 equivalents. Compound (XIII) and the condensing agent are generally used in an amount of 1 to 100 equivalents to compound (Ij2). The reaction terminates usually in 10 minutes to 24 hours at 0 to 30° C.

(Step 16)

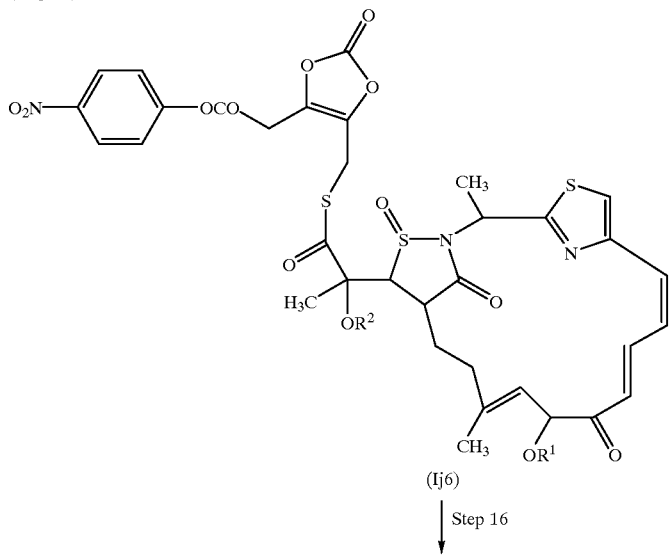

(Ij6)

Step 16

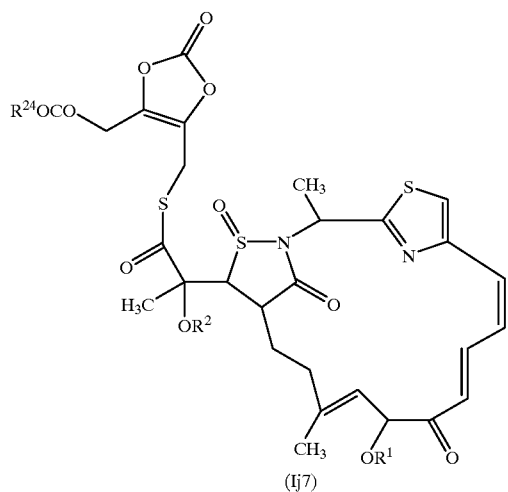

(Ij7)

{In the formulae, $R^1$ and $R^2$ have the same meaning as defined above; and $R^{24}$ represents alkylamino, (hydroxyalkyl)amino, or a nitrogen-containing alicyclic heterocyclic group.}

Among compounds (Ij), compound (Ij7) in which $R^{24}$ is alkylamino, (hydroxyalkyl)amino, or nitrogen-containing alicyclic heterocyclic group can be produced by reacting compound (Ij6) in which $R^{24}$OCO of compound (Ij7) is p-nitrophenyloxycarbonyl with alkylamine, (hydroxyalkyl)amine, or a nitrogen-containing alicyclic heterocyclic compound in an inert solvent. Although any of the above-described inert solvents may be used for the reaction, chloroform or dichloromethane is preferably used. The alkylamine, (hydroxyalkyl)amine, or nitrogen-containing alicyclic heterocyclic compound is generally used in an amount of 1 to 10 equivalents. The reaction terminates usually in 10 minutes to 24 hours at 0 to 30° C.

Process 6

Among compounds (I), compounds (IL) in which $R^3$ is represented by

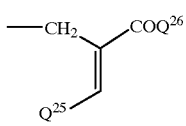

(wherein $R^{25}$ represents hydrogen, lower alkyl, or aryl; and $R^{26}$ represents hydroxy), $R^2$ is hydrogen, and W is oxygen can be also produced by the following steps:

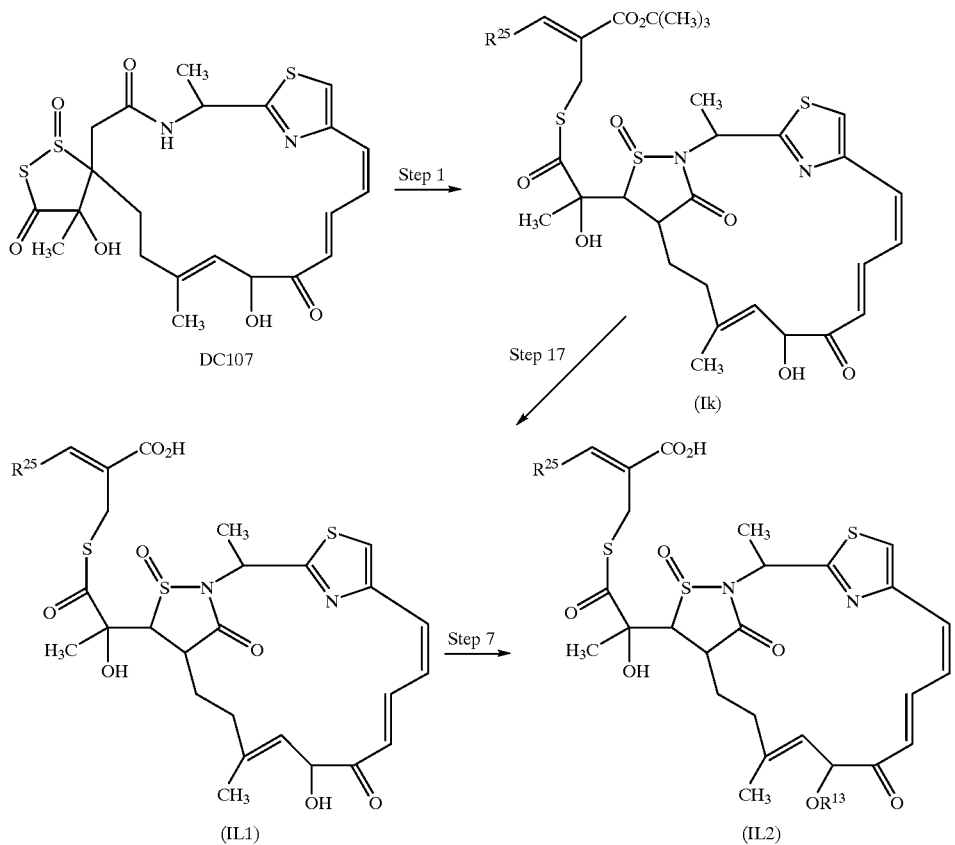

(In the formulae, $R^{13}$ and $R^{25}$ have the same meaning as defined above.)

Compound (Ik) obtained from DC107 by the method according to step 1 is treated by the method according to step 17 shown below, whereby compound (IL1) can be obtained. Compound (IL1) can be converted to compound (IL2) by the method according to step 7. (Step 17)

Compound (Ik) is treated in a solvent (for example, dichloromethane, chloroform, tetrahydrofuran, acetonitrile, or the like) with 0.1 to 100 equivalents of an organic acid (for example, trifluoroacetic acid, formic acid, acetic acid, p-toluenesulfonic acid, camphorsulfonic acid, or the like) or an inorganic acid (for example, hydrochloric acid, hydrobromic acid, sulfuric acid, or the like), whereby the starting compound can be converted to compound (IL1) having carboxylic acid. The reaction terminates usually in 5 minutes to 100 hours at −30 to 100° C.

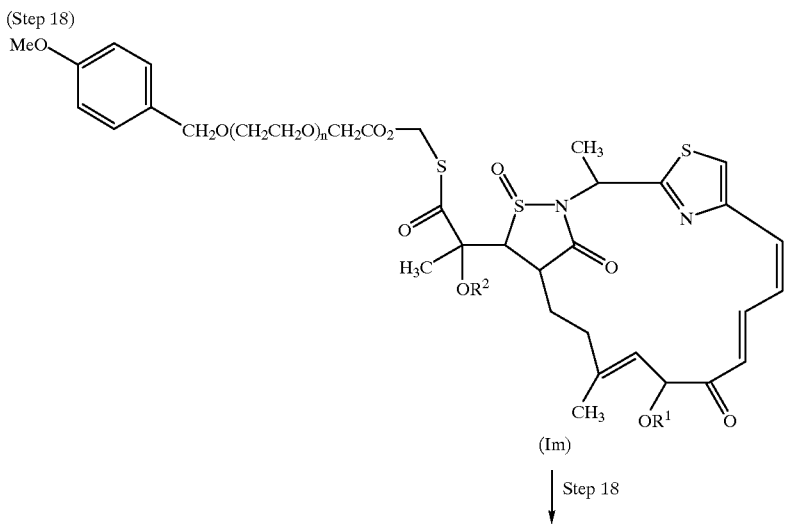

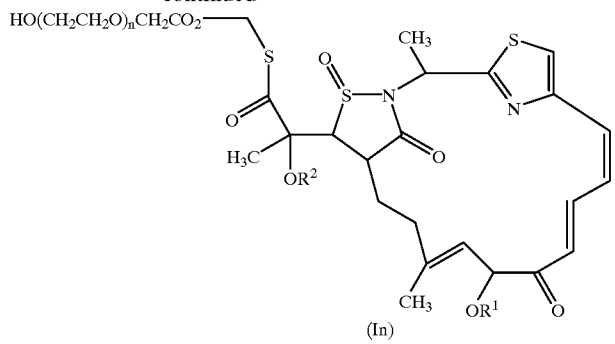

(In)

(In the formulae, $R^1$ and $R^2$ have the same meaning as defined above; and n represents an integer of 1 to 10.)

Compound (In) can be obtained by reacting compound (Im) with 2,3-dichloro-5,6-dicyano-1,4-benzoquinone (DDQ). DDQ is generally used in an amount of at least 1 equivalent, preferably 1 to 10 equivalents, to compound (Im). A mixed solvent, such as 1,4-dioxane or dichloromethane/water, is used for the reaction. This reaction terminates usually in 5 minutes to 24 hours at −20 to 50° C.

For converting a functional group of $R^1$, $R^2$, $R^3$, or W in producing compound (I), known methods {e.g. *Comprehensive Organic Transformations*, R. C. Larock (1989)} can be used besides the steps described above.

The target compounds produced by the processes described above can be isolated and purified by purification techniques ordinarily used in organic synthesis chemistry, for example, neutralization, filtration, extraction, washing, drying, concentration, recrystallization, various chromatography, and the like.

Although some of the compounds (I) can exist as stereoisomers, e.g., diastereomers, the present invention includes all possible isomers including these and mixtures thereof.

Furthermore, compounds (I) and pharmaceutically acceptable salts thereof may be present in the form of an adduct with water or any of various solvents. However, these compounds also are included in the present invention.

Specific examples of compounds (I) obtained by the processes described above are shown in Table 1.

TABLE 1

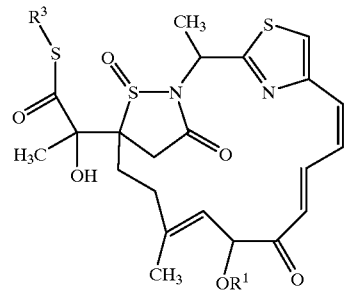

| Compound | $R^1$ | $R^3$ |
|---|---|---|
| Examples (1) of Compounds (I) | | |
| 1 | H | $CH_2OCO(CH_2)_2CO_2CH_3$ |
| 2 | H | $CH_2OCO(CH_2)_3CO_2CH_3$ |
| 3 | H | $CH_2OCOC(CH_3)_2NHCO_2CH_2C_6H_5$ |
| 4 | THP* | $CH_2OCOC(CH_3)_2NHCO_2CH_2C_6H_5$ |
| 5 | H | $CH_2OCOC(CH_3)_2NHCO_2C(CH_3)_3$ |
| 6 | H | $CH_2OCOC_6H_5$ |
| 7 | THP | $CH_2OCOC_6H_5$ |
| 8 | H | $CH_2OCO\text{-}C_6H_4\text{-}CO_2C(CH_3)_3$ |
| 9 | H | $CH_2OCO\text{-}C_6H_4\text{-}CO_2H$ |

TABLE 1-continued

| | | |
|---|---|---|
| 10 | H | CH₂OCO—[cyclohexyl]—CO₂CH₂—[phenyl]—OCH₃ |
| 11 | H | CH₂OCO—[cyclohexyl]—CO₂H |
| 12 | THP | CH₂OCO—[cyclohexyl]—CO₂H |
| 13 | H | CH₂OCOCH₂OCH₂—[phenyl]—OCH₃ |
| 14 | H | CH₂OCCCH₂OH |
| 15 | THP | CH₂OCOCH₂OH |

Examples (2) of Compounds (I)

| | | |
|---|---|---|
| 16 | H | CH₂OCOCH₂NHCO₂C(CH₃)₃ |
| 17 | H | CH₂OCOCH₂NHCO₂CH₃ |
| 18 | CH₂OCOCH₂NHCO₂CH₃ | CH₂OCOCH₂NHCO₂CH₃ |
| 19 | H | CH₂OCOCH₂NHCO—[diacetonide sugar] |
| 20 | H | CH₂OCO(CH₂)₂NHCO—[diacetonide sugar] |
| 21 | H | CH₂OCO(CH₂)₂NHCO—[diacetonide sugar] |
| 22 | H | CH₂OCO(CH₂)₂—CH(NHCO₂C(CH₃)₃)(CO₂C(CH₃)₃) |
| 23 | H | CH₂OCO(CH₂)₂—CH(NHCO₂CH₃)(CO₂CH₃) |

TABLE 1-continued
| | | |
|---|---|---|
| 24 | H | 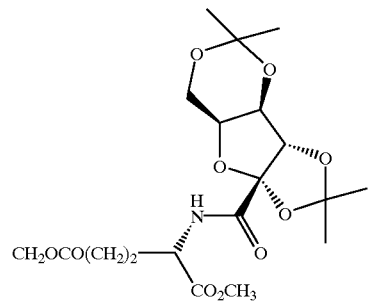 |
| 25 | H | 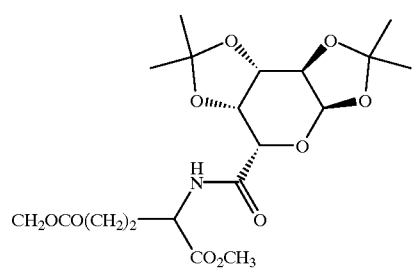 |
| 26 | H | 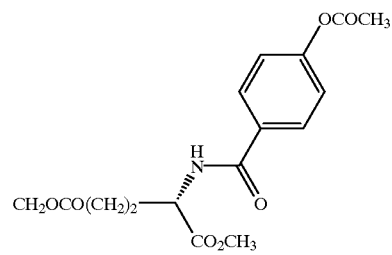 |
Examples (3) of Compounds (I)
| | | |
|---|---|---|
| 27 | H | 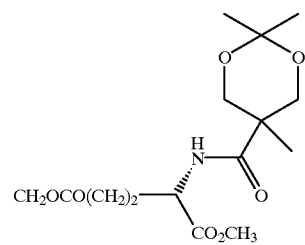 |
| 28 | H | 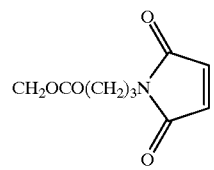 |
| 29 | H | 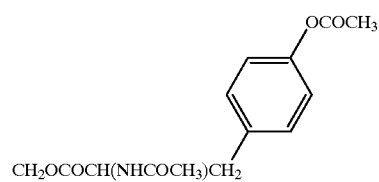 |

TABLE 1-continued

| | | |
|---|---|---|
| 30 | H | CH$_2$OCO—⟨C$_6$H$_4$⟩—OCOCH$_3$ (para) |
| 31 | H | CH$_2$OCO—⟨C$_6$H$_4$⟩—OCOCH$_3$ (with OCOCH$_3$ ortho) |
| 32 | H | CH$_2$OCO(CH$_2$)$_2$—⟨C$_6$H$_4$⟩—OCOCH$_3$ |
| 33 | H | CH$_2$OCO(CH$_2$)$_3$—⟨C$_6$H$_4$⟩—OCOCH$_3$ |
| 34 | H | CH$_2$OCO—⟨C$_6$H$_4$⟩—NHCO$_2$CH$_3$ |
| 35 | H | CH$_2$OCOCH$_2$(OCH$_2$CH$_2$)$_2$OCH$_3$ |
| 36 | CH$_2$OCOCH$_2$(OCH$_2$CH$_2$)$_2$OCH$_3$ | CH$_2$OCOCH$_2$(OCH$_2$CH$_2$)$_2$OCH$_3$ |
| 37 | H | CH$_2$OCOCH$_2$(OCH$_2$CH$_2$)$_5$OCH$_3$ |

Examples (4) of Compounds (I)

| | | |
|---|---|---|
| 38 | THP | CH$_2$OCOCH$_2$NHCO$_2$C(CH$_3$)$_3$ |
| 39 | MTHP | CH$_2$OCOCH$_2$NHCO$_2$C(CH$_3$)$_3$ |
| 40 | THP | CH$_2$OCOCH$_2$NHCO$_2$CH$_3$ |
| 41 | THP* | CH$_2$OCOCH$_2$NHCO$_2$CH$_3$ |
| 42 | THP** | CH$_2$OCOCH$_2$NHCO$_2$CH$_3$ |
| 43 | THP | CH$_2$OCOCH$_2$NHCO—(diacetone sugar) |
| 44 | THP | CH$_2$OCO(CH$_2$)$_2$NHCO—(diacetone sugar) |
| 45 | THP | CH$_2$OCO(CH$_2$)$_2$NHCO—(diacetone sugar) |

TABLE 1-continued

| 46 | THP | CH₂OCO(CH₂)₂—[C*H]—NHCO₂C(CH₃)₃ / CO₂C(CH₃)₃ |
| 47 | MTHP | CH₂OCO(CH₂)₂—[C*H]—NHCO₂C(CH₃)₃ / CO₂C(CH₃)₃ |
| 48 | THP | CH₂OCO(CH₂)₂—[C*H]—NHCO₂CH₃ / CO₂CH₃ |
| 49 | THP | CH₂OCO(CH₂)₂—C*H(NH-C(=O)-[diacetonide sugar])—CO₂CH₃ |
| 50 | THP* | CH₂OCO(CH₂)₂—C*H(NH-C(=O)-[diacetonide sugar])—CO₂CH₃ |

Examples (5) of Compounds (I)

| 51 | THP | CH₂OCO(CH₂)₂—C*H(NH-C(=O)-[diacetone galactopyranose])—CO₂CH₃ |
| 52 | THP | CH₂OCO(CH₂)₂—C*H(NH-C(=O)-C₆H₄-OCOCH₃)—CO₂CH₃ |

TABLE 1-continued
| 53 | THP | 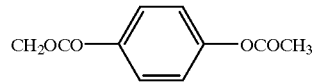 |
| --- | --- | --- |
| 54 | THP | 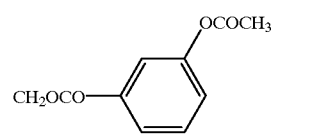 |
| 55 | MTHP | 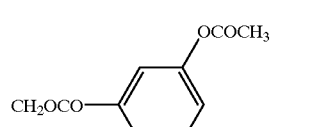 |
| 56 | THP | 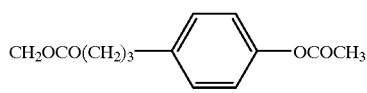 |
| 57 | THP | 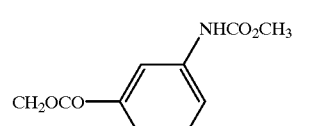 |
| 58 | MTHP | 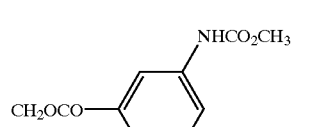 |
Examples (6) of Compounds (I)
| 59 | H | 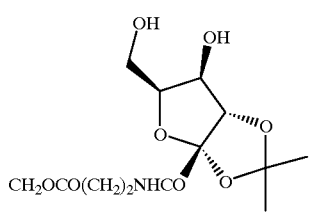 |
| --- | --- | --- |
| 60 | H | 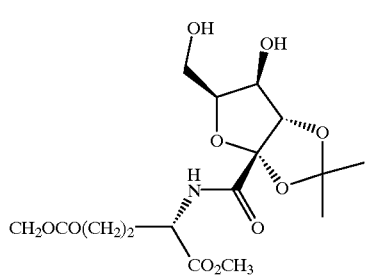 |
| 61 | H | 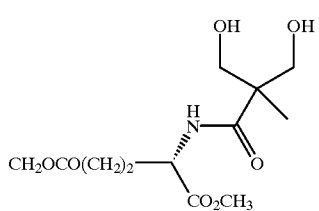 |

TABLE 1-continued

| | | |
|---|---|---|
| 62 | THP* | [structure: furanose with isopropylidene, CH₂OCOCH₂NHCO substituent] |
| 63 | THP** | [structure: furanose with isopropylidene, CH₂OCOCH₂NHCO substituent] |
| 64 | THP | [structure: furanose with isopropylidene, CH₂OCO(CH₂)₂NHCO substituent] |
| 65 | THP* | [structure: furanose with isopropylidene, CH₂OCO(CH₂)₂-CH(CO₂CH₃)-NH-CO substituent] |
| 66 | THP** | [structure: furanose with isopropylidene, CH₂OCO(CH₂)₂-CH(CO₂CH₃)-NH-CO substituent] |

Examples (7) of Compounds (I)

| | | |
|---|---|---|
| 67 | H | CH₂OCO—C₆H₄—OH |
| 68 | THP | CH₂OCO—C₆H₄—OH |

TABLE 1-continued
| | | |
|---|---|---|
| 69 | THP | (CH₂OCO-phenyl-OH, meta-hydroxy) |
| 70 | H | (CH₂OCO(CH₂)₂-phenyl-OH, para-hydroxy) |
| 71 | THP | (CH₂OCO(CH₂)₂-CH(CO₂CH₃)-NH-CO-phenyl-OH) |
| 72 | THP | (CH₂OCO-phenyl-O-P(=O)(OH)₂, para) |
| 73 | THP | (CH₂OCO-phenyl-O-P(=O)(OH)₂, meta) |
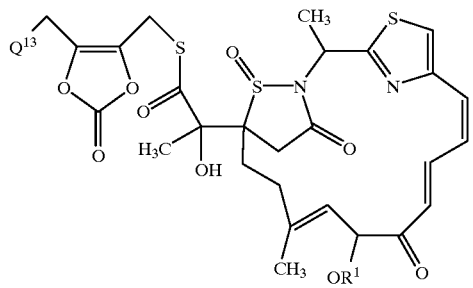
| Compound | R¹ | Q¹³ |
|---|---|---|
| Examples (8) of Compounds (I) | | |
| 74 | THP | Cl |
| 75 | H | TESO |
| 76 | THP | TESO |
| 77 | H | MOMO |
| 78 | THP | MOMO |
| 79 | H | (methyl tetrahydropyran with TBDMSO groups and CH₃) |

TABLE 1-continued

| | | |
|---|---|---|
| 80 | THP | (sugar with TBDMSO, TBDMSO, OMe, CH₃) |
| 81 | H | (sugar with TESO, TESO, OTES, OMe) |
| 82 | THP | (sugar with TESO, TESO, OTES, OMe) |
| 83 | THP | (sugar with HO, HO, OH, OMe) |
| 84 | H | (glycal with AcO, OAc, OMe) |
| 85 | THP | (glycal with AcO, OAc, OMe) |

Examples (9) of Compounds (I)

| | | |
|---|---|---|
| 86 | H | OH |
| 87 | THP | OH |
| 88 | H | OCHO |
| 89 | THP | OCHO |
| 90 | H | OAc |
| 91 | THP | OAc |
| 92 | THP | (N,N-dimethylglycine methyl ester) |
| 93 | THP | (methyl nicotinate) |

TABLE 1-continued
| 94 | THP | 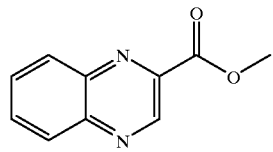 |
| 95 | THP | 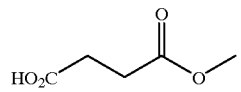 |
| 96 | H |  |
| 97 | H | 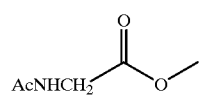 |
| 98 | THP | 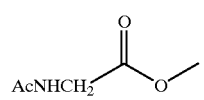 |
| 99 | H | 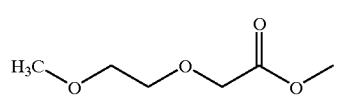 |
| 100 | THP | 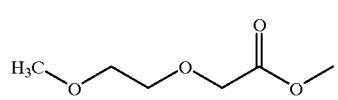 |
Examples (10) of Compounds (I)
| 101 | H | 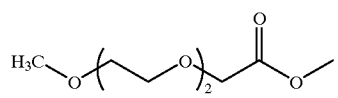 |
| 102 | THP | 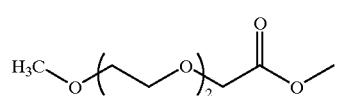 |
| 103 | MTHP | 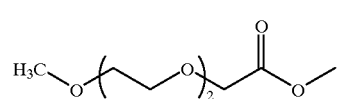 |
| 104 | THP | 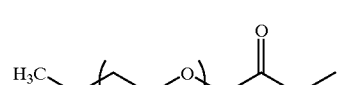 |
| 105 | THP |  |
| 106 | THP | 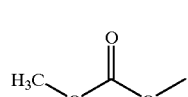 |

TABLE 1-continued
| | | |
|---|---|---|
| 107 | THP | 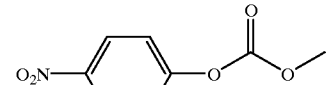 |
| 108 | THP | 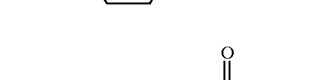 |
| 109 | THP | 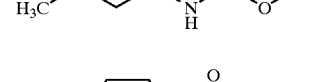 |
| 110 | THP | 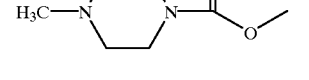 |
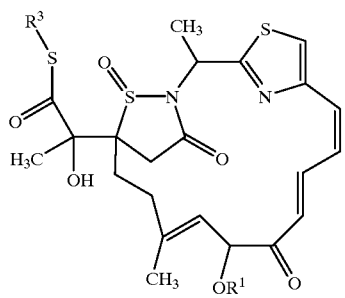
| Compound | $R^1$ | $R^3$ |
|---|---|---|
Examples (11) of Compounds (I)
| 111 | H | —CH$_2$—C(=CH$_2$)—CO$_2$CH$_3$ |
| 112 | THP | —CH$_2$—C(=CH$_2$)—CO$_2$CH$_3$ |
| 113 | MTHP | —CH$_2$—C(=CH$_2$)—CO$_2$CH$_3$ |
| 114 | H | —CH$_2$—C(=CH$_2$)—CO$_2$C(CH$_3$)$_3$ |
| 115 | H | —CH$_2$—C(=CH$_2$)—CO$_2$H |
| 116 | MTHP | —CH$_2$—C(=CH$_2$)—CO$_2$H |

TABLE 1-continued
| | | |
|---|---|---|
| 117 | H | 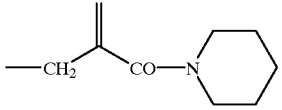 |
| 118 | H | 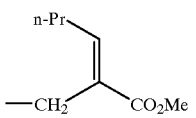 |
| 119 | MTHP | 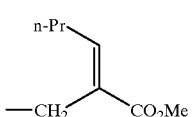 |
| 120 | H | 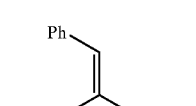 |
| 121 | H | 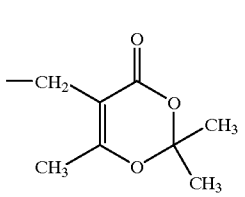 |
| 122 | MTHP | 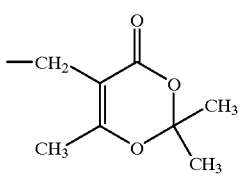 |
| 123 | THP | 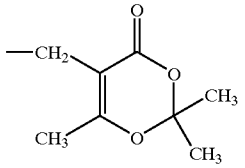 |
| | Examples (12) of Compounds (I) | |
| 124 | H | 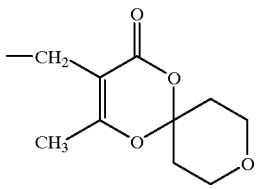 |
| 125 | THP | 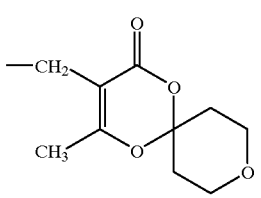 |

TABLE 1-continued
| 126 | H | 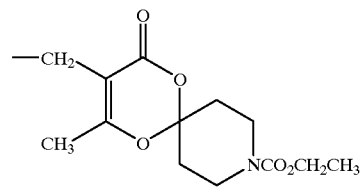 |
| --- | --- | --- |
| 127 | THP | 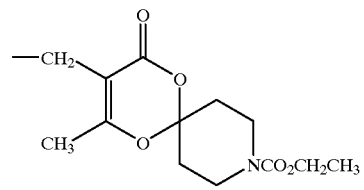 |
| 128 | H | 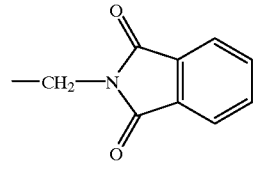 |
| 129 | THP | 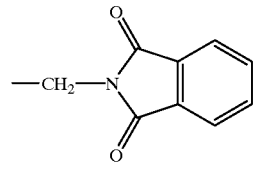 |
| 130 | THP | 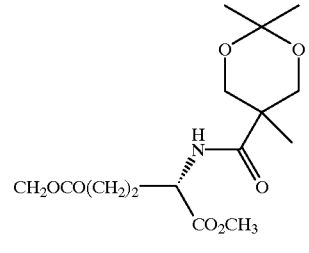 |
| 131 | THP | 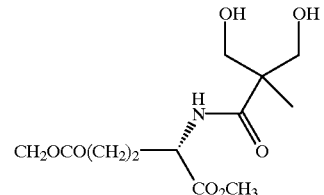 |

TABLE 1-continued

[Structure of compound (I) with Q¹³ and OR¹ substituents]

| Compound | R¹ | Q¹³ |
|---|---|---|

Examples (13) of Compounds (I)

| Compound | R¹ | Q¹³ |
|---|---|---|
| 132 | H | [methoxy tetrahydropyran with HO (dashed), HO, and CH₂OH substituents] |
| 133 | H | [methoxy dihydropyran with AcO (dashed) and CH₃ substituents] |
| 134 | THP | [methoxy dihydropyran with AcO (dashed) and CH₃ substituents] |
| 135 | H | [methoxy tetrahydropyran with TESO (dashed), TESO, and CH₃ substituents] |
| 136 | THP | [methoxy tetrahydropyran with TESO (dashed), TESO, and CH₃ substituents] |
| 137 | THP | [methoxy tetrahydropyran with HO (dashed), HO, and CH₃ substituents] |

TABLE 1-continued
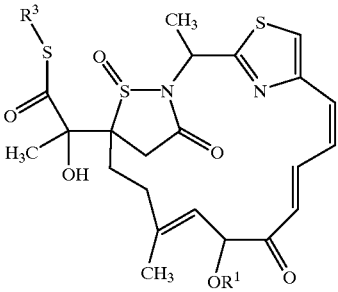
| Compound | R¹ | R³ |
|---|---|---|
Examples (14) of Compounds (I)
| 138 | H | 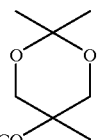 |
| 139 | H | 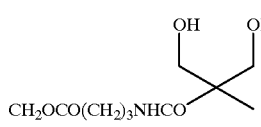 |
| 140 | H | 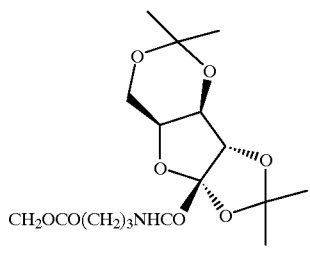 |
| 141 | H | 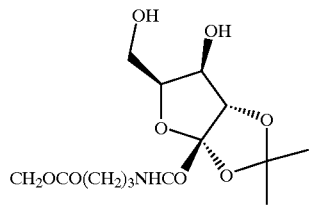 |
| 142 | H | 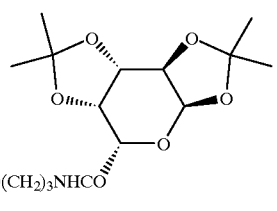 |
| 143 | H | 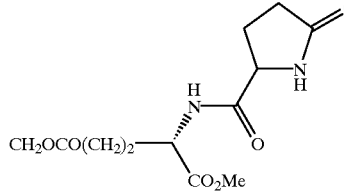 |

TABLE 1-continued

| 144 | H | [structure: CH₂OCO(CH₂)₃NHCO-pyrrolidinone] |

$\text{144} \quad \text{H} \quad \text{CH}_2\text{OCO(CH}_2)_3\text{NHCO-(5-oxopyrrolidin-2-yl)}$ $\text{145} \quad \text{H} \quad \text{CH}_2\text{OCO(CH}_2)_3\text{-N(2-oxopyrrolidin-1-yl)}$ $\text{146} \quad \text{H} \quad \text{CH}_2\text{OCO(CH}_2)_2\text{-N(2-oxopyrrolidin-1-yl)}$

| 147 | H | CH₂OCOCH₂(OCH₂CH₂)₃OCH₃ |
| 148 | H | CH₂OCO(OCH₂CH₂)₂OCH₃ |
| 149 | H | CH₂OCO(OCH₂CH₂)₃OCH₃ |

| 150 | H | CH₂OCOCH₂(OCH₂CH₂)₂OCH₂—C₆H₄—CH₃ |

| 151 | H | CH₂OCOCH₂(OCH₂CH₂)₂OH |

[Macrocyclic structure shown with substituents $Q^{13}$ and $OR^1$]

| Compound | R¹ | Q¹³ |

Examples (15) of Compounds (I)

| 152 | H | [sugar structure with HO, HO, OH, CH₂OH, O—] |

| 153 | H | [sugar structure with HO, HO, OH, CH₂OH, O—] |

TABLE 1-continued
| | | |
|---|---|---|
| 154 | H | 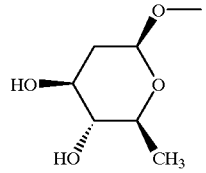 |
| 155 | H | 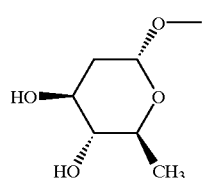 |
| 156 | H | 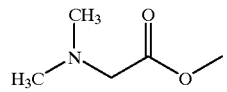 |
| 157 | 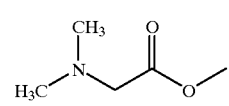 | 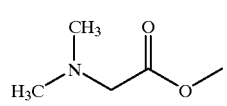 |
| 158 | H | 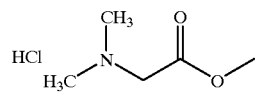 |
| 159 | THP | 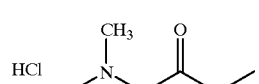 |
| 160 | 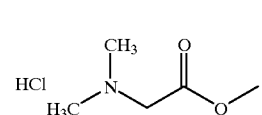 | 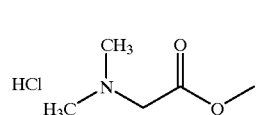 |
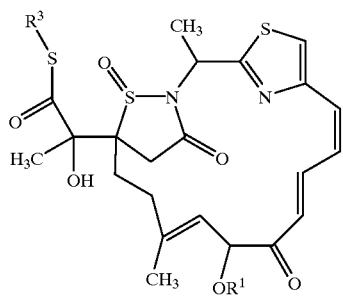
| Compound | R¹ | R³ |
|---|---|---|
Examples (16) of Compounds (I)
| 161 | H |  |

TABLE 1-continued

162  H

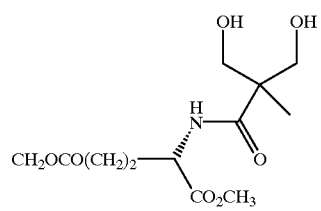

Abbreviations in Table 1 have the following structures:

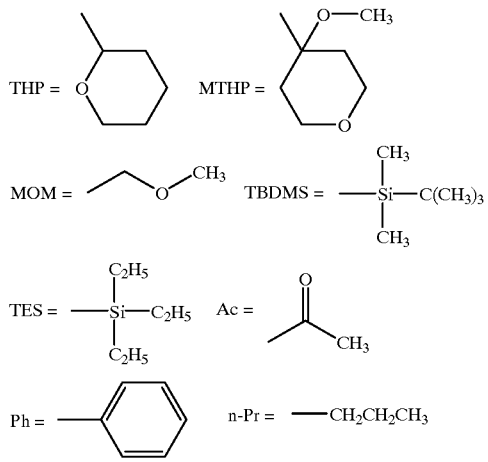

THP*=Tetrahydropyranyl group in which the asymmetric carbon atom on the substituent has a single stereo formula.

THP**=Tetrahydropyranyl group in which the asymmetric carbon atom on the substituent has a single stereo formula (the substituent has a different stereo formula corresponding to THP*).

The antimicrobial activity and antitumor activity of representative compounds (I) will be demonstrated below with Test Examples.

TEST EXAMPLE 1

Antimicrobial Activity

Antimicrobial activity was determined by the agar dilution method using a culture medium (pH 7) prepared by dissolving 3 g of Bacto-Tryptone (manufactured by Difco, Co.), 3 g of meat extract, 1 g of yeast extract, 1 g of glucose, and 16 g of agar in 1 l of water. The antimicrobial activities of representative compounds are shown in Table 2 in terms of minimum inhibitory concentration (MIC).

TABLE 2

Antimicrobial Activity
Microorganisms and MIC (μg/mL)

| Compound | EH | SA | BS | KP | EC |
|---|---|---|---|---|---|
| 17 | 1.3 | 0.65 | 0.65 | 0.65 | 42 |
| 18 | 5.7 | 11 | 11 | 2.9 | — |
| 24 | 23 | 23 | 23 | 46 | — |

TABLE 2-continued

Antimicrobial Activity
Microorganisms and MIC (μg/mL)

| Compound | EH | SA | BS | KP | EC |
|---|---|---|---|---|---|
| 35 | 0.39 | 0.39 | 0.39 | 0.39 | 13 |
| 60 | 7.3 | 15 | 15 | 15 | — |
| 70 | 0.91 | 0.91 | 0.057 | 0.91 | 29 |
| 77 | 0.18 | 0.36 | 0.36 | 0.36 | 11 |
| 80 | 3.4 | 3.4 | 0.42 | 27 | — |
| 82 | 4.2 | 2.1 | — | 33 | — |
| 83 | 0.59 | 0.32 | 0.037 | 4.7 | 4.7 |
| 86 | 0.16 | 0.33 | 0.16 | 0.16 | 10 |
| 100 | 0.33 | 0.081 | 0.041 | 0.65 | 2.6 |
| 139 | 12 | 25 | 12 | 25 | — |
| 143 | 0.29 | 0.29 | 0.29 | 0.59 | 19 |
| 144 | 5.8 | 12 | 12 | 12 | — |
| 145 | 7.7 | 15 | 7.7 | 7.7 | — |
| 158 | 0.33 | 0.33 | <0.041 | 1.3 | — |

EH: *Enterococcus hirae* ATCC 10541
SA: *Staphylococcus aureus* ATCC 6538P
BS: *Bacillus substilis* No. 10707
KP: *Klebisiella pneumoniae* ATCC 10031
EC: *Escherichia coli* ATCC 26

TEST EXAMPLE 2

HeLa $S_3$ Cell Growth Inhibition Test

In each well of a 96-well microtiter plate was placed 0.1 mL of HeLa $S_3$ cells having a concentration of $8 \times 10^3$ cells/mL and prepared in an MEM culture medium containing 10% fetal bovine serum and 2 mM glutamine. After the cells were incubated overnight at 37° C. in a carbon dioxide incubator, a test compound suitably diluted with a medium was added to the wells in an amount of 0.05 mL for each well. The cells were incubated at 37° C. for 72 hours in a carbon dioxide incubator. After the culture supernatant was removed, 0.1 mL of a culture medium containing 0.02% Neutral Red was added to each well. The cells were then incubated at 37° C. for 1 hour in a carbon dioxide incubator to dye the cells. After the culture supernatant was removed, each residue was rinsed once with physiological saline and the pigment was extracted with 0.001 N hydrochloric acid/30% ethanol. The absorbance at 550 nm of each extract was measured with a microplate reader. The drug concentration required for the 50% inhibition of cell growth, which is referred to as $IC_{50}$, was calculated by comparing the absorbance for untreated cells with those for cells treated with the drug in known concentrations. The values of $IC_{50}$ of representative compounds are shown in Table 3.

TABLE 3

HeLa S₃ Cell Growth Inhibition Activity

| Compound | IC$_{50}$ ($\mu$M) |
|---|---|
| 1 | 0.0070 |
| 2 | 0.0075 |
| 3 | 0.13 |
| 4 | 0.039 |
| 5 | 0.055 |
| 6 | 0.018 |
| 7 | 0.050 |
| 9 | 0.15* |
| 11 | 0.10* |
| 12 | 0.87 |
| 13 | 0.011 |
| 14 | 0.38 |
| 15 | 0.014 |
| 16 | 0.0061 |
| 17 | 0.015 |
| 18 | 0.15 |
| 19 | 0.057 |
| 20 | 0.11 |
| 21 | 0.38 |
| 22 | 0.0074 |
| 23 | 0.058 |
| 24 | 0.55 |
| 25 | 0.80 |
| 26 | 0.068 |
| 28 | 0.75 |
| 29 | 0.40 |
| 30 | 0.015 |
| 31 | 0.0062 |
| 32 | 0.0013 |
| 33 | 0.011 |
| 34 | 0.055 |
| 35 | 0.022 |
| 36 | 0.020 |
| 38 | 0.0038 |
| 39 | 0.0022 |
| 40 | 0.015 |
| 41 | 0.0040 |
| 42 | 0.047 |
| 43 | 0.024 |
| 44 | 0.0086 |
| 45 | 0.044 |
| 46 | 0.011 |
| 47 | 0.014 |
| 48 | 0.044 |
| 49 | 0.030 |
| 50 | 0.016 |
| 51 | 0.034 |
| 53 | 0.035 |
| 54 | 0.015 |
| 55 | 0.011 |
| 56 | 0.00052 |
| 57 | 0.036 |
| 58 | 0.038 |
| 59 | 1.3 |
| 60 | 0.55 |
| 61 | 0.72 |
| 62 | 0.071 |
| 63 | 0.27 |
| 64 | 0.035 |
| 65 | 0.0031 |
| 66 | 0.048 |
| 67 | 0.050 |
| 68 | 0.035 |
| 69 | 0.076 |
| 70 | 0.0026 |
| 71 | 0.0012 |
| 72 | 0.65 |
| 73 | 1.9 |
| 74 | 0.019 |
| 75 | 0.24 |
| 76 | 0.26 |
| 77 | 0.0077 |
| 78 | 0.0022 |
| 79 | 0.79 |
| 80 | 0.33 |
| 81 | 0.21 |
| 82 | 0.80 |
| 83 | 0.011 |
| 86 | 0.61 |
| 87 | 0.033 |
| 88 | 0.32 |
| 89 | 0.041 |
| 90 | 0.13 |
| 91 | 0.051 |
| 92 | 0.0027 |
| 93 | 0.0092 |
| 94 | 0.033 |
| 95 | 0.027 |
| 96 | 0.029 |
| 97 | 0.12 |
| 98 | 0.070 |
| 99 | 0.087 |
| 100 | 0.018 |
| 101 | 0.10 |
| 102 | 0.038 |
| 103 | 0.026 |
| 104 | 0.020 |
| 106 | 0.011 |
| 107 | 0.021 |
| 108 | 0.013 |
| 109 | 0.052 |
| 110 | 0.022 |
| 111 | 0.020 |
| 112 | 0.064 |
| 113 | 0.042 |
| 115 | >10 |
| 116 | 8.5 |
| 117 | 2.1 |
| 118 | 0.58 |
| 119 | 0.87 |
| 120 | 0.27 |
| 121 | 1.5 |
| 122 | 1.8 |
| 123 | 0.60 |
| 124 | 0.96 |
| 125 | 0.047 |
| 126 | 5.5 |
| 127 | 0.033 |

*Value after 72 hours of drug treatment

TEST EXAMPLE 3

Antitumor Activity of Test Compounds against Sarcoma 180 Mouse Solid Tumor

To a ddY mouse were intraperitoneally transplanted 5×10⁶ sarcoma 180 cells. On the seventh day from the transplant, the cells were collected from the ascites, washed once with sterilized physiological saline, and then diluted with sterilized physiological saline to prepare a cell suspension having a concentration of 5×10⁷ cells/mL. This suspension was transplanted in an amount of 0.01 mL to a subcutaneous part of the right axilla of each of male ddY mice each weighing 20±1 g.

A test compound was dissolved in physiological saline containing polyoxyethylene sorbitan monolaurate. At 24 hours after the tumor transplant, 0.2 mL of the solution was intravenously administered to the tail of each of a group of five mice.

The antitumor activity of each test compound was evaluated by measuring the major diameter (a) and minor diameter (b) of the tumor on the seventh day from the transplant and determining from these diameter values the value of a×b²/2, which corresponds to the volume of the tumor. The antitumor activity was expressed in terms of T/C ratio, i.e., the ratio of the volume for the group to which the test compound had been administered (T) to the volume for a control (untreated) group (C). The results are shown in Table 4.

TABLE 4

Antitumor Activity against S-180 Mouse Solid Tumor

| Compound | Dose (mg/kg) | T/C |
|---|---|---|
| 3 | 16 | 0.21 |
| 4 | 8.0 | 0.30 |
| 7 | 4.0 | 0.23 |
| 11 | 4.0 | 0.48 |
| 12 | 8.0 | 0.47 |
| 14 | 2.0 | 0.44 |
| 15 | 1.0 | 0.45 |
| 16 | 2.0 | 0.47 |
| 18 | 4.0 | 0.38 |
| 22 | 4.0 | 0.42 |
| 24 | 16 | 0.12 |
| 25 | 16 | 0.30 |
| 27 | 2.0 | 0.46 |
| 29 | 4.0 | 0.47 |
| 35 | 2.0 | 0.44 |
| 37 | 8.0 | 0.36 |
| 40 | 4.0 | 0.36 |
| 41 | 4.0 | 0.32 |
| 45 | 8.0 | 0.45 |
| 46 | 8.0 | 0.32 |
| 50 | 8.0 | 0.41 |
| 51 | 16 | 0.31 |
| 53 | 8.0 | 0.50 |
| 54 | 4.0 | 0.47 |
| 60 | 8.0 | 0.31 |
| 64 | 8.0 | 0.43 |
| 77 | 8.0 | 0.36 |
| 78 | 8.0 | 0.50 |
| 79 | 8.0 | 0.45 |
| 80 | 16.0 | 0.37 |
| 82 | 16.0 | 0.36 |
| 87 | 16.0 | 0.40 |
| 88 | 8.0 | 0.49 |
| 94 | 8.0 | 0.43 |
| 98 | 16.0 | 0.40 |
| 99 | 8.0 | 0.40 |
| 100 | 16.0 | 0.30 |
| 101 | 16 | 0.27 |
| 102 | 16 | 0.46 |
| 112 | 8.0 | 0.24 |
| 122 | 16 | 0.37 |
| 123 | 16 | 0.14 |
| 125 | 16 | 0.43 |
| 127 | 16 | 0.29 |
| 138 | 4.0 | 0.34 |
| 139 | 4.0 | 0.33 |
| 141 | 4.0 | 0.31 |
| 143 | 8.0 | 0.27 |
| 144 | 8.0 | 0.26 |
| 145 | 4.0 | 0.23 |
| 146 | 4.0 | 0.38 |
| 147 | 2.0 | 0.43 |
| 149 | 8.0 | 0.42 |
| 152 | 16 | 0.17 |
| 154 | 4.0 | 0.40 |
| 155 | 8.0 | 0.37 |
| 158 | 32 | 0.31 |
| 159 | 32 | 0.33 |

The compounds obtained according to the present invention are useful as antimicrobial agents and antitumor agents, and can be used as such or in various administration forms (with a pharmaceutically acceptable carrier). For example, if compound (I) is used as a parenteral agent, it may be used as a solution in a diluent ordinarily employed in this field, such as physiological saline, glucose parenteral solution, lactose parenteral solution, mannitol parenteral solution, or the like, or as an injectable powder comprising a mixture of the compound with a freeze-dried parenteral agent according to the Japanese Pharmacopeia or with sodium chloride or the like. An auxiliary agent, e.g., polyethylene glycol or HCO-60 (surfactant, manufactured by Nikko Chemicals Co., Ltd.), or a carrier, e.g., ethanol and/or liposome and cyclodextrin, may be added to those parenteral agents. Although those parenteral agents are usually administered intravenously, they can be also administered intraarterially, intraperitoneally, or intrathoracically.

The compounds (I) can be used also as a peroral agent after being mixed with an appropriate excipient, disintegrator, binder, lubricants, or the like, and molded into tablets, granules, powder, syrup, or the like.

The dose varies depending on administration method, kind of compound (I), age, condition, and the like, and the administration either method can be varied according to the condition and the dose. However, the compound can usually be administered parenterally as a parenteral agent or perorally. For example, it can be administered in a dose of 0.006 to 6 mg/kg at an interval of 1 to 3 weeks.

EXAMPLES

Physicochemical properties of each of the compounds shown in the following Examples and Reference Examples were determined with the following apparatuses.

MS JEOL: JMS-D300 (measured by FAB method)
    JEOL: JMS-SX-102 (measured by FAB method)
    JEOL: HX/HX110A (measured by FAB method)
    Shimadzu: QP-1000 (measured by EI method)
$^1$H NMR Bruker: DMX500 (500 MHz)
    JEOL: α400 (400 MHz)
    JEOL: JNM-GX270 (270 MHz)
    JEOL: JNM-EX270 (270 MHz)
    JEOL:FX-100 (100 MHz)
IR JASCO: IR-810

In the physical data for compounds given in the following Examples and Reference Examples, "FABMS" means mass spectrum by the "FAB" method; "HRFABMS" means high-resolution mass spectrum by the "FAB" method; "calcd" means the theoretical value based on the molecular formula; and "found" means found value. In the Examples and Reference Examples, "Cbz" means carbobenzoxy, "Gly" means a glycine residue, "Glu" means a glutamic acid residue, "Bu$^t$" means tert-butyl, "Boc" means tert-butoxycarbonyl, "Ph" means phenyl, and "Me" means methyl. "ODS" means silica gel with modified with an octadecyl group. With respect to the NMR data for separated stereoisomers, those for the major and minor isomers are often indicated by "major isomer" and "minor isomer", respectively. If peak overlapping occurred, the peak is indicated by "overlapped with other peaks". Furthermore, "ca." and "approx." mean "approximately". A mixture of two diastereomers is indicated to this effect.

In the following Examples and Reference Examples, the term "ordinary post-treatment" means the following post-reaction treatment.

After completion of the reaction in each step, water, an acid, a buffer solution, or the like is added if necessary to the reaction mixture before the reaction mixture is extracted with a water-insoluble solvent, for example, ethyl acetate, ether, chloroform, dichloromethane, or the like. The extract is washed with water, brine, or the like, dried with anhydrous sodium sulfate, and then distilled under reduced pressure to remove the solvent.

Example 1

Synthesis of Compound 1

DC107 (105 mg, 0.21 mmol) was dissolved in acetonitrile (10 mL). Thereto were added potassium carbonate (0.28 g, 2.1 mmol), chloromethyl methyl succinate (370 mg, 2.1 mmol), and potassium iodide (34 mg, 0.21 mmol). This mixture was stirred at 25° C. for 1 day. After the ordinary post-treatment, the reaction product was purified by thin-layer chromatography (developed with chloroform/methanol=97/3) to obtain Compound 1 (13 mg, yield 9.6%).

IR (KBr) 3430, 2934, 1735, 1649, 1610, 1439, 1365, 1265, 1149, 980, 847 cm$^{-1}$ $^1$H NMR (CDCl$_3$, 400 MHz)δ ppm; 8.46 (ddd, J=16.4, 11.5, 1.0 Hz, 1H), 7.34 (s, 1H), 6.58 (d, J=12.0 Hz, 1H), 6.23 (dd, J=12.0, 11.5, 1H), 6.17 (d, J=16.4 Hz, 1H), 5.73 (br d, J=8.8 Hz, 1H), 5.52 (br s, 1H), 5.43 (d, J=11.0 Hz, 1H), 5.41 (q, J=6.8 Hz, 1H), 5.38 (d, J=11.0 Hz, 1H), 4.94 (dd, J=8.8, 3.4 Hz, 1H), 3.88 (d, J=17.8 Hz, 1H), 3.73 (br d, J=3.4 Hz, 1H), 3.67 (s, 3H), 2.61 (br s, 4H), 2.35–1.70 (m, 4H), 2.33 (d, J=17.8 Hz, 1H), 2.02 (d, J=6.8 Hz, 3H), 1.79 (s, 3H), 1.75 (d, J=1.2 Hz, 3H)

FABMS m/z 655 (M+H)$^+$

HRFABMS calcd for C$_{28}$H$_{35}$N$_2$O$_{10}$S$_3$ (M+H)$^+$ 655.1454, found 655.1443

Example 2

Synthesis of Compound 2

In the same manner as in Example 1, Compound 2 (10 mg, yield 9.2%) was obtained from DC107 (80 mg, 0.16 mmol), potassium carbonate (0.30 g, 2.2 mmol), chloromethyl methyl adipate (330 mg, 1.6 mmol), and potassium iodide (30 mg, 0.18 mmol).

IR (KBr) 3420, 2944, 1730, 1693, 1649, 1611, 1441, 1374, 1263, 1135, 1085, 979 cm$^{-1}$ $^1$H NMR (CDCl$_3$, 400 MHz)δ ppm; 8.46 (dd, J=16.4, 11.5 Hz, 1H), 7.35 (s, 1H), 6.58 (d, J=11.7 Hz, 1H), 6.23 (dd, J=11.7, 11.5 Hz, 1H), 6.17 (d, J=16.4 Hz, 1H), 5.73 (br d, J=8.8 Hz, 1H), 5.51 (br s, 1H), 5.41 (q, J=6.7 Hz, 1H), 5.43–5.34 (m, 2H), 4.94 (dd, J=8.8, 3.5 Hz, 1H), 3.88 (d, J=17.8 Hz, 1H), 3.74 (br d, J=3.5 Hz, 1H), 3.65 (s, 3H), 2.35–1.60 (m, 12H), 2.27 (d, J=17.8 Hz, 1H), 2.02 (d, J=6.7 Hz, 3H), 1.78 (s, 3H), 1.75 (d, J=1.0 Hz, 3H)

FABMS m/z 683 (M+H)$^+$

HRFABMS calcd for C$_{30}$H$_{39}$N$_2$O$_{10}$S$_3$ (M+H)$^+$ 683.1767, found 683.1744

Example 3

Synthesis of Compound 3

DC107 (64 mg, 0.13 mmol) was dissolved in acetonitrile (15 mL). Thereto were added potassium carbonate (0.15 g, 1.1 mmol), chloromethyl 2-(N-Cbz-amino)isobutyrate (280 mg, 0.98 mmol), and potassium iodide (30 mg, 0.18 mmol). This mixture was stirred at 25° C. for 3 days. After the ordinary post-treatment, the reaction product was purified by thin-layer chromatography (developed with chloroform/methanol=97/3) to obtain Compound 3 (23 mg, yield 24%).

IR (KBr) 3410, 3100, 2932, 1710, 1650, 1611, 1516, 1455, 1386, 1273, 1132, 1088, 1018, 979, 735, 698 cm$^{-1}$ $^1$H NMR (CDCl$_3$, 400 MHz)δ ppm; 8.45 (dd, J=16.3, 11.5 Hz, 1H), 7.40–7.25 (m, 5H), 7.33 (s, 1H), 6.55 (d, J=12.0 Hz, 1H), 6.21 (dd, J=12.0, 11.5 Hz, 1H), 6.16 (d, J=16.3 Hz, 1H), 5.73 (br d, J=9.0 Hz, 1H), 5.39 (q, J=7.0 Hz, 1H), 5.50–5.20 (m, 4H), 5.05 (br s, 2H), 4.93 (dd, J=9.0, 3.7 Hz, 1H), 3.87 (d, J=18.1 Hz, 1H), 3.74 (d, J=3.7 Hz, 1H), 2.35 (d, J=18.1 Hz, 1H), 2.35–1.45 (m, 4H), 2.02 (d, J=7.0 Hz, 3H), 1.77 (s, 3H), 1.73 (d, J=1.2 Hz, 3H), 1.49 (s, 3H), 1.48 (s, 3H)

FABMS m/z 760 (M+H)$^+$

HRFABMS calcd for C$_{35}$H$_{42}$N$_3$O$_{10}$S$_3$ (M+H)$^+$ 760.2032, found 760.2021

Example 4

Synthesis of Compound 4

In the same manner as in Example 1, Compound 4 (19 mg, yield 20%) was obtained from Compound S-1 (65 mg, 0.11 mmol) obtained in Reference Example 1, potassium carbonate (0.15 g, 1.1 mmol), chloromethyl 2-(N-Cbz-amino)isobutyrate (350 mg, 1.23 mmol), and potassium iodide (20 mg, 0.12 mmol).

IR (KBr) 3360, 3092, 2942, 1720, 1648, 1607, 1504, 1454, 1376, 1272, 1253, 1120, 1072, 1024, 967, 911, 886, 868, 805, 736, 698 cm$^{-1}$ $^1$H NMR (CDCl$_3$, 500 MHz)δ ppm; 9.59 (dd, J=16.5, 11.3 Hz, 1H), 7.40 (s, 1H), 7.39–7.25 (m, 5H), 6.60 (d, J=11.6 Hz, 1H), 6.34 (dd, J=11.6, 11.3 Hz, 1H), 6.00 (d, J=16.5 Hz, 1H), 5.82 (br d, J=9.5 Hz, 1H), 5.58 (q, J=6.7 Hz, 1H), 5.49 (br s, 1H), 5.52–5.18 (m, 3H), 5.10 (br s, 2H), 5.01 (dd, J=9.5, 1.2 Hz, 1H), 4.56 (br t, J=4.0 Hz, 1H), 4.02 (d, J=17.7 Hz, 1H), 3.87–3.79 (m, 1H), 3.52–3.46 (m, 1H), 2.44–2.30 (m, 3H), 2.36 (d, J=17.7 Hz, 1H), 1.93 (d, J=6.7 Hz, 3H), 1.90–1.35 (m, 7H), 1.75 (d, J=1.2 Hz, 3H), 1.70 (s, 3H), 1.52 (s, 3H), 1.51 (s, 3H)

FABMS m/z 844 (M+H)$^+$

HRFABMS calcd for C$_{40}$H$_{50}$N$_3$O$_{11}$S$_3$ (M+H)$^+$ 844.2607, found 844.2592

Example 5

Synthesis of Compound 5

In the same manner as in Example 1, Compound 5 (10 mg, yield 13%) was obtained from DC107 (55 mg, 0.11 mmol), potassium carbonate (0.14 g, 1.0 mmol), chloromethyl 2-(N-Boc-amino)isobutyrate (270 mg, 1.1 mmol), and potassium iodide (16 mg, 0.10 mmol).

IR (KBr) 3400, 2984, 2930, 1740, 1705, 1692, 1611, 1507, 1455, 1380, 1368, 1257, 1166, 1128, 1083, 978, 856 cm$^{-1}$ $^1$H NMR (CDCl$_3$, 500 MHz)δ ppm; 8.47 (ddd, J=16.3, 11.3, 1.0 Hz, 1H), 7.34 (s, 1H), 6.58 (d, J=11.6 Hz, 1H), 6.23 (dd, J=11.6, 11.3 Hz, 1H), 6.17 (d, J=16.3 Hz, 1H), 5.74 (br d, J=8.6 Hz, 1H), 5.45 (d, J=10.9 Hz, 1H), 5.43 (br s, 1H), 5.40 (d, J=10.9 Hz, 1H), 5.40 (q, J=6.9 Hz, 1H), 4.94 (dd, J=8.6, 3.7 Hz, 1H), 4.91 (br s, 1H), 3.87 (d, J=17.8 Hz, 1H), 3.74 (br d, J=3.7 Hz, 1H), 2.36–1.40 (m, 4H), 2.29 (d, J=17.8 Hz, 1H), 2.02 (d, J=6.9 Hz, 3H), 1.77 (s, 3H), 1.74 (d, J=1.2 Hz, 3H), 1.45 (s, 3H), 1.44 (s, 3H), 1.42 (s, 9H)

FABMS m/z 726 (M+H)$^+$

HRFABMS calcd for C$_{32}$H$_{44}$N$_3$O$_{10}$S$_3$ (M+H)$^+$ 726.2189, found 726.2170

Example 6

Synthesis of Compound 6

In the same manner as in Example 1, Compound 6 (26 mg, yield 29%) was obtained from DC107 (70 mg, 0.14 mmol), potassium carbonate (97 mg, 0.70 mmol), chloromethyl benzoate (110 mg, 0.70 mmol), and potassium iodide (12 mg, 0.07 mmol).

IR (KBr) 3402, 2936, 1720, 1649, 1610, 1451, 1380, 1325, 1262, 1156, 1090, 1068, 1023, 983, 712 cm$^{-1}$ $^1$H NMR (CDCl$_3$, 500 MHz)δ ppm; 8.45 (ddd, J=16.5, 11.5, 1.0 Hz, 1H), 8.04–7.96 (m, 2H), 7.59–7.54 (m, 1H), 7.46–7.39 (m, 2H), 7.34 (s, 1H), 6.58 (d, J=11.6 Hz, 1H), 6.23 (dd, J=16.3, 11.6 Hz, 1H), 6.17 (d, J=16.5 Hz, 1H), 5.73 (br d, J=8.5 Hz, 1H), 5.66 (d, J=11.0 Hz, 1H), 5.62 (d, J=11.0 Hz, 1H), 5.48 (br s, 1H), 5.41 (q, J=7.0 Hz, 1H), 4.94 (dd, J=8.5, 3.7 Hz, 1H), 3.90 (d, J=17.7 Hz, 1H), 3.73 (br d, J=3.7 Hz, 1H), 2.36–1.90 (m, 4H), 2.27 (d, J=17.7 Hz, 1H), 2.01 (d, J=7.0 Hz, 3H), 1.80 (s, 3H), 1.74 (d, J=1.2 Hz, 3H)

FABMS m/z 645 (M+H)$^+$

HRFABMS calcd for C$_{30}$H$_{33}$N$_2$O$_8$S$_3$ (M+H)$^+$ 645.1399, found 645.1411

Example 7

Synthesis of Compound 7

Compound 6 (22 mg, 0.034 mmol) obtained in Example 6 was dissolved in dichloromethane (3.0 mL). Thereto were added 3,4-dihydro-2H-pyran (0.016 mL, 0.17 mmol) and camphorsulfonic acid (8.0 mg, 0.034 mmol). This mixture was stirred at 0° C. for 20 minutes. After the ordinary post-treatment, the reaction product was purified by thin-layer chromatography (developed with chloroform/methanol=97/3) to obtain Compound 7 (19 mg, yield 76%). $^1$H NMR revealed that Compound 7 was an approximately 5:4 mixture of diastereomers.

IR (KBr) 3400, 2944, 1720, 1647, 1609, 1452, 1376, 1261, 1177, 1152, 1090, 1068, 1024, 970, 868, 712 cm$^{-1}$ $^1$H NMR (CDCl$_3$, 400 MHz)δ ppm; major isomer 9.39 (ddd, J=16.6, 11.5, 1.0 Hz, 1H), 8.04–7.98 (m, 2H), 7.63–7.55 (m, 1H), 7.47–7.40 (m, 2H), 7.39 (s, 1H), 6.60 (d, J=11.5 Hz, 1H), 6.37 (t, J=11.5 Hz, 1H), 6.04 (d, J=16.6 Hz, 1H), 5.80 (br d, J=9.0 Hz, 1H), 5.70–5.43 (m, 4H), 4.73 (dd, J=9.0, 1.2 Hz, 1H), 4.58 (m, 1H), 4.03 (d, J=17.6 Hz, 1H), 3.90–3.35 (m, 2H), 2.50–1.40 (m, 10H), 2.31 (d, J=17.6 Hz, 1H), 1.87 (d, J=6.6 Hz, 3H), 1.73 (d, J=1.2 Hz, 3H), 1.72 (s, 3H); minor isomer 9.58 (ddd, J=16.6, 11.5, 1.0 Hz, 1H), 8.04–7.98 (m, 2H), 7.63–7.55 (m, 1H), 7.47–7.40 (m, 2H), 7.40 (s, 1H), 6.61 (d, J=11.5 Hz, 1H), 6.34 (t, J=11.5 Hz, 1H), 6.00 (d, J=16.6 Hz, 1H), 5.83 (br d, J=9.0 Hz, 1H), 5.70–5.43 (m, 4H), 5.01 (dd, J=9.0, 1.2 Hz, 1H), 4.70 (m, 1H), 4.04 (d, J=17.6 Hz, 1H), 3.90–3.35 (m, 2H), 2.50–1.40 (m, 10H), 2.30 (d, J=17.6 Hz, 1H), 1.93 (d, J=6.6 Hz, 3H), 1.76 (d, J=1.2 Hz, 3H), 1.72 (s, 3H)

FABMS m/z 729 (M+H)$^+$

HRFABMS calcd for C$_{35}$H$_{41}$N$_2$O$_9$S$_3$ (M+H)$^+$ 729.1974, found 729.1983

Example 8

Synthesis of Compound 8

In the same manner as in Example 1, Compound 8 (12 mg, yield 8.2%) was obtained from DC107 (100 mg, 0.20 mmol), potassium carbonate (0.27 g, 2.0 mmol), chloromethyl methyl terephthalate (0.53 g, 2.0 mmol), and potassium iodide (32 mg, 0.20 mmol).

$^1$H NMR (CDCl$_3$, 400 MHz)δ ppm; 8.46 (ddd, J=16.3, 11.4, 1.0 Hz, 1H), 8.03 (br s, 4H), 7.34 (s, 1H), 6.58 (d, J=11.7 Hz, 1H), 6.23 (dd, J=11.7, 11.4 Hz, 1H), 6.14 (d, J=16.3 Hz, 1H), 5.73 (br d, J=8.6 Hz, 1H), 5.67 (d, J=11.0 Hz, 1H), 5.63 (d, J=11.0 Hz, 1H), 5.50 (br s, 1H), 5.40 (q, J=6.8 Hz, 1H), 4.94 (dd, J=8.6, 3.8 Hz, 1H), 3.90 (d, J=17.8 Hz, 1H), 3.74 (br d, J=3.8 Hz, 1H), 2.35–1.50 (m, 4H), 2.20 (d, J=17.8 Hz, 1H), 2.01 (d, J=6.8 Hz, 3H), 1.80 (s, 3H), 1.74 (d, J=1.2 Hz, 3H), 1.60 (s, 9H)

FABMS m/z 745 (M+H)$^+$

HRFABMS calcd for C$_{35}$H$_{41}$N$_2$O$_{10}$S$_3$ (M+H)$^+$ 745.1923, found 745.1910

Example 9

Synthesis of Compound 9

Compound 8 (25 mg, 0.034 mmol) obtained in Example 8 was dissolved in dichloromethane (3.0 mL) and trifluoroacetic acid (0.5 ml). This solution was stirred at 0° C. for 1 hour. After the solvents were distilled off under reduced pressure, the residue was purified by thin-layer chromatography (developed with chloroform/methanol=92/8) to obtain Compound 9 (8.0 mg, yield 34%).

$^1$H NMR (CD$_3$OD, 400 MHz)δ ppm; 8.93 (dd, J=16.4, 11.5 Hz, 1H), 8.04–7.89 (m, 4H), 7.54 (s, 1H), 6.58 (d, J=11.5 Hz, 1H), 6.22 (t, J=11.5 Hz, 1H), 5.91 (d, J=16.4 Hz, 1H), 5.64 (br d, J=8.9 Hz, 1H), 5.55–5.46 (m, 2H), 5.43 (q, J=6.6 Hz, 1H), 4.76 (d, J=8.9 Hz, 1H), 3.89 (br d, J=17.8 Hz, 1H), 2.60–1.40 (m, 4H), 2.40 (d, J=17.8 Hz, 1H), 1.83 (d, J=6.6 Hz, 3H), 1.58 (s, 3H), 1.46 (s, 3H)

FABMS m/z 689 (M+H)$^+$

HRFABMS calcd for C$_{31}$H$_{33}$N$_2$O$_{10}$S$_3$ (M+H)$^+$ 689.1297, found 689.1283

Example 10

Synthesis of Compound 10

In the same manner as in Example 1, Compound 10 (21 mg, yield 16%) was obtained from DC107 (81 mg, 0.16 mmol), potassium carbonate (0.16 g, 1.2 mmol), chloromethyl (4-methoxyphenyl)methyl 1,4-cyclohexane-dicarboxylate (0.40 g, 1.2 mmol), and potassium iodide (26 mg, 0.16 mmol).

FABMS m/z 815 (M+H)$^+$

HRFABMS calcd for C$_{39}$H$_{47}$N$_2$O$_{11}$S$_3$ (M+H)$^+$ 815.2342, found 815.2339

Example 11

Synthesis of Compound 11

Compound 10 (20 mg, 0.025 mmol) obtained in Example 10 was dissolved in dichloromethane (1.5 mL) and trifluoroacetic acid (0.5 mL). Thereto was added p-anisole (0.010 mL, 0.095 mmol). This mixture was stirred at 0° C. for 20 minutes. After the solvents were distilled off under reduced pressure, the residue was purified by thin-layer chromatography (developed with chloroform/methanol=92/8) to obtain Compound 11 (8.0 mg, yield 46%).

IR (KBr) 3420, 2942, 1720, 1690, 1612, 1453, 1378, 1258, 1155, 1105, 1024, 978 cm$^{-1}$ $^1$H NMR (CDCl$_3$, 400 MHz)δ ppm; 8.45 (dd, J=16.6, 11.5 Hz, 1H), 7.35 (s, 1H), 6.58 (d, J=11.7 Hz, 1H), 6.25 (dd, J=11.7, 11.5 Hz, 1H), 6.17 (d, J=16.6 Hz, 1H), 5.73 (br d, J=8.5 Hz, 1H), 5.50–5.35 (m, 2H), 5.41 (d, J=11.0 Hz, 1H), 5.36 (d, J=11.0 Hz, 1H), 4.95 (d, J=8.5 Hz, 1H), 3.88 (d, J=17.8 Hz, 1H), 2.37–1.35 (m, 15H), 2.02 (d, J=6.8 Hz, 3H), 1.78 (s, 3H), 1.75 (d, J=1.0 Hz, 3H)

FABMS m/z 695 (M+H)$^+$

HRFABMS calcd for $C_{31}H_{39}N_2O_{10}S_3$ (M+H)$^+$ 695.1767, found 695.1782

Example 12

Synthesis of Compound 12

Compound 11 (25 mg, 0.036 mmol) obtained in Example 11 was dissolved in dichloromethane (2.0 mL). Thereto were added 3,4-dihydro-2H-pyran (0.016 mL, 0.18 mmol) and camphorsulfonic acid (4.2 mg, 0.018 mmol). This mixture was stirred at 0° C. for 35 minutes. After the ordinary post-treatment, the reaction product was purified by thin-layer chromatography (developed with chloroform/methanol=92/8) to obtain Compound 12 (15 mg, yield 53%). $^1$H NMR revealed that Compound 12 was an approximately 4:3 mixture of diastereomers.

IR (KBr) 3430, 2944, 2868, 1740, 1689, 1642, 1454, 1377, 1258, 1155, 1110, 1073, 1020, 974, 755 cm$^{-1}$ $^1$H NMR (CDCl$_3$ 500 MHz)δ ppm; major isomer 9.39 (ddd, J=16.5, 11.5, 1.0 Hz, 1H), 7.39 (s, 1H), 6.60 (d, J=11.5 Hz, 1H), 6.37 (t, J=11.5 Hz, 1H), 6.05 (d, J=16.5 Hz, 1H), 5.80 (br d, J=9.4 Hz, 1H), 5.57 (q, J=6.6 Hz, 1H), 5.44 (br s, 1H), 5.46–5.34 (m, 2H), 4.74 (dd, J=9.4, 1.2 Hz, 1H), 4.71 (br s, 1H), 4.03 (d, J=17.8 Hz, 1H), 3.90–3.40 (m, 2H), 2.45–1.38 (m, 20H), 2.29 (d, J=17.8 Hz, 1H), 1.88 (d, J=6.6 Hz, 3H), 1.74 (d, J=1.2 Hz, 3H), 1.70 (s, 3H); minor isomer 9.59 (ddd, J=16.5, 11.5, 1.0 Hz, 1H), 7.40 (s, 1H), 6.61 (d, J=11.5 Hz, 1H), 6.35 (t, J=11.5 Hz, 1H), 6.00 (d, J=16.5 Hz, 1H), 5.83 (br d, J=9.4 Hz, 1H), 5.59 (q, J=6.6 Hz, 1H), 5.51 (br s, 1H), 5.46–5.34 (m, 2H), 5.02 (dd, J=9.4, 1.2 Hz, 1H), 4.56 (br s, 1H) 4.04 (d, J=17.8 Hz, 1H), 3.90–3.40 (m, 2H), 2.45–1.38 (m, 20H), 2.28 (d, J=17.8 Hz, 1H), 1.94 (d, J=6.6 Hz, 3H), 1.77 (d, J=1.2 Hz, 3H), 1.70 (s, 3H)

FABMS m/z 779 (M+H)$^+$

HRFABMS calcd for $C_{36}H_{47}N_2O_{11}S_3$ (M+H)$^+$ 779.2342, found 779.2342

Example 13

Synthesis of Compound 13

In the same manner as in Example 1, Compound 13 (15 mg, yield 9.0%) was obtained from DC107 (120 mg, 0.24 mmol), potassium carbonate (0.23 g, 1.7 mmol), chloromethyl p-methoxybenzyloxyacetate (0.40 g, 1.7 mmol), and potassium iodide (40 mg, 0.24 mmol).

IR (KBr) 3420, 2936, 1720, 1692, 1650, 1610, 1513, 1455, 1358, 1252, 1175, 1108, 1031, 974, 816 cm$^{-1}$ $^1$H NMR (CDCl$_3$, 400 MHz)δ ppm; 8.47 (ddd, J=16.3, 11.2, 1.0 Hz, 1H), 7.35 (s, 1H), 7.30–7.23 (m, 2H), 6.90–6.83 (m, 2H), 6.58 (d, J=11.7 Hz, 1H), 6.23 (dd, J=11.7, 11.2 Hz, 1H), 6.17 (d, J=16.3 Hz, 1H), 5.73 (br d, J=8.5 Hz, 1H), 5.53 (br s, 1H), 5.48 (d, J=11.2 Hz, 1H), 5.45 (d, J=11.2 Hz, 1H), 5.41 (q, J=6.8 Hz, 1H) 4.94 (dd, J=8.5, 3.4 Hz, 1H), 4.53 (s, 2H), 4.05 (s, 2H), 3.88 (d, J=17.8 Hz, 1H), 3.79 (s, 3H), 3.74 (br d, J=3.4 Hz, 1H), 2.26 (d, J=17.8 Hz, 1H), 2.34–1.70 (m, 4H), 2.01 (d, J=6.8 Hz, 3H), 1.78 (s, 3H), 1.74 (d, J=1.0 Hz, 3H)

FABMS m/z 719 (M+H)$^+$

HRFABMS calcd for $C_{33}H_{39}N_2O_{10}S_3$ (M+H)$^+$ 719.1767, found 719.1776

Example 14

Synthesis of Compound 14

Compound 13 (25 mg, 0.035 mmol) obtained in Example 13 was dissolved in dichloromethane (3.0 mL). Thereto were added water (0.15 mL) and 2,3-dichloro-5,6-dicyano-p-benzoquinone (8.0 mg, 0.035 mmol). This mixture was stirred at 25° C. for 28 hours. After the ordinary post-treatment, the reaction product was purified by thin-layer chromatography (developed with chloroform/methanol=95/5) to obtain Compound 14 (9.0 mg, yield 43%).

IR (KBr) 3420, 2928, 1750, 1688, 1640, 1610, 1450, 1365, 1265, 1175, 1091, 967, 731 cm$^{-1}$ $^1$H NMR (CDCl$_3$, 500 MHz)δ ppm; 8.44 (ddd, J=16.5, 11.3, 1.0 Hz, 1H), 7.35 (s, 1H), 6.58 (d, J=11.8 Hz, 1H) 6.23 (dd, J=11.8, 11.3 Hz, 1H), 6.18 (d, J=16.5 Hz, 1H), 5.74 (br d, J=8.5 Hz, 1H), 5.51 (d, J=11.0 Hz, 1H), 5.49 (d, J=11.0 Hz, 1H), 5.46 (br s, 1H), 5.41 (q, J=7.0 Hz, 1H), 4.95 (dd, J=8.5, 3.1 Hz, 1H), 4.16 (br d, J=4.9 Hz, 1H), 3.88 (d, J=17.7 Hz, 1H), 3.77 (br d, J=3.1 Hz, 1H), 2.34 (br t, J=4.9 Hz, 1H), 2.27 (d, J=17.7 Hz, 1H), 2.35–1.88 (m, 4H), 2.02 (d, J=7.0 Hz, 3H), 1.78 (s, 3H), 1.75 (d, J=1.0 Hz, 3H)

FABMS m/z 599 (M+H)$^+$

HRFABMS calcd for $C_{25}H_{31}N_2O_9S_3$ (M+H)$^+$ 599.1192, found 599.1211

Example 15

Synthesis of Compound 15

Compound 13 (32 mg, 0.045 mmol) obtained in Example 13 was dissolved in dichloromethane (2.0 mL). Thereto were added 3,4-dihydro-2H-pyran (0.020 mL, 0.22 mmol) and camphorsulfonic acid (4.6 mg, 0.020 mmol). This mixture was stirred at 0° C. for 100 minutes. After the ordinary post-treatment, the reaction product was purified by thin-layer chromatography (developed with chloroform/methanol=97/3) to obtain a compound (26 mg, yield 72%).

FABMS m/z 803 (M+H)$^+$

The compound obtained was dissolved in dichloromethane (2.0 mL). Thereto were added water (0.5 mL) and 2,3-dichloro-5,6-dicyano-p-benzoquinone (22 mg, 0.097 mmol). This mixture was stirred at 25° C. for 20 hours. After the ordinary post-treatment, the reaction product was purified by thin-layer chromatography (developed with chloroform/methanol=95/5) to obtain Compound 15 (12 mg, yield 55%). $^1$H NMR revealed that Compound 15 was an approximately 5:4 mixture of diastereomers.

IR (KBr) 3400, 2944, 1756, 1694, 1643, 1608, 1441, 1377, 1262, 1178, 1075, 1019, 969, 866 cm$^{-1}$ $^1$H NMR (CDCl$_3$, 500 MHz)δ ppm; major isomer 9.39 (dd, J=16.5, 11.5 Hz, 1H), 7.39 (s, 1H), 6.60 (d, J=11.5 Hz, 1H), 6.37 (t, J=11.5 Hz, 1H), 6.04 (d, J=16.5 Hz, 1H), 5.80 (br d, J=9.2 Hz, 1H), 5.57 (q, J=6.6 Hz, 1H), 5.55–5.46 (m, 2H), 4.74 (dd, J=9.2, 1.3 Hz, 1H), 4.70 (br, 1H), 4.17 (d, J=5.6 Hz, 2H), 4.03 (d, J=17.6 Hz, 1H), 3.77–3.70 (m, 1H), 3.46–3.40 (m, 1H), 2.46–1.40 (m, 10H), 2.30 (d, J=17.6 Hz, 1H), 1.88 (d, J=6.6 Hz, 3H), 1.74 (d, J=6.3 Hz, 3H), 1.70 (s, 3H); minor isomer 9.58 (dd, J=16.5, 11.5 Hz, 1H), 7.40 (s, 1H), 6.61 (d, J=11.5 Hz, 1H), 6.35 (t, J=11.5 Hz, 1H), 6.01 (d, J=16.5 Hz, 1H), 5.83 (br d, J=9.2 Hz, 1H), 5.59 (q, J=6.6 Hz, 1H), 5.55–5.46 (m, 2H), 5.01 (dd, J=9.2, 1.3 Hz, 1H), 4.56 (br, 1H), 4.17 (d, J=5.6 Hz, 2H), 4.04 (d, J=17.6 Hz, 1H), 3.86–3.80 (m, 1H), 3.54–3.47 (m, 1H), 2.46–1.40 (m, 10H), 2.29 (d, J=17.6 Hz, 1H), 1.94 (d, J=6.6 Hz, 3H), 1.77 (d, J=6.3 Hz, 3H), 1.71 (s, 3H)

FABMS m/z 683 (M+H)$^+$

HRFABMS calcd for $C_{30}H_{39}N_2O_{10}S_3$ (M+H)$^+$ 683.1767, found 683.1741

Example 16

Synthesis of Compound 16

To a solution of chloromethyl N-Boc-aminoacetate (Compound S-3 obtained in Reference Example 3) (2.24 g, 10.0 mmol) and DC107 (510 mg, 1.00 mmol) in acetone (50 mL) were added powdered potassium iodide (1.66 g, 10.0 mmol) and potassium carbonate (1.38 g, 10.0 mmol). The resultant suspension was stirred at 25° C. for 7 hours. The reaction mixture was subjected to the ordinary post-treatment and then purified by column chromatography (silica gel; eluted with chloroform/methanol=20/1) to obtain a crude reaction product (325 mg) containing the target compound. This crude product was purified by HPLC for fractionation (ODS; eluted with acetonitrile/water=45/55) to obtain Compound 16 (182 mg, yield 26%).

$^1$H NMR (CDCl$_3$, 270 MHz)δ ppm; 8.47 (dd, J=11.4, 16.6 Hz, 1H), 7.35 (s, 1H), 6.59 (d, J=11.4 Hz, 1H), 6.23 (t, J=11.4 Hz, 1H), 6.17 (d, J=16.6 Hz, 1H), 5.74 (br d, J=8.9 Hz, 1H), 5.5 (br s, 1H), 5.45 (s, 2H), 5.41 (q, J=6.9 Hz, 1H), 5.0 (br s, 1H), 4.95 (d, J=8.9 Hz, 1H), 3.90 (d, J=ca. 7 Hz, 2H), 3.88 (d, J=17.8 Hz, 1H), 3.8 (br s, 1H), 2.3–1.5 (m, 4H), 2.28 (d, J=17.8 Hz, 1H), 2.02 (d, J=6.9 Hz, 3H), 1.78 (s, 3H), 1.75 (d, J=1.0 Hz, 3H), 1.44 (s, 9H)

FABMS m/z 698 (M+H)$^+$ calcd for C$_{30}$H$_{39}$N$_3$O$_{10}$S$_3$=697

Example 17

Syntheses of Compound 17 and Compound 18

To a solution of chloromethyl N-(methoxy-carbonyl) aminoacetate (Compound S-4 obtained in Reference Example 4) (1.06 g, 5.84 mmol) and DC107 (262 mg, 0.513 mmol) in acetone (25 mL) were added powdered potassium iodide (848 mg, 5.11 mmol) and potassium carbonate (706 mg, 5.12 mmol). The resultant suspension was stirred at 25° C. for 12 hours. The reaction mixture was subjected to the ordinary post-treatment and then purified by column chromatography (silica gel; eluted with chloroform/methanol=20/1) to obtain a crude reaction product (121 mg) containing the target compounds. This crude product was purified by HPLC for fractionation (ODS; eluted with acetonitrile/water=45/55) to obtain Compound 17 (24 mg, yield 7.0%) and Compound 18 (21 mg, yield 5.2%). Compound 17

$^1$H NMR (CDCl$_3$, 270 MHz)δ ppm; 8.45 (dd, J=11.9, 16.3 Hz, 1H), 7.35 (s, 1H), 6.59 (d, J=11.9 Hz, 1H), 6.23 (t, J=11.6 Hz, 1H), 6.17 (d, J=16.8 Hz, 1H), 5.73 (br d, J=8.9 Hz, 1H), 5.48 (d, J=11.2 Hz, 1H), 5.48 (br s, 1H), 5.42 (d, J=11.2 Hz, 1H), 5.41 (q, J=6.9 Hz, 1H), 5.25 (br s, 1H), 4.94 (dd, J=3.0, 8.9 Hz, 1H), 3.94 (br d, J=5.9 Hz, 2H), 3.89 (d, J=17.8 Hz, 1H), 3.85 (s, 1H), 3.68 (s, 3H), 2.4–1.6 (m, 4H), 2.30 (d, J=17.8 Hz, 1H), 2.02 (d, J=6.9 Hz, 3H), 1.75 (s, 6H)

FABMS m/z 656 (M+H)$^+$ calcd for C$_{27}$H$_{33}$N$_3$O$_{10}$S$_3$=655 Compound 18

$^1$H NMR (CDCl$_3$, 270 MHz)δ ppm; 9.46 (dd, J=11.4, 16.6 Hz, 1H), 7.41 (s, 1H), 6.64 (d, J=11.4 Hz, 1H), 6.34 (t, J=11.4 Hz, 1H), 6.02 (d, J=16.6 Hz, 1H), 5.79 (br d, J=ca. 9 Hz, 1H), 5.58 (q, J=6.4 Hz, 1H), 5.52 (br s, 1H), 5.49 (d, J=11.4 Hz, 1H), 5.42 (d, J=11.4 Hz, 1H), 5.35 (br s, 2H), 5.16 (br s, 1H), 5.12 (br s, 1H), 4.78 (br d, J=9.4 Hz, 1H), 4.03 (d, J=17.3 Hz, 1H), 3.96 (br d, J=5.9 Hz, 2H), 3.92 (br d, J=5.4 Hz, 2H), 3.71 (s, 3H), 3.70 (s, 3H), 2.5–2.3 (m, 2H) 2.34 (d, J=17.3 Hz, 1H), 2.1–1.4 (m, 2H), 1.86 (d, J=6.4 Hz, 3H), 1.75 (d, J=1.0 Hz, 3H), 1.70 (s, 3H)

FABMS m/z 801 (M+H)$^+$ calcd for C$_{32}$H$_{40}$N$_4$O$_{14}$S$_3$=800

Example 18

Synthesis of Compound 19

To a solution of Compound S-5 (965 mg, 2.54 mmol) obtained in Reference Example 5 and DC107 (128 mg, 0.254 mmol) in acetone (7.6 mL) were added powdered potassium iodide (422 mg, 2.54 mmol) and potassium carbonate (176 mg, 1.28 mmol). The resultant suspension was stirred at 25° C. for 14 hours. The reaction mixture was subjected to the ordinary post-treatment and then purified by column chromatography (silica gel; eluted with chloroform/methanol=100/1 to 50/1) to obtain a crude reaction product (160 mg) containing the target compound. This crude product was purified by HPLC for fractionation (ODS; eluted with acetonitrile/water=50/50) to obtain Compound 19 (27 mg, yield 12%).

$^1$H NMR (CDCl$_3$, 270 MHz)δ ppm; 8.34 (dd, J=11.6, 16.2 Hz, 1H), 7.43 (br t, J=ca. 5 Hz, 1H), 7.22 (s, 1H) 6.45 (d, J=11.9 Hz, 1H), 6.10 (t, J=11.7 Hz, 1H) 6.03 (d, J=16.2 Hz, 1H), 5.61 (br d, J=ca. 9 Hz, 1H), 5.40 (br s, 1H), 5.32 (s, 2H), 5.28 (q, J=6.9 Hz, 1H), 4.81 (br d, J=ca. 7 Hz, 1H), 4.45 (s, 1H), 4.20 (d, J=2.3 Hz, 1H), 4.05 (br s, 1H), 3.99 (s, 2H), 3.93 (d, J=5.6 Hz, 2H), 3.74 (d, J=17.8 Hz, 1H), 3.67 (br s, 1H), 2.17 (d, J=17.8 Hz, 1H), 1.89 (d, J=6.9 Hz, 3H), 1.63 (s, 3H), 1.61 (s, 3H), 2.3–1.4 (m, 4H), 1.39 (s, 3H), 1.37 (s, 3H), 1.30 (s, 3H), 1.19 (s, 3H)

FABMS m/z 854 (M+H)$^+$ calcd for C$_{37}$H$_{47}$N$_3$O$_{14}$S$_3$=853

Example 19

Synthesis of Compound 20

To a solution of Compound S-6 (187 mg, 0.476 mmol) obtained in Reference Example 6 and DC107 (52 mg, 0.10 mmol) in acetone (2.5 mL) were added powdered potassium iodide (169 mg, 1.02 mmol) and potassium carbonate (71 mg, 0.51 mmol). The resultant suspension was stirred at 25° C. for 12 hours. After the reaction mixture was subjected to the ordinary post-treatment, the reaction product was purified by thin-layer chromatography (silica gel; developed with chloroform/methanol=20/1) to obtain Compound 20 (33 mg, yield 38%).

$^1$H NMR (CDCl$_3$, 270 MHz)δ ppm; 8.46 (dd, J=11.4, 16.3 Hz, 1H), 7.48 (br t, J=6.2 Hz, 1H), 7.35 (s, 1H), 6.59 (d, J=11.9 Hz, 1H), 6.23 (t, J=11.6 Hz, 1H), 6.17 (d, J=16.3 Hz, 1H), 5.73 (br d, J=8.9 Hz, 1H), 5.5–5.3 (m, 2H), 5.41 (s, 2H), 4.95 (dd, J=4.0, 8.9 Hz, 1H), 4.56 (s, 1H), 4.31 (d, J=2.5 Hz, 1H), 4.17 (d, J=2.5 Hz, 1H), 4.10 (s, 2H), 3.89 (d, J=17.8 Hz, 1H), 3.78 (d, J=4.0 Hz, 1H), 3.67 (m, 1H), 3.46 (m, 1H), 2.59 (m, 2H), 2.4–1.4 (m, 4H), 2.28 (d, J=17.8 Hz, 1H), 2.02 (d, J=6.9 Hz, 3H), 1.76 (s, 3H), 1.75 (d, J=1.5 Hz, 3H), 1.53 (s, 6H), 1.42 (s, 3H), 1.30 (s, 3H)

FABMS m/z 868 (M+H)$^+$ calcd for C$_{38}$H$_{49}$N$_3$O$_{14}$S$_3$=867

Example 20

Synthesis of Compound 21

To a solution of Compound S-7 (197 mg, 0.500 mmol) obtained in Reference Example 7 and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 15.5 hours. After the reaction mixture was subjected to the ordinary post-treatment, the reaction product was purified by thin-layer chromatography (silica gel; developed with chloroform/methanol=20/1) to obtain Compound 21 (31 mg, yield 36%).

$^1$H NMR (CDCl$_3$, 270 MHz)δ ppm; 8.45 (dd, J=11.9, 16.5 Hz, 1H), 7.36 (s, 1H), 6.99 (br t, J=5.9 Hz, 1H), 6.59 (d, J=11.9 Hz, 1H), 6.23 (t, J=11.9 Hz, 1H), 6.18 (d, J=16.5 Hz, 1H), 5.73 (br d, J=8.9 Hz, 1H), 5.60 (d, J=4.8 Hz, 1H), 5.49 (br s, 1H), 5.40 (s, 2H), 5.4 (q, 1H, overlapped with other peaks), 4.96 (dd, J=4.0, 8.9 Hz, 1H), 4.64 (s, 2H), 4.36 (br d, J=4.8 Hz, 1H), 4.27 (s, 1H), 3.89 (d, J=17.8 Hz, 1H), 3.81 (d, J=4.0 Hz, 1H), 3.7–3.4 (m, 2H), 2.57 (br t, J=6.1 Hz, 2H), 2.4–1.4 (m, 4H), 2.28 (d, J=17.8 Hz, 1H), 2.02 (d, J=6.9 Hz, 3H), 1.77 (s, 3H), 1.76 (s, 3H), 1.51 (s, 3H), 1.38 (s, 3H), 1.33 (s, 3H), 1.32 (s, 3H)

FABMS m/z 868 (M+H)$^+$ calcd for $C_{38}H_{49}N_3O_{14}S_3$=867

Example 21

Synthesis of Compound 22

To a solution of Boc-L-Glu(OCH$_2$Cl)-OBu$^t$ (Compound S-8 obtained in Reference Example 8) (176 mg, 0.500 mmol) and DC107 (26 mg, 0.051 mmol) in acetone (2.5 mL) were added powdered potassium iodide (83 mg, 0.50 mmol) and potassium carbonate (70 mg, 0.51 mmol). The resultant suspension was stirred at 25° C. for 6.5 hours. After the reaction mixture was subjected to the ordinary post-treatment, the reaction product was purified by thin-layer chromatography (silica gel; developed with chloroform/methanol=20/1) to obtain Compound 22 (15 mg, yield 36%).

$^1$H NMR (CDCl$_3$, 270 MHz)δ ppm; 8.46 (dd, J=10.6, 16.1 Hz, 1H), 7.35 (s, 1H), 6.59 (d, J=11.9 Hz, 1H), 6.23 (t, J=11.6 Hz, 1H), 6.17 (d, J=16.2 Hz, 1H), 5.73 (br d, J=8.4 Hz, 1H), 5.50 (br s, 1H), 5.41 (q, 1H, overlapped with other peaks), 5.40 (s, 2H), 5.08 (br d, J=5.9 Hz, 1H), 4.95 (dd, J=4.0, 8.4 Hz, 1H), 4.16 (m, 1H), 3.89 (d, J=17.8 Hz, 1H), 3.77 (d, J=4.0 Hz, 1H), 2.4–1.2 (m, 8H), 2.28 (d, J=17.8 Hz, 1H), 2.02 (d, J=6.9 Hz, 3H), 1.78 (s, 3H), 1.75 (d, J=1.5 Hz, 3H), 1.45 (s, 9H), 1.43 (s, 9H)

FABMS m/z 826 (M+H)$^+$ calcd for $C_{37}H_{51}N_3O_{12}S_3$=825

Example 22

Synthesis of Compound 23

To a solution of MeOCO-L-Glu(OCH$_2$Cl)-OMe (Compound S-9 obtained in Reference Example 9) (248 mg, 0.927 mmol) and DC107 (51 mg, 0.10 mmol) in acetone (5.0 mL) were added powdered potassium iodide (171 mg, 1.03 mmol) and potassium carbonate (140 mg, 1.01 mmol). The resultant suspension was stirred at 25° C. for 11 hours. After the reaction mixture was subjected to the ordinary post-treatment, the reaction product was purified by thin-layer chromatography (developed with chloroform/methanol=20/1) to obtain Compound 23 (23 mg, yield 31%).

$^1$H NMR (CDCl$_3$, 270 MHz)δ ppm; 8.44 (dd, J=11.2, 16.5 Hz, 1H), 7.35 (s, 1H), 6.59 (d, J=11.9 Hz, 1H), 6.23 (dd, J=11.2, 11.9 Hz, 1H), 6.18 (d, J=16.5 Hz, 1H), 5.73 (br d, J=8.7 Hz, 1H), 5.5–5.3 (3H, overlapped with other peaks), 5.39 (s, 2H), 4.95 (dd, J=3.9, 8.7 Hz, 1H), 4.4 (m, 1H), 3.88 (d, J=17.8 Hz, 1H), 3.82 (d, J=3.9 Hz, 1H), 3.74 (s, 3H), 3.66 (s, 3H), 2.5–1.6 (m, 8H), 2.30 (d, J=17.8 Hz, 1H), 2.02 (d, J=6.9 Hz, 3H), 1.78 (s, 3H), 1.76 (s, 3H)

FABMS m/z 742 (M+H)$^+$ calcd for $C_{31}H_{39}N_3O_{12}S_3$=741

Example 23

Synthesis of Compound 24

To a solution of Compound S-10 (2.50 g, 5.37 mmol) obtained in Reference Example 10 and DC107 (250 mg, 0.490 mmol) in acetone (13 mL) were added powdered potassium iodide (830 mg, 5.00 mmol) and potassium carbonate (346 mg, 2.51 mmol). The resultant suspension was stirred at 25° C. for 15 hours. The reaction mixture was subjected to the ordinary post-treatment and then purified by column chromatography (silica gel; eluted with chloroform/methanol=100/1 to 50/1) to obtain a crude reaction product (716 mg). This crude product was purified by HPLC for fractionation (ODS; eluted with acetonitrile/water=50/50) to obtain Compound 24 (64 mg, yield 14%).

$^1$H NMR (CDCl$_3$, 270 MHz)δ ppm; 8.46 (dd, J=11.2, 16.5 Hz, 1H), 7.57 (br d, J=8.3 Hz, 1H), 7.36 (s, 1H), 6.59 (d, J=11.6 Hz, 1H), 6.23 (t, J=11.4 Hz, 1H), 6.18 (d, J=16.2 Hz, 1H), 5.73 (br d, J=9.2 Hz, 1H), 5.54 (br S, 1H), 5.41 (q, J=6.9 Hz, 1H), 5.38 (s, 2H), 4.96 (dd, J=3.8, 8.7 Hz, 1H), 4.62 (m, 1H), 4.57 (s, 1H), 4.32 (br d, J=2.0 Hz, 1H), 4.17 (br d, J=2.0 Hz, 1H), 4.12 (br s, 2H), 3.89 (d, J=17.8 Hz, 1H), 3.79 (d, J=3.8 Hz, 1H), 3.74 (s, 3H), 2.5–1.4 (m, 8H), 2.28 (d, J=17.8 Hz, 1H), 2.02 (d, J=6.9 Hz, 3H), 1.77 (s, 3H), 1.76 (d, J=1.0 Hz, 3H), 1.53 (s, 3H), 1.52 (s, 3H), 1.43 (s, 3H), 1.31 (s, 3H)

FABMS m/z 940 (M+H)$^+$ calcd for $C_{41}H_{53}N_3O_{16}S_3$=939

Example 24

Synthesis of Compound 25

To a solution of Compound S-11 (899 mg, 1.93 mmol) obtained in Reference Example 11 and DC107 (200 mg, 0.392 mmol) in acetone (10 mL) were added powdered potassium iodide (651 mg, 3.92 mmol) and potassium carbonate (271 mg, 1.96 mmol). The resultant suspension was stirred at 25° C. for 15 hours. The reaction mixture was subjected to the ordinary post-treatment and then purified by column chromatography (silica gel; eluted with chloroform/methanol=100/1) to obtain a crude reaction product (261 mg) containing the target compound. This crude product was purified by HPLC for fractionation (ODS; eluted with acetonitrile/water=55/45) to obtain Compound 25 (71 mg, yield 19%).

$^1$H NMR (CDCl$_3$, 270 MHz)δ ppm; 8.45 (dd, J=11.5, 16.3 Hz, 1H), 7.35 (s, 1H), 7.08 (br d, J=ca. 8 Hz, 1H), 6.59 (d, J=11.5 Hz, 1H), 6.23 (t, J=11.5 Hz, 1H) 6.18 (d, J=16.8 Hz, 1H), 5.73 (br d, J=8.9 Hz, 1H) 5.61 (d, J=5.0 Hz, 1H), 5.58 (s, 1H), 5.41 (q, J=6.9 Hz, 1H), 5.37 (s, 2H), 4.95 (dd, J=3.8, 8.9 Hz, 1H) 4.8–4.6 (m, 2H), 4.36 (dd, J=2.3, 5.0 Hz, 1H), 4.29 (s, 1H), 4.07 (br d, J=ca. 8 Hz, 1H), 3.88 (d, J=17.8 Hz, 1H), 3.81 (d, J=3.8 Hz, 1H), 3.75 (s, 3H), 2.6–1.5 (m, 8H), 2.28 (d, J=17.8 Hz, 1H), 2.02 (d, J=6.9 Hz, 3H), 1.76 (s, 6H), 1.51 (s, 3H), 1.39 (s, 3H), 1.34 (s, 3H) 1.31 (s, 3H)

FABMS m/z 940 (M+H)$^+$ calcd for $C_{41}H_{53}N_3O_{16}S_3$=939

Example 25

Synthesis of Compound 26

To a solution of Compound S-12 (372 mg, 1.00 mmol) obtained in Reference Example 12 and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 13 hours. After the reaction mixture was subjected to the ordinary post-treatment, the reaction product was purified by thin-layer chromatography (silica gel; developed with chloroform/methanol=20/1) to obtain Compound 26 (24 mg, yield 28%).

$^1$H NMR (CDCl$_3$, 270 MHz)δ ppm; 8.42 (dd, J=11.4, 16.6 Hz, 1H), 7.85 (m, 2H), 7.34 (s, 1H), 7.16 (m, 2H), 7.08 (br d, J=7.6 Hz, 1H), 6.58 (d, J=11.9 Hz, 1H), 6.21 (t, J=11.7 Hz, 1H), 6.16 (d, J=16.6 Hz, 1H), 5.67 (br d, J=ca. 9 Hz, 1H), 5.5–5.3 (2H, overlapped with other peaks), 5.39 (d, J=10.9 Hz, 1H), 5.35 (d, J=10.9 Hz, 1H), 4.93 (dd, J=3.3, 8.6 Hz, 1H), 4.77 (m, 1H), 3.91 (br d, J=3.3 Hz, 1H), 3.84 (d, J=17.8

Hz, 1H), 3.78 (s, 3H), 2.32 (s, 3H), 2.00 (d, J=6.9 Hz, 3H), 1.72 (d, J=1.0 Hz, 3H), 1.68 (s, 3H), 2.5–1.6 (m, 9H)

FABMS m/z 846 (M+H)$^+$ calcd for $C_3BH_{43}N_3O_{13}S_3$=845

Example 26

Synthesis of Compound 27

To a solution of Compound S-13 (365 mg, 1.00 mmol) obtained in Reference Example 13 and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 16.5 hours. After the reaction mixture was subjected to the ordinary post-treatment, the reaction product was purified by thin-layer chromatography (silica gel; developed with chloroform/methanol=20/1) to obtain Compound 27 (40 mg, yield 47%).

$^1$H NMR (CDCl$_3$, 270 MHz)δ ppm; 8.47 (dd, J=11.2, 16.4 Hz, 1H), 7.74 (br d, J=7.6 Hz, 1H), 7.36 (s, 1H), 6.59 (d, J=11.6 Hz, 1H), 6.23 (t, J=11.4 Hz, 1H), 6.17 (d, J=16.4 Hz, 1H), 5.72 (d, J=8.6 Hz, 1H), 5.58 (br s, 1H), 5.42 (q, J=6.9 Hz, 1H), 5.39 (s, 2H), 4.95 (br d, J=8.6 Hz, 1H), 4.71 (m, 1H), 4.0–3.7 (m, 6H), 3.75 (s, 3H), 2.5–1.6 (m, 9H), 2.02 (d, J=6.9 Hz, 3H), 1.75 (s, 6H), 1.47 (s, 6H), 0.98 (s, 3H)

FABMS m/z 840 (M+H)$^+$ calcd for $C_{37}H_{49}N_3O_{13}S_3$=839

Example 27

Synthesis of Compound 28

To a solution of Compound S-14 (383 mg, 1.65 mmol) obtained in Reference Example 14 and DC107 (169 mg, 0.33 mmol) in acetone (8.3 mL) were added powdered potassium iodide (548 mg, 3.30 mmol) and potassium carbonate (228 mg, 1.65 mmol). The resultant suspension was stirred at 25° C. for 14.5 hours. The reaction mixture was subjected to the ordinary post-treatment and then purified by column chromatography (silica gel; eluted with chloroform/methanol=100/1 to 50/1) to obtain a crude reaction product (86 mg) containing the target compound. This crude product was purified by HPLC for fractionation (ODS; eluted with acetonitrile/water=45/55) to obtain Compound 28 (4.1 mg, yield 1.8%).

$^1$H NMR (CDCl$_3$, 270 MHz)δ ppm; 8.46 (dd, J=11.2, 16.2 Hz, 1H), 7.36 (s, 1H), 6.69 (s, 2H), 6.59 (d, J=11.9 Hz, 1H), 6.23 (dd, J=11.2, 16.2 Hz, 1H), 6.18 (d, J=16.2 Hz, 1H), 5.74 (br d, J=8.3 Hz, 1H), 5.55 (br s, 1H), 5.42 (q, J=6.9 Hz, 1H), 5.39 (s, 2H), 4.95 (dd, J=3.6, 8.6 Hz, 1H), 3.90 (d, J=17.8 Hz, 1H), 3.78 (br d, J=ca. 4.0 Hz, 1H), 3.57 (d, J=6.6 Hz, 2H), 2.4–1.2 (m, 9H), 2.02 (d, J=6.9 Hz, 3H), 1.79 (s, 3H), 1.76 (d, J=1.3 Hz, 3H)

FABMS m/z 706 (M+H)$^+$ calcd for $C_{31}H_{35}N_3O_{10}S_3$=705

Example 28

Synthesis of Compound 29

To a solution of chloromethyl 3-(4-acetoxy-phenyl)-2-(acetylamino)propionate (Compound S-15 obtained in Reference Example 15) (157 mg, 0.502 mmol) and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 15 hours. The reaction mixture was subjected to the ordinary post-treatment and then purified by column chromatography (silica gel; eluted with chloroform/methanol=20/1) to obtain a crude reaction product (39 mg) containing the target compound. This crude product was purified by HPLC for fractionation (ODS; eluted with acetonitrile/water=45/55) to obtain Compound 29 (11 mg, yield 14%). Compound 29 was obtained as a mixture of diastereomers with respect to the configuration of acetylamino in the side chain R$^3$; they were in the ratio of approximately 1:1.

$^1$H NMR (CDCl$_3$, 270 MHz)δ ppm; (a mixture of two diastereomers, approx. 1:1) 8.46 (dd, J=11.3, 16.5 Hz, 1H), 7.35 (s) and 7.34 (s) (total 1H), 7.2–7.0 (m, 4H) 6.58 (d, J=11.9 Hz, 1H), 6.22 (t, J=11.7 Hz, 1H) 6.17 (d, J=16.5 Hz, 1H), 5.99 (br d, J=ca. 6 Hz) and 5.96 (br d, J=ca. 6 Hz) (total 1H), 5.72 (br d, J=ca. 9 Hz, 1H), 5.6–5.3 (m, 4H), 4.95 (br d, J=ca. 9 Hz, 1H), 4.83 (br q, J=ca. 7 Hz, 1H), 3.91 (d, J=ca. 18 Hz) and 3.90 (d, J=ca. 18 Hz) (total 1H), 3.86 (s, 1H), 3.2–3.0 (m, 2H), 2.4–1.6 (m, 5H), 2.29 (s) and 2.28 (s) (total 3H), 2.00 (d, J=6.9 Hz, 3H), 1.97 (s, 3H), 1.74 (s) and 1.74 (s) (total 3H), 1.71 (s) and 1.69 (s) (total 3H)

FABMS m/z 788 (M+H)$^+$ calcd for $C_{36}H_{41}N_3O_{11}S_3$=787

Example 29

Synthesis of Compound 30

To a solution of chloromethyl 4-acetoxybenzoate (Compound S-16 obtained in Reference Example 16) (2.11 g, 9.23 mmol) and DC107 (511 mg, 1.00 mmol) in acetone (50 mL) were added powdered potassium iodide (1.67 mg, 1.01 mmol) and potassium carbonate (1.40 mg, 1.01 mmol). The resultant suspension was stirred at 25° C. for 13 hours. After the reaction mixture was subjected to the ordinary post-treatment, the reaction product was purified by column chromatography (silica gel; eluted with chloroform/methanol=100/1) to obtain Compound 30 (392 mg, yield 56%).

$^1$H NMR (CDCl$_3$, 270 MHz)δ ppm; 8.46 (dd, J=11.9, 16.3 Hz, 1H), 8.03 (m, 2H), 7.34 (s, 1H), 7.17 (m, 2H), 6.58 (d, J=11.9 Hz, 1H), 6.23 (t, J=11.9 Hz, 1H), 6.17 (d, J=16.3 Hz, 1H), 5.72 (br d, J=8.9 Hz, 1H), 5.65 (d, J=11.4 Hz, 1H), 5.60 (d, J=11.4 Hz, 1H), 5.47 (br s, 1H), 5.41 (q, J=6.9 Hz, 1H), 4.94 (dd, J=4.0, 8.9 Hz, 1H), 3.90 (d, J=17.8 Hz, 1H), 3.76 (br d, J=4.0 Hz, 1H), 2.32 (s, 3H), 2.3–1.5 (m, 5H), 2.01 (d, J=6.9 Hz, 3H), 1.79 (s, 3H), 1.74 (d, J=1.0 Hz, 3H)

FABMS m/z 703 (M+H)$^+$ calcd for $C_{32}H_{34}N_2O_{10}S_3$=702

Example 30

Synthesis of Compound 31

To a solution of chloromethyl 3-acetoxybenzoate (Compound S-17 obtained in Reference Example 17) (2.48 g, 10.8 mmol) and DC107 (515 mg, 1.01 mmol) in acetone (50 mL) were added powdered potassium iodide (1.71 g, 10.3 mmol) and potassium carbonate (1.40 g, 10.1 mmol). The resultant suspension was stirred at 25° C. for 12 hours. The reaction mixture was subjected to the ordinary post-treatment and then purified by column chromatography (silica gel; eluted with chloroform/methanol=100/1) to obtain a crude reaction product (411 mg) containing the target compound. This crude product was purified by HPLC for fractionation (ODS; eluted with acetonitrile/water=60/40) to obtain Compound 31 (246 mg, yield 35%).

$^1$H NMR (CDCl$_3$, 270 MHz)δ ppm; 8.47 (dd, J=11.1, 16.2 Hz, 1H), 7.87 (dt, J=7.4, 1.0 Hz, 1H), 7.71 (t, J=2.0 Hz, 1H), 7.45 (t, J=7.9 Hz, 1H), 7.35 (s, 1H), 7.30 (m, 1H), 6.58 (d, J=11.9 Hz, 1H), 6.23 (t, J=11.6 Hz, 1H), 6.17 (d, J=16.2 Hz, 1H), 5.73 (br d, J=8.4 Hz, 1H), 5.66 (d, J=11.4 Hz, 1H), 5.59 (d, J=11.4 Hz, 1H), 5.51 (br s, 1H), 5.41 (q, J=6.9 Hz, 1H)

4.94 (dd, J=4.0, 8.4 Hz, 1H), 3.90 (d, J=17.8 Hz, 1H), 3.74 (d, J=4.0 Hz, 1H), 2.4–1.4 (m, 4H), 2.30 (s, 3H), 2.28 (d, J=17.8 Hz, 1H), 2.01 (d, J=6.9 Hz, 3H), 1.79 (s, 3H), 1.74 (d, J=1.0 Hz, 3H)

FABMS m/z 703 (M+H)$^+$ calcd for $C_{32}H_{34}N_2O_{10}S_3$=702

Example 31

Synthesis of Compound 32

To a solution of chloromethyl 4-(acetoxyphenyl) propionate (Compound S-18 obtained in Reference Example 18) (257 mg, 1.00 mmol) and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 14.5 hours. After the reaction mixture was subjected to the ordinary post-treatment, the reaction product was purified by thin-layer chromatography (silica gel; developed with chloroform/methanol=20/1) to obtain Compound 32 (14 mg, yield 19%).

$^1$H NMR (CDCl$_3$, 270 MHz)δ ppm; 8.50 (dd, J=11.2, 16.7 Hz, 1H), 7.35 (s, 1H), 7.18 (m, 2H), 6.98 (m, 2H), 6.58 (d, J=11.9 Hz, 1H), 6.22 (t, J=11.7 Hz, 1H), 6.16 (d, J=16.7 Hz, 1H), 5.72 (br d, J=8.6 Hz, 1H), 5.5–5.4 (1H, overlapped with other peaks), 5.45 (br s, 1H), 5.40 (d, J=10.9 Hz, 1H), 5.36 (d, J=10.9 Hz, 1H), 4.94 (dd, J=3.3, 8.6 Hz, 1H), 3.89 (d, J=17.8 Hz, 1H), 3.79 (br d, J=3.3 Hz, 1H), 2.92 (d, J=6.6 Hz, 2H), 2.62 (d, J=7.6 Hz, 2H), 2.28 (s, 3H), 2.26 (d, J=17.8 Hz, 1H), 2.01 (d, J=6.6 Hz, 3H), 1.74 (d, J=1.3 Hz, 3H), 1.72 (s, 3H), 2.4–1.6 (m, 4H)

FABMS m/z 731 (M+H)$^+$ calcd for $C_{34}H_3N_2O_{10}S_3$=730

Example 32

Synthesis of Compound 33

To a solution of chloromethyl 4-(acetoxy-phenyl)butyrate (Compound S-19 obtained in Reference Example 19) (1.87 g, 6.89 mmol) and DC107 (352 mg, 0.690 mmol) in acetone (17 mL) were added powdered potassium iodide (1.15 g, 6.93 mmol) and potassium carbonate (477 mg, 3.46 mmol). The resultant suspension was stirred at 25° C. for 16 hours. After the reaction mixture was subjected to the ordinary post-treatment, the reaction product was purified by column chromatography (silica gel; eluted with chloroform/methanol=20/1) to obtain Compound 33 (489 mg, yield 95%).

$^1$H NMR (CDCl$_3$, 270 MHz)δ ppm; 8.53 (dd, J=12.0, 16.4 Hz, 1H), 7.36 (s, 1H), 7.20 (m, 2H), 6.98 (m, 2H), 6.59 (d, J=11.9 Hz, 1H), 6.24 (t, J=11.9 Hz, 1H), 6.16 (d, J=16.4 Hz, 1H), 5.73 (br d, J=ca. 8 Hz, 1H), 5.53 (br s, 1H), 5.42 (q, J=6.9 Hz, 1H), 5.40 (d, J=11.1 Hz, 1H), 5.35 (d, J=11.1 Hz, 1H), 4.94 (dd, J=3.9, 8.7 Hz, 1H), 3.90 (d, J=17.8 Hz, 1H), 3.81 (d, J=3.9 Hz, 1H), 2.7–2.6 (m, 2H), 2.4–1.5 (m, 9H), 2.28 (s, 3H), 2.01 (d, J=6.9 Hz, 3H), 1.77 (s, 3H), 1.72 (d, J=1.3 Hz, 3H)

FABMS m/z 745 (M+H)$^+$ calcd for $C_{35}H_{40}N_2O_{10}S_3$=744

Example 33

Synthesis of Compound 34

To a solution of chloromethyl 3-(methoxycarbonylamino) benzoate (Compound S-20 obtained in Reference Example 20) (244 mg, 1.00 mmol) and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 16 hours. After the reaction mixture was subjected to the ordinary post-treatment, the reaction product was purified by thin-layer chromatography (silica gel; developed with chloroform/methanol=20/1) to obtain Compound 34 (20 mg, yield 28%).

$^1$H NMR (CDCl$_3$, 270 MHz)δ ppm; 8.44 (dd, J=10.9, 16.5 Hz, 1H), 7.89 (m, 1H), 7.71 (br d, J=ca. 8 Hz, 1H), 7.70 (m, 1H), 7.38 (t, J=7.9 Hz, 1H), 7.35 (s, 1H), 6.83 (br s, 1H), 6.59 (d, J=11.9 Hz, 1H), 6.23 (t, J=11.4 Hz, 1H), 6.17 (d, J=16.5 Hz, 1H), 5.71 (br d, J=ca. 9 Hz, 1H), 5.67 (d, J=11.2 Hz, 1H), 5.59 (d, J=11.2 Hz, 1H), 5.48 (br s, 1H), 5.41 (q, J=6.9 Hz, 1H) 4.94 (dd, J=3.8, 8.6 Hz, 1H), 3.90 (d, J=17.8 Hz, 1H), 3.80 (d, J=3.8 Hz, 1H), 3.75 (s, 3H), 2.4–1.8 (m, 4H), 2.34 (d, J=17.8 Hz, 1H), 2.02 (d, J=6.9 Hz, 3H), 1.80 (s, 3H), 1.73 (d, J=1.0 Hz, 3H)

FABMS m/z 718 (M+H)$^+$ calcd for $C_{32}H_{35}N_3O_{10}S_3$=717

Example 34

Syntheses of Compound 35 and Compound 36

To a solution of Compound S-21 (113 mg, 0.500 mol) obtained in Reference Example 21 and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 14 hours. After the reaction mixture was subjected to the ordinary post-treatment, the reaction product was purified by thin-layer chromatography (silica gel; developed with chloroform/methanol=20/1) to obtain Compound 35 (13 mg, yield 19%) and Compound 36 (10 mg, yield 11%).

Compound 35

$^1$H NMR (CDCl$_3$, 270 MHz)δ ppm; 8.46 (dd, J=11.9, 16.5 Hz, 1H), 7.36 (s, 1H), 6.59 (d, J=11.9 Hz, 1H), 6.23 (t, J=11.9 Hz, 1H), 6.17 (d, J=16.5 Hz, 1H), 5.73 (d, J=ca. 8 Hz, 1H), 5.57 (br s, 1H), 5.46 (s, 2H), 5.41 (q, J=6.9 Hz, 1H), 4.95 (br d, J=ca. 7 Hz, 1H), 4.15 (s, 2H), 3.89 (d, J=17.8 Hz, 1H), 3.81 (br s, 1H), 3.8–3.5 (m, 8H), 3.37 (s, 3H), 2.27 (d, J=17.8 Hz, 1H), 2.02 (d, J=6.9 Hz, 3H), 1.77 (s, 3H), 1.75 (d, J=1.0 Hz, 3H), 2.4–1.6 (m, 4H)

FABMS m/z 701 (M+H)$^+$ calcd for $C_{30}H_{40}N_2O_{11}S_3$=700

Compound 36

$^1$H NMR (CDCl$_3$, 270 MHz)δ ppm; 9.49 (dd, J=11.3, 16.4 Hz, 1H), 7.42 (s, 1H), 6.64 (d, J=11.5 Hz, 1H), 6.34 (t, J=11.4 Hz, 1H), 6.02 (d, J=16.4 Hz, 1H), 5.80 (br d, J=8.9 Hz, 1H), 5.59 (s, 1H), 5.58 (q, J=6.6 Hz, 1H), 5.46 (s, 2H), 5.40 (d, J=6.3 Hz, 1H), 5.28 (d, J=6.3 Hz, 1H), 4.78 (br d, J=8.9 Hz, 1H), 4.17 (s, 2H), 4.2–4.1 (2H, overlapped with other peaks), 4.03 (d, J=17.5 Hz, 1H), 3.8–3.5 (m, 16H), 3.38 (s, 6H), 2.30 (d, J=17.5 Hz, 1H), 1.87 (d, J=6.6 Hz, 3H), 1.74 (s, 3H), 1.69 (s, 3H), 2.5–1.4 (m, 4H)

FABMS m/z 913 (M+Na)$^+$ calcd for $C_{38}H_{54}N_2O_{16}S_3$=890

Example 35

Synthesis of Compound 37

To a solution of Compound S-22 (434 mg, 1.21 mmol) obtained in Reference Example 22 and DC107 (124 mg, 0.24 mmol) in acetone (6.0 mL) were added powdered potassium iodide (402 mg, 2.42 mmol) and potassium carbonate (167 mg, 1.21 mmol). The resultant suspension was stirred at 25° C. for 14.5 hours. The reaction mixture was subjected to the ordinary post-treatment and then purified by column chromatography (silica gel; eluted with chloroform/methanol=100/1 to 50/1) to obtain a crude reaction product (251 mg). This crude product was purified by HPLC for fractionation (ODS; eluted with acetonitrile/water=40/60), and a fraction obtained was further purified by preparative TLC (silica gel; developed with chloroform/methanol=20/1) to obtain Compound 37 (28 mg, yield 14%).

$^1$H NMR (CDCl$_3$, 270 MHz)δ ppm; 8.48 (dd, J=11.6, 16.6 Hz, 1H), 7.37 (s, 1H), 6.59 (d, J=11.6 Hz, 1H), 6.23 (t, J=11.6 Hz, 1H), 6.17 (d, J=16.6 Hz, 1H), 5.73 (br d, J=ca. 9 Hz, 1H), 5.63 (br s, 1H), 5.46 (s, 2H), 5.42 (q, J=6.9 Hz, 1H), 4.96 (br d, J=ca. 9 Hz, 1H), 4.15 (s, 2H), 3.89 (d, J=17.8 Hz, 1H), 3.86 (br s, 1H), 3.8–3.5 (m, 20H), 3.38 (s, 3H), 2.4–1.5 (m, 4H), 2.28 (d, J=17.8 Hz, 1H), 2.02 (d, J=6.9 Hz, 3H), 1.75 (s, 6H)

FABMS m/z 833 (M+H)$^+$ calcd for C$_{36}$H$_{52}$N$_2$O$_{14}$S$_3$=832

Example 36

Synthesis of Compound 38

Compound 16 (26 mg, 0.037 mmol) obtained in Example 16 was dissolved in dichloromethane (4.0 mL). Thereto were added 3,4-dihydro-2H-pyran (100 μL) and camphorsulfonic acid (15 mg). This mixture was stirred at 25° C. for 20 minutes. After the reaction mixture was subjected to the ordinary post-treatment, the reaction product was purified by thin-layer chromatography (developed with chloroform/methanol=20/1) to obtain Compound 38 (19 mg, yield 64%). Compound 38 was obtained as a mixture of diastereomers due to the asymmetric carbon of the tetrahydropyranyl group; they were found through HPLC to be in the ratio of approximately 4:3.

$^1$H NMR (CDCl$_3$, 270 MHz)δ ppm; (a mixture of two diastereomers, approx. 4:3) 9.61 (dd, J=11.4, 16.5 Hz) and 9.41 (dd, J=11.4, 16.5 Hz) (total 1H), 7.41 (s) and 7.40 (s) (total 1H), 6.62 (d, J=11.4 Hz) and 6.61 (d, J=11.4 Hz) (total 1H), 6.37 (t, J=11.4 Hz) and 6.35 (t, J=11.4 Hz) (total 1H), 6.05 (d, J=16.5 Hz) and 6.00 (d, J=16.5 Hz) (total 1H), 5.83 (br d, J=ca. 8 Hz) and 5.81 (br d, J=ca. 8 Hz) (total 1H), 5.6–5.5 (br, 1H), 5.59 (q, J=6.4 Hz) and 5.55 (q, J=6.4 Hz) (total 1H), 5.48 (d, J=11.4 Hz, 1H), 5.43 (d, J=11.4 Hz, 1H), 5.02 (br d, J=ca. 9 Hz) and 4.74 (br d, J=ca. 9 Hz) (total 1H), 5.0 (br s, 1H), 4.71 (br s) and 4.57 (br s) (total 1H), 4.05 (d, J=17.8 Hz) and 4.04 (d, J=17.8 Hz) (total 1H), 3.9–3.4 (m, 2H), 3.72 (d, J=6.9 Hz, 2H), 2.5–2.2 (m, 3H), 1.94 (d, J=6.4 Hz) and 1.88 (d, J=6.4 Hz) (total 3H), 1.77 (s) and 1.74 (d, J=1.0 Hz) (total 3H), 1.8–1.4 (m, 8H), 1.70 (s, 3H), 1.45 (s, 9H)

FABMS m/z 782 (M+H)$^+$ calcd for C$_{35}$H$_{47}$N$_3$O$_{11}$S$_3$=781

Example 37

Synthesis of Compound 39

Compound 16 (26 mg, 0.037 mmol) obtained in Example 16 was dissolved in dichloromethane (4.0 mL). Thereto were added 5,6-dihydro-4-methoxy-2H-pyran (100 μL) and camphorsulfonic acid (15 mg). This mixture was stirred at 25° C. for 20 minutes. After the reaction mixture was subjected to the ordinary post-treatment, the reaction product was purified by thin-layer chromatography (developed with chloroform/methanol=20/1) to obtain Compound 39 (12 mg, yield 41%).

$^1$H NMR (CDCl$_3$, 270 MHz)δ ppm; 9.56 (dd, J=11.4, 16.8 Hz, 1H), 7.43 (s, 1H), 6.63 (d, J=11.4 Hz, 1H), 6.37 (t, J=11.4 Hz, 1H), 6.01 (d, J=16.8 Hz, 1H), 5.86 (d, J=9.7 Hz, 1H), 5.58 (q, J=6.4 Hz, 1H), 5.50 (br s, 1H), 5.48 (d, J=10.9 Hz, 1H), 5.43 (d, J=10.9 Hz, 1H), 5.00 (br s, 1H), 4.98 (dd, J=1.5, 9.7 Hz, 1H), 4.04 (d, J=17.8 Hz, 1H), 3.91 (d, J=5.9 Hz, 2H), 3.7–3.5 (m, 4H), 3.11 (s, 3H), 2.5–2.2 (m, 3H), 2.32 (d, J=17.8 Hz, 1H), 2.0–1.6 (m, 5H), 1.95 (d, J=6.4 Hz, 3H), 1.79 (d, J=1.0 Hz, 3H), 1.69 (s, 3H), 1.45 (s, 9H)

FABMS m/z 812 (M+H)$^+$ calcd for C$_{36}$H$_{49}$N$_3$O$_{12}$S$_3$=811

Example 38

Syntheses of Compounds 40 to 42

Compound 17 (10 mg, 0.015 mmol) obtained in Example 17 was dissolved in dichloromethane (2.0 mL). Thereto were added 3,4-dihydro-2H-pyran (40 μL) and camphorsulfonic acid (0.8 mg). This mixture was stirred at 25° C. for 25 minutes. The reaction mixture was subjected to the same post-treatment and purification as in Example 36 to obtain Compound 40 (11 mg, yield 97%). Compound 40 was obtained as a mixture of diastereomers due to the asymmetric carbon of the tetrahydropyranyl group; they were found through HPLC to be in the ratio of approximately 5:4. The Compound 40 was further treated with HPLC for fractionation (ODS, eluted with acetonitrile/water=60/40) to separate the diastereomers, thereby giving Compound 41 and Compound 42.

Compound 40

$^1$H NMR (CDCl$_3$, 270 MHz)δ ppm; major isomer 9.41 (dd, J=11.4, 16.6 Hz, 1H), 7.40 (s, 1H), 6.60 (d, J=11.4 Hz, 1H), 6.37 (t, J=11.4 Hz, 1H), 6.05 (d, J=16.6 Hz, 1H), 5.81 (br d, J=ca. 9 Hz, 1H), 5.7–5.4 (1H, overlapped with other peaks), 5.59 (q, J=6.4 Hz, 1H), 5.49 (d, J=11.2 Hz, 1H), 5.43 (d, J=11.2 Hz, 1H), 5.16 (br s, 1H), 4.74 (br d, J=ca. 9 Hz, 1H), 4.71 (br s, 1H), 4.03 (d, J=17.8 Hz, 1H), 3.96 (d, J=5.9 Hz, 2H), 3.9–3.3 (m, 2H), 3.71 (s, 3H), 2.5–2.2 (m, 3H), 2.0–1.4 (m, 8H), 1.88 (d, J=6.4 Hz, 3H), 1.75 (s, 3H), 1.70 (s, 3H); minor isomer 9.60 (dd, J=11.4, 16.3 Hz, 1H), 7.41 (s, 1H), 6.61 (d, J=11.4 Hz, 1H), 6.35 (t, J=11.4 Hz, 1H), 6.00 (d, J=16.3 Hz, 1H), 5.83 (br d, J=8.9 Hz, 1H), 5.7–5.4 (1H, overlapped with other peaks), 5.57 (q, J=6.4 Hz, 1H), 5.49 (d, J=11.2 Hz, 1H), 5.43 (d, J=11.2 Hz, 1H), 5.02 (br d, J=8.9 Hz, 1H), 4.90 (br s, 1H), 4.56 (br s, 1H), 4.04 (d, J=17.8 Hz, 1H), 3.96 (d, J=5.9 Hz, 2H), 3.9–3.3 (m, 2H), 3.71 (s, 3H), 2.5–2.2 (m, 3H), 2.0–1.4 (m, 8H), 1.94 (d, J=6.4 Hz, 3H), 1.77 (d, J=1.0 Hz, 3H), 1.70 (s, 3H)

FABMS m/z 740 (M+H)$^+$ calcd for C$_{32}$H$_{41}$N$_3$O$_{11}$S$_3$=739

Compound 41

$^1$H NMR (CDCl$_3$, 270 MHz)δ ppm; 9.63 (dd, J=11.6, 16.5 Hz, 1H), 7.42 (s, 1H), 6.62 (d, J=11.4 Hz, 1H), 6.35 (t, J=11.4 Hz, 1H), 6.01 (d, J=16.5 Hz, 1H), 5.84 (br d, J=9.6 Hz, 1H), 5.7–5.5 (1H, overlapped with other peaks), 5.59 (q, J=6.6 Hz, 1H), 5.49 (d, J=11.2 Hz, 1H), 5.43 (d, J=11.2 Hz, 1H), 5.24 (br s, 1H), 5.02 (d, J=9.2 Hz, 1H), 4.57 (br s, 1H), 4.05 (d, J=17.8 Hz, 1H), 3.97 (d, J=5.6 Hz, 2H), 3.9–3.8 (m, 1H), 3.71 (s, 3H), 3.6–3.4 (m, 1H), 2.5–2.2 (m, 3H), 2.0–1.4 (m, 8H), 1.94 (d, J=6.6 Hz, 3H), 1.78 (d, J=1.0 Hz, 3H), 1.70 (s, 3H)

FABMS m/z 740 (M+H)$^+$ calcd for C$_{32}$H$_{41}$N$_3$O$_{11}$S$_3$=739

Compound 42

FABMS m/z 740 (M+H)$^+$ calcd for C$_{32}$H$_{41}$N$_3$O$_{11}$S$_3$=739

Example 39

Synthesis of Compound 43

Compound 19 (24 mg, 0.028 mmol) obtained in Example 18 was dissolved in dichloromethane (3.0 mL). Thereto were added 3,4-dihydro-2H-pyran (82 μL) and camphorsulfonic acid (1 mg). This mixture was stirred at 0° C. for 45 minutes. The reaction mixture was subjected to the same post-treatment and purification as in Example 36 to obtain Compound 43 (17 mg, yield 65%). Compound 43 was obtained as a mixture of diastereomers due to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.54 (dd, J=11.6, 16.9 Hz) and 9.35 (dd, J=11.6, 16.9 Hz) (total 1H), 7.49 (br t, J=5.6 Hz, 1H), 7.34 (s) and 7.33 (s) (total 1H), 6.54 (d, J=11.4 Hz) and 6.54 (d, J=11.4 Hz) (total 1H), 6.30 (t, J=11.5 Hz) and 6.27 (t, J=11.5 Hz) (total 1H), 5.97 (d, J=16.9 Hz) and 5.93 (d, J=16.9 Hz) (total 1H), 5.76 (br d, J=ca. 9 Hz) and 5.73 (br d, J=ca. 9 Hz) (total 1H), 5.6–5.4 (m, 2H), 5.41 (d, J=11.2 Hz, 1H), 5.36 (d, J=11.2 Hz, 1H), 4.95 (dd, J=1.3, 9.2 Hz) and 4.67 (br d, J=9.2 Hz) (total 1H), 4.54 (s, 1H), 4.64 (br s) and 4.50 (br s) (total 1H), 4.27 (d, J=1.9 Hz, 1H), 4.12 (d, J=1.9 Hz, 1H), 4.06 (s, 2H), 4.01 (d, J=5.6 Hz, 2H), 3.97 (d, overlapped with other peaks) and 3.96 (d, overlapped with other peaks) (total 1H), 3.8–3.3 (m, 2H), 2.5–1.2 (m, 10H), 2.27 (d, J=17.8 Hz) and 2.26 (d, J=17.8 Hz) (total 1H), 1.86 (d, J=6.6 Hz) and 1.80 (d, J=6.6 Hz) (total 3H), 1.70 (d, J=1.0 Hz) and 1.67 (d, J=1.0 Hz) (total 3H), 1.62 (s, 3H), 1.46 (s, 3H), 1.45 (s, 3H), 1.37 (s, 3H), 1.27 (s, 3H)

FABMS m/z 960 (M+Na)$^+$ calcd for C$_{42}$H$_{55}$N$_3$O$_{15}$S$_3$=937

Example 40

Synthesis of Compound 44

Compound 20 (28 mg, 0.032 mmol) obtained in Example 19 was dissolved in dichloromethane (5.0 mL). Thereto were added 3,4-dihydro-2H-pyran (100 μL) and camphorsulfonic acid (2 mg). This mixture was stirred at 25° C. for 30 minutes. The reaction mixture was subjected to the same post-treatment and purification as in Example 36-to obtain Compound 44 (19 mg, yield 64%). Compound 44 was obtained as a mixture of diastereomers due to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.62 (dd, J=11.4, 16.8 Hz) and 9.42 (dd, J=11.4, 16.8 Hz) (total 1H), 7.48 (br t, J=6.9 Hz, 1H), 7.41 (s) and 7.40 (s) (total 1H), 6.61 (br d, J=11.4 Hz, 1H), 6.37 (t, J=11.4 Hz) and 6.34 (t, J=11.4 Hz) (total 1H), 6.04 (d, J=16.8 Hz) and 6.00 (d, J=16.8 Hz) (total 1H), 5.84 (br d, J=ca. 9 Hz) and 5.81 (br d, J=ca. 9 Hz) (total 1H), 5.59 (q, J=6.4 Hz) and 5.57 (q, J=6.4 Hz) (total 1H), 5.49 (s) and 5.47 (s) (total 1H), 5.41 (s, 2H), 5.02 (br d, J=9.4 Hz) and 4.74 (br d, J=9.4 Hz) (total 1H), 4.72 (br s) and 4.57 (br s) (total 1H), 4.57 (s, 1H), 4.32 (d, J=2.0 Hz, 1H), 4.17 (d, J=2.0 Hz, 1H), 4.11 (s, 2H), 4.06 (d, J=17.8 Hz) and 4.05 (d, J=17.8 Hz) (total 1H), 3.9–3.6 (m, 2H), 3.67 (m, 1H), 3.47 (m, 1H), 2.61 (m, 2H), 2.5–1.3 (m, 10H), 2.30 (d, J=17.8 Hz) and 2.29 (d, J=17.8 Hz) (total 1H), 1.94 (d, J=6.4 Hz) and 1.87 (d, J=6.4 Hz) (total 3H), 1.77 (s) and 1.75 (s) (total 3H), 1.69 (br s, 3H), 1.54 (s, 3H), 1.53 (s, 3H), 1.43 (s, 3H), 1.31 (s, 3H)

FABMS m/z 952 (M+H)$^+$ calcd for C$_{43}$H$_{57}$N$_3$O$_5$S$_3$=951

Example 41

Synthesis of Compound 45

Compound 21 (24 mg, 0.028 mmol) obtained in Example 20 was dissolved in dichloromethane (3.0 mL). Thereto were added 3,4-dihydro-2H-pyran (75 μL) and camphorsulfonic acid (1 mg). This mixture was stirred at 0° C. for 25 minutes. The reaction mixture was subjected to the same post-treatment and purification as in Example 36 to obtain Compound 45 (18 mg, yield 67%). Compound 45 was obtained as a mixture of diastereomers due to the asymmetric carbon of the tetrahydropyranyl group; they were found through HPLC to be in the ratio of approximately 3:2.

$^1$H NMR (CDCl$_3$, 270 MHz)δ ppm; (a mixture of two diastereomers, approx. 3:2) 9.62 (dd, J=11.3, 16.5 Hz) and 9.43 (dd, J=11.6, 16.5 Hz) (total 1H), 7.42 (s) and 7.41 (s) (total 1H), 6.98 (br t, J=ca. 6 Hz, 1H), 6.62 (d, J=11.2 Hz) and 6.61 (d, J=11.2 Hz) (total 1H), 6.37 (t, J=11.4 Hz) and 6.35 (t, J=11.4 Hz) (total 1H), 6.05 (d, J=16.5 Hz) and 6.00 (d, J=16.5 Hz) (total 1H), 5.84 (br d, J=ca. 8 Hz) and 5.81 (br d, J=ca. 8 Hz) (total 1H), 5.6–5.5 (m, 3H), 5.41 (s, 2H), 5.02 (br d, J=ca. 9 Hz) and 4.73 (br d, J=ca. 9 Hz) (total 1H), 4.65 (s, 2H), 4.71 (br s) and 4.57 (br s) (total 1H), 4.36 (d, J=5.0 Hz, 1H), 4.27 (s, 1H), 4.06 (d, J=17.5 Hz) and 4.05 (d, J=17.5 Hz) (total 1H), 3.9–3.4 (m, 4H), 2.58 (br d, J=ca. 6 Hz, 2H), 2.5–2.3 (m, 2H), 2.31 (d, J=17.5 Hz) and 2.30 (d, J=17.5 Hz) (total 1H), 2.0–1.4 (m, 8H), 1.94 (d, J=6.6 Hz) and 1.88 (d, J=6.3 Hz) (total 3H), 1.77 (s) and 1.74 (s) (total 3H), 1.69 (s, 3H), 1.51 (s, 3H), 1.39 (s, 3H), 1.33 (s, 6H)

FABMS m/z 952 (M+H)$^+$ calcd for C$_{43}$H$_{57}$N$_3$O$_{15}$S$_3$=951

Example 42

Synthesis of Compound 46

Compound 22 (23 mg, 0.028 mmol) obtained in Example 21 was dissolved in dichloromethane (4.0 mL). Thereto were added 3,4-dihydro-2H-pyran (100 μL) and camphorsulfonic acid (3 mg). This mixture was stirred at 0° C. for 25 minutes. The reaction mixture was subjected to the same post-treatment and purification as in Example 36 to obtain Compound 46 (23 mg, yield 91%). Compound 46 was obtained as a mixture of diastereomers due to the asymmetric carbon of the tetrahydropyranyl group; they were found through HPLC to be in the ratio of approximately 1:1.

$^1$H NMR (CDCl$_3$, 270 MHz)δ ppm; (a mixture of two diastereomers, approx. 1:1) 9.61 (dd, J=11.6, 16.6 Hz) and 9.41 (dd, J=11.9, 16.3 Hz) (total 1H), 7.41 (s) and 7.40 (s) (total 1H), 6.61 (d, J=11.9 Hz) and 6.61 (d, J=11.4 Hz) (total 1H), 6.37 (t, J=11.4 Hz) and 6.34 (t, J=11.4 Hz) (total 1H), 6.05 (d, J=16.8 Hz) and 6.00 (d, J=16.3 Hz) (total 1H), 5.84 (br d, J=8.4 Hz) and 5.81 (br d, J=7.9 Hz) (total 1H), 5.6–5.5 (br, 1H), 5.59 (q, J=6.0 Hz) and 5.57 (q, J=6.4 Hz) (total 1H), 5.40 (s, 2H), 5.08 (br d, J=6.9 Hz, 1H), 5.02 (dd, J=1.0, 9.4 Hz) and 4.74 (dd, J=1.0, 9.4 Hz) (total 1H), 4.71 (br s) and 4.57 (br s) (total 1H), 4.07 (m, 1H), 4.04 (d, J=17.8 Hz, 1H), 3.9–3.4 (m, 2H), 2.5–1.4 (m, 12H), 1.94 (d, J=6.4 Hz, 3H), 1.88 (d, J=6.9 Hz, 3H), 1.74 (d, J=1.0 Hz, 3H), 1.70 (s, 3H), 1.47 (s, 9H), 1.44 (s, 9H)

FABMS m/z 910 (M+H)$^+$ calcd for C$_{42}$H$_{59}$N$_3$O$_{13}$S$_3$=909

Example 43

Synthesis of Compound 47

Compound 22 (28 mg, 0.028 mmol) obtained in Example 21 was dissolved in dichloromethane (4.0 mL). Thereto were added 5,6-dihydro-4-methoxy-2H-pyran (100 μL) and camphorsulfonic acid (3 mg). This mixture was stirred at 0° C. for 15 minutes. The reaction mixture was subjected to the same post-treatment and purification as in Example 37 to obtain Compound 47 (19 mg, yield 60%).

$^1$H NMR (CDCl$_3$, 270 MHz)δ ppm; 9.56 (dd, J=11.4, 17.1 Hz, 1H), 7.49 (s, 1H), 6.63 (d, J=11.4 Hz, 1H), 6.37 (t, J=11.4 Hz, 1H), 6.01 (d, J=17.1 Hz, 1H), 5.86 (d, J=9.9 Hz, 1H), 5.57 (q, J=6.4 Hz, 1H), 5.51 (br s, 1H), 5.40 (s, 2H), 5.07 (br d, J=6.9 Hz, 1H), 4.98 (dd, J=1.5, 9.9 Hz, 1H), 4.18 (m, 1H), 4.05 (d, J=18.1 Hz, 1H), 3.8–3.5 (m, 4H), 3.10 (s, 3H), 2.5–1.2 (m, 12H), 2.32 (d, J=18.1 Hz, 1H), 1.95 (d, J=6.4 Hz, 3H), 1.79 (d, J=1.0 Hz, 3H), 1.68 (s, 3H), 1.47 (s, 9H), 1.44 (s, 9H)

FABMS m/z 940 (M+H)$^+$ calcd for $C_{43}H_{61}N_3O_{14}S_3$=939

Example 44

Synthesis of Compound 48

Compound 23 (23 mg, 0.032 mmol) obtained in Example 22 was dissolved in dichloromethane (3.0 mL). Thereto were added 3,4-dihydro-2H-pyran (75 μL) and camphorsulfonic acid (1 mg). This mixture was stirred at 0° C. for 30 minutes. The reaction mixture was subjected to the same post-treatment and purification as in Example 36 to obtain Compound 48 (18 mg, yield 69%). Compound 48 was obtained as a mixture of diastereomers due to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.61 (dd, J=11.4, 16.7 Hz) and 9.43 (dd, J=11.4, 16.7 Hz) (total 1H), 7.41 (s) and 7.41 (s) (total 1H), 6.62 (d, J=11.4 Hz) and 6.61 (d, J=11.4 Hz) (total 1H), 6.37 (t, J=11.4 Hz) and 6.35 (t, J=11.4 Hz) (total 1H), 6.06 (d, J=16.7 Hz) and 6.00 (d, J=16.7 Hz) (total 1H), 5.84 (br d, J=ca. 9 Hz) and 5.81 (br d, J=ca. 9 Hz) (total 1H), 5.7–5.5 (m, 2H), 5.40 (s, 2H), 5.4–5.3 (m, 1H), 5.02 (d, J=9.2 Hz) and 4.74 (d, J=9.2 Hz) (total 1H), 4.72 (br s) and 4.57 (br s) (total 1H), 4.4 (m, 1H), 4.04 (br d, J=17.8 Hz, 1H), 3.9–3.4 (m, 2H), 3.76 (s, 3H), 3.69 (s, 3H), 2.5–1.4 (m, 14H), 2.32 (d, J=17.8 Hz) and 2.31 (d, J=17.8 Hz) (total 1H), 1.94 (d, J=6.6 Hz) and 1.88 (d, J=6.6 Hz) (total 3H), 1.77 (d, J=1.0 Hz) and 1.74 (d, J=1.0 Hz) (total 3H), 1.70 (s, 3H)

FABMS m/z 826 (M+H)$^+$ calcd for $C_{36}H_{47}N_3O_{13}S_3$=825

Example 45

Syntheses of Compound 49 and Compound 50

Compound 24 (40 mg, 0.043 mmol) obtained in Example 23 was dissolved in dichloromethane (3.6 mL). Thereto were added 3,4-dihydro-2H-pyran (100 μL) and camphorsulfonic acid (2 mg). This mixture was stirred at 0 to 25° C. for 30 minutes. The reaction mixture was subjected to the same post-treatment and purification as in Example 36 to obtain Compound 49 (31 mg, yield 70%). Compound 49 was obtained as a mixture of diastereomers due to the asymmetric carbon of the tetrahydropyranyl group; they were found through HPLC to be in the ratio of approximately 5:4. The Compound 49 was treated with HPLC for fractionation (ODS; eluted with acetonitrile/water=55/45) to separate the diastereomers to thereby obtain Compound 50.

Compound 49

$^1$H NMR (CDCl$_3$, 270 MHz)δ ppm; (a mixture of two diastereomers, approx. 5:4) 9.62 (dd, J=11.6, 16.5 Hz) and 9.43 (dd, J=11.6, 16.5 Hz) (total 1H), 7.57 (br d, J=8.6 Hz, 1H), 7.42 (s) and 7.41 (s) (total 1H), 6.62 (d, J=11.5 Hz) and 6.61 (d, J=11.5 Hz) (total 1H), 6.37 (t, J=11.5 Hz) and 6.34 (t, J=11.5 Hz) (total 1H), 6.04 (d, J=16.5 Hz) and 6.00 (d, J=16.5 Hz) (total 1H), 5.84 (br d, J=ca. 9 Hz) and 5.81 (br d, J=ca. 9 Hz) (total 1H), 5.6–5.5 (m, 2H), 5.39 (s, 2H), 5.02 (br d, J=ca. 9 Hz) and 4.73 (br d, J=ca. 9 Hz) (total 1H), 4.7–4.6 (m, 2H), 4.58 (s, 1H), 4.33 (d, J=1.8 Hz, 1H), 4.17 (d, J=1.8 Hz, 1H), 4.13 (s, 2H), 4.05 (d, J=17.8 Hz) and 4.04 (d, J=17.8 Hz) (total 1H), 3.9–3.3 (m, 2H), 3.75 (s, 3H), 2.5–1.4 (m, 15H), 1.93 (d, J=6.6 Hz) and 1.87 (d, J=6.6 Hz) (total 3H), 1.80 (s) and 1.77 (s) (total 3H), 1.69 (s, 3H), 1.53 (s, 3H), 1.53 (s, 3H), 1.44 (s, 3H), 1.32 (s, 3H)

FABMS m/z 1024 (M+H)$^+$ calcd for $C_{46}H_{61}N_3O_{17}S_3$=1023

Compound 50

$^1$H NMR (CDCl$_3$, 270 MHz)δ ppm; 9.62 (dd, J=11.5, 16.5 Hz, 1H), 7.57 (br d, J=8.3 Hz, 1H), 7.42 (s, 1H), 6.63 (d, J=11.2 Hz, 1H), 6.35 (t, J=11.4 Hz, 1H), 6.01 (d, J=16.5 Hz, 1H), 5.84 (br d, J=ca. 9 Hz, 1H), 5.60 (q, J=6.6 Hz, 1H), 5.56 (s, 1H), 5.40 (s, 2H), 5.03 (br d, J=ca. 9 Hz, 1H), 4.65 (m, 1H), 4.7–4.6 (m, 1H), 4.59 (s, 1H), 4.34 (d, J=2.0 Hz, 1H), 4.18 (d, J=2.0 Hz, 1H), 4.14 (s, 2H), 4.05 (d, J=17.8 Hz, 1H), 3.8–3.4 (m, 2H), 3.76 (s, 3H), 2.5–1.4 (m, 14H), 2.31 (d, J=17.8 Hz, 1H), 1.94 (d, J=6.6 Hz, 3H), 1.78 (s, 3H), 1.70 (s, 3H), 1.54 (s, 3H), 1.54 (s, 3H), 1.45 (s, 3H), 1.32 (s, 3H)

FABMS m/z 1024 (M+H)$^+$ calcd for $C_{46}H_{61}N_3O_{17}S_3$=1023

Example 46

Synthesis of Compound 51

Compound 25 (35 mg, 0.037 mmol) obtained in Example 24 was dissolved in dichloromethane (5.5 mL). Thereto were added 3,4-dihydro-2H-pyran (143 μL) and camphorsulfonic acid (2 mg). This mixture was stirred at 0° C. to 25° C. for 1 hour. The reaction mixture was subjected to the same post-treatment and purification as in Example 36 to obtain Compound 51 (17 mg, yield 45%). Compound 51 was obtained as a mixture of diastereomers due to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.63 (dd, J=11.6, 16.5 Hz) and 9.43 (dd, J=11.6, 16.5 Hz) (total 1H), 7.42 (s) and 7.41 (s) (total 1H), 7.09 (br d, J=ca. 8 Hz, 1H), 6.62 (d, J=11.5 Hz) and 6.61 (d, J=11.5 Hz) (total 1H), 6.37 (t, J=11.5 Hz) and 6.34 (t, J=11.5 Hz) (total 1H), 6.04 (d, J=16.5 Hz) and 6.00 (d, J=16.5 Hz) (total 1H), 5.84 (br d, J=ca. 9 Hz) and 5.81 (br d, J=ca. 9 Hz) (total 1H), 5.7–5.5 (m, 2H), 5.7–5.5 (m, overlapped with other peaks) and 5.57 (q, J=6.3 Hz) (total 1H), 5.37 (s, 2H), 4.8–4.5 (m, 3H), 5.02 (br d, J=ca. 9 Hz) and 4.8–4.5 (m, overlapped with other peaks) (total 1H), 4.37 (d, J=5.0 Hz) and 4.36 (d, J=5.0 Hz) (total 1H), 4.29 (s) and 4.29 (s) (total 1H), 4.16 (br d, J=ca. 8 Hz, 1H), 4.05 (d, J=17.8 Hz) and 4.04 (d, J=17.8 Hz) (total 1H), 3.9–3.4 (m, 2H), 3.77 (s, 3H), 2.32 (d, J=17.8 Hz) and 2.31 (d, J=17.5 Hz) (total 1H), 1.94 (d, J=6.6 Hz) and 1.87 (d, J=6.6 Hz) (total 3H), 1.77 (s) and 1.74 (s) (total 3H), 1.68 (s, 3H), 1.51 (s, 3H), 1.41 (s, 3H), 1.34 (s, 3H), 1.33 (s, 3H), 2.6–1.0 (m, 14H)

FABMS m/z 1024 (M+H)$^+$ calcd for $C_{46}H_{61}N_3O_{17}S_3$=1023

Example 47

Synthesis of Compound 52

Compound 26 (53 mg, 0.063 mmol) obtained in Example 25 was dissolved in dichloromethane (5.3 mL). Thereto were added 3,4-dihydro-2H-pyran (145 μL) and camphorsulfonic acid (3.5 mg). This mixture was stirred at 25° C. for 30 minutes. The reaction mixture was subjected to the same post-treatment and purification as in Example 36 to obtain Compound 52 (51 mg, 0.055 mmol, 87%). Compound 52 was obtained as a mixture of diastereomers due to the asymmetric carbon of the THP group; they were found through HPLC to be in the ratio of approximately 5:4.

¹H NMR (CDCl₃, 270 MHz)δ ppm; (a mixture of two diastereomers, approx. 5:4) 9.62 (dd, J=11.6, 16.8 Hz) and 9.41 (dd, J=11.6, 16.8 Hz) (total 1H), 7.85 (m, 2H), 7.40 (s) and 7.39 (s) (total 1H), 7.18 (m, 2H), 6.92 (br d, J=7.3 Hz, 1H), 6.61 (d, J=11.6 Hz) and 6.60 (d, J=6.6 Hz) (total 1H), 6.36 (t, J=11.6 Hz) and 6.34 (t, J=11.6 Hz) (total 1H), 6.04 (d, J=16.8 Hz) and 6.00 (d, J=16.8 Hz) (total 1H), 5.83 (d, J=ca. 9 Hz) and 5.80 (d, J=ca. 9 Hz) (total 1H), 5.58 (q, J=6.6 Hz) and 5.56 (q, J=6.6 Hz) (total 1H), 5.45 (br s, 1H), 5.41 (d, J=11.4 Hz, 1H), 5.35 (d, J=11.4 Hz, 1H), 5.01 (br d, J=ca. 9 Hz) and 4.8–4.7 (overlapped with other peaks) (total 1H), 4.8–4.7 (m, 1H), 4.71 (br s) and 4.56 (br s) (total 1H), 4.01 (d, J=17.8 Hz) and 4.00 (d, J=17.8 Hz) (total 1H), 3.9–3.4 (m, 2H), 3.79 (s, 3H), 2.6–1.4 (m, 15H), 2.32 (s, 3H), 1.93 (d, J=6.6 Hz) and 1.86 (d, J=6.6 Hz) (total 3H), 1.75 (s) and 1.72 (s) (total 3H), 1.65 (s, 3H)

FABMS m/z 952 (M+Na)⁺ calcd for C₄₃H₅₁N₃O₁₃S₃=929

Example 48

Synthesis of Compound 53

Compound 30 (148 mg, 0.028 mmol) obtained in Example 29 was dissolved in dichloromethane (4.0 mL). Thereto were added 3,4-dihydro-2H-pyran (0.6 mL) and camphorsulfonic acid (10 mg). This mixture was stirred at 25° C. for 30 minutes. The reaction mixture was subjected to the same post-treatment and purification as in Example 36 to obtain Compound 53 (114 mg, yield 69%). Compound 53 was obtained as a mixture of diastereomers due to the asymmetric carbon of the tetrahydropyranyl group; they were found through HPLC to be in the ratio of approximately 1:1.

¹H NMR (CDCl₃, 270 MHz)δ ppm; (a mixture of two diastereomers, approx. 1:1) 9.61 (dd, J=11.4, 16.8 Hz) and 9.41 (dd, J=11.4, 16.8 Hz) (total 1H), 8.04 (m, 2H), 7.41 (s) and 7.40 (s) (total 1H), 7.18 (m, 2H), 6.60 (d, J=11.4 Hz, 1H), 6.37 (t, J=11.4 Hz) and 6.34 (t, J=11.4 Hz) (total 1H), 6.05 (d, J=16.8 Hz) and 6.00 (d, J=16.8 Hz) (total 1H), 5.83 (br d, J=ca. 9 Hz) and 5.81 (br d, J=ca. 9 Hz) (total 1H), 5.7–5.4 (2H, overlapped with other peaks), 5.67 (d, J=10.9 Hz, 1H), 5.60 (d, J=10.9 Hz, 1H), 5.01 (br d, J=9.4 Hz) and 4.73 (br d, J=8.9 Hz) (total 1H), 4.71 (br s) and 4.56 (br s) (total 1H), 4.05 (d, J=17.3 Hz) and 4.04 (d, J=17.8 Hz) (total 1H), 3.9–3.3 (m, 2H), 2.5–2.2 (m, 3H), 2.33 (s, 3H), 2.0–1.3 (m, 8H), 1.93 (d, J=6.4 Hz) and 1.87 (d, J=6.4 Hz) (total 3H), 1.76 (s) and 1.73 (s) (total 3H), 1.71 (s, 3H)

FABMS m/z 787 (M+H)⁺ calcd for C₃₇H₄₂N₂O₁₁S₃=786

Example 49

Synthesis of Compound 54

Compound 31 (30 mg, 0.042 mmol) obtained in Example 30 was dissolved in dichloromethane (4.0 mL). Thereto were added 3,4-dihydro-2H-pyran (100 μL) and camphorsulfonic acid (2 mg). This mixture was stirred at 25° C. for 15 minutes. The reaction mixture was subjected to the same post-treatment and purification as in Example 36 to obtain Compound 54 (30 mg, yield 91%). Compound 54 was obtained as a mixture of diastereomers due to the asymmetric carbon of the tetrahydropyranyl group; they were found through HPLC to be in the ratio of approximately 3:2.

¹H NMR (CDCl₃, 270 MHz)δ ppm; (a mixture of two diastereomers, approx. 3:2) 9.61 (dd, J=11.4, 16.3 Hz) and 9.41 (dd, J=11.4, 16.3 Hz) (total 1H), 7.89 (br d, J=7.9 Hz, 1H), 7.73 (br s, 1H), 7.47 (t, J=7.9 Hz, 1H), 7.40 (s) and 7.39 (s) (total 1H), 7.32 (m, 1H), 6.61 (d, J=11.4 Hz) and 6.60 (d, J=11.4 Hz) (total 1H), 6.38 (t, J=11.4 Hz) and 6.34 (t, J=11.4 Hz) (total 1H), 6.05 (d, J=16.3 Hz) and 6.00 (d, J=16.3 Hz) (total 1H), 5.83 (br d, J=ca. 9 Hz) and 5.80 (br d, J=ca. 8 Hz) (total 1H), 5.7–5.5 (m, 2H), 5.67 (d, J=11.4 Hz, 1H), 5.60 (d, J=11.4 Hz, 1H), 5.01 (br d, J=ca. 8 Hz) and 4.73 (br d, J=ca. 10 Hz) (total 1H), 4.70 (br s) and 4.56 (br s) (total 1H), 4.05 (d, J=17.8 Hz) and 4.04 (d, J=17.8 Hz) (total 1H), 3.9–3.4 (m, 2H), 1.4–2.4 (m, 10H), 2.32 (s, 3H), 2.31 (d, J=17.8 Hz) and 2.30 (d, J=17.8 Hz) (total 1H), 1.93 (d, J=6.4 Hz) and 1.87 (d, J=6.4 Hz) (total 3H), 1.76 (s) and 1.72 (s) (total 3H), 1.72 (s) and 1.72 (s) (total 3H)

FABMS m/z 787 (M+H)⁺ calcd for C₃₇H₄₂N₂O₁₁S₃=786

Example 50

Synthesis of Compound 55

Compound 31 (30 mg, 0.042 mmol) obtained in Example 30 was dissolved in dichloromethane (4.0 mL). Thereto were added 5,6-dihydro-4-methoxy-2H-pyran (100 μL) and camphorsulfonic acid (2 mg). This mixture was stirred at 25° C. for 15 minutes. The reaction mixture was subjected to the same post-treatment and purification as in Example 37 to obtain Compound 55 (31 mg, yield 86%).

¹H NMR (CDCl₃, 270 MHz)δ ppm; 9.57 (dd, J=11.6, 16.6 Hz, 1H), 7.90 (dt, J=7.5, 1.5 Hz, 1H), 7.73 (t, J=2.0 Hz, 1H), 7.47 (t, J=7.9 Hz, 1H), 7.43 (s, 1H), 7.32 (m, 1H), 6.63 (d, J=11.6 Hz, 1H), 6.37 (t, J=11.6 Hz, 1H), 6.01 (d, J=16.6 Hz, 1H), 5.85 (br d, J=ca. 10 Hz, 1H), 5.68 (d, J=10.9 Hz, 1H), 5.58 (d, J=10.9 Hz, 1H), 5.57 (q, J=6.4 Hz, 1H), 5.47 (br s, 1H), 4.97 (d, J=9.9 Hz, 1H), 4.05 (d, J=17.8 Hz, 1H), 3.7–3.5 (m, 4H), 3.09 (s, 3H), 2.4–1.2 (m, 8H), 2.32 (d, J=17.8 Hz, 1H), 2.32 (s, 3H), 1.94 (d, J=6.4 Hz, 3H), 1.76 (d, J=1.0 Hz, 3H), 1.70 (s, 3H)

FABMS m/z 817 (M+H)⁺ calcd for C₃₈H₄₄N₂O₁₂S₃=816

Example 51

Synthesis of Compound 56

Compound 33 (200 mg, 0.269 mmol) obtained in Example 32 was dissolved in dichloromethane (23 mL). Thereto were added 3,4-dihydro-2H-pyran (620 μL) and camphorsulfonic acid (15 mg). This mixture was stirred at 25° C. for 30 minutes. After the reaction mixture was subjected to the ordinary post-treatment, the reaction product was purified by column chromatography (silica gel; eluted with chloroform/methanol=100/1) to obtain Compound 56 (216 mg, yield 97%). Compound 56 was obtained as a mixture of diastereomers due to the asymmetric carbon of the tetrahydropyranyl group; they were found through HPLC to be in the ratio of approximately 4:3.

¹H NMR (CDCl₃, 270 MHz)δ ppm; (a mixture of two diastereomers, approx. 4:3) 9.62 (dd, J=11.5, 16.5 Hz) and 9.43 (dd, J=11.5, 16.5 Hz) (total 1H), 7.41 (s) and 7.40 (s) (total 1H), 7.17 (m, 2H), 6.99 (m, 2H), 6.62 (d, J=11.6 Hz) and 6.61 (d, J=11.6 Hz) (total 1H), 6.37 (t, J=11.6 Hz) and 6.35 (t, J=11.6 Hz) (totral 1H), 6.05 (d, J=16.5 Hz) and 6.00 (d, J=16.5 Hz) (total 1H), 5.83 (br d, J=ca. 8 Hz) and 5.80 (br d, J=ca. 8 Hz) (total 1H), 5.57 (q, J=6.6 Hz, 1H), 5.6–5.5 (1H, overlapped with other peaks), 5.41 (d, J=10.9 Hz, 1H), 5.36 (d, J=10.9 Hz, 1H), 5.02 (d, J=9.2 Hz) and 4.73 (d, J=9.2 Hz) (total 1H), 4.71 (br s) and 4.56 (br s) (total 1H), 4.04 (d, J=17.5 Hz) and 4.03 (d, J=17.5 Hz) (total 1H), 3.9–3.4 (m, 2H), 2.64 (m, 2H), 2.5–1.4 (m, 15H), 2.29 (s, 3H), 1.94 (d, J=6.6 Hz) and 1.87 (d, J=6.6 Hz) (total 3H), 1.76 (d, J=1.0 Hz) and 1.73 (d, J=1.0 Hz) (total 3H), 1.69 (s, 3H)

FABMS m/z 829 (M+H)⁺ calcd for C₄₀H₄₈N₂O₁₁S₃=828

Example 52

Synthesis of Compound 57

Compound 34 (25 mg, 0.035 mmol) obtained in Example 33 was dissolved in dichloromethane (3.0 mL). Thereto were added 3,4-dihydro-2H-pyran (82 µL) and camphorsulfonic acid (1 mg). This mixture was stirred at 0° C. for 30 minutes. The reaction mixture was subjected to the same post-treatment and purification as in Example 36 to obtain Compound 57 (21 mg, yield 68%). Compound 57 was obtained as a mixture of diastereomers due to the asymmetric carbon of the tetrahydropyranyl group; they were found through HPLC to be in the ratio of approximately 3:2.

$^1$H NMR (CDCl$_3$, 270 MHz)δ ppm; (a mixture of two diastereomers, approx. 3:2) 9.62 (dd, J=11.6, 16.5 Hz) and 9.43 (dd, J=11.4, 16.3 Hz) (total 1H), 7.94 (m, 1H), 7.73 (br d, J=ca. 8 Hz, 1H), 7.70 (br d, J=7.9 Hz, 1H), 7.41 (t, J=7.9 Hz, 1H), 7.40 (s) and 7.39 (s) (total 1H), 7.00 (br s, 1H), 6.62 (d, J=11.5 Hz) and 6.61 (d, J=11.6 Hz) (total 1H), 6.37 (t, J=11.5 Hz) and 6.34 (t, J=11.6 Hz) (total 1H), 6.05 (d, J=16.2 Hz) and 6.01 (d, J=16.5 Hz) (total 1H), 5.82 (br d, J=ca. 8 Hz) and 5.79 (br d, J=ca. 8 Hz) (total 1H), 5.7–5.5 (m, 2H), 5.67 (d, J=11.2 Hz, 1H), 5.60 (d, J=11.2 Hz) and 5.59 (d, J=11.2 Hz) (total 1H), 5.02 (d, J=ca. 9 Hz) and 4.73 (br d, J=ca. 9 Hz) (total 1H), 4.71 (br s) and 4.57 (br s) (total 1H), 4.05 (d, J=17.8 Hz) and 4.04 (d, J=17.8 Hz) (total 1H), 3.9–3.4 (m, 2H), 3.78 (s, 3H), 2.5–1.4 (m, 10H), 2.37 (d, J=17.8 Hz, 1H), 1.93 (d, J=6.6 Hz) and 1.87 (d, J=6.6 Hz) (total 3H), 1.75 (s) and 1.71 (s) (total 3H), 1.71 (s) and 1.71 (s) (total 3H)

FABMS m/z 802 (M+H)$^+$ calcd for C$_{37}$H$_{43}$N$_3$O$_{11}$S$_3$=801

Example 53

Synthesis of Compound 58

Compound 34 (25 mg, 0.035 mmol) obtained in Example 33 was dissolved in dichloromethane (3.0 mL). Thereto were added 5,6-dihydro-4-methoxy-2H-pyran (82 µL) and camphorsulfonic acid (1 mg). This mixture was stirred at 0° C. for 10 minutes. The reaction mixture was subjected to the same post-treatment and purification as in Example 37 to obtain Compound 58 (25 mg, yield 86%).

$^1$H NMR (CDCl$_3$, 270 MHz)δ ppm; 9.57 (dd, J=11.7, 16.9 Hz, 1H), 7.93 (m, 1H), 7.73 (br d, 1H), 7.70 (m, 1H) 7.43 (s, 1H), 7.39 (t, J=7.9 Hz, 1H), 6.63 (d, J=11.5 Hz, 1H), 6.37 (t, J=11.6 Hz, 1H), 6.01 (d, J=16.9 Hz, 1H), 6.96 (br s, 1H), 5.85 (br d, J=ca. 10 Hz, 1H), 5.67 (d, J=11.2 Hz, 1H), 5.60 (q, J=6.6 Hz, 1H), 5.59 (d, J=11.2 Hz, 1H), 5.47 (br s, 1H), 4.97 (br d, J=ca. 10 Hz, 1H), 4.05 (d, J=17.8 Hz, 1H), 3.78 (s, 3H), 3.7–3.5 (m, 4H), 3.09 (s, 3H), 2.5–1.6 (m, 8H), 2.37 (d, J=17.8 Hz, 1H), 1.94 (d, J=6.6 Hz, 3H), 1.75 (s, 3H), 1.70 (s, 3H)

FABMS m/z 832 (M+H)$^+$ calcd for C$_{38}$H$_{45}$N$_3$O$_{12}$S$_3$=831

Example 54

Synthesis of Compound 59

Compound 20 (12 mg, 0.015 mmol) obtained in Example 19 was dissolved in THF (2.5 mL). Thereto was added hydrochloric acid (1 M, 2.5 mL). This mixture was stirred at 25° C. for 1 hour and 40 minutes. After the reaction mixture was subjected to the ordinary post-treatment, the reaction product was purified by thin-layer chromatography (silica gel; developed with chloroform/methanol=20/1) to obtain Compound 59 (10 mg, yield 86%).

$^1$H NMR (CDCl$_3$, 270 MHz)δ ppm; 8.54 (dd, J=11.1, 16.6 Hz, 1H), 7.45 (br t, J=ca. 6 Hz, 1H), 7.36 (s, 1H), 6.60 (d, J=11.9 Hz, 1H), 6.24 (t, J=11.4 Hz, 1H), 6.17 (d, J=16.6 Hz, 1H), 5.71 (d, J=8.4 Hz, 1H), 5.55 (br s, 1H), 5.41 (q, J=6.9 Hz, 1H), 5.41 (s, 2H), 5.00 (dd, J=3.5, 8.4 Hz, 1H), 4.77 (br d, J=ca. 8 Hz, 1H), 4.56 (s, 1H), 4.45 (m, 1H), 4.31 (dd, J=2.5, 7.9 Hz, 1H), 4.1–3.9 (m, 4H), 3.7–3.5 (m, 2H), 3.10 (br s, 1H), 2.58 (br t, J=ca. 6 Hz, 2H), 2.5–1.4 (m, 4H), 2.28 (d, J=17.8 Hz, 1H), 2.01 (d, J=6.9 Hz, 3H), 1.75 (s, 3H), 1.67 (s, 3H), 1.55 (s, 3H), 1.46 (s, 3H)

FABMS m/z 828 (M+H)$^+$ calcd for C$_{35}$H$_{45}$N$_3$O$_{14}$S$_3$=827

Example 55

Synthesis of Compound 60

Compound 24 (15.9 mg, 0.017 mmol) obtained in Example 23 was dissolved in THF (5.0 mL) and hydrochloric acid (1 M, 5.0 mL). This solution was stirred at 25° C. for 2 hours. After the reaction mixture was subjected to the ordinary post-treatment, the reaction product was purified by thin-layer chromatography (silica gel; developed with chloroform/methanol=9/1) to obtain Compound 60 (12 mg, yield 76%).

$^1$H NMR (CDCl$_3$, 270 MHz)δ ppm; 8.49 (dd, J=11.1, 16.5 Hz, 1H), 7.55 (br d, J=8.4 Hz, 1H), 7.36 (s, 1H), 6.59 (d, J=11.9 Hz, 1H), 6.24 (t, J=11.6 Hz, 1H), 6.18 (d, J=16.5 Hz, 1H), 5.72 (br d, J=8.9 Hz, 1H), 5.48 (br s, 1H), 5.41 (s, 2H), 5.40 (q, J=6.9 Hz, 1H), 4.98 (d, J=8.9 Hz, 1H), 4.62 (m, 1H), 4.52 (s, 1H), 4.43 (m, 1H), 4.28 (m, 1H), 4.00 (dd, J=3.0, 5.0 Hz, 2H), 3.95 (d, J=17.8 Hz, 1H), 4.1–3.8 (m, 3H), 3.76 (s, 3H) 2.5–1.4 (m, 8H), 2.29 (d, J=17.8 Hz, 1H), 2.02 (d, J=6.9 Hz, 3H), 1.75 (d, J=1.0 Hz, 3H), 1.73 (s, 3H), 1.56 (s, 3H), 1.48 (s, 3H)

FABMS m/z 900 (M+H)$^+$ calcd for C$_{38}$H$_{49}$N$_3$O$_{16}$S$_3$=899

Example 56

Synthesis of Compound 61

Compound 27 (40 mg, 0.048 mmol) obtained in Example 26 was dissolved in THF (5 mL). Thereto was added hydrochloric acid (1 M, 5 mL). This mixture was stirred at 25° C. for 80 minutes. The reaction mixture was subjected to the same post-treatment and purification as in Example 55 to obtain Compound 61 (28 mg, yield 57%).

$^1$H NMR (CDCl$_3$, 270 MHz)δ ppm; 8.43 (dd, J=11.5, 16.5 Hz, 1H), 7.62 (br d, J=7.6 Hz, 1H), 7.36 (s, 1H), 6.59 (d, J=11.9 Hz, 1H), 6.23 (t, J=11.7 Hz, 1H), 6.17 (d, J=16.5 Hz, 1H), 5.69 (br d, J=ca. 8 Hz, 1H), 5.68 (br s, 1H), 5.41 (q, J=6.6 Hz, 1H), 5.40 (s, 2H), 4.96 (br d, J=8.6 Hz, 1H), 4.60 (m, 1H), 3.96 (br s, 1H) 3.8–3.5 (m, 6H), 3.93 (d, J=17.8 Hz, 1H), 3.75 (s, 3H), 2.5–1.6 (m, 8H), 2.31 (d, J=17.8 Hz, 1H), 2.01 (d, J=6.6 Hz, 3H), 1.76 (s, 3H), 1.70 (s, 3H), 1.09 (s, 3H)

FABMS m/z 800 (M+H)$^+$ calcd for C$_{34}$H$_{45}$N$_3$O$_{13}$S$_3$=799

Example 57

Syntheses of Compound 62 and Compound 63

Compound 43 (10 mg, 0.011 mmol) obtained in Example 39 was dissolved in THF (5 mL). Thereto was added hydrochloric acid (1 M, 5 mL). This mixture was stirred at 25° C. for 30 minutes. The reaction mixture was subjected to the same post-treatment and purification as in Example 55 to obtain a mixture (4.0 mg) of the target compounds. This mixture was treated with HPLC for fractionation (ODS; eluted with chloroform/methanol=45/55) to separate the diastereomers attributable to the asymmetric carbon of the tetrahydropyranyl group. Thus, Compound 62 (1.8 mg, yield 19%) and Compound 63 (1.8 mg, yield 19%) were obtained.
Compound 62

$^1$H NMR (CDCl$_3$, 270 MHz)δ ppm; (major peaks) 9.60 (dd, J=11.5, 16.5 Hz, 1H), 7.44 (br t, J=ca. 6 Hz, 1H), 7.41 (s, 1H), 6.62 (d, J=11.5 Hz, 1H), 6.34 (t, J=11.5 Hz, 1H), 6.00 (d, J=16.5 Hz, 1H), 5.83 (br d, J=ca. 9 Hz, 1H), 5.60 (q, J=6.6 Hz, 1H), 5.51 (d, J=11 Hz, 1H), 5.42 (d, J=11 Hz, 1H), 5.36 (br s, 1H), 5.01 (br d, J=ca. 9 Hz, 1H), 4.58 (s, 1H), 4.56 (br s, 1H), 4.45 (m, 1H), 4.38 (m, 1H), 4.2–4.0 (m, 5H), 3.9–3.4 (m, 2H), approx. 2.7 (br s, 1H), 2.5–1.4 (m, 10H), 2.30 (d, J=17.5 Hz, 1H), 1.94 (d, J=6.6 Hz, 3H), 1.78 (d, J=1.0 Hz, 3H), 1.70 (s, 3H), approx. 1.6 (3H, overlapped with other peaks), 1.48 (s, 3H)

FABMS m/z 898 (M+H)$^+$ calcd for C$_{39}$H$_{51}$N$_3$O$_{15}$S$_3$=897
Compound 63

FABMS m/z 898 (M+H)$^+$ calcd for C$_{39}$H$_{51}$N$_3$O$_{15}$S$_3$=897

Example 58

Synthesis of Compound 64

Compound 44 (23 mg, 0.024 mmol) obtained in Example 40 was dissolved in THF (10 mL). Thereto was added hydrochloric acid (1 M, 10 mL). This mixture was stirred at 25° C. for 30 minutes. The reaction mixture was subjected to the same post-treatment and purification as in Example 55 to obtain Compound 64 (9.2 mg, yield 42%). Compound 64 was obtained as a mixture of diastereomers due to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.61 (dd, J=11.3, 16.7 Hz) and 9.42 (dd, J=11.3, 16.7 Hz) (total 1H), 7.44 (br t, J=6.3 Hz, 1H), 7.41 (s) and 7.40 (s) (total 1H), 6.62 (d, J=11.7 Hz) and 6.61 (d, J=11.7 Hz) (total 1H), 6.36 (t, J=11.3 Hz) and 6.34 (t, J=11.3 Hz) (total 1H), 6.04 (d, J=16.7 Hz) and 6.00 (d, J=16.7 Hz) (total 1H), 5.83 (br d, J=ca. 9 Hz) and 5.80 (br d, J=ca. 9 Hz) (total 1H), 5.57 (q, J=6.6 Hz) and 5.55 (q, J=6.6 Hz) (total 1H), 5.50 (br s, 1H), 5.39 (s, 2H), 4.90 (br s, 1H), 5.01 (br d, J=ca. 9 Hz) and 4.74 (br d, J=ca. 9 Hz) (total 1H), 4.72 (br s) and 4.56 (br s) (total 1H), 4.54 (s, 1H), 4.42 (m, 1H), 4.25 (br d, J=5.6 Hz), 4.14 (d, J=17.5 Hz) and 4.13 (d, J=17.5 Hz) (total 1H), 4.1–3.9 (m, 2H), 3.9–3.4 (m, 4H), 2.82 (br s, 1H), 2.58 (m, 2H), 2.5–1.4 (m, 10H), 2.32 (d, J=17.5 Hz) and 2.31 (d, J=17.5 Hz) (total 1H), 1.93 (d, J=6.6 Hz) and 1.87 (d, J=6.6 Hz) (total 3H), 1.77 (d, J=1.0 Hz) and 1.74 (d, J=1.0 Hz) (total 3H), 1.64 (s) and 1.64 (s) (total 3H), 1.54 (s, 3H), 1.46 (s, 3H)

FABMS m/z 912 (M+H)$^+$ calcd for C$_{40}$H$_{53}$N$_3$O$_{15}$S$_3$=911

Example 59

Synthesis of Compound 65

Compound 50 (29 mg, 0.029 mmol) obtained in Example 45 was dissolved in THF (10 mL). Thereto was added hydrochloric acid (1 M, 10 mL). This mixture was stirred at 25° C. for 50 minutes. The reaction mixture was subjected to the same post-treatment and purification as in Example 55 to obtain Compound 65 (12 mg, yield 41%).

$^1$H NMR (CDCl$_3$, 270 MHz)δ ppm; 9.61 (dd, J=11.5, 16.5 Hz, 1H), 7.56 (d, J=8.3 Hz, 1H), 7.41 (s, 1H), 6.62 (d, J=11.5 Hz, 1H), 6.34 (t, J=11.5 Hz, 1H), 6.00 (d, J=16.5 Hz, 1H), 5.83 (br d, J=ca. 9 Hz, 1H), 5.58 (q, J=6.6 Hz, 1H), 5.53 (br s, 1H), 5.43 (d, J=10.9 Hz, 1H), 5.37 (d, J=10.9 Hz, 1H), 5.02 (d, J=9.2 Hz, 1H), 4.64 (m, 1H), 4.56 (br s, 1H), 4.54 (s, 1H), 4.44 (m, 1H), 4.30 (br s, 1H), 4.1–3.9 (m, 2H), 4.07 (d, J=17.8 Hz, 1H), 3.9–3.7 (m, 1H), 3.78 (s, 3H), 3.6–3.4 (m, 1H), 3.0–2.6 (br, 2H), 2.5–1.4 (m, 14H), 2.31 (d, J=17.8 Hz, 1H), 1.94 (d, J=6.6 Hz, 3H), 1.78 (s, 3H), 1.70 (s, 3H), 1.57 (s, 3H), 1.48 (s, 3H)

FABMS m/z 984 (M+H)$^+$ calcd for C$_{43}$H$_{57}$N$_3$O$_{17}$S$_3$=983

Example 60

Synthesis of Compound 66

Compound 50 (13 mg, 0.012 mmol), which is a stereoisomer with respect to the tetrahydropyranyl moiety, was dissolved in THF (5.0 mL) and hydrochloric acid (1 M, 5.0 mL). This solution was stirred at 0° C. to 25° C. for 4.5 hours. The reaction mixture was subjected to the same post-treatment and purification as in Example 55 to obtain Compound 66 (2.4 mg, yield 20%). Compound 60 (6.7 mg, yield 61%) was simultaneously obtained as a by-product.

$^1$H NMR (CDCl$_3$, 270 MHz)δ ppm; 9.41 (dd, J=11.4, 16.8 Hz, 1H), 7.54 (br d, J=ca. 8 Hz, 1H), 7.40 (s, 1H), 6.60 (d, J=11.4 Hz, 1H), 6.37 (t, J=11.4 Hz, 1H), 6.05 (d, J=16.8 Hz, 1H), 5.81 (br d, J=ca. 8 Hz, 1H), 5.56 (q, J=6.9 Hz, 1H), 5.49 (br s, 1H), 5.44 (d, J=10.9 Hz, 1H), 5.37 (d, J=10.9 Hz, 1H), 4.74 (d, J=8.9 Hz, 1H), 4.72 (br s, 1H), 4.65 (m, 1H), 4.54 (s, 1H), 4.40 (m, 1H), 4.30 (m, 1H), 4.05 (d, J=17.8 Hz, 1H), 4.1–3.9 (m, 2H), 3.8–3.4 (m, 2H), 3.78 (s, 3H), 3.0–2.6 (m, 2H), 2.5–1.4 (m, 14H), 2.32 (d, J=17.8 Hz, 1H), 1.88 (d, J=6.9 Hz, 3H), 1.75 (s, 3H), 1.69 (s, 3H), 1.57 (s, 3H), 1.48 (s, 3H)

FABMS m/z 984 (M+H)$^+$ calcd for C$_{43}$H$_{57}$N$_3$O$_{17}$S$_3$=983

Example 61

Synthesis of Compound 67

Compound 30 (101 mg, 0.144 mmol) obtained in Example 29 was dissolved in methanol (40 mL). Thereto was added a mixed solution (20 mL) consisting of saturated aqueous sodium bicarbonate solution/water (1:100). This mixture was stirred at 25° C. for 1 hour and 40 minutes. After the reaction mixture was subjected to the ordinary post-treatment, the reaction product was purified by thin-layer chromatography (silica gel; developed with chloroform/methanol=20/1) to obtain Compound 67 (29 mg, yield 30%).

$^1$H NMR (CDCl$_3$, 270 MHz)δ ppm; 8.38 (dd, J=10.9, 16.3 Hz, 1H), 7.88 (m, 2H), 7.33 (s, 1H), 6.81 (m, 2H), 6.59 (d, J=11.9 Hz, 1H), 6.4–5.9 (br, 1H), 6.24 (t, J=11.4 Hz, 1H), 6.17 (d, J=16.3 Hz, 1H), 5.64 (d, J=11.0 Hz, 1H), 5.61 (br d, 1H, overlapped with other peaks), 5.55 (d, J=11.0 Hz, 1H), 5.40 (q, J=6.9 Hz, 1H), 5.30 (br s, 1H), 4.94 (br d, J=8.4 Hz, 1H), 3.89 (d, J=17.8 Hz, 1H), 3.85 (br s, 1H), 2.4–1.5 (m, 4H), 2.28 (d, J=18.1 Hz, 1H), 2.01 (d, J=6.9 Hz, 3H), 1.79 (s, 3H), 1.69 (d, J=1.0 Hz, 3H)

FABMS m/z 661 (M+H)$^+$ calcd for C$_{30}$H$_{32}$N$_2$O$_9$S$_3$ 660

Example 62

Synthesis of Compound 68

Compound 53 (74 mg, 0.094 mmol) obtained in Example 48 was dissolved in methanol (30 mL). Thereto was added a mixed solution (15 mL) consisting of saturated aqueous sodium bicarbonate solution/water (1:100). This mixture was stirred at 25° C. for 2 hours. The reaction mixture was subjected to the same post-treatment and purification as in Example 61 to obtain Compound 68 (40 mg, 0.054 mmol, 58%). Compound 68 was obtained as a mixture of diastereomers due to the asymmetric carbon of the tetrahydropyranyl group; they were found through HPLC to be in the ratio of approximately 1:1.

$^1$H NMR (CDCl$_3$, 270 MHz)δ ppm; (a mixture of two diastereomers, approx. 1:1, major peaks) 9.51 (dd, J=11.4, 16.6 Hz) and 9.34 (dd, J=11.4, 16.3 Hz) (total 1H), 7.87 (m, 2H), 7.41 (s) and 7.40 (s) (total 1H), 6.79 (m, 2H), 6.64 (d, J=11.4 Hz, 1H), 6.38 (t, J 11.4 Hz) and 6.36 (t, J=11.4 Hz) (total 1H), 6.06 (d, J=16.3 Hz) and 6.01 (d, J=16.6 Hz) (total 1H), 5.8–5.5 (1H, overlapped with other peaks), 5.74 (br d, J=ca. 9 Hz) and 5.71 (br d, J=ca. 9 Hz) (total 1H), 5.60 (br s, 2H), 5.56 (q, overlapped with other peaks) and 5.54 (q, J=6.9 Hz) (total 1H), 5.00 (br d) and 4.72 (br d) (total 1H), 4.71 (br s) and 4.57 (br s) (total 1H), 4.0–3.3 (m, 3H), 2.4–1.3 (m, 10H), 2.35 (d, J=17.8 Hz) and 2.33 (d, J=17.8 Hz) (total 1H), 1.94 (d, J=6.9 Hz) and 1.88 (d, J=6.9 Hz) (total 3H), 1.72 (s, 6H)

FABMS m/z 745 (M+H)$^+$ calcd for C$_{35}$H$_{40}$N$_2$O$_{10}$S$_3$=744

Example 63

Synthesis of Compound 69

Compound 54 (160 mg, 0.203 mmol) obtained in Example 49 was dissolved in methanol (50 mL). Thereto was added a mixed solution (15 mL) consisting of saturated aqueous sodium bicarbonate solution/water (1:100). This mixture was stirred at 25° C. for 2 hours. The reaction mixture was subjected to the same post-treatment and purification as in Example 61 to obtain Compound 69 (66 mg, yield 44%). Compound 69 was obtained as a mixture of diastereomers due to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.57 (dd, J=11.5, 16.6 Hz) and 9.37 (dd, J=11.5, 16.6 Hz) (total 1H), 7.58 (m, 1H), 7.5–7.3 (m, 3H), 7.40 (s) and 7.39 (s) (total 1H), 7.07 (m, 1H), 6.62 (d, J=11.2 Hz) and 6.61 (d, J=11.2 Hz) (total 1H), 6.37 (t, J=11.5 Hz) and 6.35 (t, J=11.5 Hz) (total 1H), 6.06 (d, J=16.6 Hz) and 6.01 (d, J=16.6 Hz) (total 1H), 5.79 (br d, J=ca. 9 Hz) and 5.77 (br d, J=ca. 9 Hz) (total 1H), 5.69 (d, J=11.1 Hz, 1H), 5.58 (d, J=11.1 Hz, 1H), 5.56 (1H, overlapped with other peaks), 5.4–5.2 (br, 1H), 5.01 (dd, J=1.3, 9.2 Hz) and 4.74 (dd, J=1.3, 9.2 Hz) (total 1H), 4.70 (br s) and 4.56 (br s) (total 1H), 4.03 (d, J=17.5 Hz) and 4.01 (d, J=17.8 Hz) (total 1H), 3.9–3.4 (m, 2H), 2.4–1.4 (m, 11H), 1.93 (d, J=6.6 Hz) and 1.87 (d, J=6.6 Hz) (total 3H), 1.72 (s, 3H), 1.72 (d, overlapped with other peaks) and 1.69 (d, J=1.0 Hz) (total 3H)

FABMS m/z 745 (M+H)$^+$ calcd for C$_{35}$H$_{40}$N$_2$O$_{10}$S$_3$=744

Example 64

Synthesis of Compound 70

Compound 32 (29 mg, 0.040 mmol) obtained in Example 31 was dissolved in methanol (7.5 mL). Thereto was added a mixed solution (3.8 mL) consisting of saturated aqueous sodium bicarbonate solution/water (1:50). This mixture was stirred at 25° C. for 3 hours. The reaction mixture was subjected to the same post-treatment and purification as in Example 61 to obtain Compound 70 (5.3 mg, yield 18%).

$^1$H NMR (CDCl$_3$, 270 MHz)δ ppm; 8.44 (dd, J=11.6, 16.2 Hz, 1H), 7.36 (s, 1H), 7.01 (m, 2H), 6.71 (m, 2H), 6.60 (d, J=11.6 Hz, 1H), 6.24 (t, J=11.6 Hz, 1H), 6.18 (d, J=16.2 Hz, 1H), 5.72 (br d, J=ca. 9 Hz, 1H), 5.46 (br s, 2H), 5.43 (q, J=6.9 Hz, 1H), 5.37 (d, J=11.5 Hz, 1H), 5.33 (d, J=11.5 Hz, 1H), 4.95 (br d, J=ca. 9 Hz, 1H), 3.84 (d, J=17.8 Hz, 1H), 3.9–3.7 (br, 1H), 3.0–2.5 (m, 2H), 2.4–1.4 (m, 6H), 2.19 (d, J=17.8 Hz, 1H), 2.03 (d, J=6.9 Hz, 3H), 1.76 (s, 3H), 1.74 (d, J=1.3 Hz, 3H)

FABMS m/z 689 (M+H)$^+$ calcd for C$_{32}$H$_{36}$N$_2$O$_9$S$_3$=688

Example 65

Synthesis of Compound 71

Compound 52 (49 mg, 0.052 mmol) obtained in Example 47 was dissolved in methanol (9.8 mL). Thereto was added a mixed solution (4.9 mL) consisting of saturated aqueous sodium bicarbonate solution/water (1:50). This mixture was stirred at 25° C. for 2 hours. The reaction mixture was subjected to the same post-treatment and purification as in Example 61 to obtain Compound 71 (25 mg, 0.028 mmol, 53%). Compound 71 was obtained as a mixture of diastereomers attributable to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.69 (dd, J=11.5, 16.8 Hz) and 9.43 (dd, J=11.5, 16.8 Hz) (total 1H), 7.67 (m, 2H), 7.41 (s) and 7.38 (s) (total 1H), 7.10 (m, 1H), 6.83 (m, 2H), 6.62 (d, J=11.5 Hz) and 6.59 (d, J=11.5 Hz) (total 1H), 6.34 (t, J=11.5 Hz, 1H), 6.05 (d, J=16.8 Hz) and 6.01 (d, J=16.8 Hz) (total 1H), 5.79 (br d, J=ca. 8 Hz) and 5.77 (br d, J=ca. 8 Hz) (total 1H), 5.7–5.5 (br, 1H), 5.57 (q, J=6.6 Hz) and 5.54 (q, J=6.6 Hz) (total 1H), 5.36 (br s, 2H), 5.08 (d, J=9.2 Hz) and 4.9–4.7 (overlapped with other peaks) (total 1H), 4.9–4.7 (m, 2H), 4.9–4.7 (overlapped with other peaks) and 4.53 (br s) (total 1H), 4.05 (br d, J=17.8 Hz, 1H), 3.77 (s, 3H), 3.8–3.4 (m, 2H), 2.6–1.4 (m, 14H), 2.32 (d, J=17.8 Hz, 1H), 1.96 (d, J=6.6 Hz) and 1.85 (d, J=6.6 Hz) (total 3H), 1.67 (s, 3H), 1.60 (s, 3H)

FABMS m/z 888 (M+H)$^+$ calcd for C$_{41}$H$_{49}$N$_3$O$_{13}$S$_3$=887

Example 66

Synthesis of Compound 72

Compound 68 (71 mg, 0.095 mmol) obtained in Example 62 was dissolved in THF (2.5 mL). Thereto were added phosphorus oxychloride (150 μL) and triethylamine (150 μL). This mixture was allowed to stand at 0° C. to 25° C. for 20 minutes. After the reaction mixture was subjected to the ordinary post-treatment, the reaction product was purified by HPLC for fractionation (ODS; eluted with acetonitrile/water=20/80 to 50/50) to obtain Compound 72 (40 mg, yield 50%).

$^1$H NMR (CD$_3$OD, 270 MHz)δ ppm; (major peaks) 9.68 (dd, J=11.4, 16.5 Hz) and 9.56 (dd, J=11.4, 16.5 Hz) (total 1H), 8.0–7.8 (m, 2H), 7.71 (s) and 7.70 (s) (total 1H), 7.4–7.2 (m, 2H), 6.73 (br d, J=11.4 Hz, 1H), 6.37 (t, J=11.4 Hz) and 6.36 (t, J=11.4 Hz) (total 1H), 6.00 (m, 1H), 5.86 (br d, J=ca. 10 Hz) and 5.81 (br d, J=ca. 10 Hz) (total 1H), 5.7–5.5 (1H, overlapped with other peaks), 5.59 (d, J=11 Hz, 1H), 5.52 (d, J=11 Hz, 1H), 5.0–4.7 (1H, overlapped with other peaks), 4.72 (br s) and 4.59 (br s) (total 1H), 4.3–3.6 (m, 2H), 2.7–1.4 (m, 10H), 2.49 (d, J=17.8 Hz, 1H), 1.94 (d, J=6.4 Hz) and 1.87 (d, J=6.4 Hz) (total 3H), 1.72 (s, 3H), 1.69 (s, 3H)

FABMS m/z 869 [(M−2H+2Na)+H]$^+$ calcd for $C_{35}H_{41}N_2O_{13}PS_3$=824

Example 67

Synthesis of Compound 73

Compound 69 (30 mg, 0.040 mmol) obtained in Example 63 was dissolved in THF (1.0 mL). Thereto were added phosphorus oxychloride (60 μL) and triethylamine (60 μL). This mixture was allowed to stand at 25° C. for 10 minutes. After the reaction mixture was subjected to the ordinary post-treatment, the reaction product was purified by HPLC for fractionation (ODS, eluted with acetonitrile/water=20/80 to 30/70) to obtain Compound 73 (10 mg, yield 32%).

$^1$H NMR (CD$_3$OD, 270 MHz)δ ppm; (major peaks) 9.69 (dd, J=11.9, 16.3 Hz) and 9.52 (dd, J=11.9, 16.3 Hz) (total 1H), 7.80 (br s, 1H), 7.73 (s) and 7.72 (s) (total 1H), 7.6–7.5 (m, 3H), 7.32 (m, 1H), 6.75 (d, J=11.9 Hz) and 6.75 (d, J=11.9 Hz) (total 1H), 6.38 (t, J=11.9 Hz) and 6.39 (t, J=11.9 Hz) (total 1H), 5.98 (d, J=16.3 Hz) and 5.97 (d, J=16.3 Hz) (total 1H), 5.84 (br d, J=ca. 10 Hz) and 5.80 (br d, J=ca. 10 Hz) (total 1H), 5.6–5.5 (1H, overlapped with other peaks), 5.59 (d, J=10.9 Hz, 1H), 5.52 (d, J=10.9 Hz, 1H), 5.0–4.7 (1H, overlapped with other peaks), 4.71 (br s) and 4.58 (br s) (total 1H), 4.2–3.6 (m, 2H), 2.7–1.3 (m, 10H), 2.51 (d, J=17.8 Hz, 1H), 1.92 (d, J=6.4 Hz) and 1.86 (d, J=6.4 Hz) (total 3H), 1.71 (s) and 1.68 (s) (total 3H), 1.51 (s, 3H)

FABMS m/z 869 [(M−2H+2Na)+H]$^+$ calcd for $C_{35}H_{41}N_2O_{13}PS_3$=824

Example 68

Synthesis of Compound 74

Compound S-1 (17 mg, 0.029 mmol) obtained in Reference Example 1 and Compound S-28 (37 mg, 0.11 mmol) obtained in Reference Example 28 were dissolved in acetonitrile (2.5 mL). Thereto was added potassium carbonate (16 mg, 0.11 mmol). This mixture was stirred at 25° C. for 2 hours. After the ordinary post-treatment, the reaction product was purified by silica gel chromatography (eluted with n-hexane/ethyl acetate=1/1) to obtain Compound 74 (15 mg, yield 80%). $^1$H NMR revealed that Compound 74 was an approximately 1:1 mixture of diastereomers.

$^1$H NMR (CDCl$_3$, 400 MHz)δ ppm; 9.59 (ddd, J=16.6, 11.5, 0.8 Hz) and 9.39 (ddd, J=16.6, 11.5, 0.8 Hz) (total 1H), 7.41 (s) and 7.40 (s) (total 1H), 6.61 (d, J=11.5 Hz) and 6.60 (d, J=11.5 Hz) (total 1H), 6.37 (dd, J=11.5, 11.5 Hz) and 6.34 (dd, J=11.5, 11.5 Hz) (total 1H), 6.07 (d, J=16.6 Hz) and 6.00 (d, J=16.6 Hz) (total 1H), 5.83 (d, J=9.8 Hz) and 5.80 (d, J=9.8 Hz) (total 1H), 5.57 (m, 1H), 5.52 (d, J=4.2 Hz, 1H), 5.02 (dd, J=9.8, 1.3 Hz) and 4,74 (dd, J=9.8, 1.0 Hz) (total 1H), 4.70 (m) and 4.58 (m) (total 1H), 4.56 (d, J=13.5 Hz) and 4.44 (d, J=13.5 Hz) (total 2H), 4.04 (d, J=17.6 Hz) and 4.03 (d, J=17.6 Hz) (total 1H), 3.86 (d, J=15.4 Hz) and 3.78 (d, J=15.4, 2.2 Hz) (total 2H), 3.87–3.40 (m, 2H), 2.46–2.25 (m, 5H), 1.93 (d, J=6.6 Hz) and 1.88 (d, J=6.6 Hz) (total 3H), 1.80–1.40 (m, 6H), 1.78 (s) and 1.74 (s) (total 3H), 1.67 (s, 3H)

FABMS m/z 741M$^+$ calcd for $C_{32}H_{37}N_2O_{10}{}^{35}ClS_3$=741

Example 69

Synthesis of Compound 75

DC107 (9.8 mg, 0.016 mmol) and Compound S-24 (21 mg, 0.063 mmol) obtained in Reference Example 24 were dissolved in acetonitrile (1.5 mL). Thereto was added potassium carbonate (9.1 mg, 0.063 mmol). This mixture was stirred at 25° C. for 3 hours. After the ordinary post-treatment, the reaction product was purified by silica gel chromatography (eluted with n-hexane/ethyl acetate=3/2) to obtain Compound 69 (14 mg, yield 98%).

$^1$H NMR (CDCl$_3$, 400 MHz)δ ppm; 8.47 (dd, J=16.6, 11.7 Hz, 1H), 7.54 (s, 1H), 6.59 (d, J=11.7 Hz, 1H), 6.23 (dd, J=11.7, 11.7 Hz, 1H), 6.18 (d, J=16.6 Hz, 1H), 5.74 (d, J=8.6 Hz, 1H), 5.53 (s, 1H), 5.41 (q, J=6.8 Hz, 1H), 4.95 (dd, J=8.6, 3.1 Hz, 1H), 4.50 (s, 2H), 3.89 (d, J=19.0 Hz, 1H), 3.89 (s, 1H), 3.87 (s, 1H), 3.77 (d, J=3.1 Hz, 1H), 2.25 (d, J=19.0 Hz, 1H), 2.38–2.13 (m, 4H), 2.02 (d, J=6.8 Hz, 3H), 1.77 (s, 3H), 1.75 (d, -J=1.2 Hz, 3H), 0.98 (m, 9H), 0.65 (m, 6H)

FABMS m/z 753 (M+H)$^+$ calcd for $C_{33}H_{44}N_2O_{10}S_3Si$=752

Example 70

Synthesis of Compound 76

Compound S-1 (86 mg, 1.4 mmol) obtained in Reference Example 1 and Compound S-24 (186 mg, 0.575 mmol) obtained in Reference Example 24 were dissolved in acetonitrile (13 mL). Thereto was added potassium carbonate (80 mg, 0.58 mmol). This mixture was stirred at 25° C. for 2 hours. After the ordinary post-treatment, the reaction mixture was purified by silica gel chromatography (eluted with n-hexane/ethyl acetate=3/2) to obtain Compound 76 (106 mg, yield 89%). $^1$H NMR revealed that Compound 76 was an approximately 1:1 mixture of diastereomers.

$^1$H NMR (CDCl$_3$, 400 MHz)δ ppm; 9.58 (dd, J=16.6, 11.5 Hz) and 9.39 (dd, J=16.6, 11.5 Hz) (total 1H), 7.49 (s) and 7.41 (s) (total 1H), 6.61 (d, J=11.5 Hz) and 6.60 (d, J=11.5 Hz) (total 1H), 6.38 (dd, J=11.5, 11.5 Hz) and 6.34 (dd, J=11.5, 11.5 Hz) (total 1H), 6.04 (d, J=16.6 Hz) and 6.00 (d, J=16.6 Hz) (total 1H), 5.83 (d, J=9.5 Hz) and 5.81 (d, J=9.5 Hz) (total 1H), 5.58 (q, J=6.6 Hz, 1H), 5.53 (d, J=8.3 Hz, 1H), 5.02 (dd, J=9.5, 1.4 Hz) and 4.74 (dd, J=9.5, 1.4 Hz) (total 1H), 4.71 (m) and 4.58 (m) (total 1H), 4.51 (s, 2H), 4.05 (d, J=17.5 Hz) and 4.04 (d, J=17.5 Hz) (total 1H), 3.89 (s, 2H), 3.88–3.40 (m, 2H), 2.45–2.28 (m, 4H), 2.31 (d, J=17.5 Hz) and 2.30 (d, J=17.5 Hz) (total 1H), 1.94 (d, J=6.6 Hz) and 1.88 (d, J=6.6 Hz) (total 3H), 1.70–1.25 (m, 6H), 1.78 (s) and 1.74 (s) (total 3H), 1.69 (s, 3H), 0.98 (m, 9H), 0.66 (m, 6H)

FABMS m/z 837 M+calcd for $C_{38}H_{52}N_2O_{11}S_3Si$=837

Example 71

Synthesis of Compound 77

According to Example 69, Compound 77 (20 mg, yield 48%) was obtained from DC107 (32 mg, 0.062 mmol), Compound S•25 (31 mg, 0.12 mmol) obtained in Reference Example 25, acetonitrile (4.8 mL), and potassium carbonate (17 mg, 0.12 mmol).

$^1$H NMR (CDCl$_3$, 400 MHz)δ ppm; 8.45 (ddd, J=16.3, 11.9, 0.9 Hz, 1H), 7.35 (s, 1H), 6.58 (d, J=11.9 Hz, 1H) 6.23 (dd, J=11.9, 11.9 Hz, 1H), 6.18 (d, J=16.3 Hz, 1H), 5.73 (d, J=8.7 Hz, 1H), 5.52 (br, 1H), 5.42 (q, J=6.8 Hz, 1H), 4.67 (m, 1H), 4.43 (m, 1H), 4.94 (d, J=8.7 Hz, 1H), 3.87 (d, J=17.5 Hz, 1H), 3.85 (m, 4H), 3.38 (s, 3H), 2.42–2.13 (m, 4H), 2.27 (d, J=17.5 Hz, 1H), 2.02 (d, J=6.8 Hz, 3H), 1.77 (s, 3H), 1.75 (s, 3H)

FABMS m/z 683 (M+H)$^+$ calcd for $C_{29}H_{34}N_2O_{11}S_3$=682

Example 72

Synthesis of Compound 78

According to Example 70, Compound 78 (30 mg, yield 93%) was obtained from Compound S-1 (25 mg, 0.042 mmol) obtained in Reference Example 1, Compound S-25 (22 mg, 0.085 mmol) obtained in Reference Example 25, acetonitrile (3.8 mL), and potassium carbonate (12 mg, 0.085 mmol). $^1$H NMR revealed that Compound 78 was an approximately 1:1 mixture of diastereomers.

$^1$H NMR (CDCl$_3$, 400 MHz)δ ppm; 9.58 (dd, J=16.6, 11.5 Hz) and 9.48 (dd, J=16.6, 11.5 Hz) (total 1H), 7.41 (s) and 7.39 (s) (total 1H), 6.62 (d, J=11.5 Hz) and 6.60 (d, J=11.5 Hz) (total 1H), 6.38 (dd, J=11.5, 11.5 Hz) and 6.34 (dd, J=11.5, 11.5 Hz) (total 1H), 6.04 (d, J=16.6 Hz) and 5.99 (d, J=16.6 Hz) (total 1H), 5.84 (d, J=10.0 Hz) and 5.81 (d, J=10.0 Hz) (total 1H), 5.58 (q, J=6.6 Hz) and 5.56 (q, J=6.6 Hz) (total 1H), 5.53 (d, J=8.3 Hz, 1H), 5.02 (dd, J=10.0, 1.4 Hz) and 4.74 (dd, J=10.0, 1.4 Hz) (total 1H), 4.71 (m) and 4.57 (m) (total 1H), 4.67 (s, 2H), 4.43 (s, 2H), 4.04 (d, J=17.6 Hz) and 4.03 (d, J=17.6 Hz) (total 1H), 3.87 (d, J=1.3 Hz) and 3.85 (d, J=1.0 Hz) (total 2H), 3.90–3.35 (m, 2H), 3.42 (s, 3H), 2.44–2.26 (m, 4H), 2.29 (d, J=17.6 Hz) and 2.28 (d, J=17.6 Hz) (total 1H), 1.94 (d, J=6.6 Hz) and 1.87 (d, J=6.6 Hz) (total 3H), 1.70–1.25 (m, 6H), 1.76 (s) and 1.74 (s) (total 3H), 1.68 (s, 3H)

FABMS m/z 767 (M+H)$^+$ calcd for C$_{34}$H$_{42}$N$_2$O$_{12}$S$_3$=766

Example 73

Synthesis of Compound 79

According to Example 69, Compound 79 (68 mg, yield 65%) was obtained from DC107 (54 mg, 0.11 mmol), Compound S-26 (240 mg, 0.42 mmol) obtained in Reference Example 26, acetonitrile (8.1 mL), and potassium carbonate (58 mg, 0.42 mmol). $^1$H NMR revealed that Compound 79 was an approximately 1:1 mixture of diastereomers.

$^1$H NMR (CDCl$_3$, 400 MHz)δ ppm; 8.47 (dd, J=16.4, 11.6 Hz, 1H), 7.35 (s, 1H), 6.59 (d, J=11.6 Hz, 1H), 6.23 (dd, J=11.6, 11.6 Hz, 1H), 6.17 (d, J=16.4 Hz, 1H), 5.75 (d, J=8.0 Hz, 1H), 5.52 (d, J=6.9 Hz, 1H), 5.41 (q, J=6.9 Hz, 1H), 4.95 (d, J=8.6 Hz, 1H), 4.82 (d, J=2.1 Hz, 1H), 4.59 (d, J=14.0 Hz) and 4.45 (d, J=14.0 Hz) (total 1H), 4.52 (dd, J=9.6 Hz, 1H), 4.41 (d, J=14.0 Hz) and 4.32 (d, J=14.0 Hz) (total 1H), 3.89 (s, 3H), 3.89 (d, J=17.7 Hz) and 3.88 (d, J=17.7 Hz) (total 1H) 1.9 Hz, 1H), 3.60 (m, 1H), 3.20 (m, 1H), 2.30–1.53 (m, 6H), 2.25 (d, J=17.7 Hz, 1H), 2.01 (d, J=6.9 Hz, 3H), 1.75 (s, 3H), 1.74 (s, 3H), 1.28 (d, J=6.9 Hz) and 1.21 (d, J=6.9 Hz) (total 3H), 0.90 (m, 18H), 0.19 (m, 12H)

FABMS m/z 997 (M+H)$^+$ calcd for C$_{45}$H$_{68}$N$_2$O$_{13}$S$_3$Si$_2$=996

Example 74

Synthesis of Compound 80

According to Example 70, Compound 80 (30 mg, yield 76%) was obtained from Compound S-1 (22 mg, 0.036 mmol) obtained in Reference Example 1, Compound S-26 (83 mg, 0.15 mmol) obtained in Reference Example 26, acetonitrile (3.2 mL), and potassium carbonate (20 mg, 0.15 mmol). $^1$H NMR revealed that Compound 80 was an approximately 1:1 mixture of diastereomers.

$^1$H NMR (CDCl$_3$, 400 MHz)δ ppm; 9.59 (dd, J=16.4, 11.5 Hz) and 9.39 (dd, J=16.4, 11.5 Hz) (total 1H), 7.40 (s) and 7.39 (s) (total 1H), 6.61 (d, J=11.5 Hz) and 6.60 (d, J=11.5 Hz) (total 1H), 6.37 (dd, J=11.5, 11.5 Hz) and 6.34 (dd, J=11.5, 11.5 Hz) (total 1H), 6.04 (d, J=16.4 Hz) and 6.00 (d, J=16.4 Hz) (total 1H), 5.83 (d, J=10.0 Hz) and 5.81 (d, J=10.0 Hz) (total 1H), 5.57 (m, 1H), 5.54 (m, 1H), 5.02 (dd, J=10.0, 1.4 Hz) and 4.74 (d, J=10.0 Hz) (total 1H), 4.84 (m) and 4.70 (m) (total 1H), 4.62–4.33 (m, 3H), 4.04 (d, J=17.6 Hz) and 4.03 (d, J=17.6 Hz) (total 1H), 3.85 (m, 2H), 3.91–3.16 (m, 4H), 2.45–2.04 (m, 4H), 2.30 (d, J=17.6 Hz) and 2.28 (d, J=17.6 Hz) (total 1H), 2.18–2.04 (m, 2H), 1.94 (d, J=6.6 Hz) and 1.87 (d, J=6.6 Hz) (total 3H), 1.77 (d, J=1.2 Hz) and 1.72 (d, J=1.2 Hz) (total 3H), 1.69 (s, 3H), 1.60–1.40(m, 6H), 1.28 (d, J=6.3 Hz) and 1.23 (d, J=6.3 Hz) (total 3H), 0.90 (m, 18H), 0.09 (m, 12H)

FABMS m/z 1103 (M+Na)$^+$ calcd for C$_{50}$H$_{76}$N$_2$O$_{14}$S$_3$Si$_2$=1080

Example 75

Synthesis of Compound 81

According to Example 69, Compound 81 (105 mg, yield 76%) was obtained from DC107 (63 mg, 0.12 mmol), Compound S-27 (342 mg, 0.49 mmol) obtained in Reference Example 27, acetonitrile (9.4 mL), and potassium carbonate (68 mg, 0.49 mmol).

$^1$H NMR (CDCl$_3$, 400 MHz)δ ppm; 8.49 (ddd, J=16.4, 11.4, 1.0 Hz, 1H), 7.36 (s, 1H), 6.58 (d, J=11.4 Hz, 1H) 6.24 (dd, J=11.4, 11.4 Hz, 1H), 6.17 (d, J=16.4 Hz, 1H), 5.76 (d, J=8.8 Hz, 1H), 5.42 (q, J=6.8 Hz, 1H), 4.95 (d, J=8.8 Hz, 1H), 4.84 (m, 1H), 4.46 (d, J=13.9 Hz, 1H), 4.33 (d, J=13.9 Hz, 1H), 3.93 (d, J=15.4 Hz, 1H), 3.87 (d, J=15.1 Hz, 1H), 3.89 (d, J=15.4 Hz, 2H), 3.86 (d, J=18.8 Hz, 1H), 3.92–3.13 (m, 3H), 2.38–1.92 (m, 6H), 2.26 (d, J=18.1 Hz, 1H), 2.02 (d, J=6.8 Hz, 3H), 1.78 (s, 3H), 1.75 (s, 3H), 0.96 (m, 27H), 0.63 (m, 18H)

FABMS m/z 1149 (M+Na)$^+$ calcd for C$_{51}$H$_{82}$N$_2$O$_{14}$S$_3$Si$_3$=1126

Example 76

Synthesis of Compound 82

According to Example 70, Compound 82 (44 mg, yield 46%) was obtained from Compound S-1 (47 mg, 0.080 mmol) obtained in Reference Example 1, Compound S-27 (222 mg, 0.32 mmol) obtained in Reference Example 27, acetonitrile (7.1 mL), and potassium carbonate (44 mg, 0.32 mmol). $^1$H NMR revealed that Compound 82 was an approximately 1:1 mixture of diastereomers.

$^1$H NMR (CDCl$_3$, 400 MHz)δ ppm; 9.59 (dd, J=16.6, 11.4 Hz) and 9.40 (dd, J=16.6, 11.4 Hz) (total 1H), 7.41 (s) and 7.39 (s) (total 1H), 6.62 (d, J=11.4 Hz) and 6.60 (d, J=11.4 Hz) (total 1H), 6.37 (dd, J=11.4, 11.4 Hz) and 6.34 (dd, J=11.4, 11.4 Hz) (total 1H) 6.05 (d, J=16.6 Hz) and 6.01 (d, J=16.6 Hz) (total 1H), 5.84 (d, J=10.2 Hz) and 5.80 (d, J=10.2 Hz) (total 1H), 5.58 (m, 1H), 5.56 (m, 1H), 5.32 (br s, 1H), 5.03 (d, J=10.2 Hz) and 4.73 (d, J=10.2 Hz) (total 1H), 4.85 (m, 2H), 4.71 (m) and 4.57 (m) (total 1H), 4.62–4.25 (m, 3H), 4.04 (d, J=17.6 Hz) and 4.03 (d, J=17.6 Hz) (total 1H), 3.86 (m, 2H), 3.92–3.10 (m, 4H), 2.45–2.04 (m, 6H), 2.28 (d, J=17.6 Hz) and 2.27 (d, J=17.6 Hz) (total 1H), 1.93 (d, J=6.6 Hz) and 1.87 (d, J=6.6 Hz) (total 3H), 1.77 (d, J=1.4 Hz) and 1.74 (d, J=1.4 Hz) (total 3H), 1.81–1.25 (m, 6H), 1.68 (s, 3H), 1.00–0.92 (m, 27H), 0.70–0.55 (m, 18H)

FABMS m/z 1211 (M+H)$^+$ calcd for C$_{56}$H$_{90}$N$_2$O$_{15}$S$_3$Si$_3$=1210

Example 77

Synthesis of Compound 83

Compound 82 (56 mg, 0.046 mmol) obtained in Example 76 was dissolved in tetrahydrofuran (5.6 mL). Thereto were added acetic acid (13 μL, 0.23 mmol) and 1.0 N tetrabutylammonium fluoride/tetrahydrofuran solution (0.23 mL, 0.23 mmol). This mixture was stirred at 25° C. for 3 hours. After the ordinary post-treatment, the reaction mixture was purified by thin-layer chromatography (developed with chloroform/methanol 10/1) to obtain Compound 83 (12 mg, yield 30%). $^1$H NMR revealed that Compound 83 was an approximately 1:1 mixture of diastereomers.

$^1$H NMR (CDCl$_3$, 400 MHz)δ ppm; 9.56 (dd, J=16.8, 11.5 Hz) and 9.37 (dd, J=16.8, 11.5 Hz) (total 1H), 7.41 (s) and 7.40 (s) (total 1H), 6.62 (d, J=11.5 Hz) and 6.61 (d, J=11.5 Hz) (total 1H), 6.36 (dd, J=11.5, 11.5 Hz) and 6.33 (dd, J=11.5, 11.5 Hz) (total 1H), 6.04 (d, J=16.8 Hz) and 5.98 (d, J=16.8 Hz) (total 1H), 5.82 (d, J=9.3 Hz) and 5.77 (d, J=9.3 Hz) (total 1H), 5.56 (m, 1H), 5.49 (m, 1H), 5.02–4.35 (m, 3H), 5.01 (d, J=9.3 Hz) and 4.74 (d, J=9.3 Hz) (total 1H), 4.96 (d, J=2.9 Hz, 2H), 4.71 (m) and 4.58 (m) (total 1H), 4.07 (d, J=17.5 Hz) and 4.04 (d, J=16.6 Hz) (total 1H), 3.63 (m, 2H), 3.94–3.19 (m, 4H), 2.50–2.28 (m, 4H), 2.37 (d, J=17.5 Hz) and 2.35 (d, J=17.5 Hz) (total 1H), 2.13 (m, 2H), 1.93 (d, J=6.6 Hz) and 1.87 (d, J=6.6 Hz) (total 3H), 1.77 (s) and 1.72 (s) (total 3H), 1.80–1.24 (m, 6H), 1.65 (s, 3H)

FABMS m/z 869 (M+H)$^+$ calcd for C$_{38}$H$_{48}$N$_2$O$_{15}$S$_3$=868

Example 78

Synthesis of Compound 84

According to Example 69, Compound 84 (69 mg, yield 91%) was obtained from DC107 (47 mg, 0.092 mmol), Compound S-29 (150 mg, 0.37 mmol) obtained in Reference Example 29, acetonitrile (7.0 mL), and potassium carbonate (51 mg, 0.37 mmol).

$^1$H NMR (CDCl$_3$, 400 MHz)δ ppm; 8.45 (ddd, J=16.3, 11.5, 1.0 Hz, 1H), 7.36 (s, 1H), 6.59 (d, J=11.5 Hz, 1H), 6.23 (dd, J=11.5, 11.5 Hz, 1H), 6.18 (d, J=16.3 Hz, 1H), 5.93 (d, J=10.3 Hz, 1H), 5.79 (ddd, J=9.9, 2.7, 2.0 Hz, 1H), 5.72 (d, J=7.6 Hz, 1H), 5.52 (br s, 1H), 5.42 (q, J=6.9 Hz, 1H), 5.32 (ddd, J=9.9, 3.2, 2.0 Hz, 1H), 5.10 (m, 1H), 4.95 (d, J=10.3 Hz, 1H), 4.59 (d, J=13.7 Hz, 1H), 4.51 (d, J=13.7 Hz, 1H), 4.28–4.03 (m, 4H), 3.92 (d, J=15.4 Hz, 1H), 3.80 (d, J=15.4 Hz, 1H), 3.39 (d, J=17.8 Hz, 1H), 2.32–2.03 (m, 4H), 2.28 (d, J=17.8 Hz, 1H), 2.17 (s, 3H), 2.09 (s, 3H), 2.02 (d, J=6.8 Hz, 3H), 1.75 (s, 3H), 1.74 (s, 3H)

FABMS m/z 851 (M+H)$^+$ calcd for C$_{37}$H$_{42}$N$_2$O$_{15}$S$_3$=850

Example 79

Synthesis of Compound 85

According to Example 70, Compound 85 (54 mg, yield 85%) was obtained from Compound S-1 (41 mg, 0.069 mmol) obtained in Reference Example 1, Compound S-29 (110 mg, 0.28 mmol) obtained in Reference Example 29, acetonitrile (6.2 mL), and potassium carbonate (38 mg, 0.28 mmol). $^1$H NMR revealed that Compound 85 was an approximately 1:1 mixture of diastereomers.

$^1$H NMR (CDCl$_3$, 400 MHz)δ ppm; 9.58 (ddd, J=16.6, 11.5, 0.7 Hz) and 9.38 (ddd, J=16.6, 11.5, 0.7 Hz) (total 1H), 7.41 (s) and 7.39 (s) (total 1H), 6.61 (d, J=11.5 Hz) and 6.60 (d, J=11.5 Hz) (total 1H), 6.37 (dd, J=11.5, 11.5 Hz) and 6.34 (dd, J=11.5, 11.5 Hz) (total 1H), 6.03 (d, J=16.6 Hz) and 6.00 (d, J=16.6 Hz) (total 1H), 5.82 (m, 2H), 5.58 (m, 1H), 5.52 (d, J=6.8 Hz, 1H), 5.32 (ddd, J=10.2, 3.2, 1.7 Hz, 1H), 5.11 (m, 1H), 5.02 (dd, J=9.3, 1.2 Hz) and 4.73 (d, J=9.3, 1.2 Hz) (total 1H), 4.70 (m) and 4.58 (m) (total 1H), 4.30–3.40 (m, 6H), 4.58 (d, J=13.6 Hz) and 4.0 (dd, J=13.6, 1.7 Hz) (total 2H), 4.06 (d, J=17.5 Hz) and 4.05 (d, J=17.5 Hz) (total 1H), 3.90 (dd, J=15.3, 1.9 Hz) and 3.81 (dd, J=15.3, 2.2 Hz) (total 2H), 2.50–2.27 (m, 4H), 2.31 (d, J=17.5 Hz) and 2.30 (d, J=17.5 Hz) (total 1H), 2.18 (s, 3H), 2.10 (s, 3H), 1.93 (d, J=6.6 Hz) and 1.87 (d, J=6.6 Hz) (total 3H), 1.75–1.48 (m, 6H), 1.77 (d, J=1.2 Hz) and 1.73 (d, J=1.2 Hz) (total 3H), 1.68 (s, 3H)

FABMS m/z 935 (M+H)$^+$ calcd for C$_{42}$H$_{50}$N$_2$O$_{10}$S$_3$=934

Example 80

Synthesis of Compound 86

Compound 75 (9.1 mg, 0.012 mmol) obtained in Example 69 was dissolved in tetrahydrofuran (0.3 mL). Thereto were added acetic acid (0.0014 mL, 0.024 mmol) and 1.0 N tetrabutylammonium fluoride/tetrahydrofuran solution (0.024 mL, 0.024 mmol). This mixture was stirred at 0° C. for 5 minutes. After the ordinary post-treatment, the reaction product was purified by silica gel chromatography (eluted with n-hexane/ethyl acetate=1/5) to obtain Compound 86 (9.0 mg, yield 100%).

$^1$H NMR (CDCl$_3$, 400 MHz)δ ppm; 8.43 (dd, J=16.4, 11.3 Hz, 1H), 7.35 (s, 1H), 6.59 (d, J=11.3 Hz, 1H), 6.23 (dd, J=11.3, 11.3 Hz, 1H), 6.18 (d, J=16.4 Hz, 1H), 5.72 (d, J=8.3 Hz, 1H), 5.41 (q, J=6.9 Hz, 1H), 5.22 (br s, 1H), 4.96 (d, J=8.3 Hz, 1H), 4.49 (d, J=5.4 Hz, 2H), 3.98 (d, J=17.8 Hz, 1H), 3.92 (d, J=15.3 Hz, 1H), 3.85 (br s, 1H), 3.79 (d, J=15.3 Hz, 1H), 2.88 (br, 1H), 2.34–2.15 (m, 4H), 2.28 (d, J=17.8 Hz, 1H), 2.00 (d, J=6.9 Hz, 3H), 1.74 (s, 3H), 1.70 (s, 3H)

FABMS m/z 639 (M+H)1 calcd for C$_{27}$H$_{30}$N$_2$O$_{10}$S$_3$=638

Example 81

Synthesis of Compound 87

Compound 89 (20 mg, 0.027 mmol) obtained in Example 83 shown below was dissolved in methanol (6.0 mL). This solution was stirred at 25° C. for 30 hours. The methanol was distilled off under reduced pressure, and the resultant residue was purified by thin-layer chromatography (developed with chloroform/methanol 96/4) to obtain Compound 87 (5.0 mg, yield 26%).

$^1$H NMR (CDCl$_3$, 400 MHz)δ ppm; major isomer 9.38 (dd, J 16.6, 11.5 Hz, 1H), 7.39 (s, 1H), 6.60 (d, J=11.5 Hz, 1H), 6.36 (t, J=11.5 Hz, 1H), 6.04 (d, J=16.6 Hz, 1H), 5.79 (br d, J=9.5 Hz, 1H), 5.55 (q, J=9.5 Hz, 1H), 5.12 (br s, 1H), 4.73 (dd, J=9.5, 1.2 Hz, 1H), 4.71 (br s, 1H), 4.55–4.44 (m, 2H), 4.10 (d, J=17.8 Hz, 1H), 3.92 (d, J=15.4 Hz, 1H), 3.78 (d, J=15.4 Hz, 1H), 3.87–3.36 (m, 2H), 2.50–1.35 (m, 10H), 2.31 (d, J=17.6 Hz, 1H), 1.87 (d, J=6.6 Hz, 3H), 1.74 (d, J=1.2 Hz, 3H), 1.66 (s, 3H); minor isomer 9.57 (dd, J=16.6, 11.5 Hz, 1H), -7.40 (s, 1H), 6.61 (d, J=11.5 Hz, 1H), 6.33 (t, J=11.5 Hz, 1H), 5.99 (d, J=16.6 Hz, 1H), 5.82 (br d, J=9.5 Hz, 1H), 5.57 (q, J=9.5 Hz, 1H), 5.12 (br s, 1H), 5.01 (dd, J=9.5, 1.2 Hz, 1H), 4.56 (br s, 1H), 4.55–4.44 (m, 2H), 4.12 (d, J=17.8 Hz, 1H), 3.92 (d, J=15.4 Hz, 1H), 3.78 (d, J=15.4 Hz, 1H), 3.87–3.36 (m, 2H), 2.50–1.35 (m, 10H), 2.30 (d, J=17.6 Hz, 1H), 1.93 (d, J=6.6 Hz, 3H), 1.77 (d, J=1.2 Hz, 3H), 1.66 (s, 3H)

FABMS m/z 723 (M+H)$^+$

HRFABMS calcd for C$_{32}$H$_{39}$N$_2$O$_{11}$S$_3$ (M+H)$^+$ 723.1716, found 723.1710

Example 82

Synthesis of Compound 88

DC107 (60 mg, 0.11 mmol) was dissolved in acetonitrile (5.0 mL). Thereto were added potassium carbonate (39 mg, 0.28 mmol) and 4-bromomethyl-5-formyloxymethyl-2-oxo-1,3-dioxolene (Compound S-30 obtained in Reference Example 30) (68 mg, 0.28 mmol). This mixture was stirred at 25° C. for 5 hours. After the ordinary post-treatment, the reaction product was purified by thin-layer chromatography (developed with chloroform/methanol=96/4) to obtain Compound 88 (9.2 mg, yield 13%).

$^1$H NMR (CDCl$_3$, 400 MHz)δ ppm; 8.45 (ddd, J=16.3, 11.5, 1.0 Hz, 1H), 8.07 (t, J=0.7 Hz, 1H), 7.35 (s, 1H), 6.58 (d, J=12.0 Hz, 1H), 6.24 (dd, J=12.0, 11.5 Hz, 1H), 6.17 (d, J=16.3 Hz, 1H), 5.74 (br d, J=8.8 Hz, 1H), 5.48 (br s, 1H), 5.41 (q, J=6.8 Hz, 1H), 5.09 (dd, J=11.2, 0.7 Hz, 1H), 5.04 (dd, J=11.2, 0.7 Hz, 1H) 4.95 (d, J=8.8 Hz, 1H), 3.95–3.73 (m, 3H), 3.89 (d, J=17.8 Hz, 1H), 2.30–1.50 (m, 4H), 2.26 (d, J=17.8 Hz, 1H), 2.02 (d, J=6.8 Hz, 3H), 1.75 (s, 3H), 1.75 (s, 3H)

FABMS m/z 667 (M+H)$^+$

HRFABMS calcd for C$_{28}$H$_{31}$N$_2$O$_{11}$S$_3$ (M+H)$^+$ 667.1090, found 667.1116

Example 83

Synthesis of Compound 89

Compound 88 (50 mg, 0.075 mmol) obtained in Example 82 was dissolved in dichloromethane (5.0 mL). Thereto were added 3,4-dihydro-2H-pyran (0.034 mL, 0.38 mmol) and camphorsulfonic acid (10 mg, 0.038 mmol). This mixture was stirred at 25° C. for 30 minutes. After the ordinary post-treatment, the reaction product was purified by thin-layer chromatography (developed with chloroform/methanol=96/4) to obtain Compound 89 (24 mg, yield 43%). $^1$H NMR revealed that Compound 89 was an approximately 4:3 mixture of diastereomers.

$^1$H NMR (CDCl$_3$, 400 MHz)δ ppm; major isomer 9.40 (dd, J=16.6, 11.5 Hz, 1H), 8.09 (s, 1H), 7.40 (s, 1H), 6.60 (d, J=11.5 Hz, 1H), 6.37 (t, J=11.5 Hz, 1H), 6.04 (d, J=16.6 Hz, 1H), 5.80 (br d, J=9.3 Hz, 1H), 5.56 (q, J=6.6 Hz, 1H), 5.12–5.00 (m, 2H), 4.73 (dd, J=9.3, 1.2 Hz, 1H), 4.70 (br s, 1H), 4.03 (d, J=17.6 Hz, 1H), 3.95–3.40 (m, 4H), 2.60–1.40 (m, 11H), 1.88 (d, J=6.6 Hz, 3H), 1.74 (d, J=1.2 Hz, 3H), 1.68 (s, 3H); minor isomer 9.59 (dd, J=16.6, 11.5 Hz, 1H), 8.09 (s, 1H), 7.41 (s, 1H), 6.61 (d, J=11.5 Hz, 1H), 6.34 (t, J=11.5 Hz, 1H), 6.00 (d, J=16.6 Hz, 1H), 5.83 (br d, J=9.3 Hz, 1H), 5.59 (q, J=6.6 Hz, 1H), 5.12–5.00 (m, 2H), 5.02 (dd, J=9.3, 1.2 Hz, 1H), 4.56 (br s, 1H), 4.04 (d, J=17.6 Hz, 1H), 3.95–3.40 (m, 4H), 2.60–1.40 (m, 11H), 1.94 (d, J=6.6 Hz, 3H), 1.77 (d, J=1.2 Hz, 3H), 1.67 (s, 3H)

FABMS m/z 751 (M+H)$^+$ calcd for C$_{33}$H$_{38}$N$_2$O$_{12}$S$_3$=750

Example 84

Synthesis of Compound 90

DC107 (51 mg, 0.10 mmol) was dissolved in acetonitrile (7.0 mL). Thereto were added potassium carbonate (41 mg, 0.30 mmol) and 4-acetoxymethyl-5-bromomethyl-2-oxo-1,3-dioxolene (Compound S-31 obtained in Reference Example 31) (75 mg, 0.30 mmol). This mixture was stirred at 25° C. for 6 hours. After the ordinary post-treatment, the reaction product was purified by thin-layer chromatography (developed with chloroform/methanol=96/4) to obtain Compound 90 (11 mg, yield 16%).

$^1$H NMR (CDCl$_3$, 500 MHz) ppm; 8.46 (ddd, J=16.4, 11.5, 1.0, 1H), 7.35 (s, 1H), 6.59 (d, J=11.5 Hz, 1H), 6.24 (t, J=11.5 Hz, 1H), 6.17 (d, J=16.4 Hz, 1H), 5.74 (br d, J=9.0 Hz, 1H), 5.52 (br s, 1H), 5.41 (q, J=6.9 Hz, 1H), 4.97 (d, J=14.0 Hz, 1H), 4.94 (br d, J=9.0 Hz, 1H), 4.91 (d, J=14.0 Hz, 1H), 3.93 (d, J=15.3 Hz, 1H), 3.89 (d, J=17.8 Hz, 1H), 3.87 (d, J=15.3 Hz, 1H), 3.76 (br s, 1H), 2.34–1.50 (m, 4H), 2.27 (d, J=17.8 Hz, 1H), 2.09 (s, 3H), 2.02 (d, J=6.9 Hz, 3H), 1.77 (s, 3H), 1.75 (d, J=1.2 Hz, 3H)

FABMS m/z 681 (M+H)$^+$

HRFABMS calcd for C$_{29}$H$_{33}$N$_2$O$_{11}$S$_3$ (M+H)$^+$ 681.1246, found 681.1221

Example 85

Synthesis of Compound 91

In the same manner as in Example 84, Compound 91 (12 mg, yield 21%) was obtained from Compound S-1 (45 mg, 0.076 mmol) obtained in Reference Example 1, potassium carbonate (32 mg, 0.30 mmol), and 4-acetoxymethyl-5-bromomethyl-2-oxo-1,3-dioxolene (Compound S-31 obtained in Reference Example 31) (57 mg, 0.23 mmol).

$^1$H NMR (CDCl$_3$, 400 MHz)δ ppm; 9.58 (dd, J=16.6, 11.5 Hz) and 9.39 (dd, J=16.6, 11.5 Hz) (total 1H), 7.40 (s) and 7.39 (s) (total 1H), 6.61 (d, J=11.5 Hz) and 6.60 (d, J=11.5 Hz) (total 1H), 6.37 (t, J=11.5 Hz) and 6.34 (t, J=11.5 Hz) (total 1H), 6.05 (d, J=16.6 Hz) and 6.00 (d, J=16.6 Hz)(total 1H), 5.83 (br d, J=9.3 Hz) and 5.81 (br d, J=9.3 Hz) (total 1H), 5.59 (q, J=6.6 Hz) and 5.56 (q, J=6.6 Hz) (total 1H), 5.55 (br s) and 5.53 (br s) (total 1H), 5.02 (d, J=9.3 Hz) and 4.74 (d, J=9.3 Hz) (total 1H), 5.01–4.88 (m, 2H), 4.71 (br s) and 4.57 (br s) (total 1H), 4.04 (d, J=17.6) and 4.03 (d, J=17.6 Hz) (total 1H), 3.92 (br s, 2H), 3.90–3.70 (m, 1H), 3.53–3.40 (m, 1H), 2.45–1.40 (m, 10H), 2.31 (d, J=17.6 Hz) and 2.30 (d, J=17.6 Hz) (total 1H), 2.12 (s, 3H), 1.94 (d, J=6.6 Hz) and 1.88 (d, J=6.6 Hz) (total 3H), 1.77 (d, J=1.0 Hz) and 1.75 (d, J=1.0 Hz) (total 3H), 1.70 (s) and 1.69 (s) (total 3H)

FABMS m/z 765 (M+H)$^+$

HRFABMS calcd for C$_{34}$H$_{41}$N$_2$O$_{12}$S$_3$ (M+H)$^+$ 765.1821, found 765.1816

Example 86

Synthesis of Compound 92

Compound 87 (40 mg, 0.034 mmol) obtained in Example 81 was dissolved in dichloromethane (4.0 mL). Thereto were added N,N-dimethylglycine (12 mg, 0.111 mmol), 1-ethyl-3-(3-dimethylaminopropyl)carbodiimide hydrochloride (34 mg, 0.18 mmol), and 4-dimethyl-aminopyridine (1.4 mg, 0.011 mmol). This mixture was stirred at 40° C. for 2 hours. After the ordinary post-treatment, the reaction product was purified by silica gel chromatography (eluted with n-hexane/ethyl acetate=1/3) to obtain Compound 92 (63 mg, yield 100%). $^1$H NMR revealed that Compound 92 was an approximately 1:1 mixture of diastereomers.

$^1$H NMR (CDCl$_3$, 400 MHz)δ ppm; 9.58 (dd, J=16.5, 11.5 Hz) and 9.38 (dd, J=16.5, 11.5 Hz) (total 1H), 7.40 (s) and 7.39 (s) (total 1H), 6.62 (d, J=11.5 Hz) and 6.57 (d, J=11.5 Hz) (total 1H), 6.37 (dd, J=11.5, 11.5 Hz) and 6.34 (dd, J=11.5, 11.5 Hz) (total 1H), 6.03 (d, J=16.5 Hz) and 5.99 (d, J=16.5 Hz) (total 1H), 5.82 (d, J=10.0 Hz) and 5.79 (d, J=10.0 Hz) (total 1H), 5.57 (m, 1H), 5.04 (d, J=14.0 Hz) and 4.98 (d, J=14.0 Hz) (total 2H), 5.03 (m) and 4.73 (d, J=10.0 Hz) (total 1H), 4.69 (m) and 4.56 (m) (total 1H), 4.03 (d, J=17.7 Hz) and 4.02 (d, J=17.7 Hz) (total 1H), 3.94 (dd, J=15.3, 1.0 Hz) and 3.87 (dd, J=15.3, 1.5 Hz) (total 2H), 3.84–3.38 (m, 2H), 2.45–2.25 (m, 4H), 2.35 (s, 2H), 2.30 (d, J=17.7 Hz) and 2.29 (d, J=17.6 Hz) (total 1H), 1.93 (d, J=6.6

Hz) and 1.86 (d, J=6.6 Hz) (total 3H), 1.70–1.20 (m, 6H), 1.73 (d, J=1.1 Hz) and 1.70 (d, J=1.1 Hz) (total 3H), 1.67 (s, 3H), 1.23 (s, 6H)

FABMS m/z 808 (M+H)$^+$ calcd for $C_{36}H_{45}N_3O_{12}S_3$=807

Example 87

Synthesis of Compound 93

According to Example 86, Compound 93 (32 mg, yield 94%) was obtained from Compound 87 (30 mg, 0.041 mmol) obtained in Example 81, dichloromethane (1.5 mL), nicotinic acid (20 mg, 0.16 mmol), 1-ethyl-3-(3-dimethylaminopropyl)carbodiimide hydrochloride (50 mg, 0.32 mmol), and 4-dimethylaminopyridine (1.2 mg, 0.010 mmol). $^1$H NMR revealed that Compound 93 was an approximately 1:1 mixture of diastereomers.

$^1$H NMR (CDCl$_3$, 400 MHz)δ ppm; 9.58 (dd, J=16.9, 11.5 Hz) and 9.39 (dd, J=16.9, 12.2 Hz) (total 1H), 9.23 (s) and 9.22 (s) (total 1H), 8.82 (d, J=1.7 Hz) and 8.81 (d, J=1.7 Hz) (total 1H), 8.32 (dd, J=4.9, 1.7 Hz) and 8.31 (dd, J=4.9, 1.7 Hz) (total 1H), 7.43 (d, J=4.9 Hz) and 7.42 (d, J=4.9 Hz) (total 1H), 7.40 (s) and 7.39 (s) (total 1H), 6.62 (d, J=11.5 Hz) and 6.59 (d, J=11.5 Hz) (total 1H), 6.37 (dd, J=11.5, 11.5 Hz) and 6.34 (dd, J=11.5, 11.5 Hz) (total 1H), 6.04 (d, J=16.9 Hz) and 6.00 (d, J=16.9 Hz) (total 1H), 5.82 (d, J=9.8 Hz) and 5.79 (d, J=9.8 Hz) (total 1H), 5.60 (br s, 1H), 5.58 (m, 1H), 5.28 (d, J=13.7 Hz) and 5.22 (d, J=13.7 Hz) (total 2H), 5.01 (dd, J=9.8, 1.5 Hz) and 4.73 (dd, J=9.8, 1.2 Hz) (total 1H), 4.70 (m) and 4.57 (m) (total 1H), 4.06 (d, J=17.6 Hz) and 4.05 (d, J=17.6 Hz) (total 1H), 4.03 (dd, J=15.4, 2.0 Hz) and 3.95 (dd, J=15.4, 2.0 Hz) (total 2H), 3.90–3.40 (m, 2H), 2.45–2.25 (m, 4H), 2.31 (d, J=17.6 Hz) and 2.30 (d, J=17.6 Hz) (total 1H), 1.94 (d, J=6.6 Hz) and 1.90 (d, J=6.6 Hz) (total 3H), 1.78–1.24 (m, 6H), 1.77 (d, J=1.2 Hz) and 1.72 (d, J=1.2 Hz) (total 3H), 1.68 (s, 3H)

FABMS m/z 828 (M+H)$^+$ calcd for $C_{38}H_{41}N_3O_{12}S_3$=827

Example 88

Synthesis of Compound 94

Compound 87 (25 mg, 0.034 mmol) obtained in Example 81 was dissolved in dichloromethane (2.5 mL) and pyridine (0.068 mL, 0.85 mmol). Thereto was added 2-quinoxaloyl chloride (46 mg, 0.24 mmol). This mixture was stirred at 25° C. for 0.5 hours. After the ordinary post-treatment, the reaction product was purified by silica gel chromatography (eluted with n-hexane/ethyl acetate=1/2) to obtain Compound 94 (56 mg, yield 100%).

$^1$H NMR revealed that Compound 94 was an approximately 1:1 mixture of diastereomers.

$^1$H NMR (CDCl$_3$, 400 MHz)δ ppm; 9.58 (dd, J=16.5, 11.5 Hz) an 9.39 (dd, J=16.5, 11.5 Hz) (total 1H), 9.54 (s, 1H), 8.24–7.70 (m, 4H), 7.40 (s) and 7.39 (s) (total 1H), 6.61 (d, J=11.5 Hz) and 6.59 (d, J=11.5 Hz) (total 1H), 6.35 (dd, J=11.5, 11.5 Hz) and 6.33 (dd, J=11.5, 11.5 Hz) (total 1H), 6.02 (d, J=16.5 Hz) and 5.99 (d, J=16.5 Hz) (total 1H), 5.80 (d, J=9.2 Hz) and 5.78 (d, J=9.2 Hz) (total 1H), 5.56 (m, 1H), 5.42 (d, J=13.9 Hz) and 5.38 (d, J=13.9 Hz) (total 2H), 5.00 (dd, J=9.2, 1.3 Hz) and 4.72 (dd, J=9.2, 1.3 Hz) (total 1H), 4.68 (m) and 4.56 (m) (total 1H), 4.22 (m, 2H), 4.06 (m, 1H), 3.40–3.84 (m, 3H), 2.44–2.25 (m, 4H), 2.32 (d, J=17.7 Hz) and 2.31 (d, J=17.7 Hz) (total 1H), 1.93 (d, J=6.6 Hz) and 1.86 (d, J=6.6 Hz) (total 3H), 1.72–1.25 (m, 6H), 1.74 (s) and 1.70 (s) (total 3H), 1.66 (s, 3H)

FABMS m/z 879 (M+H)$^+$ calcd for $C_{41}H_{42}N_4O_{12}S_3$=878

Example 89

Synthesis of Compound 95

Compound 87 (50 mg, 0.069 mmol) obtained in Example 81 was dissolved in N,N-dimethylformamide (5.0 mL). Thereto were added succinic anhydride (35 mg, 0.35 mmol) and 4-dimethylaminopyridine (42 mg, 0.35 mmol). This mixture was stirred at 70° C. for 3 hours. After the ordinary post-treatment, the reaction product was purified by thin-layer chromatography (developed with chloroform/methanol=10/1) to obtain Compound 95 (60 mg, yield 100%). $^1$H NMR revealed that Compound 95 was an approximately 1:1 mixture of diastereomers.

$^1$H NMR (CDCl$_3$, 400 MHz)δ ppm; 9.54 (dd, J=16.9, 11.5 Hz) and 9.36 (dd, J=16.9, 11.5 Hz) (total 1H), 7.51 (s) and 7.49 (s) (total 1H), 6.61 (d, J=11.5 Hz) and 6.60 (d, J=11.5 Hz) (total 1H), 6.37 (dd, J=11.5, 11.5 Hz) and 6.34 (dd, J=11.5, 11.5 Hz) (total 1H) 6.07 (d, J=16.9 Hz) and 6.04 (d, J=16.9 Hz) (total 1H), 5.81 (d, J=10.0 Hz) and 5.78 (d, J=10.0 Hz) (total 1H), 5.56 (m, 1H), 5.42 (m, 1H), 5.02 (d, J=13.9 Hz) and 4.93 (d, J=13.9 Hz) (total 2H),4.96 (m) and 4.76 (d, J=9.3 Hz) (total 1H), 4.79 (m) and 4.53 (m) (total 1H), 4.07 (d, J=17.8 Hz) and 4.02 (d, J=17.8 Hz) (total 1H), 4.02 (d, J=15.2 Hz) and 3.78 (d, J=15.2 Hz) (total 2H), 3.97–3.45 (m, 3H), 2.67 (m, 4H), 2.52–2.28 (m, 4H), 2.47 (d, J=7.3 Hz) and 2.42 (d, J=7.3 Hz) (total 1H), 1.94 (d, J=6.6 Hz) and 1.88 (d, J=6.6 Hz) (total 3H), 1.80–1.20 (m, 6H), 1.77 (s) and 1.74 (s) (total 3H), 1.69 (s, 3H)

FABMS m/z 823 (M+H)$^+$ calcd for $C_{36}H_{42}N_2O_{14}S_3$=822

Example 90

Synthesis of Compound 96

In the same manner as in Example 84, Compound 96 (9.0 mg, yield 11%) was obtained from DC107 (51 mg, 0.10 mmol), potassium carbonate (13.8 mg, 0.10 mmol), and 4-bromomethyl-5-(N-Boc-aminoisobutyryloxy)methyl-2-oxo-1,3-dioxolene (Compound S-33 obtained in Reference Example 33) (40 mg, 0.10 mmol).

$^1$H NMR (CDCl$_3$, 400 MHz)δ ppm; 8.47 (dd, J=16.4, 11.4 Hz, 1H), 7.35 (s, 1H), 6.58 (d, J=11.4 Hz, 1H), 6.24 (t, J=11.4 Hz, 1H), 6.17 (d, J=16.4 Hz, 1H), 5.74 (br d, J=9.3 Hz, 1H), 5.54 (br s, 1H), 5.40 (q, J=6.8 Hz, 1H), 5.05 (d, J=13.9 Hz, 1H), 4.94 (d, J=13.9 Hz, 1H), 4.94 (dd, J=9.4, 3.7 Hz, 1H), 3.95 (d, J=15.4 Hz, 1H), 3.90 (d, J=15.4 Hz, 1H), 3.89 (d, J=17.8 Hz, 1H), 3.73 (d, J=3.7 Hz, 1H), 2.35–1.70 (m, 4H), 2.31 (d, J=17.8 Hz, 1H), 2.02 (d, J=6.8 Hz, 3H), 1.77 (s, 3H), 1.75 (d, J=1.2 Hz, 3H), 1.47 (s, 3H), 1.46 (s, 3H), 1.41 (s, 9H)

FABMS m/z 824 (M+H)$^+$ calcd for $C_{36}H_{45}N_3O_{13}S_3$=823

Example 91

Synthesis of Compound 97

In the same manner as in Example 84, Compound 97 (5.0 mg, yield 14%) was obtained from DC107 (33 mg, 0.066 mmol), potassium carbonate (9.1 mg, 0.066 mmol), and 4-(N-acetylglycyl)methyl-5-bromomethyl-2-oxo-1,3-dioxolene (Compound S-34 obtained in Reference Example 34) (15 mg, 0.049 mmol)

FABMS m/z 738 (M+H)$^+$

HRFABMS calcd for $C_{31}H_{36}N_3O_{12}S_3$ (M+H)$^+$ 738.1453, found 738.1461

Example 92

Synthesis of Compound 98

In the same manner as in Example 84, Compound 98 (9.4 mg, yield 18%) was obtained from Compound S-1 (38 mg, 0.065 mmol) obtained in Reference Example 1, potassium carbonate (18 mg, 0.13 mmol), and 4-(N-acetylglycyl)methyl-5-bromomethyl-2-oxo-1,3-dioxolene (40 mg, 0.13 mmol).

$^1$H NMR (CDCl$_3$, 400 MHz)δ ppm; major isomer 9.38 (dd, J=16.4, 11.5 Hz, 1H), 7.39 (s, 1H), 6.60 (d, J=11.5 Hz, 1H), 6.37 (d, J=11.5 Hz, 1H), 6.10 (br s, 1H), 6.05 (d, J=16.4 Hz, 1H), 5.80 (br d, J=9.0 Hz, 1H), 5.60–5.52 (m, 2H), 5.09 (d, J=13.9 Hz, 1H), 4.96 (d, J=13.9 Hz, 1H), 4.74 (dd, J=9.0, 1.2 Hz, 1H), 4.70 (br s, 1H), 4.15–3.35 (m, 7H), 2.45–1.35 (m, 11H), 2.05 (s, 3H), 1.88 (d, J=6.6 Hz, 3H), 1.75 (d, J=1.2 Hz, 3H), 1.68 (s, 3H); minor isomer 9.57 (dd, J=16.4, 11.5 Hz, 1H), 7.40 (s, 1H), 6.61 (d, J=11.5 Hz, 1H), 6.34 (d, J=11.5 Hz, 1H), 6.00 (br s, 1H), 6.05 (d, J=16.4 Hz, 1H), 5.83 (br d, J=9.3 Hz, 1H), 5.60–5.52 (m, 2H), 5.10 (d, J=13.9 Hz, 1H), 5.02 (dd, J=9.3, 1.5 Hz, 1H), 4.96 (d, J=13.9 Hz, 1H), 4.56 (br s, 1H), 4.15–3.35 (m, 7H), 2.45–1.35 (m, 11H), 2.05 (s, 3H), 1.94 (d, J=6.6 Hz, 3H), 1.78 (d, J=1.2 Hz, 3H), 1.68 (s, 3H)

FABMS m/z 822 (M+H)$^+$

HRFABMS calcd for C$_{36}$H$_{44}$N$_3$O$_{13}$S$_3$ (M+H)$^+$ 822.2036, found 822.2046

Example 93

Synthesis of Compound 99

In the same manner as in Example 84, Compound 99 (15 mg, yield 21%) was obtained from DC107 (51 mg, 0.10 mmol), potassium carbonate (19 mg, 0.14 mmol), and 4-bromomethyl-5-(2-methoxyethoxy)acetoxymethyl-2-oxo-1,3-dioxolene (Compound S-32 obtained in Reference Example 32) (45 mg, 0.14 mmol).

$^1$H NMR (CDCl$_3$, 400 MHz)δ ppm; 8.47 (dd, J=16.6, 11.3 Hz, 1H), 7.35 (s, 1H), 6.58 (d, J=11.7 Hz, 1H), 6.24 (dd, J=11.7, 11.3 Hz, 1H), 6.17 (d, J=16.6 Hz, 1H) 5.74 (br d, J=8.7 Hz, 1H), 5.51 (br s, 1H), 5.41 (q, J=7.0 Hz, 1H), 5.07 (d, J=13.9 Hz, 1H), 5.00 (d, J=13.9 Hz, 1H), 4.94 (br d, J=8.7 Hz, 1H), 4.20 (s, 2H), 3.96 (d, J=15.4 Hz, 1H), 3.88 (d, J=17.8 Hz, 1H), 3.87 (d, J=15.4 Hz, 1H), 3.74 (br s, 1H), 3.72–3.64 (m, 4H), 3.37 (s, 3H), 2.27 (d, J=17.8 Hz, 1H), 2.34–1.70 (m, 4H), 2.02 (d, J=7.0 Hz, 3H), 1.76 (s, 3H), 1.75 (d, J=1.2 Hz, 3H)

FABMS m/z 755 (M+H)$^+$

HRFABMS calcd for C$_{32}$H$_{39}$N$_2$O$_{13}$S$_3$ (M+H)$^+$ 755.1614, found 755.1600

Example 94

Synthesis of Compound 100

According to Example 86, Compound 100 (27 mg, yield 81%) was obtained from Compound 87 (30 mg, 0.041 mmol) obtained in Example 81, dichloromethane (3.0 mL), 3,6-dioxaheptanoic acid (0.0093 mL, 0.082 mmol), 1-ethyl-3-(3-dimethylaminopropyl)carbodiimide hydro-chloride (24 mg, 1.2 mmol), and 4-dimethylaminopyridine (1.0 mg, 0.0081 mmol). $^1$H NMR revealed that Compound 100 was an approximately 1:1 mixture of diastereomers.

$^1$H NMR (CDCl$_3$, 400 MHz)δ ppm; 9.59 (dd, J=16.4, 11.5 Hz) and 9.39 (dd, J=16.4, 11.5 Hz) (total 1H), 7.41 (s) and 7.39 (s) (total 1H), 6.61 (d, J=11.5 Hz) and 6.60 (d, J=11.5 Hz) (total 1H), 6.37 (dd, J=12.2, 12.2 Hz) and 6.34 (dd, J=11.5, 11.5 Hz) (total 1H), 6.04 (d, J=16.4 Hz) and 6.00 (d, J=16.4 Hz) (total 1H), 5.83 (d, J=9.6 Hz) and 5.80 (d, J=9.6 Hz) (total 1H), 5.58 (m, 1H), 5.52 (d, J=6.3 Hz, 1H), 5.06 (dd, J=14.0, 1.5 Hz) and 5.02 (d, J=14.0 Hz) (total 2H), 5.03 (d, J=9.6 Hz) and 4.74 (d, J=9.6 Hz) (total 2H), 4.70 (m) and 4.57 (m) (total 1H), 4.21 (s, 2H), 4.04 (d, J=17.6 Hz) and 4.03 (d, J=17.6 Hz) (total 1H), 3.89–3.40 (m, 8H), 3.45 (s, 3H), 2.45–2.26 (m, 4H), 2.29 (d, J=17.6 Hz) and 2.28 (d, J=17.6 Hz) (total 1H), 1.94 (d, J=6.6 Hz) and 1.88 (d, J=6.6 Hz) (total 3H), 1.80–1.25 (m, 6H), 1.78 (s) and 1.75 (s) (total 3H), 1.68 (s, 3H)

FABMS m/z 839 (M+H)$^+$ calcd for C$_{37}$H$_{46}$N$_2$O$_{14}$S$_3$=838

Example 95

Synthesis of Compound 101

Compound 86 (51 mg, 0.079 mmol) obtained in Example 80 was dissolved in dichloromethane (5.1 mL). Thereto were added 3,6,9-trioxadecanoic acid (0.012 mL, 0.079 mmol), 1-ethyl-3-(3-dimethylaminopropyl)-carbodiimide hydrochloride (15 mg, 0.079 mmol), and 4-dimethylaminopyridine (14.5 mg, 0.12 mmol). This mixture was stirred at 0° C. for 20 minutes. After the ordinary post-treatment, the reaction product was purified by thin-layer chromatography (developed with chloroform/methanol=10/1) to obtain Compound 101 (9.7 mg, yield 15%).

$^1$H NMR (CDCl$_3$, 400 MHz)δ ppm; 8.47 (ddd, J=16.4, 11.4, 0.9 Hz, 1H), 7.35 (s, 1H), 6.59 (d, J=11.4 Hz, 1H), 6.23 (dd, J=11.4, 11.4 Hz, 1H), 6.18 (d, J=16.4 Hz, 1H), 5.74 (d, J=9.0 Hz, 1H), 5.53 (br s, 1H), 5.41 (q, J=7.0 Hz, 1H), 5.07 (d, J=14.0 Hz, 1H), 5.01 (d, J=14.0 Hz, 1H), 4.96 (d, J=9.0 Hz, 1H), 4.20 (s, 2H), 3.88 (d, J=17.8 Hz, 1H), 3.96 (d, J=15.3 Hz, 1H), 3.88 (d, J=15.3 Hz, 1H), 3.80–3.54 (m, 8H), 3.38 (s, 3H), 2.42–2.17 (m, 4H), 2.28 (d, J=17.8 Hz, 1H), 2.01 (d, J=7.0 Hz, 3H), 1.75 (s, 6H)

FABMS m/z 799 (M+H)$^+$ calcd for C$_{34}$H$_{42}$N$_2$O$_{14}$S$_3$=798

Example 96

Synthesis of Compound 102

According to Example 86, Compound 102 (45 mg, yield 99%) was obtained from Compound 87 (36 mg, 0.050 mmol) obtained in Example 81, dichloromethane (3.6 mL), 3,6,9-trioxadecanoic acid (0.015 mL, 0.10 mmol), 1-ethyl-3-(3-dimethylaminopropyl)carbodiimide hydro-chloride (19 mg, 0.10 mmol), and 4-dimethylaminopyridine (18 mg, 0.15 mmol). $^1$H NMR revealed that Compound 102 was an approximately 1:1 mixture of diastereomers.

$^1$H NMR (CDCl$_3$, 400 MHz)δ ppm; 9.59 (ddd, J=16.9, 11.5, 0.9 Hz) and 9.40 (ddd, J=16.9, 11.5, 0.7 Hz) (total 1H), 7.42 (s) and 7.41 (s) (total 1H), 6.61 (d, J=11.5 Hz) and 6.60 (d, J=11.5 Hz) (total 1H), 6.37 (dd, J=11.5, 11.5 Hz) and 6.34 (dd, J=11.5, 11.5 Hz) (total 1H), 6.04 (d, J=16.9 Hz) and 5.99 (d, J=16.9 Hz) (total 1H), 5.83 (d, J=9.5 Hz) and 5.79 (d, J=9.5 Hz) (total 1H), 5.57 (m, 1H), 5.06 (d, J=14.1 Hz) and 5.02 (d, J=14.1 Hz) (total 2H), 5.02 (dd, J=9.5, 1.2 Hz) and 4.73 (dd, J=9.5, 1.2 Hz) (total 1H), 4.71 (m) and 4.57 (m) (total 1H), 4.22 (s, 2H), 4.07 (d, J=17.6 Hz) and 4.06 (d, J=17.6 Hz) (total 1H), 3.95–3.35 (m, 11H), 3.94 (dd, J=15.4, 1.7 Hz) and 3.88 (d, J=15.4 Hz) (total 2H), 3.38 (s, 3H), 2.52–2.26 (m, 4H), 2.01 (d, J=17.6 Hz) and 2.00 (d, J=17.6 Hz) (total 1H), 1.94 (d, J=6.6 Hz) and 1.87 (d, J=6.6 Hz) (total 3H), 1.82–1.22 (m, 6H), 1.77 (d, J=1.2 Hz) and 1.74 (d, J=1.2 Hz) (total 3H), 1.68 (s, 3H)

FABMS m/z 905 (M+Na)$^+$ calcd for C$_{39}$H$_{50}$N$_2$O$_{15}$S$_3$=882

Example 97

Synthesis of Compound 103

Compound 101 (17 mg, 0.021 mmol) was dissolved in dichloromethane (3.0 mL). Thereto were added 5,6-dihydro- 4-methoxy-2H-pyran (0.0071 mL, 0.064 mmol) and camphorsulfonic acid (2.6 mg, 0.011 mmol). This mixture was stirred at 0° C. for 90 minutes. After the ordinary post-treatment, the reaction product was purified by thin-layer chromatography (developed with chloroform/methanol=96/4) to obtain Compound 103 (5.0 mg, yield 26%).

$^1$H NMR (CDCl$_3$, 400 MHz)δ ppm; 9.53 (ddd, J=16.6, 11.5, 1.0 Hz, 1H), 7.42 (s, 1H), 6.63 (d, J=11.4 Hz, 1H), 6.37 (t, J=11.5 Hz, 1H), 6.00 (d, J=16.6 Hz, 1H), 5.86 (br d, J=9.5 Hz, 1H), 5.57 (q, J=6.6 Hz, 1H), 6.48 (br s, 1H), 5.04 (d, J=13.9 Hz, 1H), 5.02 (d, J=13.9 Hz, 1H), 4.98 (dd, J=9.5, 1.2 Hz, 1H), 4.22 (s, 2H), 4.04 (d, J=17.8 Hz, 1H), 3.96 (d, J=13.7 Hz, 1H), 3.92 (d, J=13.7 Hz, 1H), 3.74–3.50 (m, 12H), 3.38 (s, 3H), 3.11 (s, 3H), 2.42–1.40 (m, 8H), 2.31 (d, J=17.8 Hz, 1H), 1.95 (d, J=6.6 Hz, 3H), 1.79 (d, J=1.2 Hz, 3H), 1.67 (s, 3H)

FABMS m/z 913 (M+H)$^+$

HRFABMS calcd for C$_{40}$H$_{53}$N$_2$O$_{16}$S$_3$ (M+H)$^+$ 913.2557, found 913.2577

Example 98

Synthesis of Compound 104

According to Example 86, Compound 104 (9.4 mg, yield 23%) was obtained from Compound 87 (31 mg, 0.043 mmol) obtained in Example 81, dichloromethane (3.1 mL), 3,6,9,12-tetraoxatridecanoic acid (19 mg, 0.087 mmol), 1-ethyl-3-(3-dimethylaminopropyl)carbodiimide hydrochloride (17 mg, 0.087 mmol), and 4-dimethylaminopyridine (16 mg, 0.13 mmol). $^1$H NMR revealed that Compound 104 was an approximately 1:1 mixture of diastereomers.

$^1$H NMR (CDCl$_3$, 400 MHz)δ ppm; 9.59 (dd, J=16.6, 11.6 Hz) and 9.39 (dd, J=16.6, 11.6 Hz) (total 1H), 7.41 (s) and 7.39 (s) (total 1H), 6.61 (d, J=11.6 Hz) and 6.59 (d, J=11.6 Hz) (total 1H), 6.37 (dd, J=11.6, 11.6 Hz) and 6.34 (dd, J=11.6, 11.6 Hz) (total 1H), 6.03 (d, J=16.6 Hz) and 6.00 (d, J=16.6 Hz) (total 1H), 5.83 (d, J=8.9 Hz) and 5.80 (d, J=8.9 Hz) (total 1H), 5.58 (m, 1H), 5.56 (m, 2H), 5.08 (dd, J 14.1, 2.0 Hz) and 5.01 (d, J=13.9 Hz) (total 2H), 5.00 (d, J=8.9 Hz) and 4.74 (d, J=8.9 Hz) (total 1H), 4.72 (m) and 4.59 (m) (total 1H), 4.23 (s, 2H), 4.04 (d, J=17.6 Hz) and 4.03 (d, J=17.6 Hz) (total 1H), 3.97–3.40 (m, 14H), 3.39 (s, 3H), 2.45–2.26 (m, 4H), 2.28 (d, J=17.6 Hz) and 2.27 (d, J=17.6 Hz) (total 1H), 2.03–1.22 (m, 6H), 1.93 (d, J=6.6 Hz) and 1.86 (d, J=6.6 Hz) (total 3H), 1.78 (d, J=1.0 Hz) and 1.74 (d, J=1.0 Hz) (total 3H), 1.68 (s, 3H)

FABMS m/z 927 (M+H)$^+$ calcd for C$_{41}$H$_{54}$N$_2$O$_{16}$S$_3$=926

Example 99

Synthesis of Compound 105

According to Example 86, Compound 105 (16 mg, yield 40%) was obtained from Compound 87 (30 mg, 0.041 mmol) obtained in Example 81, dichloromethane (3.0 mL), 3,6,9,12,15-pentaoxahexadecanoic acid (21 mg, 0.082 mmol), 1-ethyl-3-(3-dimethylaminopropyl)carbodiimide hydrochloride (24 mg, 1.2 mmol), and 4-dimethylaminopyridine (1.0 mg, 0.0081 mmol). $^1$H NMR revealed that Compound 105 was an approximately 1:1 mixture of diastereomers.

$^1$H NMR (CDCl$_3$, 400 MHz)δ ppm; 9.59 (dd, J=16.8, 11.5 Hz) and 9.39 (dd, J=16.8, 11.2 Hz) (total 1H), 7.41 (s) and 7.39 (s) (total 1H), 6.61 (d, J=11.2 Hz) and 6.59 (d, J=11.2 Hz) (total 1H), 6.38 (dd, J=11.2, 11.2 Hz) and 6.33 (dd, J=11.2, 11.2 Hz) (total 1H), 6.03 (d, J=16.8 Hz) and 6.00 (d, J=16.8 Hz) (total 1H), 5.183 (d, J=10.3 Hz) and 5.80 (d, J=10.3 Hz) (total 1H), 5.58 (m, 1H), 5.02 (d, J=12.5 Hz) and 5.0 3 (d, J=12.5 Hz) (total 2H), 5.00 (d, J=10.3 Hz) and 4.74 (d, J=10.3 Hz) (total H), 4.71 (m) and 4.57 (m) (total 1H), 4.30–3.53 (m, 4H), 4.22 (s, 2H), 4.05 (d, J=17.5 Hz) and 4.04 (d, J=17.5 Hz) (total 1H), 3.63 (m, 16H), 3.38 (s, 3H), 2.42–2.25 (m, 5H), 1.94 (d, J=6.8 Hz) and 1.988 (d, J=6.8 Hz) (total 3H), 1.80–1.22 (m, 6H), 1.78 (s) and 1.69 (s) (total 3H), 1.69 (s, 3H)

FABMS M/z 971 (M+H)$^+$ calcd for C$_{43}$H$_{58}$N$_2$O$_{17}$S$_3$=970

Example 100

Synthesis of Compound 106

According to Example 88, Compound 106 (20 mg, yield 59%) was obtained from Compound 87 (24 mg, 0.033 mmol) obtained in Example 81, dichloromethane (2.4 mL), pyridine (0.081 mL, 1.0 mmol), and methyl chloroformate (77 mL, 1.0 mmol). $^1$H NMR revealed that Compound 106 was an approximately 1:1 mixture of diastereomers.

$^1$H NMR (CDCl$_3$, 400 MHz)δ ppm; 9.59 (ddd, J=16.6, 11.5, 1.0 Hz) and 9.39 (ddd, J=16.6, 11.5, 0.9 Hz) (total 1H), 7.41 (s) and 7.39 (s) (total 1H), 6.62 (d, J=11.5 Hz) and 6.59 (d, J=11.5 Hz) (total 1H), 6.37 (dd, J=11.5, 11.5 Hz) and 6.33 (dd, J=11.5, 11.5 Hz) (total 1H), 6.05 (d, J=16.6 Hz) and 6.00 (d, J=16.6 Hz) (total 1H), 5.83 (d, J=10.2 Hz) and 5.80 (d, J=10.2 Hz) (total 1H), 5.58 (m, 1H), 5.54 (dd, J=7.4, 7.4 Hz) and 3.63 (dd, J=7.4, 7.4 Hz) (total 2H), 5.34 (m) and 4.74 (dd, J=10.2, 1.5 Hz) (total 1H), 5.04 (dd, J=13.9, 2.0 Hz) and 4.98 (d, J=13.9 Hz) (total 2H), 4.70 (m) and 4.58 (m) (total 1H), 4.03 (d, J=17.5 Hz) and 4.02 (d, J=17.5 Hz) (total 1H), 3.92 (s) and 3.83 (s) (total 3H), 3.90–3.40 (m, 2H), 2.44–2.26 (m, 4H), 2.30 (d, J=17.5 Hz) and 2.29 (d, J=17.5 Hz) (total 1H), 1.94 (d, J=6.6 Hz) and 1.88 (d, J=6.6 Hz) (total 3H), 1.78 (d, J=1.2 Hz) and 1.75 (d, J=1.2 Hz) (total 3H), 1.80–1.22 (m, 6H), 1.69 (s) and 1.68 (s) (total 3H)

FABMS m/z 781 (M+H)$^+$ calcd for C$_{34}$H$_{40}$N$_2$O$_{13}$S$_3$=780

Example 101

Synthesis of Compound 107

According to Example 88, Compound 107 (55 mg, yield 72%) was obtained from Compound 87 (51 mg, 0.070 mmol) obtained in Example 81, dichloromethane (5.1 mL), pyridine (0.14 mL, 1.8 mmol), and 4-nitrophenyl chloroformate (234 mg, 1.3 mmol). $^1$H NMR revealed that Compound 107 was an approximately 1:1 mixture of diastereomers.

$^1$H NMR (CDCl$_3$, 400 MHz)δ ppm; 9.59 (dd, J=16.5, 11.4 Hz) and 9.40 (dd, J=16.5, 12.3 Hz) (total 1H), 8.35 (m) and 7.41 (m) (total 4H), 7.42 (s) and 7.40 (s) (total 1H), 6.77 (br s, 1H), 6.62 (d, J -=11.3 Hz) and 6.61 (d, J=11.3 Hz) (total 1H), 6.36 (dd, J=11.3, 11.3 Hz) and 6.33 (dd, J=11.3, 11.3 Hz) (total 1H), 6.03 (d, J=16.6 Hz) and 6.00 (d, J=16.6 Hz) (total 1H), 5.81 (d, J=9.1 Hz) and 5.79 (d, J=9.1 Hz) (total 1H), 5.57 (m, 1H), 5.25–5.15 (m, 2H), 5.02 (dd, J=9.1, 1.3 Hz) and 4.75 (dd, J=9.1, 1.2 Hz) (total 1H), 4.69 (m) and 4.57 (m) (total 1H), 4.06 (d, J=17.6 Hz) and 4.05 (d, J=17.6 Hz) (total 1H), 3.90–3.41 (m, 2H), 3.66 (d, J=6.7 Hz) and 3.65 (d, J=6.7 Hz) (total 2H), 2.44–2.23 (m, 4H), 2.29 (d, J=17.6 Hz) and 2.28 (d, J=17.6 Hz) (total 1H), 1.94 (d, J=6.6 Hz) and 1.85 (d, J=6.6 Hz) (total 3H), 1.77–1.23 (m, 6H), 1.75 (d, J=1.2 Hz) and 1.71 (d, J=1.2 Hz) (total 3H), 1.60 (s, 3H)

FABMS m/z 888 (M+H)$^+$ calcd for C$_{39}$H$_{41}$N$_3$O$_{15}$S$_3$=887

Example 102

Synthesis of Compound 108

Compound 107 (40 mg, 0.065 mmol) obtained in Example 101 was dissolved in N,N-dimethylformamide (4.0

ML). Thereto, was added n-butylamine (5.4 mg, 0.054 mmol). This mixture was stirred at 0° C. for 5 minutes. After the ordinary post-treatment, the reaction product was purified by silica gel chromatography (eluted with n-hexane/ethyl acetate=1/1) to obtain Compound 108 (32 mg, yield 97%). $^1$H NMR revealed that Compound 108 was an approximately 1:1 mixture of diastereomers.

$^1$H NMR (CDCl$_3$, 400 MHz)δ ppm; 9.59 (dd, J=16.6, 11.5 Hz) and 9.40 (dd, J=16.6, 11.5 Hz) (total 1H), 7.41 (s) and 7.39 (s) (total 1H), 6.98 (s, 1H), 6.61 (d, J=11.5 Hz) and 6.60 (d, J=11.5 Hz) (total 1H), 6.37 (dd, J=11.5, 11.5 Hz) and 6.34 (dd, J=11.5, 11.5 Hz) (total 1H), 6.04 (d, J=16.6 Hz) and 6.02 (d, J=16.6 Hz) (total 1H), 5.83 (d, J=9.8 Hz) and 5.80 (d, J=9.8 Hz) (total 1H), 5.58 (m, 1H), 5.52 (d, J=7.1 Hz, 1H), 5.02 (d, J=9.8 Hz) and 4.74 (d, J=9.8 Hz) (total 1H), 4.92 (d, J=14.4 Hz) and 4.88 (d, J=14.4 Hz) (total 2H), 4.70 (m) and 4.57 (m) (total 1H), 4.05 (d, J=17.6 Hz) and 4.04 (d, J=17.6 Hz) (total 1H), 3.96 (s, 2H), 3.87–3.40 (m, 2H), 2.45–2.28 (m, 5H), 2.03–1.20 (m, 6H), 1.94 (d, J=6.6 Hz) and 1.87 (d, J=6.6 Hz) (total 3H), 1.80–0.80 (m, 9H), 1.78 (d, J=1.2 Hz) and 1.74 (d, J=1.2 Hz) (total 3H), 1.39 (s, 3H)

FABMS m/z 822 (M+H)$^+$ calcd for C$_{37}$H$_{47}$N$_3$O$_{12}$S$_3$=821

Example 103

Synthesis of Compound 109

According to Example 102, Compound 109 (33 mg, yield 76%) was obtained from Compound 107 (45 mg, 0.051 mmol) obtained in Example 101, N,N-dimethylformamide (4.5 mL), and 1-methylpiperazine (0.0067 mL, 0.061 mmol).

$^1$H NMR revealed that Compound 109 was an approximately 1:1 mixture of diastereomers.

$^1$H NMR (CDCl$_3$, 400 MHz)δ ppm; 9.59 (dd, J=16.6, 11.5 Hz) and 9.40 (dd, J=16.6, 11.5 Hz) (total 1H), 7.41 (s) and 7.39 (s) (total 1H), 6.62 (d, J=11.5 Hz) and 6.60 (d, J=11.5 Hz) (total 1H), 6.37 (dd, J=11.5, 11.5 Hz) and 6.33 (dd, J=11.5, 11.5 Hz) (total 1H), 6.04 (d, J=16.6 Hz) and 6.00 (d, J=16.6 Hz) (total 1H), 5.83 (d, J=10.5 Hz) and 5.80 (d, J=10.5 Hz) (total 1H), 5.58 (m, 1H), 5.02 (m) and 4.74 (dd, J=9.0, 1.0 Hz) (total 1H), 4.99 (dd, J=13.7, 2.0 Hz) and 4.93 (d, J=13.7 Hz) (total 2H), 4.71 (m) and 4.57 (m) (total 1H), 4.50 (d, J=17.6 Hz) and 4.49 (d, J=17.6 Hz) (total 1H), 3.99 (d, J=15.4 Hz) and 3.94 (d, J=15.4 Hz) (total 2H), 3.50 (m, 8H), 3.90–3.40 (m, 2H), 2.46–2.26 (m, 5H), 2.30 (s, 3H), 1.93 (d, J=6.6 Hz) and 1.88 (d, J=6.6 Hz) (total 3H), 1.78 (s) and 1.74 (s) (total 3H), 1.80–1.25 (m, 6H), 1.69 (s, 3H)

FABMS m/z 849 (M+H)$^+$ calcd for C$_{38}$H$_{48}$N$_4$O$_{12}$S$_3$=848

Example 104

Synthesis of Compound 110

According to Example 102, Compound 110 (33 mg, yield 90%) was obtained from Compound 107 (40 mg, 0.065 mmol) obtained in Example 101, N,N-dimethylformamide (4.0 mL), and ethanolamine (0.0032 mL, 0.054 mmol). $^1$H NMR revealed that Compound 110 was an approximately 1:1 mixture of diastereomers.

$^1$H NMR (CDCl$_3$, 400 MHz)δ ppm; 9.59 (dd, J=17.1, 11.5 Hz) and 9.38 (dd, J=17.1, 11.5 Hz) (total 1H), 7.41 (s) and 7.40 (s) (total 1H), 6.62 (d, J=11.5 Hz) and 6.60 (d, J=11.5 Hz) (total 1H), 6.36 (dd, J=11.5, 11.5 Hz) and 6.34 (dd, J=11.5, 11.5 Hz) (total 1H), 6.03 (d, J=17.1 Hz) and 6.00 (d, J=17.1 Hz) (total 1H), 5.83 (m, 1H), 5.82 (d, J=9.5 Hz) and 5.79 (d, J=9.5 Hz) (total 1H), 5.56 (m, 1H), 5.02 (dd, J=9.5, 1.2 Hz) and 4.73 (dd, J=9.5, 1.3 Hz) (total 1H), 4.97 (d, J=13.9 Hz) and 4.90 (dd, J=13.9, 3.4 Hz) (total 2H), 4.71 (m) and 4.57 (m) (total 1H), 4.08 (d, J=17.6 Hz) and 4.07 (d, J=17.6 Hz) (total 1H), 3.98 (d, J=15.1 Hz) and 3.97 (d, J=15.1 Hz) (total 2H), 3.94 (d, J=17.6 Hz) and 3.93 (d, J=17.6 Hz) (total 1H), 3.89–3.30 (m, 6H), 2.48–2.28 (m, 4H), 1.94 (d, J=6.6 Hz) and 1.88 (d, J=6.6 Hz) (total 3H), 1.80–1.24 (m, 6H), 1.78 (d, J=1.2 Hz) and 1.74 (d, J=1.2 Hz) (total 3H), 1.68 (s, 3H)

FABMS m/z 810 (M+H)$^+$ calcd for C$_{35}$H$_{43}$N$_3$O$_{13}$S$_3$=809

Example 105

Synthesis of Compound 111

DC107 (55 mg, 0.11 mmol) was dissolved in acetonitrile (5.0 mL). Thereto were added potassium carbonate (45 mg, 0.33 mmol) and methyl 2-bromomethylacrylate (0.040 mL, 0.33 mmol). This mixture was stirred at 25° C. for 4.5 hours. After the ordinary post-treatment, the reaction product was purified by thin-layer chromatography (developed with chloroform/methanol=97/3) to obtain Compound 111 (36 mg, yield 54%).

IR (KBr) 3420, 3104, 2938, 1712, 1680, 1609, 1439, 1377, 1333, 1255, 1204, 1105, 986, 813 cm$^{-1}$ $^1$H NMR (CDCl$_3$, 400 MHz)δ ppm; 8.45 (ddd, J=16.4, 11.2, 1.0 Hz, 1H), 7.34 (s, 1H), 6.57 (d, J=11.7 Hz, 1H), 6.23 (br s, 1H), 6.23 (dd, J=11.7, 11.2 Hz, 1H), 6.17 (d, J=16.4 Hz, 1H), 5.85 (br s, 1H), 5.72 (br d, J=8.8 Hz, 1H), 5.47 (br s, 1H), 5.40 (q, J=6.8 Hz, 1H), 4.94 (dd, J=8.8, 3.7 Hz, 1H), 3.90 (d, J=17.8 Hz, 1H), 3.78–3.65 (m, 3H), 3.76 (s, 3H), 2.36–1.82 (m, 4H), 2.25 (d, J=17.8 Hz, 1H), 2.02 (d, J=6.8 Hz, 3H) 1.77 (s, 3H), 1.75 (d, J=1.0 Hz, 3H)

FABMS m/z 609 (M+H)$^+$

HRFABMS calcd for C$_{27}$H$_{33}$N$_2$OBS$_3$ (M+H)$^+$ 609.1399, found 609.1418

Example 106

Synthesis of Compound 112

Compound S-1 (84 mg, 0.14 mmol) obtained in Reference Example 1 was dissolved in acetonitrile (7.0 mL). Thereto were added potassium carbonate (58 mg, 0.42 mmol) and methyl 2-bromomethylacrylate (0.051 mL, 0.42 mmol). This mixture was stirred at 25° C. for 5 hours. After the ordinary post-treatment, the reaction product was purified by thin-layer chromatography (developed with chloroform/methanol=97/3) to obtain Compound 112 (67 mg, yield 69%). $^1$H NMR revealed that Compound 112 was an approximately 5:4 mixture of diastereomers.

IR (KBr) 3430, 2942, 1712, 1680, 1650, 1608, 1439, 1258, 1201, 1117, 1074, 1020, 974 cm$^{-1}$ $^1$H NMR (CDCl$_3$, 400 MHz)δ ppm; major isomer 9.59 (dd, J=16.4, 11.5 Hz, 1H), 7.40 (s, 1H), 6.60 (d, J=11.5 Hz, 1H), 6.37 (t, J=11.5 Hz, 1H), 6.24 (br s, 1H), 6.04 (d, J=16.4 Hz, 1H), 5.86 (br s, 1H), 5.82 (br d, J=9.3 Hz, 1H), 5.58 (q, J=6.6 Hz, 1H), 5.50 (br s, 1H), 5.01 (dd, J=9.3, 1.2 Hz, 1H), 4.70 (br, 1H), 4.05 (d, J=17.8 Hz, 1H), 3.86–3.40 (m, 2H), 3.78 (s, 3H), 3.77 (d, J=13.5 Hz, 1H), 3.68 (d, J=13.5 Hz, 1H), 2.46–1.35 (m, 10H), 2.29 (d, J=17.8 Hz, 1H), 1.93 (d, J=6.6 Hz, 3H), 1.77 (d, J=1.2 Hz, 3H), 1.69 (s, 3H); minor isomer 9.39 (dd, J=16.6, 11.5 Hz, 1H), 7.39 (s, 1H), 6.59 (d, J=11.5 Hz, 1H), 6.34 (t, J=11.5 Hz, 1H), 6.24 (br s, 1H), 5.99 (d, J=16.6 Hz, 1H), 5.86 (br s, 1H), 5.80 (br d, J=9.3 Hz, 1H), 5.56 (q, J=6.6 Hz, 1H), 5.48 (br s, 1H), 4.73 (dd, J=9.3, 1.2 Hz, 1H), 4.57 (br, 1H), 4.04 (d, J=17.8 Hz, 1H), 3.86–3.40 (m, 2H), 3.78 (s, 3H), 3.77 (d, J=13.5 Hz, 1H), 3.68 (d, J=13.5 Hz, 1H), 2.46–1.35 (m, 10H), 2.28 (d, J=17.8 Hz, 1H), 1.87 (d, J=6.6 Hz, 3H), 1.74 (d, J=1.2 Hz, 3H), 1.69 (s, 3H)

FABMS m/z 693 (M+H)$^+$

HRFABMS calcd for $C_{32}H_{41}N_2O_9S_3$ (M+H)$^+$ 693.1974, found 693.1960

Example 107

Synthesis of Compound 113

Compound S-2 (70 mg, 0.11 mmol) obtained in Reference Example 2 was dissolved in acetonitrile (8.0 mL). Thereto were added potassium carbonate (47 mg, 0.34 mmol) and methyl 2-bromomethylacrylate (0.040 mL, 0.34 mmol). This mixture was stirred at 25° C. for 5 hours. After the ordinary post-treatment, the reaction product was purified by thin-layer chromatography (developed with chloroform/methanol=97/3) to obtain Compound 113 (49 mg, yield 61%).

IR (KBr) 3400, 3092, 2942, 2870, 1710, 1670, 1640, 1608, 1440, 1354, 1333, 1306, 1256, 1202, 1140, 1095, 1051, 989, 812 cm$^{-1}$ $^1$H NMR (CDCl$_3$, 400 MHz)δ ppm; 9.54 (ddd, J=16.6, 11.5, 1.0 Hz, 1H), 7.42 (s, 1H), 6.63 (d, J=11.5 Hz, 1H), 6.37 (t, J=11.5 Hz, 1H), 6.24 (d, J=1.0 Hz, 1H), 6.00 (d, J=16.6 Hz, 1H), 5.86 (bs, 1H), 5.85 (br d, J=9.5 Hz, 1H), 5.56 (q, J=6.6 Hz, 1H), 5.44 (br s, 1H), 4.97 (dd, J=9.5, 1.4 Hz, 1H), 4.05 (d, J=17.8 Hz, 1H), 3.78 (s, 3H), 3.77 (dd, J=14.0, 1.0 Hz, 1H), 3.68 (dd, J=14.0, 1.0 Hz, 1H), 3.68–3.46 (m, 4H), 3.10 (s, 3H), 2.40–1.30 (m, 8H), 2.30 (d, J=17.8 Hz, 1H), 1.94 (d, J=6.6 Hz, 3H), 1.78 (d, J=1.0 Hz, 3H), 1.67 (s, 3H)

FABMS m/z 723 (M+H)$^+$

HRFABMS calcd for $C_{33}H_{43}N_2O_{10}S_3$ (M+H)$^+$ 723.2080, found 723.2093

Example 108

Synthesis of Compound 114

DC107 (100 mg, 0.20 mmol) was dissolved in acetonitrile (4.0 mL). Thereto were added potassium carbonate (200 mg, 1.5 mmol) and t-butyl 2-bromomethylacrylate (220 mg, 1.0 mmol). This mixture was stirred at 25° C. for 5 hours. After the ordinary post-treatment, the reaction product was purified by thin-layer chromatography (developed with chloroform/methanol=97/3) to obtain Compound 114 (75 mg, yield 59%).

FABMS m/z 651 (M+H)$^+$

HRFABMS calcd for $C_{30}H_{39}N_2O_8S_3$ (M+H)$^+$ 651.1868, found 651.1864

Example 109

Synthesis of Compound 115

Compound 114 (56 mg, 0.086 mmol) obtained in Example 108 was dissolved in dichloromethane (4.0 mL). Thereto was added trifluoroacetic acid (0.40 mL). This mixture was stirred at 25° C. for 85 minutes. After the reaction mixture was concentrated, the residue was purified by thin-layer chromatography (developed with chloroform/methanol=85/15) to obtain Compound 115 (31 mg, yield 61%).

IR (KBr) 3400, 2936, 1705, 1680, 1610, 1450, 1378, 1262, 1195, 1087, 989 cm$^{-1}$ $^1$H NMR (CDCl$_3$+CD$_3$OD, 500 MHz)δ ppm; 8.44 (dd, J=16.4, 11.4 Hz, 1H), 7.35 (s, 1H), 6.58 (d, J=11.9 Hz, 1H), 6.23 (bs, 1H), 6.23 (dd, J=11.9, 11.4 Hz, 1H), 6.16 (d, J=16.4 Hz, 1H), 5.84 (bs, 1H), 5.67 (br d, J=8.5 Hz, 1H), 5.40 (q, J=6.9 Hz, 1H), 4.93 (d, J=8.5 Hz, 1H), 3.84 (d, J=17.8 Hz, 1H), 3.81 (d, J=13.8 Hz, 1H), 3.64 (d, J=13.8 Hz, 1H), 2.32 (d, J=17.8 Hz, 1H), 2.30–1.70 (m, 4H), 2.01 (d, J=6.9 Hz, 3H), 1.73 (d, J=1.0 Hz, 3H), 1.72 (s, 3H)

FABMS m/z 595 (M+H)$^+$

HRFABMS calcd for $C_{26}H_{31}N_2O_8S_3$ (M+H)$^+$ 595.1242, found 595.1224

Example 110

Synthesis of Compound 116

Compound 115 (35 mg, 0.059 mmol) obtained in Example 109 was dissolved in dichloromethane (3.0 mL). Thereto were added 5,6-dihydro-4-methoxy-2H-pyran (0.033 mL, 0.29 mmol) and camphorsulfonic acid (6.8 mg, 0.029 mmol). This mixture was stirred at 0° C. for 40 minutes. After the ordinary post-treatment, the reaction product was purified by thin-layer chromatography (developed with chloroform/methanol=9/1) to obtain Compound 116 (24 mg, yield 57%).

IR (KBr) 3420, 2940, 1711, 1680, 1640, 1608, 1450, 1356, 1263, 1141, 1093, 989 cm$^{-1}$ $^1$H NMR (CDCl$_3$, 400 MHz)δ ppm; 9.53 (dd, J=16.5, 11.5 Hz, 1H), 7.42 (s, 1H), 6.62 (d, J=11.5 Hz, 1H), 6.36 (t, J=11.5 Hz, 1H), 6.34 (br s, 1H), 6.01 (d, J=16.5 Hz, 1H), 5.96 (br s, 1H), 5.85 (br d, J=9.8 Hz, 1H), 5.56 (q, J=6.6 Hz, 1H), 5.43 (br s, 1H), 4.97 (dd, J=9.8, 1.0 Hz, 1H), 4.05 (d, J=17.8 Hz, 1H), 3.78 (d, J=14.0 Hz, 1H), 3.70–3.48 (m, 4H), 3.67 (d, J=14.0 Hz, 1H), 3.10 (s, 3H), 2.40–1.30 (m, 8H), 2.32 (d, J=17.8 Hz, 1H), 1.95 (d, J=6.6 Hz, 3H), 1.78 (d, J=1.0 Hz, 3H), 1.68 (s, 3H)

FABMS m/z 709 (M+H)$^+$

HRFABMS calcd for $C_{32}H_{41}N_2O_{10}S_3$ (M+H)$^+$ 709.1923, found 709.1921

Example 111

Synthesis of Compound 117

DC107 (51 mg, 0.10 mmol) was dissolved in acetonitrile (7.0 mL). Thereto were added potassium carbonate (138 mg, 0.10 mmol) and 1-[2-(bromomethyl)-1-oxo-2-propenyl]piperidine (200 mg, 0.86 mmol). This mixture was stirred at 25° C. for 26 hours. After the ordinary post-treatment, the reaction product was purified by thin-layer chromatography (developed with chloroform/methanol=97/3) to obtain Compound 117 (5.0 mg, yield 7.6%).

$^1$H NMR (CDCl$_3$, 400 MHz)δ ppm; 8.46 (ddd, J=16.4, 11.5, 1.0 Hz, 1H), 7.34 (s, 1H), 6.58 (d, J=11.5 Hz, 1H), 6.23 (t, J=11.5 Hz, 1H), 6.17 (d, J=16.4 Hz, 1H), 5.73 (br d, J=9.3 Hz, 1H), 5.53 (br s, 1H), 5.41 (q, J=6.7 Hz, 1H), 5.40 (br s, 1H), 5.13 (br s, 1H), 4.94 (br d, J=9.3 Hz, 1H), 3.90 (d, J=17.8 Hz, 1H), 3.77 (d, J=14.2 Hz, 1H), 3.74 (br s, 1H), 3.66 (d, J=14.2 Hz, 1H), 3.60–3.40 (m, 4H), 2.35 (d, J=17.8 Hz, 1H), 2.34–1.45 (m, 10H), 2.02 (d, J=6.7 Hz, 3H), 1.76 (s, 3H), 1.74 (d, J=1.2 Hz, 3H)

FABMS m/z 662 (M+H)$^+$

HRFABMS calcd for $C_{31}H_{40}N_3O_7S_3$ (M+H)$^+$ 662.2028, found 662.1999

Example 112

Synthesis of Compound 118

DC107 (26 mg, 0.051 mmol) was dissolved in acetonitrile (2.0 mL). Thereto were added potassium carbonate (21 mg, 0.15 mmol) and methyl 2-bromomethyl-2-hexenoate (34 mg, 0.15 mmol). This mixture was stirred at 25° C. for 4.5 hours. After the ordinary post-treatment, the reaction product was purified by thin-layer chromatography (developed with chloroform/methanol=95/5) to obtain Compound 118 (21 mg, yield 63%).

IR (KBr) 3420, 3104, 2936, 2874, 1715, 1680, 1642, 1610, 1439, 1376, 1262, 1195, 1153, 1053, 986, 780 cm$^{-1}$ $^1$H NMR (CDCl$_3$, 500 MHz)δ ppm; 8.48 (ddd, J=16.4, 11.2, 1.0 Hz, 1H), 7.36 (s, 1H), 6.90 (t, J=7.7 Hz, 1H), 6.60 (d, J=11.5 Hz, 1H), 6.25 (dd, J=11.5, 11.2 Hz, 1H), 6.19 (d, J=16.4 Hz, 1H), 5.75 (br d, J=8.7 Hz, 1H), 5.46 (br s, 1H), 5.42 (q, J=6.9 Hz, 1H), 4.96 (dd, J=8.7, 3.7 Hz, 1H), 3.93 (d, J=17.8 Hz, 1H), 3.82 (d, J=13.3 Hz, 1H), 3.77 (d, J=13.3 Hz, 1H), 3.75 (s, 3H), 3.74 (d, J=3.7 Hz, 1H), 2.40–1.90 (m, 6H), 2.29 (d, J=17.8 Hz, 1H), 2.04 (d, J=6.9 Hz, 3H), 1.80 (s, 3H), 1.76 (d, J=1.2 Hz, 3H), 1.53–1.45 (m, 2H), 0.96 (t, J=7.4 Hz, 3H)

FABMS m/z 651 (M+H)$^+$

HRFABMS calcd for C$_{30}$H$_{39}$N$_2$O$_8$S$_3$ (M+H)$^+$ 651.1868, found 651.1861

Example 113

Synthesis of Compound 119

Compound 118 (44 mg, 0.068 mmol) obtained in Example 112 was dissolved in dichloromethane (4.0 mL). Thereto were added 5,6-dihydro-4-methoxy-2H-pyran (0.023 mL, 0.20 mmol) and camphorsulfonic acid (7.9 mg, 0.034 mmol). This mixture was stirred at 0° C. for 40 minutes. After the ordinary post-treatment, the reaction product was purified by thin-layer chromatography (developed with chloroform/methanol=97/3) to obtain Compound 119 (38 mg, yield 73%).

IR (KBr) 3400, 3092, 2962, 2872, 1709, 1670, 1640, 1609, 1438, 1355, 1259, 1165, 1141, 1096, 1070, 989, 782 cm$^{-1}$ $^1$H NMR (CDCl$_3$, 400 MHz)δ ppm; 9.55 (ddd, J=16.6, 11.5, 0.8 Hz, 1H), 7.42 (s, 1H), 6.90 (t, J=7.8 Hz, 1H), 6.63 (d, J=11.5 Hz, 1H), 6.37 (t, J=11.5 Hz, 1H), 6.00 (d, J=16.6 Hz, 1H), 5.85 (br dd, J=9.8, 1.0 Hz, 1H), 5.57 (q, J=6.6 Hz, 1H), 5.39 (br s, 1H), 4.98 (dd, J=9.8, 1.2 Hz, 1H), 4.05 (d, J=17.8 Hz, 1H), 3.83 (d, J=13.2 Hz, 1H), 3.75 (s, 3H), 3.74 (d, J=13.2 Hz, 1H), 3.67–3.48 (m, 4H), 3.10 (s, 3H), 2.40–1.35 (m, 12H), 2.33 (d, J=17.8 Hz, 1H), 1.95 (d, J=6.6 Hz, 3H), 1.78 (d, J=1.2 Hz, 3H), 1.69 (s, 3H), 0.95 (t, J=7.4 Hz, 3H)

FABMS m/z 765 (M+H)$^+$

HRFABMS calcd for C$_{36}$H$_{49}$N$_2$O$_{10}$S$_3$ (M+H)$^+$ 765.2549, found 765.2566

Example 114

Synthesis of Compound 120

DC107 (51 mg, 0.110 mmol) was dissolved in acetonitrile (4.0 mL). Thereto were added potassium carbonate (41 mL, 0.30 mmol) and methyl α-bromomethylcinnamate (0.076 mL, 0.30 mmol). This mixture was stirred at 25° C. for 4 hours. After the ordinary post-treatment, the reaction product was purified by thin-layer chromatography (developed with chloroform/methanol=97/3) to obtain Compound 120 (47 mg, yield 68%).

IR (KBr) 3420, 2938, 1711, 1680, 1645, 1611, 1494, 1436, 1373, 1268, 1204, 1157, 1082, 983, 783, 759, 699 cm$^{-1}$ $^1$H NMR (CDCl$_3$, 400 MHz)δ ppm; 8.48 (ddd, J=16.4, 11.2, 0.8 Hz, 1H), 7.82 (s, 1H), 7.43–7.30 (m, 6H), 6.59 (d, J=12.0 Hz, 1H), 6.24 (dd, J=12.0, 11.2 Hz, 1H), 6.18 (d, J=16.4 Hz, 1H), 5.74 (br d, J=8.8 Hz, 1H), 5.51 (br s, 1H), 5.41 (q, J=6.8 Hz, 1H), 4.95 (dd, J=8.8, 3.7 Hz, 1H), 4.02 (d, J=12.7 Hz, 1H), 3.93 (d, J=18.0 Hz, 1H), 3.79 (d, J=12.7 Hz, 1H), 3.81 (s, 3H), 3.73 (d, J=3.7 Hz, 1H), 2.27 (d, J=18.0 Hz, 1H), 2.38–1.80 (m, 4H), 2.02 (d, J=6.8 Hz, 3H), 1.80 (s, 3H), 1.75 (d, J=1.0 Hz, 3H)

FABMS m/z 685 (M+H)$^+$

HRFABMS calcd for C$_{33}$H$_{37}$N$_2$O$_8$S$_3$ (M+H)$^+$ 685.1712, found 685.1689

Example 115

Synthesis of Compound 121

DC107 (102 mg, 0.20 mmol) was dissolved in acetonitrile (5.0 mL). Thereto were added potassium carbonate (55 mg, 0.40 mmol) and 5-bromomethyl-2,2,6-trimethyl-4H-1,3-dioxin-4-one (94 mg, 0.40 mmol). This mixture was stirred at 25° C. for 9 hours. After the ordinary post-treatment, the reaction product was purified by thin-layer chromatography (developed with chloroform/methanol=97/3) to obtain Compound 121 (84 mg, yield 63%).

IR (KBr) 3420, 2936, 1711, 1670, 1637, 1611, 1393, 1356, 1274, 1205, 1160, 1054, 985, 900, 780, 730 cm$^{-1}$ $^1$H NMR (CDCl$_3$, 400 MHz)δ ppm; 8.45 (dd, J=16.4, 11.2 Hz, 1H), 7.34(s, 1H), 6.58 (d, J=11.7 Hz, 1H), 6.57 (dd, J=11.7, 11.2 Hz, 1H), 6.17 (d, J=16.4 Hz, 1H), 5.73 (br d, J=9.5 Hz, 1H), 5.40 (q, J=6.8 Hz, 1H) 5.38 (br s, 1H), 4.94 (dd, J=9.5, 3.7 Hz, 1H), 3.91 (d, J=17.8 Hz, 1H), 3.81 (d, J=13.8 Hz, 1H), 3.74 (d, J=3.7 Hz, 1H), 3.71 (d, J=13.8 Hz, 1H), 2.30 (d, J=17.8 Hz, 1H), 2.40–1.55 (m, 4H), 2.08 (s, 3H), 2.01 (d, J=6.8 Hz, 3H), 1.78 (s, 3H), 1.75 (d, J=1.0 Hz, 3H), 1.63 (s, 6H)

FABMS m/z 665 (M+H)$^+$

HRFABMS calcd for C$_{30}$H$_{37}$N$_2$O$_9$S$_3$ (M+H)$^+$ 665.1661, found 665.1635

Example 116

Synthesis of Compound 122

Compound S-2 (68 mg, 0.11 mmol) obtained in Reference Example 2 was dissolved in acetonitrile (7.0 mL). Thereto were added potassium carbonate (50 mg, 0.36 mmol) and 5-bromomethyl-2,2,6-trimethyl-4H-1,3-dioxin-4-one (84 mg, 0.36 mmol). This mixture was stirred at 25° C. for 6 hours. After the ordinary post-treatment, the reaction product was purified by thin-layer chromatography (developed with chloroform/methanol=97/3) to obtain Compound 122 (36 mg, yield 57%).

IR (KBr) 3430, 2938, 1713, 1670, 1640, 1609, 1393, 1353, 1273, 1204, 1163, 1097, 1052 cm$^{-1}$ $^1$H NMR (CDCl$_3$, 400 MHz)δ ppm; 9.55 (dd, J=16.6, 11.5 Hz, 1H), 7.42 (s, 1H), 6.63 (d, J=11.5 Hz, 1H), 6.37 (t, J=11.5 Hz, 1H), 6.00 (d, J=16.6 Hz, 1H), 5.85 (br d, J=9.7 Hz, 1H), 5.56 (q, J=6.6 Hz, 1H), 5.37 (br s, 1H), 4.97 (dd, J=9.7, 1.2 Hz, 1H), 4.05 (d, J=17.8 Hz, 1H), 3.88 (d, J=13.9 Hz, 1H), 3.68 (d, J=13.9 Hz, 1H), 3.68–3.50 (m, 4H), 3.67 (s, 3H), 2.37 (d, J=17.8 Hz, 1H), 2.44–1.35 (m, 8H), 2.08 (s, 3H), 1.94 (d, J=6.6 Hz, 3H), 1.78 (d, J=1.2 Hz, 3H), 1.69 (s, 3H), 1.68 (s, 6H)

FABMS m/z 779 (M+H)$^+$

HRFABMS calcd for C$_{36}$H$_{47}$N$_2$O$_{11}$S$_3$ (M+H)$^+$ 779.2342, found 779.2313

Example 117

Synthesis of Compound 123

Compound S-1 (70 mg, 0.11 mmol) obtained in Reference Example 1 was dissolved in dichloromethane (6.0 mL). Thereto were added 3,4-dihydro-2H-pyran (0.048 mL, 0.53 mmol) and camphorsulfonic acid (12 mg, 0.053 mmol). This mixture was stirred at 25° C. for 40 minutes. After the ordinary post-treatment, the reaction product was purified by thin-layer chromatography (developed with chloroform/methanol=98/2) to obtain Compound 123 (55 mg, yield 70%). $^1$H NMR revealed that Compound 123 was an approximately 5:4 mixture of diastereomers.

IR (KBr) 3430, 2944, 1711, 1670, 1640, 1609, 1441, 1392, 1355, 1274, 1203, 1160, 1115, 1021, 974, 736 cm$^{-1}$ $^1$H NMR (CDCl$_3$, 400 MHz)δ ppm; major isomer 9.39 (ddd, J 16.6, 11.2, 1.0 Hz, 1H), 7.39 (s, 1H), 6.60 (d, J=11.5 Hz, 1H), 6.36 (dd, J=11.5, 11.2 Hz, 1H), 6.04 (d, J=16.6 Hz, 1H), 5.79 (br d, J=9.0 Hz, 1H), 5.56 (q, J=6.6 Hz, 1H), 5.41 (br s, 1H), 4.73 (dd, J=9.0, 1.2 Hz, 1H), 4.69 (br, 1H), 4.04 (d, J=17.8 Hz, 1H), 3.85 (d, J=13.9 Hz, 1H), 3.70 (d, J=13.9 Hz, 1H), 3.86–3.39 (m, 2H), 2.35 (d, J=17.8 Hz, 1H), 2.45–1.35 (m, 10H), 2.08 (s, 3H), 1.87 (d, J=6.6 Hz, 3H), 1.74 (d, J=1.2 Hz, 3H), 1.70 (s, 3H), 1.65 (s, 6H); minor isomer 9.59 (ddd, J=16.6, 11.5, 1.0 Hz, 1H), 7.40 (s, 1H), 6.61 (d, J=11.5 Hz, 1H), 6.34 (t, J=11.5 Hz, 1H), 5.99 (d, J=16.6 Hz, 1H), 5.82 (br d, J=9.3 Hz, 1H), 5.58 (q, J=6.6 Hz, 1H), 5.43 (br s, 1H), 5.01 (dd, J=9.3, 1.5 Hz, 1H), 4.57 (br, 1H), 4.05 (d, J=17.8 Hz, 1H), 3.84 (d, J=13.8 Hz, 1H), 3.71 (d, J=13.9 Hz, 1H), 3.86–3.39 (m, 2H), 2.34 (d, J=17.8 Hz, 1H), 2.45–1.35 (m, 10H), 2.08 (s, 3H), 1.93 (d, J=6.6 Hz, 3H), 1.77 (d, J=1.5 Hz, 3H), 1.69 (s, 3H), 1.65 (s, 6H)

FABMS m/z 749 (M+H)$^+$

HRFABMS calcd for C$_{35}$H$_{45}$N$_2$O$_{10}$S$_3$ (M+H)$^+$ 749.2236, found 749.2262

Example 118

Synthesis of Compound 124

DC107 (52 mg, 0.10 mmol) was dissolved in acetonitrile (3.0 mL). Thereto were added potassium carbonate (46 mg, 0.31 mmol) and 3-bromomethyl-4-methyl-1,5,9-trioxaspiro[5.5]-3-undecen-2-one (85 mg, 0.31 mmol). This mixture was stirred at 25° C. for 2 hours. After the ordinary post-treatment, the reaction product was purified by thin-layer chromatography (developed with chloroform/methanol=97/3) to obtain Compound 124 (34 mg, yield 47%).

$^1$H NMR (CDCl$_3$, 500 MHz)δ ppm; 8.45 (ddd, J=16.4, 11.2, 1.0 Hz, 1H), 7.34 (s, 1H), 6.58 (d, J=11.2 Hz, 1H), 6.23 (t, J=11.2 Hz, 1H), 6.17 (d, J=16.4 Hz, 1H), 5.72 (br d, J=8.7 Hz, 1H), 5.40 (q, J=6.8 Hz, 1H), 4.94 (dd, J=8.7, 3.2 Hz, 1H), 4.35 (br s, 1H), 3.90 (d, J=17.8 Hz, 1H), 3.88–3.70 (m, 4H), 3.80 (d, J=13.8 Hz, 1H), 3.71 (d, J=13.8 Hz, 1H), 2.38–1.70 (m, 8H), 2.29 (d, J=17.8 Hz, 1H), 2.12 (s, 3H), 2.01 (d, J=6.8 Hz, 3H), 1.77 (s, 3H), 1.75 (d, J=1.0 Hz, 3H)

FABMS m/z 707 (M+H)$^+$

HRFABMS calcd for C$_{32}$H$_{39}$N$_2$O$_{10}$S$_3$ (M+H)$^+$ 707.1767, found 707.1781

Example 119

Synthesis of Compound 125

Compound S-1 (85 mg, 0.11 mmol) obtained in Reference Example 1 was dissolved in acetonitrile (4.0 mL). Thereto were added potassium carbonate (43 mg, 0.31 mmol) and 3-bromomethyl-4-methyl-1,5,9-trioxaspiro[5.5]-3-undecen-2-one (85 mg, 0.31 mmol). This mixture was stirred at 25° C. for 2 hours. After the ordinary post-treatment, the reaction product was purified by thin-layer chromatography (developed with chloroform/methanol=97/3) to obtain Compound 125 (48 mg, yield 55%).

$^1$H NMR (CDCl$_3$, 500 MHz)δ ppm; 9.59, 9.40 (ddd, J=16.5, 11.5, 1.0 Hz, 1H), 7.40, 7.39 (s, 1H), 6.61, 6.59 (d, J=11.5 Hz, 1H), 6.36, 6.34 (t, J=11.5 Hz, 1H), 6.04, 5.99 (d, J=16.5 Hz, 1H), 5.83, 5.79 (br d, J=9.2 Hz, 1H), 5.58, 5.56 (q, J=6.6 Hz, 1H), 5.44, 5.42 (br s, 1H), 5.01, 4.73 (dd, J=9.2, 1.2 Hz, 1H), 4.70, 4.57 (m, 1H), 4.05, 4.04 (d, J=17.8 Hz, 1H), 3.87–3.35 (m, 8H), 2.45–1.30 (m, 14H), 2.34, 2.33 (d, J=17.8 Hz, 1H), 2.12, 2.11 (s, 3H), 1.93, 1.87 (d, J=6.6 Hz, 3H), 1.77, 1.74 (d, J=1.0 Hz, 3H), 1.69, 1.68 (s, 3H)

FABMS m/z 791 (M+H)$^+$

HRFABMS calcd for C$_{37}$H$_{47}$N$_2$O$_{11}$S$_3$ (M+H)$^+$ 791.2342, found 791.2318

Example 120

Synthesis of Compound 126

DC107 (61 mg, 0.12 mmol) was dissolved in acetonitrile (4.0 mL). Thereto were added potassium carbonate (32 mg, 0.23 mmol) and 3-bromomethyl-9-ethoxycarbonyl-4-methyl-9-aza-1,5-dioxaspiro[5.5]-3-undecen-2-one (80 mg, 0.23 mmol). This mixture was stirred at 25° C. for 1 hour. After the ordinary post-treatment, the reaction product was purified by thin-layer chromatography (developed with chloroform/methanol=97/3) to obtain Compound 126 (38 mg, yield 41%).

$^1$H NMR (CDCl$_3$, 400 MHz)δ ppm; 8.46 (ddd, J=16.3, 11.5, 1.0 Hz, 1H), 7.35 (s, 1H), 6.59 (d, J=12.0 Hz, 1H) 6.23 (dd, J=12.0, 11.5 Hz, 1H), 6.17 (d, J=16.5 Hz, 1H), 5.72 (br d, J=16.3 Hz, 1H), 5.40 (q, J=6.8 Hz, 1H), 5.38 (br s, 1H), 4.94 (br d, J=8.6 Hz, 1H), 4.14 (q, J=7.1 Hz, 2H), 3.91 (d, J=17.8 Hz, 1H), 3.79 (d, J=13.9 Hz, 1H), 3.77 (br s, 1H), 3.71 (d, J=13.9 Hz, 1H), 3.65–3.50 (m, 4H), 2.40–1.70 (m, 8H), 2.30 (d, J=17.8 Hz, 1H), 2.11 (s, 3H), 2.01 (d, J=6.8 Hz, 3H) 1.77 (s, 3H), 1.75 (d, J=1.2 Hz, 3H), 1.26 (t, J=7.1 Hz, 3H)

FABMS m/z 778 (M+H)$^+$

HRFABMS calcd for C$_{35}$H$_{44}$N$_3$O$_{11}$S$_3$ (M+H)$^+$ 778.2138, found 778.2126

Example 121

Synthesis of Compound 127

Compound S-1 (59 mg, 0.10 mmol) obtained in Reference Example 1 was dissolved in acetonitrile (4.0 mL). Thereto were added potassium carbonate (28 mg, 0.20 mmol) and 3-bromomethyl-9-ethoxycarbonyl-4-methyl-9-aza-1,5-dioxaspiro[5.5]-3-undecen-2-one (70 mg, 0.20 mmol). This mixture was stirred at 25° C. for 3 hours. After the ordinary post treatment, the reaction product was purified by thin-layer chromatography (developed with chloroform/methanol=97/3) to obtain Compound 127 (51 mg, yield 59%).

$^1$H NMR (CDCl$_3$, 400 MHz)δ ppm; 1:1 mixture 9.59, 9.40 (ddd, J=16.6, 11.5, 1.0 Hz, 1H), 7.41, 7.40 (s, 1H), 6.61, 6.60 (d, J=11.5 Hz, 1H), 6.36, 6.34 (d, J=11.5 Hz, 1H), 6.04, 5.99 (d, J=16.6 Hz, 1H), 5.83, 5.80 (br d, J=9.6 Hz, 1H), 5.58, 5.56 (q, J=6.6 Hz, 1H), 5.41, 5.39 (br s, 1H), 5.01, 4.73 (dd, J=9.0, 1.2 Hz, 1H), 4.71, 4.57 (br, 1H), 4.14 (d, J=7.0 Hz, 2H), 4.06, 4.05 (d, J=17.8 Hz, 1H), 3.86–3.40 (m, 8H), 2.35, 2.34 (d, J=17.8 Hz, 1H), 2.47–1.38 (m, 14H), 2.11 (s, 3H), 1.93, 1.87 (d, J=6.6 Hz, 3H), 1.77, 1.74 (d, J=1.2 Hz, 3H), 1.69, 1.69 (s, 3H), 1.27 (t, J=7.0 Hz, 3H)

FABMS m/z 862 (M+H)$^+$

HRFABMS calcd for $C_{40}H_{52}N_3O_{12}S_3$ (M+H)$^+$ 862.2173, found 862.2724

Example 122

Synthesis of Compound 128

DC107 (51 mg, 0.10 mmol) was dissolved in dimethylformamide (10 mL). Thereto were added potassium carbonate (56 mg, 0.41 mmol), N-(chloromethyl)phthalimide (30 mg, 0.15 mmol), and potassium iodide (2.5 mg, 0.015 mmol). This mixture was stirred at 25° C. for 2.5 hours. After the ordinary post-treatment, the reaction product was purified by thin-layer chromatography (developed with chloroform/methanol=95/5) to obtain Compound 128 (17 mg, yield 25%).

IR (KBr) 3420, 2962, 2930, 1776, 1720, 1649, 1612, 1467, 1413, 1383, 1274, 1118, 1073, 985, 915, 728 cm$^{-1}$ $^1$H NMR (CDCl$_3$, 400 MHz)δ ppm; 8.51 (ddd, J=16.4, 11.3, 1.0 Hz, 1H), 7.88–7.68 (m, 4H), 7.34 (s, 1H), 6.58 (d, J=11.7 Hz, 1H), 6.25 (d, J=16.4 Hz, 1H), 6.18 (d, J=16.4 Hz, 1H), 5.75 (br d, J=8.5 Hz, 1H), 5.58 (br s, 1H), 5.41 (q, J=6.8 Hz, 1H), 4.95 (dd, J=8.5, 3.9 Hz, 1H), 4.28–4.15 (m, 2H), 3.87 (d, J=17.8 Hz, 1H), 3.69 (d, J=3.9 Hz, 1H), 2.34 (d, J=17.8 Hz, 1H), 2.40–1.60 (m, 4H), 2.00 (d, J=6.8 Hz, 3H), 1.81 (s, 3H), 1.77 (d, J=1.2 Hz, 3H)

FABMS m/z 670 (M+H)$^+$

HRFABMS calcd for $C_{31}H_{32}N_3O_8S_3$ (M+H)$^+$ 670.1351, found 670.1351

Example 123

Synthesis of Compound 129

Compound S-1 (34 mg, 0.057 mmol) obtained in Reference Example 1 was dissolved in acetonitrile (3.0 ML). Thereto were added potassium carbonate (40 mg, 0.29 mmol), N-(chloromethyl)phthalimide (57 mg, 0.29 mmol), and potassium iodide (4.7 mg, 0.028 mmol) This mixture was stirred at 25° C. for 4.5 hours. After the ordinary post-treatment, the reaction product was purified by thin-layer chromatography (developed with chloroform/methanol=95/5) to obtain Compound 129 (33 mg, yield 77%).

IR (KBr) 3420, 2938, 1777, 1721, 1648, 1608, 1467, 1416, 1383, 1261, 1115, 1073, 1022, 971, 914, 729 cm$^{-1}$ $^1$H NMR (CDCl$_3$, 500 MHz)δ ppm; 9.61 (dd, J=16.5, 11.6 Hz, 1H), 7.90–7.72 (m, 4H), 7.39 (s, 1H), 6.61 (d, J=11.3 Hz, 1H), 6.35 (dd, J=11.6, 11.3 Hz, 1H), 6.00 (dd, J=16.5, 1.0 Hz, 1H), 5.83 (br d, J=9.5 Hz, 3H), 5.58 (q, J=6.7 Hz, 1H), 5.57 (br s, 1H), 5.18 (d, J=13.4 Hz, 1H), 5.15 (d, J=13.4 Hz, 1H), 5.03 (dd, J=9.5, 1.2 Hz, 1H), 4.58 (br t, J=4.3 Hz, 1H), 4.00 (d, J=17.7 Hz, 1H), 3.86–3.81 (m, 1H), 3.54–3.47 (m, 1H), 2.52–2.42 (m, 3H), 2.46 (d, J=17.7 Hz, 1H), 1.94 (d, J=6.7 Hz, 3H) ; 1.80 (d, J=1.2 Hz, 3H), 1.74 (s, 3H), 1.76–1.38 (m, 7H)

FABMS m/z 754 (M+H)$^+$

HRFABMS calcd for $C_{36}H_{40}N_3O_9S_3$ (M+H)$^+$ 754.1926, found 754.1931

Example 124

Synthesis of Compound 130

Compound 27 (100 mg, 0.119 mmol) obtained in Example 26 was dissolved in dichloromethane (10 mL). Thereto were added dihydropyran (274 μL) and camphorsulfonic acid (6.6 mg). This mixture was stirred at 0° C. for 30 minutes. After the reaction mixture was subjected to the ordinary post-treatment, the reaction product was purified by column chromatography (silica gel; eluted with chloroform/methanol=100/1) to obtain Compound 130 (101 mg, yield 92%). Compound 130 was obtained as a mixture of diastereomers attributable to the asymmetric carbon of the tetrahydropyranyl group; they were found through HPLC to be in the ratio of approximately 4:3.

$^1$H NMR (CDCl$_3$, 270 MHz)δ ppm; (a mixture of two diastereomers, approx. 4:3) 9.62 (dd, J=11.7, 16.5 Hz) and 9.43 (dd, J=11.7, 16.5 Hz) (total 1H), 7.74 (br d, J=ca. 8 Hz, 1H), 7.42 (s) and 7.41 (s) (total 1H), 6.62 (d, J=11.5 Hz) and 6.61 (d, J=11.5 Hz) (total 1H), 6.37 (t, J=11.5 Hz) and 6.34 (t, J=11.5 Hz) (total 1H), 6.04 (d, J=16.5 Hz) and 6.00 (d, J=16.5 Hz) (total 1H), 5.84 (br d, J=8.6 Hz) and 5.81 (br d, J=8.6 Hz) (total 1H), 5.64 (s) and 5.62 (s) (total 1H), 5.59 (q, J=6.6 Hz) and 5.56 (q, J=6.6 Hz) (total 1H), 5.39 (s, 2H), 5.02 (br d, J=8.3 Hz) and 4.9–4.6 (overlapped with other peaks) (total 1H), 4.9–4.6 (1H, overlapped with other peaks), 4.9–4.6 (overlapped with other peaks) and 4.57 (br s) (total 1H), 4.06 (d, J=17.8 Hz) and 4.05 (d, J=17.8 Hz) (total 1H), 4.0–3.4 (m, 6H), 3.76 (s, 3H), 2.5–1.4 (m, 15H), 1.94 (d, J=6.6 Hz) and 1.87 (d, J=6.6 Hz) (total 3H), 1.77 (s) and 1.74 (s) (total 3H), 1.68 (s, 3H), 1.48 (s, 6H), 1.00 (s, 3H)

FABMS m/z 924 (M+H)$^+$ calcd for $C_{42}H_{57}N_3O_{14}S_3$=923

Example 125

Synthesis of Compound 131

Compound 130 (90 mg, 0.098 mmol) obtained in Example 124 was dissolved in THF (10 mL). Thereto was added hydrochloric acid (1 M, 10 mL). This mixture was stirred at room temperature for 2.5 hours. After the reaction mixture was subjected to the ordinary post-treatment, the reaction product was purified by thin-layer chromatography (silica gel; developed with chloroform/methanol=20/1) to obtain Compound 131 (33 mg, 0.037 mmol, yield 38%). Compound 131 was obtained as a mixture of diastereomers attributable to the asymmetric carbon of the tetrahydropyranyl group; they were found through HPLC to be in the ratio of approximately 5:4.

$^1$H NMR (CDCl$_3$, 270 MHz)δ ppm; (a mixture of two diastereomers, approx. 5:4) 9.63 (dd, J=11.6, 16.5 Hz) and 9.43 (dd, J=11.6, 16.5 Hz) (total 1H), 7.64 (br d, J=7.3 Hz, 1H), 7.42 (s) and 7.41 (s) (total 1H), 6.61 (d, J=11.5 Hz) and 6.60 (d, J=11.5 Hz) (total 1H), 6.37 (t, J=11.5 Hz) and 6.34 (t, J=11.5 Hz) (total 1H), 6.04 (d, J=16.5 Hz) and 6.00 (d, J=16.5 Hz) (total 1H), 5.83 (br d, J=ca. 8 Hz) and 5.80 (br d, J=ca. 8 Hz) (total 1H), 5.69 (s) and 5.67 (s) (total 1H), 5.58 (q, J=6.6 Hz) and 5.56 (q, J=6.6 Hz) (total 1H), 5.40 (s, 2H), 5.01 (d, J=9.2 Hz) and 4.74 (d, J=9.2 Hz) (total 1H), 4.88 (br s, 1H), 4.72 (br s) and 4.7–4.5 (overlapped with other peaks) (total 1H), 4.7–4.5 (m, 1H), 4.10 (d, J=17.8 Hz) and 4.09 (d, J=17.8 Hz) (toatl 1H), 4.1–3.4 (m, 6H), 3.76 (s, 3H), 3.20 (br s, 1H), 2.6–1.4 (m, 14H), 2.33 (d, J=17.8 Hz, 1H), 1.94 (d, J=6.6 Hz) and 1.87 (d, J=6.6 Hz) (total 3H), 1.77 (s) and 1.74 (s) (total 3H), 1.65 (s, 3H), 1.10 (s, 3H)

FABMS m/z 884 (M+H)$^+$ calcd for $C_{39}H_{53}N_3O_{14}S_3$=883

Example 126

Synthesis of Compound 132

Compound 81 (54 mg, 0.054 mmol) obtained in Example 75 was dissolved in methanol (6.1 mL). Thereto was added 3.0 N hydrochloric acid (0.61 mL, 1.8 mmol). This mixture was stirred at 0° C. for 30 minutes. After the ordinary post-treatment, the reaction product was purified by thin-layer chromatography (developed with chloroform/methanol=10/1) to obtain Compound 132 (34 mg, yield 83%). $^1$H NMR revealed that Compound 132 was an approximately 4:1 mixture of diastereomers.

$^1$H NMR (CD$_3$OD, 400 MHz)δ ppm; 9.22 (dd, J=16.3, 11.4 Hz) and 9.07 (dd, J=16.3, 11.4 Hz) (total 1H), 7.65 (s) and 7.64 (s) (total 1H), 6.77 (d, J=11.4 Hz) and 6.70 (d, J=11.4 Hz) (total 1H), 6.46 (dd, J=11.4, 11.4 Hz) and 6.32 (dd, J=11.4, 11.4 Hz) (total 1H), 6.26 (d, J=16.3 Hz) and 6.03 (d, J=16.3 Hz) (total 1H), 5.76 (d, J=8.8 Hz, 1H), 5.54 (q, J=6.6 Hz, 1H), 4.98 (d, J=3.0 Hz, 1H), 4.89 (d, J=8.8 Hz, 1H), 4.54 (d, J=14.0 Hz) and 4.47 (d, J=14.0 Hz) (total 1H), 4.40 (d, J=14.0 Hz) and 4.36 (d, J=14.0 Hz) (total 1H), 3.88–3.23 (m, 7H), 3.84 (d, J=18.6 Hz) and 2.49 (d, J=18.6 Hz) (total 2H), 2.13–2.05 (m, 6H), 1.93 (d, J=6.8 Hz, 3H), 1.73 (d, J=8.8 Hz, 3H), 1.50 (s, 3H)

FABMS m/z 785 (M+H)$^+$ calcd for C$_{33}$H$_{40}$N$_2$O$_{14}$S$_3$=784

Example 127

Synthesis of Compound 133

According to Example 69, Compound 133 (26 mg, yield 80%) was obtained from DC107 (24 mg, 0.047 mmol), Compound S-35 (80 mg, 0.19 mmol) obtained in Reference Example 35, acetonitrile (3.6 mL), and potassium carbonate (26 mg, 0.19 mmol). $^1$H NMR revealed that Compound 133 was an approximately 3:1 mixture of diastereomers.

$^1$H NMR (CDCl$_3$, 400 MHz)δ ppm; 8.44 (ddd, J=16.4, 11.3, 0.8 Hz, 1H), 7.36 (s, 1H), 6.59 (d, J=11.3 Hz, 1H), 6.22 (dd, J=11.3, 11.3 Hz, 1H), 6.17 (d, J=16.3 Hz, 1H), 5.93 (d, J=7.8 Hz, 1H), 5.79 (ddd, J=10.2, 2.7, 1.9 Hz, 1H), 5.72 (d, J=7.8 Hz, 1H), 5.32 (ddd, J=10.2, 3.1, 1.7 Hz, 1H), 5.51 (br s, 1H), 5.41 (q, J=6.8 Hz, 1H), 5.10 (m, 1H), 4.95 (d, J=7.8 Hz, 1H), 4.58 (d, J=13.4 Hz, 1H), 4.51 (d, J=13.4 Hz, 1H), 4.23 (m, 1H), 4.08 (m, 1H), 3.90 (d, J=15.2 Hz, 1H), 3.80 (d, J=15.2 Hz, 1H), 3.88 (d, J=17.9 Hz, 1H), 2.30–2.17 (m, 4H), 2.25 (d, J=17.6 Hz, 1H), 2.09 (s, 3H), 2.01 (d, J=6.9 Hz, 3H), 1.73 (s, 3H), 1.72 (s, 3H), 1.22 (d, J=6.0 Hz, 3H)

FABMS m/z 793 (M+H)$^+$ calcd for C$_{35}$H$_{40}$N$_2$O$_{13}$S$_3$=792

Example 128

Synthesis of Compound 134

According to Example 70, Compound 134 (20 mg, yield 89%) was obtained from Compound S-1 (18 mg, 0.030 mmol) obtained in Reference Example 1, Compound S-35 (51 mg, 0.12 mmol) obtained in Reference Example 35, acetonitrile (2.7 mL), and potassium carbonate (17 mg, 0.12 mmol). $^1$H NMR revealed that Compound 134 was an approximately 3:3:1:1 mixture of diastereomers.

$^1$H NMR (CDCl$_3$, 400 MHz)δ ppm; 9.58 (ddd, J=16.6, 11.5, 0.7 Hz) and 9.39 (ddd, J=16.6, 11.5, 0.7 Hz) (total 1H), 7.41 (s) and 7.39 (s) (total 1H), 6.62 (d, J=11.5 Hz) and 6.61 (d, J=11.5 Hz) (total 1H), 6.37 (dd, J=11.5, 11.5 Hz) and 6.34 (dd, J=11.5, 11.5 Hz) (total 1H), 6.04 (d, J=16.6 Hz) and 6.00 (d, J=16.6 Hz) (total 1H), 5.90 (d, J=9.3 Hz, 1H), 5.82 (d, J=10.5 Hz, 1H), 5.79 (ddd, J=10.5, 2.5, 2.5 Hz, 1H), 5.56 (m, 1H), 5.07 (m, 1H), 5.01 (dd, J=9.3, 1.2 Hz) and 4.73 (dd, J=9.3, 1.2 Hz) (total 1H), 4.58 (m, 1H), 4.57 (dd, J=13.9, 2.0 Hz) and 4.47 (dd, J=13.9, 2.0 Hz) (total 2H), 4.03 (d, J=17.5 Hz) and 4.02 (d, J=17.5 Hz) (total 1H), 3.96 (m, 1H), 3.87 (s, 1H), 3.83 (d, J=15.1 Hz) and 3.82 (d, J=15.1 Hz) (total 2H), 3.50–3.43 (m, 2H), 2.43–2.27 (m, 4H), 2.31 (d, J=17.5 Hz) and 2.30 (d, J=17.5 Hz) (total 1H), 2.09 (s, 3H), 1.93 (d, J=6.6 Hz) and 1.78 (d, J=6.6 Hz) (total 3H), 1.82– 1.40 (m, 6H), 1.76 (d, J=1.3 Hz) and 1.74 (d, J=1.3 Hz) (total 3H), 1.68 (s, 3H), 1.23 (d, J=6.3 Hz, 3H)

FABMS m/z 877 (M+H)$^+$ calcd for C$_{40}$H$_{48}$N$_2$O$_{14}$S$_3$=876

Example 129

Synthesis of Compound 135

According to Example 69, Compound 135 (49 mg, yield 75%) was obtained from DC107 (34 mg, 0.066 mmol), Compound S-36 (0.15 g, 0.27 mmol) obtained in Reference Example 36, acetonitrile (5.1 mL), and potassium carbonate (37 mg, 0.27 mmol). $^1$H NMR revealed that Compound 135 was an approximately 2:1 mixture of diastereomers.

$^1$H NMR (CDCl$_3$, 400 MHz)δ ppm; 8.48 (ddd, J=16.4, 11.3, 1.0 Hz, 1H), 7.36 (s, 1H), 6.59 (d, J=11.3 Hz, 1H), 6.23 (dd, J=11.3, 11.3 Hz, 1H), 6.17 (d, J=16.4 Hz, 1H), 5.75 (d, J=8.5 Hz, 1H), 5.52 (s) and 5.51 (s) (total 1H), 5.41 (q, J=6.8 Hz, 1H), 4.96 (d, J=8.6 Hz, 1H), 4.82 (d, J=2.7 Hz, 1H), 4.59 (d, J=14.2 Hz, 1H), 4.45 (d, J=14.0 Hz, 1H), 4.40 (d, J=13.9 Hz, 1H), 4.32 (d, J=13.2 Hz, 1H), 3.89 (d, J=17.9 Hz) and 3.88 (d, J=17.9 Hz) (total 1H), 3.83–3.20 (m, 3H), 2.25 (d, J=17.9 Hz, 1H), 2.20 (m, 6H), 2.02 (d, J=6.8 Hz, 3H), 1.76 (s) and 1.75 (s) (total 3H), 1.74 (s, 3H), 1.28 (d, J=6.1 Hz) and 1.22 (d, J=6.1 Hz) (total 3H), 0.95 (m, 18H), 0.70–0.58 (m, 12H)

FABMS m/z 997 (M+H)$^+$ calcd for C$_{45}$H$_{68}$N$_2$O$_{13}$S$_3$Si$_2$=996

Example 130

Synthesis of Compound 136

According to Example 70, Compound 136 (60 mg, yield 61%) was obtained from Compound S-1 (54 mg, 0.091 mmol) obtained in Reference Example 1, Compound S-36 (0.21 g, 0.35 mmol) obtained in Reference Example 36, acetonitrile (8.1 mL), and potassium carbonate (50 mg, 0.35 mmol). $^1$H NMR revealed that Compound 136 was an approximately 2:2:1:1 mixture of diastereomers.

$^1$H NMR (CDCl$_3$, 400 MHz)δ ppm; 9.58 (dd, J=16.4, 11.5 Hz) and 9.40 (dd, J=16.4, 11.5 Hz) (total 1H), 7.41 (s) and 7.39 (s) (total 1H), 6.61 (d, J=11.5 Hz) and 6.60 (d, J=11.5 Hz) (total 1H), 6.37 (dd, J=11.5, 11.5 Hz) and 6.33 (dd, J=11.5, 11.5 Hz) (total 1H), 6.05 (d, J=16.4 Hz) and 6.00 (d, J=16.4 Hz) (total 1H), 5.83 (d, J=10.5 Hz) and 5.82 (d, J=10.5 Hz) (total 1H), 5.57 (m, 1H), 5.01 (dd, J=9.3, 1.2 Hz) and 4.74 (dd, J=9.3, 1.2 Hz) (total 1H), 4.83 (d, J=3.1 Hz) and 4.59 (m) (total 1H), 4.71 (m) and 4.58 (m) (total 1H), 4.58 (d, J=14.4 Hz, 1H), 4.47 (d, J=14.4 Hz, 1H), 4.40 (dd, J=14.2, 1.5 Hz, 1H), 4.33 (d, J=14.2 Hz, 1H), 4.04 (d, J=17.6 Hz) and 4.03 (d, J=17.6 Hz) (total 1H), 3.92–3.72 (m, 2H), 3.64–3.40 (m, 2H), 3.17 (m, 1H), 2.80 (m, 4H), 2.29 (d, J=17.6 Hz) and 2.28 (d, J=17.6 Hz) (total 1H), 1.94 (d, J=6.6 Hz) and 1.88 (d, J=6.6 Hz) (total 3H), 1.60–1.40 (m, 8H), 1.78 (d, J=0.9 Hz) and 1.74 (d, J=0.9 Hz) (total 3H), 1.69 (s) and 1.68 (s) (total 3H), 1.29 (d, J=6.0 Hz) and 1.24 (d, J=6.0 Hz) (total 3H), 0.97 (m, 18H), 0.68–0.59 (m, 12H)

FABMS m/z 1081 (M+H)$^+$ calcd for C$_{50}$H$_{76}$N$_2$O$_{14}$S$_3$Si$_2$=1080

Example 131

Synthesis of Compound 137

According to Example 77, Compound 137 (12 mg, yield 37%) was obtained from Compound 136 (41 mg, 0.091 mmol) obtained in Example 130, tetrahydrofuran (4.1 mL), acetic acid (0.0086 mL, 0.15 mmol), and 1.0 N tetrabutylammonium fluoride solution in tetrahydrofuran (0.15 mL, 0.15 mmol). $^1$H NMR revealed that Compound 137 was an approximately 2:2:1:1 mixture of diastereomers.

$^1$H NMR (CDCl$_3$, 400 MHz)δ ppm; 9.56 (ddd, J=16.6, 11.7, 0.7 Hz) and 9.55 (ddd, J=16.6, 11.7, 0.7 Hz) and 9.37 (ddd, J=16.6, 11.7, 0.7 Hz) and 9.36 (ddd, J=16.6, 11.7, 0.7 Hz) (total 1H), 7.41 (s) and 7.40 (s) and 7.39 (s) (total 1H), 6.63 (d, J=11.7 Hz) and 6.61 (d, J=11.7 Hz) (total 1H), 6.36 (dd, J=11.7, 11.7 Hz) and 6.34 (dd, J=11.7, 11.7 Hz) (total 1H), 6.04 (d, J=16.6 Hz) and 6.00 (d, J=16.6 Hz) (total 1H), 5.82 (dd, J=10.5, 0.7 Hz) and 5.78 (dd, J=10.5, 0.7 Hz) (total 1H), 5.57 (m, 1H), 5.52 (br s) and 4.99 (br s) (total 1H), 4.97 (m, 1H), 5.03 (dd, J=9.3, 1.0 Hz) and 4.74 (dd, J=9.3, 1.0 Hz) (total 1H), 4.71 (m) and 4.53 (m) (total 1H), 4.62 (d, J=13.9 Hz) and 4.49 (d, J=13.9 Hz) and 4.48 (d, J=13.9 Hz) and 4.47 (d, J=13.9 Hz) and 4.32 (d, J=13.9 Hz) (total 2H), 4.04 (d, J=17.6 Hz) and 4.03 (d, J=17.6 Hz) (total 1H), 3.96 (d, J=15.3 Hz) and 3.91 (d, J=15.3 Hz) and 3.84 (d, J=15.3 Hz) and 3.77 (d, J=15.3 Hz) (total 2H), 3.90–3.57 (m, 2H), 3.53–3.40 (m, 2H), 3.20 (m) and 2.98 (m) (total 1H), 2.33 (d, J=17.6 Hz, 1H), 2.32 (m, 4H), 1.94 (d, J=6.6 Hz) and 1.88 (d, J=6.6 Hz) (total 3H), 1.74–1.58 (m, 8H), 1.79 (d, J=0.9 Hz) and 1.74 (d, J=0.9 Hz) (total 3H), 1.69 (m, 3H), 1.35 (d, J=6.1 Hz) and 1.31 (d, J=6.1 Hz) (total 3H)

FABMS m/z 853 (M+H)$^+$ calcd for C$_{38}$H$_{48}$N$_2$O$_{14}$S$_3$=852

Example 132

Synthesis of Compound 138

To a solution of Compound S-37 (1.55 g, 5.04 mmol) obtained in Reference Example 37 and DC107 (251 mg, 0.492 mmol) in acetone (15 mL) were added powdered potassium iodide (830 mg, 5.00 mmol) and potassium carbonate (348 mg, 2.52 mmol). The resultant suspension was stirred at 25° C. for 11 hours. After the reaction mixture was subjected to the ordinary post-treatment, the reaction product was purified by silica gel chromatography (eluted with chloroform/methanol=100/1 to 50/1) to obtain Compound 138 (291 mg, yield 76%).

$^1$H NMR (CDCl$_3$, 270 MHz)δ ppm; 8.46 (dd, J=11.6, 16.7 Hz, 1H), 7.36 (s, 1H), 7.17 (m, 1H), 6.59 (d, J=11.9 Hz, 1H), 6.23 (t, J=11.7 Hz, 1H), 6.17 (d, J=16.7 Hz, 1H), 5.71 (br d, J=ca. 10 Hz, 1H), 5.69 (br s, 1H), 5.41 (q, J=6.9 Hz, 1H), 5.40 (s, 2H), 4.94 (br d, J=8.6 Hz, 1H), 4.0–3.8 (2H, overlapped with other peaks), 3.89 (d, J=12.5 Hz, 2H), 3.74 (d, J=12.5 Hz, 2H), 3.33 (m, 2H), 2.5–1.6 (m, 9H), 2.01 (d, J=6.9 Hz, 3H), 1.76 (d, J=1.3 Hz, 3H), 1.73 (s, 3H), 1.46 (s, 3H) 1.41 (s, 3H), 0.98 (s, 3H)

FABMS m/z 782 (M+H)$^+$ calcd for C$_{35}$H$_{47}$N$_3$O$_{11}$S$_3$=781

Example 133

Synthesis of Compound 139

Compound 138 (213 mg, 0.273 mmol) obtained in Example 132 was dissolved in THF (18 mL). Thereto was added hydrochloric acid (1 M, 18 ml). This mixture was stirred at 25° C. for 2.5 hours. After the reaction mixture was subjected to the ordinary post-treatment, the reaction product was purified by silica gel chromatography (eluted with chloroform/methanol=100/1 to 96/4) and HPLC for fractionation (ODS; acetonitrile/water=30/70) to obtain Compound 139 (11 mg, yield, 5.3%).

$^1$H NMR (CDCl$_3$, 270 MHz)δ ppm; 8.44 (dd, J=11.2, 16.4 Hz, 1H), 7.36 (s, 1H), 7.13 (m, 1H), 6.59 (d, J=11.9 Hz, 1H), 6.24 (t, J=11.6 Hz, 1H), 6.18 (d, J=6.4 Hz, 1H), 5.70 (br d, J=8.8 Hz, 1H), 5.66 (br s, 1H), 5.43 (q, J=6.9 Hz, 1H), 5.40 (s, 2H), 4.96 (dd, J=3.6, 8.8 Hz, 1H), 3.94 (br d, J=3.6 Hz, 1H), 3.93 (d, J=17.8 Hz, 1H), 3.72 (m, 4H), 3.54 (br s, 2H), 3.30 (m, 2H), 2.4–1.7 (m, 8H), 2.31 (d, J=17.8 Hz, 1H), 2.02 (d, J=6.9 Hz, 3H), 1.76 (d, J=1.0 Hz, 3H), 1.71 (s, 3H), 1.05 (s, 3H)

FABMS m/z 742 (M+H)$^+$ calcd for C$_{32}$H$_{43}$N$_3$O$_{11}$S$_3$=741

Example 134

Synthesis of Compound 140

To a solution of Compound S-38 (852 mg, 2.09 mmol) obtained in Reference Example 38 and DC107 (107 mg, 0.210 mmol) in acetone (5.0 mL) were added powdered potassium iodide (348 mg, 2.10 mmol) and potassium carbonate (145 mg, 1.05 mmol). The resultant suspension was stirred at 25° C. for 13.5 hours. After the reaction mixture was subjected to the ordinary post-treatment, the reaction product was purified by silica gel chromatography (eluted with chloroform/methanol=100/1 to 50/1) to obtain Compound 140 (185 mg, yield 100%).

$^1$H NMR (CDCl$_3$, 270 MHz) ppm; 8.45 (dd, J=11.6, 16.5 Hz, 1H), 7.35 (s, 1H), 7.23 (m, 1H), 6.59 (d, J=11.6 Hz, 1H), 6.23 (t, J=11.6 Hz, 1H), 6.17 (d, J=16.5 Hz, 1H), 5.73 (br d, J=ca. 8 Hz, (H), 5.51 (br s, 1H) 5.41 (q, J=6.9 Hz, 1H) 5.40 (s, 2H), 4.95 (dd, J 3.6, 8.9 Hz, 1H), 4.55 (s, 1H), 4.31 (d, J=1.7 Hz, 1H), 4.18 (d, J=1.7 Hz, 1H), 4.11 (s, 2H), 3.89 (d, J=17.8 Hz, 1H) 3.80 (br d, J=3.6 Hz, 1H), 3.5–3.2 (m, 2H), 2.5–1.6 (m, 8H), 2.28 (d, J=17.8 Hz, 1H), 2.02 (d, J=6.9 Hz, 3H), 1.75 (s, 6H), 1.43 (s, 6H), 1.29 (s, 6H)

FABMS m/z 882 (M+H)$^+$ calcd for C$_{39}$H$_{51}$N$_3$O$_{14}$S$_3$=881

Example 135

Synthesis of Compound 141

Compound 140 (185 mg, 0.210 mmol) obtained in Example 134 was dissolved in THF (22 mL). Thereto was added hydrochloric acid (1 M, 22 mL). This mixture was stirred at 25° C. for 2 hours. After the reaction mixture was subjected to the ordinary post-treatment, the reaction mixture was purified by HPLC for fractionation (ODS; eluted with acetonitrile/water=30/70 to 40/60) to obtain Compound 141 (77 mg, yield 43%).

$^1$H NMR (CDCl$_3$, 270 MHz)δ ppm; 8.48 (dd, J=11.2, 16.4 Hz, 1H), 7.36 (s, 1H), 7.14 (m, 1H), 6.59 (d, J=11.9 Hz, 1H), 6.24 (t, J=11.6 Hz, 1H), 6.18 (d, J=16.4 Hz, 1H), 5.72 (br d, J=ca. 9 Hz, 1H), 5.50 (br s, 1H), 5.41 (q, J=6.9 Hz, 1H), 5.40 (s, 2H), 4.97 (dd, J=3.8, 8.6 Hz, 1H), 4.80 (d, J=8.8 Hz, 1H), 4.55 (s, 1H), 4.43 (m, 1H), 4.30 (dd, J=3.0, 8.8 Hz, 1H), 4.00 (m, 2H), 3.96 (d, J=17.8 Hz, 1H), 3.89 (d, J=3.8 Hz, 1H), 3.35 (m, 2H), 2.84 (m, 1H), 2.5–1.5 (m, 8H), 2.29 (d, J=17.8 Hz, 1H), 2.02 (d, J=6.9 Hz, 3H), 1.75 (d, j=1.0 Hz, 3H), 1.72 (s, 3H), 1.55 (s, 3H), 1.46 (s, 3H)

FABMS m/z 842 (M+H)$^+$ calcd for C$_{36}$H$_{47}$N$_3$O$_{14}$S$_3$=841

Example 136

Synthesis of Compound 142

To a solution of Compound S-39 (240 mg, 0.588 mmol) obtained in Reference Example 39 and DC107 (51 mg, 0.10 mmol) in acetone (2.5 mL) were added powdered potassium iodide (170 mg, 1.02 mmol) and potassium carbonate (70 mg, 0.51 mmol). The resultant suspension was stirred at 25° C. for 11 hours. After the reaction mixture was subjected to the ordinary post-treatment, the reaction product was purified by thin-layer chromatography (silica gel; developed with chloroform/methanol=20/1) to obtain Compound 142 (57 mg, yield 65%).

$^1$H NMR (CDCl$_3$, 270 MHz)δ ppm; 8.45 (dd, J=11.4, 16.6 Hz, 1H), 7.35 (s, 1H), 6.61 (br s, 1H), 6.59 (d, J=11.9 Hz, 1H), 6.23 (t, J=11.6 Hz, 1H), 6.18 (d, J=16.6 Hz, 1H), 5.73 (br d, J=8.9 Hz, 1H), 5.58 (d, J=4.8 Hz, 1H), 5.54 (br s, 1H), 5.41 (q, J=6.9 Hz, 1H), 5.39 (s, 2H), 4.95 (dd, J=3.8, 8.9 Hz, 1H), 4.64 (s, 2H), 4.35 (d, J=4.8 Hz, 1H), 4.27 (s, 1H), 3.89 (d, J=17.8 Hz, 1H), 3.79 (d, J=3.8 Hz, 1H), 3.5–3.1 (m, 2H), 2.5–1.5 (m, 8H), 2.28 (d, J=17.8 Hz, 1H), 2.02 (d, J=6.9 Hz, 3H), 1.76 (s, 6H), 1.51 (s, 3H), 1.39 (s, 3H), 1.34 (s, 3H), 1.32 (s, 3H)

FABMS m/z 882 (M+H)$^+$ calcd for C$_{39}$H$_{51}$N$_3$O$_{14}$S$_3$=881

Example 137

Synthesis of Compound 143

To a solution of Compound S-40 (1.54 g, 4.80 mmol) obtained in Reference Example 40 and DC107 (249 mg, 0.488 mmol) in acetone (13 mL) were added powdered potassium iodide (830 mg, 5.00 mmol) and potassium carbonate (347 mg, 2.50 mmol). The resultant suspension was stirred at 25° C. for 17.5 hours. After the reaction mixture was subjected to the ordinary post-treatment, the reaction product was purified by silica gel chromatography (eluted with chloroform/methanol=50/1 to 30/1) and HPLC for fractionation (eluted with acetonitrile/water=35/65) to obtain Compound 143 (57 mg, yield 15%).

$^1$H NMR (CDCl$_3$, 270 MHz)δ ppm; (a mixture of two diastereomers, approx. 5:4) 8.45 (dd, J=11.4, 15.8 Hz, 1H), 7.75 (br d, J=7.9 Hz) and 7.41 (br d, J=7.4 Hz) (total 1H), 7.36 (s, 1H), 7.01 (br s, 1H), 6.59 (d, J=11.4 Hz, 1H), 6.23 (t, J=1.4 Hz, 1H), 6.16 (d, J=15.8 Hz, 1H), 5.87 (br s) and 5.74 (br s) (total 1H), 5.69 (br d, J=ca. 9 Hz, 1H), 5.40 (q, J=6.9 Hz, 1H), 5.38 (s, 2H), 4.96 (br d, J=ca. 9 Hz, 1H), 4.54 (m, 1H), 4.27 (m) and 4.19 (m) (total 1H), 4.04 (br s, 1H), 3.92 (d, J=17.8 Hz, 1H), 3.74 (s) and 3.73 (s) (total 3H), 2.6–1.6 (m, 13H), 2.00 (d, J=6.9 Hz, 3H), 1.75 (s, 3H), 1.69 (s) and 1.67 (s) (total 3H)

FABMS m/z 795 (M+H)$^+$ calcd for C$_{34}$H$_{42}$N$_4$O$_{12}$S$_3$=794

Example 138

Synthesis of Compound 144

To a solution of chloromethyl 4-(L-pyroglutamylamino)butyrate (Compound S-41 obtained in Reference Example 41) (260 mg, 0.99 mmol) and DC107 (51 mg, 0.10 mmol) in acetone (2.5 mL) were added powdered potassium iodide (171 mg, 1.03 mmol) and potassium carbonate (70 mg, 0.51 mmol). The resultant suspension was stirred at 25° C. for 16.5 hours. After the reaction mixture was subjected to the ordinary post-treatment, the reaction product was purified by thin-layer chromatography (silica gel; developed with chloroform/methanol=9/1) and HPLC for fractionation (ODS; eluted with acetonitrile/water=30/70 to 35/65) to obtain Compound 144 (16 mg, yield 21%).

$^1$H NMR (CDCl$_3$, 270 MHz)δ ppm; (major peaks) 8.57 (dd, J=11.1, 16.3 Hz, 1H), 7.33 (s, 1H), 7.13 (m, 1H), 6.86 (br s, 1H), 6.58 (d, J=11.6 Hz, 1H), 6.25 (t, J=11.4 Hz, 1H), 6.15 (d, J=16.3 Hz, 1H), 5.72 (br d, J=8.8 Hz, 1H), 5.44 (q, J=6.9 Hz, 1H), 5.33 (s, 2H), 4.96 (br d, J=8.8 Hz, 1H), 4.22 (m, 1H), 4.18 (br s, 1H), 3.96 (d, J=17.8 Hz, 1H), 3.5–3.1 (m, 2H), 2.6–1.4 (m, 13H), 1.96 (d, J=6.9 Hz, 3H), 1.76 (s, 6H)

FABMS m/z 737 (M+H)$^+$ calcd for C$_{32}$H$_{40}$N$_4$O$_{10}$S$_3$=736

Example 139

Synthesis of Compound 145

To a solution of chloromethyl 4-(2-oxo-pyrrolidinyl)butyrate (Compound S-42 obtained in Reference Example 42) (2.19 g, 10.0 mmol) and DC107 (510 mg, 1.00 mmol) in acetone (25 mL) were added powdered potassium iodide (1.66 g, 10.0 mmol) and potassium carbonate (690 mg, 5.0 mmol). The resultant suspension was stirred at 25° C. for 18 hours. After the reaction mixture was subjected to the ordinary post-treatment, the reaction product was purified by silica gel chromatography (eluted with chloroform/methanol=100/1 to 50/1) and HPLC for fractionation (ODS; eluted with acetonitrile/water=30/70 to 40/60) to obtain Compound 145 (92 mg, yield 13%).

$^1$H NMR (CDCl$_3$, 270 MHz)δ ppm; 8.45 (dd, J=11.2, 16.4 Hz, 1H), 7.35 (s, 1H), 6.59 (d, J=11.9 Hz, 1H), 6.22 (t, J=11.7 Hz, 1H), 6.17 (d, J=16.4 Hz, 1H), 5.89 (br s, 1H), 5.70 (br d, J=8.9 Hz, 1H), 5.40 (s, 2H), 5.41 (q, J=6.9 Hz, 1H), 4.95 (br d, J=8.9 Hz, 1H), 3.93 (br s, 1H), 3.90 (d, J=17.8 Hz, 1H), 3.39 (m, 2H), 3.29 (m, 2H), 2.4–1.7 (m, 12H), 2.30 (d, J=17.8 Hz, 1H), 2.01 (d, J=6.9 Hz, 3H), 1.76 (d, J=1.0 Hz, 3H), 1.72 (s, 3H)

FABMS m/z 694 (M+H)$^+$ calcd for C$_{31}$H$_{39}$N$_3$O$_9$S$_3$=693

Example 140

Synthesis of Compound 146

To a solution of chloromethyl 2-oxa-4-(2-oxopyrrolidinyl)butyrate (Compound S-43 obtained in Reference Example 43) (225 mg, 1.02 mmol) and DC107 (55 mg, 0.11 mmol) in acetone (2.5 mL) were added powdered potassium iodide (166 mg, 1.00 mmol) and potassium carbonate (69 mg, 0.50 mmol). The resultant suspension was stirred at 25° C. for 14 hours. After the reaction mixture was subjected to the ordinary post-treatment, the reaction product was purified by thin-layer chromatography (silica gel; eluted with chloroform/methanol=20/1) to obtain Compound 146 (20 mg, yield 27%).

$^1$H NMR (CDCl$_3$, 270 MHz)δ ppm; 8.46 (dd, J=11.2, 16.5 Hz, 1H), 7.35 (s, 1H) 6.59 (d, J=11.9 Hz, 1H), 6.23 (t, J=11.7 Hz, 1H), 6.17 (d, J=16.5 Hz, 1H), 5.93 (br s, 1H), 5.71 (br d, J=8.6 Hz, 1H), 5.47 (d, J=11.2 Hz, 1H), 5.42 (d, J=11.2 Hz, 1H), 5.41 (q, J=6.9 Hz, 1H), 4.95 (d, J=8.9 Hz, 1H), 4.4–4.2 (m, 2H), 3.91 (d, J=17.8 Hz, 1H), 3.7–3.4 (m, 5H), 2.5–1.7 (m, 8H), 2.31 (d, J=17.8 Hz, 1H), 2.01 (d, J=6.6 Hz, 3H), 1.76 (d, J=1.0 Hz, 3H), 1.72 (s, 3H)

FABMS m/z 696 (M+H)$^+$ calcd for C$_{30}$H$_{37}$N$_3$O$_{10}$S$_3$=695

Example 141

Synthesis of Compound 147

To a solution of chloromethyl 3,6,9,12-tetraoxatridecanoate (Compound S-44 obtained in Reference Example 44) (1.62 g, 6.00 mmol) and DC107 (306 mg, 0.60 mmol) in acetone (15 mL) were added powdered potassium iodide (996 mg, 6.00 mmol) and potassium carbonate (414 mg, 3.00 mmol). The resultant suspension was stirred at 25° C. for 25.5 hours. After the reaction mixture was subjected to the ordinary post-treatment, the reaction product was purified by silica gel chromatography (eluted with chloroform/methanol=100/1 to 25/1) and HPLC for fractionation (ODS; eluted with acetonitrile/water=30/70 to 35/65) to obtain Compound 147 (66 mg, yield 15%).

$^1$H NMR (CDCl$_3$, 270 MHz)δ ppm; 8.49 (dd, J=11.2, 16.5 Hz, 1H), 7.37 (s, 1H), 6.60 (d, J=11.6 Hz, 1H), 6.23 (t, J=11.4 Hz, 1H), 6.16 (d, J=16.5 Hz, 1H), 5.72 (br d, J=8.6 Hz, 1H), 5.58 (br s, 1H), 5.45 (s, 2H), 5.42 (q, J=6.9 Hz, 1H), 4.95 (d, J=8.6 Hz, 1H), 4.15 (s, 2H), 3.92 (br s, 1H), 3.90 (d, J=17.8 Hz, 1H), 3.7–3.5 (m, 12H), 3.38 (s, 3H), 2.4–1.7 (m, 4H), 2.28 (d, J=17.8 Hz, 1H), 2.01 (d, J=6.9 Hz, 3H), 1.75 (d, J=1.0 Hz, 3H), 1.73 (s, 3H)

FABMS m/z 745 (M+H)$^+$ calcd for C$_{32}$H$_{44}$N$_2$O$_{12}$S$_3$=744

Example 142

Synthesis of Compound 148

To a solution of chloromethyl 2,5,8-trioxanonanoate (Compound S-45 obtained in Reference Example 45) (1.06 g, 5.00 mmol) and DC107 (255 mg, 0.500 mmol) in acetone (13 mL) were added powdered potassium iodide (830 mg, 5.00 mmol) and potassium carbonate (345 mg, 2.5 mmol). The resultant suspension was stirred at 25° C. for 16.5 hours. The reaction mixture was subjected to the ordinary post-treatment, and the residue was purified by silica gel chromatography (eluted with chloroform/methanol=100/1 to 50/1) and HPLC for fractionation (ODS; eluted with acetonitrile/water=45/55) to obtain Compound 148 (64 mg, yield 20%).

$^1$H NMR (CDCl$_3$, 270 MHz)δ ppm; 8.49 (dd, J=11.5, 16.7 Hz, 1H), 7.36 (s, 1H), 6.59 (d, J=11.9 Hz, 1H), 6.24 (t, J=11.7 Hz, 1H), 6.17 (d, J=16.7 Hz, 1H), 5.74 (br d, J=ca. 9 Hz, 1H), 5.60 (br s, 1H), 5.44 (s, 2H), 5.42 (q, J=6.9 Hz, 1H), 4.95 (br d, J=ca. 9 Hz, 1H), 4.31 (m, 2H), 3.90 (d, J=17.8 Hz, 1H), 3.82 (br s, 1H), 3.54 (m, 2H), 3.62 (m, 2H), 3.71 (m, 2H), 3.37 (s, 3H), 2.4–1.6 (m, 4H), 2.30 (d, J=17.8 Hz, 1H), 2.02 (d, J=6.9 Hz, 3H), 1.77 (s, 3H), 1.75 (d, J=1.3 Hz, 3H)

FABMS m/z 687 (M+H)$^+$ calcd for C$_{29}$H$_{38}$N$_2$O$_{11}$S$_3$=686

Example 143

Synthesis of Compound 149

To a solution of chloromethyl 2,5,8,11-tetraoxadodecanoate (Compound S-46 obtained in Reference Example 46) (257 mg, 1.00 mmol) and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 15 hours. After the reaction mixture was subjected to the ordinary post-treatment, the reaction product was purified by thin-layer chromatography (silica gel; developed with chloroform/methanol=20/1) to obtain Compound 149 (29 mg, yield 39%).

$^1$H NMR (CDCl$_3$, 270 MHz)δ ppm; 8.50 (dd, J=11.6, 16.7 Hz, 1H), 7.36 (s, 1H), 6.59 (d, J=11.5 Hz, 1H), 6.23 (t, J=11.6 Hz, 1H), 6.17 (d, J=16.7 Hz, 1H), 5.73 (br d, J=8.9 Hz, 1H), 5.61 (br s, 1H), 5.44 (s, 2H), 5.42 (q, J=6.9 Hz, 1H), 4.95 (dd, J=2.6, 8.0 Hz, 1H), 4.30 (m, 2H), 3.90 (d, J=17.8 Hz, 1H), 3.83 (br d, J=3.3 Hz, 1H), 3.8–3.5 (m, 10H), 3.38 (s, 3H), 2.4–1.5 (m, 4H), 2.30 (d, J=17.8 Hz, 1H), 2.02 (d, J=6.9 Hz, 3H), 1.76 (s, 3H), 1.75 (s, 3H)

FABMS m/z 731 (M+H)$^+$ calcd for C$_{31}$H$_{42}$N$_2$O$_{12}$S$_3$=730

Example 144

Synthesis of Compound 150

To a solution of chloromethyl 10-(4-methoxy-phenyl)-3,6,9-trioxadecanoate (Compound S-47 obtained in Reference Example 47) (3.32 g, 10.0 mmol) and DC107 (512 mg, 1.00 mmol) in acetone (25 mL) were added powdered potassium iodide (1.69 g, 10.0 mmol) and potassium carbonate (690 mg, 5.00 mmol). The resultant suspension was stirred at 25° C. for 26.5 hours. After the reaction mixture was subjected to the ordinary post-treatment, the reaction product was purified by silica gel chromatography (eluted with chloroform/methanol=100/1) and HPLC for fractionation (ODS; eluted with acetonitrile/water=45/55) to obtain Compound 150 (288 mg, yield 36%).

$^1$H NMR (CDCl$_3$, 270 MHz)δ ppm; 8.46 (dd, J=11.4, 16.3 Hz, 1H), 7.35 (s, 1H), 7.26 (m, 2H), 6.87 (m, 2H), 6.58 (d, J=11.9 Hz, 1H), 6.23 (t, J=11.9 Hz, 1H), 6.17 (d, J=16.3 Hz, 1H), 5.73 (br d, J=8.4 Hz, 1H), 5.53 (br s, 1H), 5.45 (s, 2H), 5.41 (q, J=6.9 Hz, 1H), 4.95 (dd, J=4.0, 8.4 Hz, 1H), 4.48 (s, 2H), 4.15 (s, 2H), 3.88 (d, J=17.8 Hz, 1H), 3.8–3.5 (m, 9H), 3.80 (s, 3H), 2.4–1.6 (m, 4H), 2.26 (d, J=17.8 Hz, 1H), 2.02 (d, J=6.9 Hz, 3H), 1.77 (s, 3H), 1.75 (d, J=1.0 Hz, 3H)

FABMS m/z 807 (M+H)$^+$ calcd for C$_{37}$H$_{46}$N$_2$O$_{12}$S$_3$=806

Example 145

Synthesis of Compound 151

Compound 150 (10 mg, 0.012 mmol) obtained in Example 144 was dissolved in chloroform (1.0 mL) and water (50 μL). Thereto was added DDQ (3.8 mg). This mixture was stirred at 25° C. for 2.5 hours. After the reaction mixture was subjected to the ordinary post-treatment, the reaction product was purified by thin-layer chromatography (silica gel; developed with chloroform/methanol=9/1) to obtain Compound 151 (6.9 mg, yield 84%).

$^1$H NMR (CDCl$_3$, 270 MHz)δ ppm; (major peaks) 8.46 (dd, J=11.2, 16.5 Hz, 1H), 7.36 (s, 1H), 6.59 (d, J=11.5 Hz, 1H), 6.23 (t, J=11.4 Hz, 1H), 6.17 (d, J=16.5 Hz, 1H), 5.72 (br d, J=ca. 9 Hz, 1H), 5.58 (br s, 1H) 5.46 (s, 2H), 5.41 (q, J=6.9 Hz, 1H), 4.95 (br d, J=ca. 9 Hz, 1H), 4.15 (s, 2H), 3.89 (d, J=17.8 Hz, 1H), 3.86 (br s, 1H), 3.8–3.6 (m, 6H), 3.60 (m, 2H), 2.4–1.7 (m, 4H), 2.29 (d, J=17.8 Hz, 1H), 2.02 (d, J=6.9 Hz, 3H), 1.75 (s, 6H)

FABMS m/z 687 (M+H)$^+$ calcd for C$_{29}$H$_{38}$N$_2$O$_{11}$S$_3$=686

Example 146

Syntheses of Compound 152 and Compound 153

Compound 132 (150 mg, 0.19 mmol) obtained in Example 126 was purified by HPLC for fractionation (ODS; acetonitrile/water=25/75) to obtain Compound 152 (51 mg, yield 34%) and Compound 153 (14 mg, yield 9%). Compound 152

$^1$H NMR (CD$_3$OD, 400 MHz)δ ppm; 9.09 (dd, J=16.3, 11.4 Hz, 1H), 7.65 (s, 1H), 6.70 (d, J=11.4 Hz, 1H), 6.33 (dd, J=11.4, 11.4 Hz, 1H), 6.02 (d, J=16.3 Hz, 1H), 5.76 (d, J=8.9 Hz, 1H), 5.54 (q, J=6.6 Hz, 1H), 4.97 (d, J=3.0 Hz, 1H), 4.87 (d, J=8.9 Hz, 1H), 4.53 (d, J=13.9 Hz, 1H), 4.39 (d, J=13.9 Hz, 1H), 4.02 (d, J=17.8 Hz, 1H), 3.88 (d, J=15.3 Hz, 1H), 3.84 (d, J=15.3 Hz, 1H), 3.83 (d, J=9.4 Hz, 2H), 3.82–3.48 (m, 4H), 3.25 (dd, J=9.4, 9.4 Hz, 1H), 2.49 (d, J=17.8 Hz, 1H), 2.32–2.06 (m, 4H), 1.93 (d, J=6.6 Hz, 3H), 1.74 (s, 3H), 1.48 (s, 3H)

FABMS m/z 785 (M+H)$^+$ calcd for C$_{33}$H$_{40}$N$_2$O$_{14}$S$_3$=784 Compound 153

$^1$H NMR (CD$_3$OD, 400 MHz)δ ppm; 9.06 (dd, J=16.1, 11.4 Hz, 1H), 7.66 (s, 1H), 6.70 (d, J=11.4 Hz, 1H), 6.32 (dd, J=11.4, 11.4 Hz, 1H), 6.03 (d, J=16.1 Hz, 1H), 5.76 (d, J=8.8 Hz, 1H), 5.53 (q, J=6.6 Hz, 1H), 4.88 (d, J=8.8 Hz, 1H), 4.66

(dd, J=9.5, 2.0 Hz, 1H), 4.64 (d, J=13.9 Hz, 1H), 4.58 (d, J=13.9 Hz, 1H), 3.90–3.17 (m, 7H), 3.72 (d, J=17.8 Hz, 1H), 2.50 (d, J=17.8 Hz, 1H), 2.35–2.18 (m, 4H), 2.11 (m, 2H), 1.93 (d, J=6.6 Hz, 3H), 1.73 (s, 3H), 1.50 (s, 3H)

FABMS m/z 807 (M+Na)$^+$ calcd for $C_{33}H_{40}N_2O_{14}S_3$=784

Example 147

Syntheses of Compound 154 and Compound 155

Compound 135 (160 mg, 0.17 mmol) obtained in Example 129 was dissolved in methanol (16 mL). Thereto was added 1.0 N hydrochloric acid (1.6 mL, 1.6 mmol). This mixture was stirred at 0° C. for 20 minutes. After the ordinary post-treatment, the reaction mixture was purified by thin-layer chromatography (developed with chloroform/methanol=10/1) to obtain a crude reaction product (120 mg) containing the target compounds. This crude product was purified by HPLC for fractionation (ODS; acetonitrile/water=30/70) to obtain Compound 154 (21 mg, yield 21%) and Compound 155 (48 mg, yield 40%). Compound 154

$^1$H NMR (CD$_3$OD, 400 MHz)δ ppm; 9.03 (dd, J=16.6, 11.8 Hz, 1H), 7.66 (s, 1H), 6.69 (d, J=11.8 Hz, 1H), 6.32 (dd, J=11.8, 11.8 Hz, 1H), 6.02 (dd, J=16.4 Hz, 0.5 Hz, 1H), 5.74 (d, J=8.8 Hz, 1H), 5.54 (q, J=6.6 Hz, 1H), 4.87 (d, J=8.8 Hz, 1H), 4.64 (dd, J=9.3 Hz, 2.2 Hz, 1H), 4.63 (d, J=13.9 Hz, 1H), 4.47 (d, J=13.9 Hz, 1H), 3.98 (d, J=17.8 Hz, 1H), 3.89 (d, J=15.3 Hz, 1H), 3.81 (d, J=15.3 Hz, 1H), 3.68–3.46 (m, 4H), 2.92 (dd, J=9.0 Hz, 9.0 Hz, 1H), 2.50 (d, J=17.8 Hz, 1H), 2.36–2.10 (m, 4H), 1.92 (d, J=6.6 Hz, 3H), 1.72 (s, 3H), 1.49 (s, 3H), 1.30 (d, J=8.1 Hz, 3H)

FABMS m/z 769 (M+H)$^+$ calcd for $C_{33}H_{40}N_2O_{13}S_3$=768 Compound 155

$^1$H NMR (CD$_3$OD, 400 MHz)δ ppm; 8.99 (dd, J=16.3, 11.4 Hz, 1H), 7.64 (s, 1H), 6.69 (d, J=11.4 Hz, 1H), 6.31 (dd, J=11.4, 11.4 Hz, 1H), 6.02 (d, J=16.3 Hz, 1H), 5.74 (d, J=8.8 Hz, 1H), 5.54 (q, J=6.6 Hz, 1H), 4.88 (d, J=8.8 Hz, 1H), 4.92 (d, J=3.1 Hz, 1H), 4.42 (d, J=13.9 Hz, 1H), 4.40 (d, J=13.9 Hz, 1H), 3.95 (m, 1H), 3.90 (d, J=15.4 Hz, 1H), 3.82 (d, J=15.4 Hz, 1H), 3.79–3.47 (m, 4H), 2.95 (dd, J=9.3 Hz, 9.3 Hz, 1H), 2.50 (d, J=17.8 Hz, 1H), 2.35–2.18 (m, 4H), 1.93 (d, J=6.6 Hz-, 3H), 1.73 (s, 3H), 1.50 (s, 3H), 1.27 (d, J=6.3 Hz, 3H)

FABMS m/z 769 (M+H)$^+$ calcd for $C_{33}H_{40}N_2O_{13}S_3$=768

Example 148

Syntheses of Compound 156 and Compound 157

Compound 86 (190 mg, 0.30 mmol) obtained in Example 80 was dissolved in dichloromethane (19 mL). Thereto were added N,N-dimethylglycine (47 mg, 0.45 mmol), 1-ethyl-3-(3-dimethylaminopropyl)carbodiimide hydrochloride (93 mg, 0.48 mmol), and 4-dimethylaminopyridine (3.7 mg, 0.030 mmol). This mixture was stirred at 40° C. for 30 minutes. After the ordinary post-treatment, the reaction mixture was purified by thin-layer chromatography (developed with chloroform/acetone=1/1), whereby a crude reaction product (80 mg) containing Compound 156 was obtained together with Compound 157 (59 mg, yield 24%). The crude product containing Compound 156 was purified by HPLC for fractionation (ODS; acetonitrile/0.1% aqueous trifluoroacetic acid solution=35/65) to obtain Compound 156 (37 mg, yield 17%). Compound 156

$^1$H NMR (CDCl$_3$, 400 MHz)δ ppm; 8.46 (ddd, J=16.6, 11.2, 1.0 Hz, 1H), 7.35 (s, 1H), 6.58 (d, J=11.2 Hz, 1H), 6.23 (dd, J=11.2, 11.2 Hz, 1H), 6.18 (d, J=16.3 Hz, 1H), 5.74 (d, J=8.5 Hz, 1H), 5.41 (q, J=6.9 Hz, 1H), 5.03 (d, J=14.0 Hz, 1H), 4.97 (d, J=14.0 Hz, 1H) 4.95 (d, J=8.5 Hz, 1H), 3.95 (d, J=15.1 Hz, 1H), 3.88 (d, J=15.1 Hz, 1H), 3.76 (d, J=18.3 Hz, 1H), 3.21 (s, 2H), 2.85 (s, 3H), 2.84 (s, 3H), 2.25 (m, 1H), 2.41–2.18 (m, 4H), 2.02 (d, J=6.9 Hz, 3H), 1.76 (s, 3H), 1.26 (s, 3H)

FABMS m/z 724 (M+H)$^+$ calcd for $C_{31}H_{37}N_3O_{11}S_3$=723 Compound 157

$^1$H NMR (CDCl$_3$, 400 MHz)δ ppm; 9.16 (ddd, J=16.3, 11.5, 0.7 Hz, 1H), 7.46 (s, 1H), 6.62 (d, J=11.5 Hz, 1H) 6.32 (dd, J=11.5, 11.5 Hz, 1H), 6.03 (d, J=16.3 Hz, 1H), 5.78 (m, 1H), 5.72 (d, J=8.8 Hz, 1H), 5.54 (q, J=6.9 Hz, 1H), 5.05 (d, J=14.2 Hz, 1H), 4.97 (d, J=14.2 Hz, 1H), 4.03 (d, J=17.8 Hz, 1H), 3.96 (d, J=15.4 Hz, 1H), 3.91 (d, J=15.4 Hz, 1H), 2.44–2.30 (m, 4H), 2.41 (s, 2H), 2.40 (m, 1H), 2.37 (s, 12H), 2.23 (s, 2H), 1.92 (d, J=6.9 Hz, 3H), 1.79 (s, 3H), 1.70 (s, 3H)

FABMS m/z 809 (M+H)$^+$ calcd for $C_{35}H_{44}N_4O_{12}S_3$=808

Example 149

Synthesis of Compound 158

Compound 156 (37 mg, 0.051 mmol) obtained in Example 148 was dissolved in ethyl acetate (3.7 mL). Thereto was added 4.0 N hydrogen chloride/ethyl acetate (13 mL, 0.45 mmol). This mixture was stirred at 0° C. for 10 minutes. The resultant precipitate was taken out by filtration to obtain Compound 158 (22 mg, yield 57%).

$^1$H NMR (DMSO-d$_6$, 400 MHz)δ ppm; 10.13 (br s, 1H), 9.09 (dd, J=16.6, 11.3 Hz, 1H), 7.11 (s, 1H), 6.72 (d, J=11.3 Hz, 1H), 6.34 (dd, J=11.3, 11.3 Hz, 1H), 5.96 (dd, J=16.6 Hz, 1H), 5.69 (br s, 1H), 5.64 (d, J=8.8 Hz, 1H), 5.53 (q, J=6.7 Hz, 1H), 5.22 (d, J=14.0 Hz, 2H), 5.12 (d, J=14.0 Hz, 2H), 4.68 (dd, J=8.8, 0.5 Hz, 1H), 3.93 (s, 2H), 3.82 (m, 1H), 2.80 (s, 6H), 2.62 (d, J=18.0 Hz, 1H), 2.30–2.03 (m, 4H),1.79 (d, J=6.7 Hz, 3H), 1.62 (s, 3H), 1.49 (s, 3H)

FABMS m/z 724 (M+H)$^+$ calcd for $C_{31}H_{37}N3O_{11}S_3$=723

Example 150

Synthesis of Compound 159

Compound 92 (88 mg, 0.11 mmol) obtained in Example 86 was dissolved in ethyl acetate (13 mL). Thereto was added 4.0 N hydrogen chloride/ethyl acetate (27 μL, 0.11 mmol). This mixture was stirred at 0° C. for 10 minutes. The resultant precipitate was taken out by filtration to obtain Compound 159 (33 mg, yield 36%). $^1$H NMR revealed that Compound 159 was an approximately 1:1 mixture of diastereomers.

$^1$H NMR (CDCl$_3$, 400 MHz)δ ppm; 9.57 (ddd, J=16.9, 11.5, 0.8 Hz) and 9.37 (ddd, J=16.9, 11.5, 0.8 Hz) (total 1H), 7.40 (s) and 7.39 (s) (total 1H), 6.61 (d, J=11.5 Hz) and 6.59 (d, J=11.5 Hz) (total 1H), 6.37 (ddd, J=11.5, 11.5, 0.5 Hz) and 6.34 (ddd, J=11.5, 11.5, 0.5 Hz) (total 1H), 6.04 (dd, J=16.9, 0.7 Hz) and 6.03 (d, J=16.9 Hz) (total 1H), 5.82 (dd, J=9.5, 0.8 Hz) and 5.80 (dd, J=9.5, 0.8 Hz) (total 1H), 5.60 (br s, 1H), 5.56(m, 1H), 5.13 (s, 2H), 5.03 (dd, J=9.5, 1.2 Hz) and 4.74 (dd, J=9.5, 1.2 Hz) (total 1H), 4.71 (m) and 4.57 (m) (total 1H), 4.07 (d, J=17.6 Hz) and 4.06 (d, J=17.6 Hz) (total 1H), 3.91 (s, 2H), 3.90 (m, 2H), 3.75 (m) and 3.50 (m) (total 2H), 2.94 (m, 2H), 2.52–2.28 (m, 4H), 2.33 (d, J=17.6 Hz) and 2.32 (d, J=17.6 Hz) (total 1H), 1.94 (d, J=6.6 Hz) and 1.88 (d, J=6.6 Hz) (total 3H), 1.77 (d, J=1.0 Hz) and 1.75 (d, J=1.0 Hz) (total 3H), 1.68 (s, 3H), 1.50 (m, 4H), 1.13 (s) and 1.12 (s) (total 6H)

FABMS m/z 808 (M+H)$^+$ calcd for $C_{35}H_{45}N_3O_{12}S_3$=807

Example 151

Synthesis of Compound 160

Compound 157 (59 mg, 0.065 mmol) obtained in Example 148 was dissolved in ethyl acetate (5.9 mL). Thereto was added 4.0 N hydrogen chloride/ethyl acetate (37 μL, 0.15 mmol). This mixture was stirred at 0° C. for 10 minutes. The resultant precipitate was taken out by filtration to obtain Compound 160 (54 mg, yield 82%).

$^1$H NMR (DMSO-d$_6$, 400 MHz)δ ppm; 10.24 (br s, 2H), 8.82 (dd, J=16.4, 11.5 Hz, 1H), 7.20 (s, 1H), 6.81 (d, J=11.7 Hz, 1H), 6.38 (dd, J=11.7, 11.7 Hz, 1H), 6.13 (d, J=16.4 Hz, 1H), 5.82 (d, J=9.5 Hz, 1H), 5.64 (m, 1H), 5.63 (m, 1H), 5.24 (d, J=14.2 Hz, 2H), 5.14 (d, J=14.2 Hz, 2H), 4.21 (s, 2H), 3.94 (s, 2H), 3.83 (m, 1H), 2.83 (s, 12H), 2.50–2.20 (m, 5H), 1.78 (d, J=6.7 Hz, 3H), 1.72 (s, 3H), 1.41 (s, 3H)

FABMS m/z 809 (M+H)$^+$ calcd for C$_{35}$H$_{44}$N$_4$O$_{12}$S$_3$=808

Example 152

Synthesis of Compound 161

To a solution of Compound S-48 (366 mg, 1.00 mmol) obtained in Reference Example 48 and DC107 (51 mg, 0.10 mmol) in acetone (2.5 mL) were added powdered potassium iodide (166 mg, 1.00 mmol) and potassium carbonate (69 mg, 0.50 mmol). The resultant suspension was stirred at 25° C. for 15.5 hours. After the reaction mixture was subjected to the ordinary post-treatment, the residue was purified by thin-layer chromatography (silica gel; developed with chloroform/methanol=20/1) to obtain Compound 161 (48 mg, yield 57%).

$^1$H NMR (CDCl$_3$, 270 MHz)δ ppm; 8.47 (dd, J=11.2, 16.4 Hz, 1H), 7.74 (br d, J=7.6 Hz, 1H), 7.36 (s, 1H), 6.59 (d, J=11.6 Hz, 1H), 6.23 (t, J=11.4 Hz, 1H), 6.17 (d, J=16.4 Hz, 1H), 5.72 (d, J=8.6 Hz, 1H), 5.58 (br s, 1H), 5.42 (q, J=6.9 Hz, 1H), 5.39 (s, 2H), 4.95 (br d, J=8.6 Hz, 1H), 4.71 (m, 1H), 4.0–3.7 (m, 6H), 3.75 (s, 3H), 2.5–1.6 (m, 9H), 2.02 (d, J=6.9 Hz, 3H), 1.75 (s, 6H), 1.47 (s, 6H), 0.98 (s, 3H)

FABMS m/z 840 (M+H)$^+$ calcd for C$_{37}$H$_{49}$N$_3$O$_{13}$S$_3$=839

Example 153

Synthesis of Compound 162

Compound 161 (25 mg, 0.030 mmol) obtained in Example 152 was dissolved in methanol (10 mL). Thereto was added trifluoroacetic acid (0.50 mL). This mixture was stirred at room temperature for 2 hours. After the reaction mixture was subjected to the ordinary post-treatment, the residue was purified by thin-layer chromatography (silica gel; developed with chloroform/methanol=20/1) to obtain Compound 162 (16 mg, yield 68%).

$^1$H NMR (CDCl$_3$, 270 MHz)δ ppm; 8.48 (dd, J=11.5, 16.8 Hz, 1H), 7.61 (br d, J=7.6 Hz, 1H), 7.36 (s, 1H), 6.59 (d, J=12.2 Hz, 1H), 6.24 (t, J=11.8 Hz, 1H), 6.17 (d, J=16.5 Hz, 1H), 5.71 (br d, J=8.6 Hz, 1H), 5.68 (br s, 1H), 5.41 (q, J=6.9 Hz, 1H), 5.40 (s, 2H), 4.96 (br d, J=8.6 Hz, 1H), 4.60 (m, 1H), 3.96 (d, J=17.8 Hz, 1H), 3.93 (br s, 1H), 3.8–3.5 (m, 6H), 3.75 (s, 3H), 2.5–1.6 (m, 8H), 2.33 (d, J=17.8 Hz, 1H), 2.01 (d, J=6.9 Hz, 3H), 1.75 (d, J=1.3 Hz, 3H), 1.70 (s, 3H), 1.09 (s, 3H)

FABMS m/z 800 (M+H)$^+$ calcd for C$_{34}$H$_{45}$N$_3$O$_{13}$S$_3$=799

Reference Examples for the present invention will be given below. The structures of the compounds synthesized in the Reference Examples are shown in Table 5.

TABLE 5

| Compound | Reference Ex. | Formula |
|---|---|---|
| Compounds in Reference Examples (1) | | |
| S.1 | 1 | 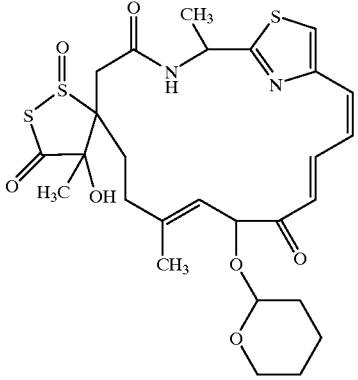 |

TABLE 5-continued
| | | |
|---|---|---|
| S.2 | 2 | 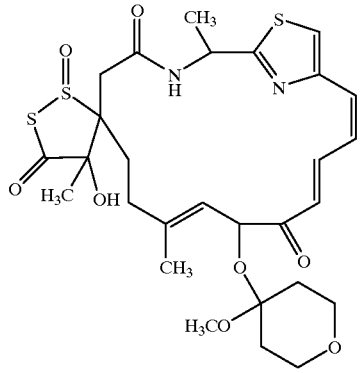 |
| S.3 | 3 | (CH₃)₃COCONHCH₂CO₂CH₂Cl |
| S.4 | 4 | CH₃COCONHCH₂CO₂CH₂Cl |
| S.5 | 5 | 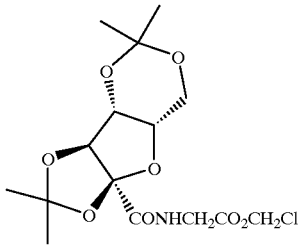 |
| S.6 | 6 | 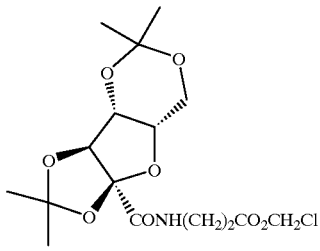 |
| S.7 | 7 | 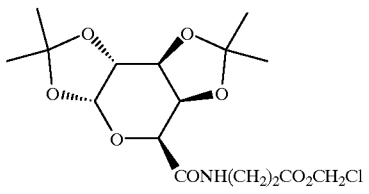 |
| S.8 | 8 | (CH₃)₃COCONH⟩—(CH₂)₂CO₂CH₂Cl<br>(CH₃)₃COCO⟩ |
| S.9 | 9 | CH₃OCONH⟩—(CH₂)₂CO₂CH₂Cl<br>CH₃COCO⟩ |

TABLE 5-continued
| | | |
|---|---|---|
| S.10 | 10 | 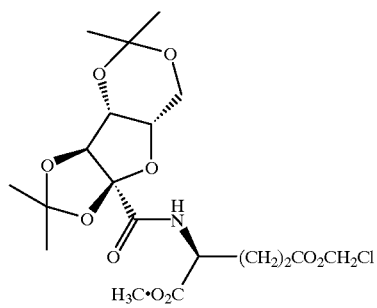 |
Compounds in Reference Examples (2)
| | | |
|---|---|---|
| S.11 | 11 | 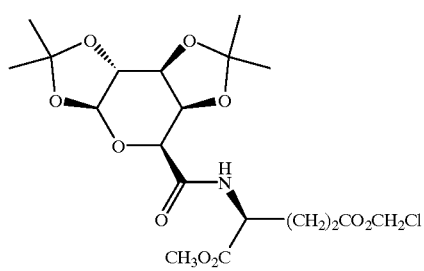 |
| S.12 | 12 | 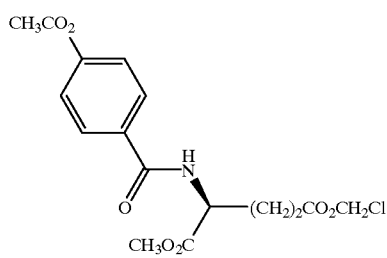 |
| S.13 | 13 | 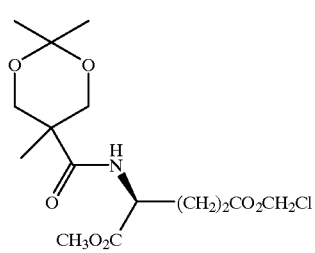 |
| S.14 | 14 | 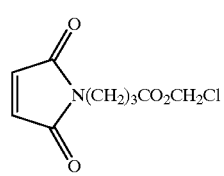 |
| S.15 | 15 | 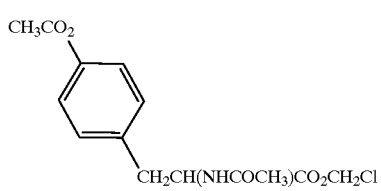 |

TABLE 5-continued

| | | |
|---|---|---|
| S.16 | 16 | CH₃CO₂—C₆H₄—CO₂CH₂Cl |
| S.17 | 17 | 3-(CH₃CO₂)-C₆H₄—CO₂CH₂Cl |
| S.18 | 18 | CH₃CO₂—C₆H₄—(CH₂)₂CO₂CH₂Cl |
| S.19 | 19 | CH₃CO₂—C₆H₄—(CH₂)₃CO₂CH₂Cl |
| S.20 | 20 | 3-(CH₃OCONH)-C₆H₄—CO₂CH₂Cl |
| S.21 | 21 | CH₃O(CH₂CH₂O)₂CH₂CO₂CH₂Cl |
| S.22 | 22 | CH₃O(CH₂CH₂O)₅CH₂CO₂CH₂Cl |

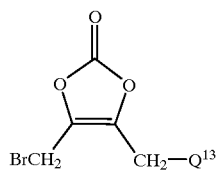

| Compound | Reference Ex. | Formula (Q¹³) |
|---|---|---|
| | | Compounds in Reference Examples (3) |
| S.23 | 23 | OH |
| S.24 | 24 | OTES |
| S.25 | 25 | OMOM |
| S.26 | 26 | (sugar structure with OTBDMS, OTBDMS, H₃C) |
| S.27 | 27 | (sugar structure with OTES, OTES, TESO) |
| S.28 | 28 | Cl |

TABLE 5-continued

| | | |
|---|---|---|
| S.29 | 29 | (structure: methyl pyranoside with OAc, OAc, and CH₂OAc substituents) |
| S.30 | 30 | OCHO |
| S.31 | 31 | OAc |
| S.32 | 32 | CH₃O-C(=O)-CH₂-O-CH₂CH₂-O-CH₃ |
| S.33 | 33 | CH₃O-C(=O)-C(CH₃)₂NHCO₂C(CH₃)₃ |
| S.34 | 34 | CH₃O-C(=O)-CH₂NHAc |
| S.35 | 35 | (structure: methyl 2,3-dihydropyran with OAc and CH₃ substituents) |
| S.36 | 36 | (structure: methyl pyranoside with TESO, TESO, and CH₃ substituents) |

| | Compounds in Reference Examples (4) | |
|---|---|---|
| Compound | Reference Ex. | Formula |
| S.37 | 37 | (structure: 2,2,5-trimethyl-1,3-dioxane with CONH(CH₂)₃CO₂CH₂Cl) |
| S.38 | 38 | (structure: diacetonide sugar derivative with CONH(CH₂)₃CO₂CH₂Cl) |

TABLE 5-continued
| | | |
|---|---|---|
| S.39 | 39 | 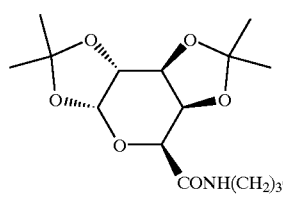 |
| S.40 | 40 | 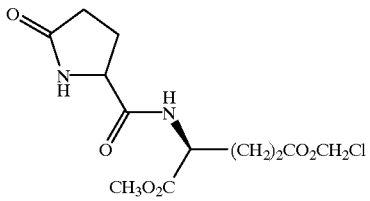 |
| S.41 | 41 | 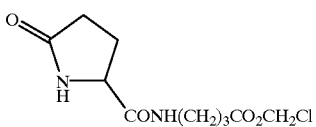 |
| S.42 | 42 | 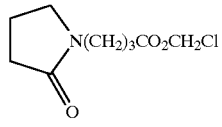 |
| S.43 | 43 | 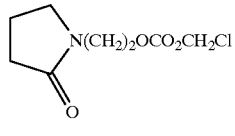 |
| S.44 | 44 | $CH_3O(CH_2CH_2O)_3CH_2CO_2CH_2Cl$ |
| S.45 | 45 | $CH_3O(CH_2CH_2O)_2CO_2CH_2Cl$ |
| S.46 | 46 | $CH_3O(CH_2CH_2O)_3CO_2CH_2Cl$ |
| S.47 | 47 | 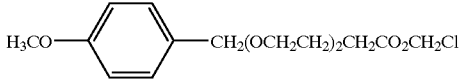 |
| S.48 | 48 | 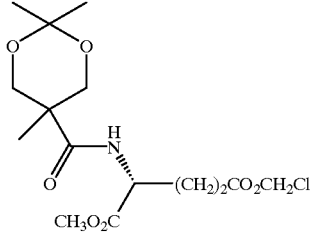 |
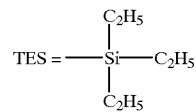
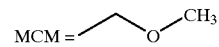

TABLE 5-continued

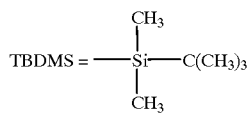

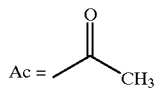

In the following Reference Examples, chloromethyl esters were synthesized from carboxylic acids according to the following typical synthesis method.

Typical Method for Synthesizing Chloromethyl Ester

Carboxylic acid (20 mmol) is dissolved in a mixture of dichloromethane (80 mL) and distilled water (80 mL). Sodium bicarbonate (4.14 g, 30 mmol) is added thereto little by little while giving care to bubbling. Thereto is further added tetrabutylammonium hydrogen sulfate (678 mg, 2.0 mmol). This mixture is stirred at 25° C. Ten minutes later, chloromethyl chlorosulfonate (3.63 g–4.95 g, 22 mmol–30 mmol) is added and this mixture is continuously stirred for 2 to 3 hours. After the progress of the reaction is confirmed by TLC, the reaction mixture is subjected to the ordinary post-treatment. The reaction product is purified by column chromatography (silica gel; eluted with n-hexane/ethyl acetate=2/1 to 9/1) to obtain a target compound as a colorless to light-yellow oily liquid or as white crystals.

REFERENCE EXAMPLE 1

Synthesis of Compound S-1

DC107 (71 mg, 0.14 mmol) was dissolved in dichloromethane (9.0 mL). Thereto were added 3,4-dihydro-2H-pyran (0.164 mL, 1.81 mmol) and camphorsulfonic acid (77 mg, 0.33 mmol). This mixture was stirred at 0° C. for 4 hours. After the ordinary post-treatment, the reaction product was purified by silica gel column chromatography (eluted with chloroform/methanol=99/1) to obtain Compound S-1 (49 mg, yield 58%). $^1$H NMR revealed that Compound S-1 was an approximately 5:4 mixture of diastereomers due to the asymmetric carbon of the tetrahydropyranyl group.

IR (KBr) 3400, 3320, 2930, 2850, 1715, 1651, 1612, 1538, 1450, 1373, 1260, 1098, 1025, 970, 890, 867, 808 cm$^{-1}$ $^1$H NMR (CDCl$_3$, 500 MHz)δ ppm; major isomer 9.25 (dd, J=16.5, 11.6 Hz, 1H), 7.25 (s, 1H), 6.88 (br d, J=6.4 Hz, 1H), 6.63 (d, J=11.6 Hz, 1H), 6.36 (dd, J=11.6, 11.6 Hz, 1H), 6.01 (d, J=16.5 Hz, 1H), 5.94 (d, J=9.7 Hz, 1H), 5.30 (dq, J=6.7, 6.4 Hz, 1H), 5.08 (dd, J=9.7, 1.2 Hz, 1H), 5.00 (br s, 1H), 4.58 (t, J=4.6 Hz, 1H), 3.78–3.74 (m, 1H), 3.50–3.45 (m, 1H), 3.25 (d, J=15.0 Hz, 1H), 2.90 (d, J=15.0 Hz, 1H), 2.35–2.28 (m, 1H), 2.12–2.06 (m, 1H), 1.95–1.44 (m, 8H), 1.88 (s, 3H), 1.79 (d, J=6.7 Hz, 3H), 1.72 (d, J=1.2 Hz, 3H); minor isomer 9.04 (dd, J=16.5, 11.6 Hz, 1H), 7.25 (s, 1H), 6.86 (br d, J=6.4 Hz, 1H), 6.63 (d, J=11.6 Hz, 1H), 6.39 (dd, J=11.6, 11.6 Hz, 1H), 6.05 (d, J=16.5 Hz, 1H), 5.87 (d, J=9.8 Hz, 1H), 5.27 (dq, J=6.4, 6.4 Hz, 1H), 4.93 (br s, 1H), 4.91 (dd, J=9.8, 1.2 Hz, 1H), 4.63 (br s, 1H), 3.72–3.67 (m, 1H), 3.45–3.39 (m, 1H), 3.22 (d, J=14.6 Hz, 1H), 2.88 (d, J=14.6 Hz, 1H), 2.35–2.28 (m, 1H), 2.14–2.06 (m, 1H), 1.90–1.40 (m, 8H), 1.90 (s, 3H), 1.72 (d, J=6.4 Hz, 3H), 1.72 (s, 3H)

FABMS m/z 595 (M+H)$^+$

HRFABMS calcd for C$_{27}$H$_{35}$N$_2$O$_7$S$_3$ (M+H)$^+$ 595.1606, found 595.1606

REFERENCE EXAMPLE 2

Synthesis of Compound S-2

According to the method used in Reference Example 1, Compound S-2 (30 mg, yield 49%) was obtained from DC107 (50 mg, 0.1 mmol), 5,6-dihydro-4-methoxy-2H-pyran (0.056 mL, 0.50 mmol), and camphorsulfonic acid (23 mg, 0.1 mmol).

IR (KBr) 3420, 3330, 2944, 1726, 1642, 1609, 1529, 1453, 1357, 1306, 1261, 1231, 1142, 1097, 1048, 949, 886, 807, 732 cm$^{-1}$ $^1$H NMR (CDCl$_3$, 400 MHz)δ ppm; 9.31 (ddd, J=16.5, 11.5, 1.0 Hz, 1H), 7.29 (s, 1H), 6.88 (br d, J=6.3 Hz, 1H) 6.65 (d, J=11.5 Hz, 1H), 6.39 (t, J=11.5 Hz, 1H), 6.01 (d, J=16.5 Hz, 1H), 5.95 (br d, J=9.8 Hz, 1H), 5.26 (dq, J=6.3, 6.5 Hz, 1H), 5.22 (br s, 1H), 5.03 (dd, J=9.8, 1.2 Hz, 1H), 3.64–3.44 (m, 4H), 3.24 (d, J=14.8 Hz, 1H), 3.06 (s, 3H), 2.86 (d, J=14.8 Hz, 1H), 2.35–1.50 (m, 8H), 1.90 (s, 3H), 1.80 (d, J=6.5 Hz, 3H), 1.74 (d, J=1.2 Hz, 3H)

FABMS m/z 625 (M+H)$^+$

HRFABMS calcd for C$_{28}$H$_{37}$N$_2$O$_8$S$_3$ (M+H)$^+$ 625.1712, found 625.1738

REFERENCE EXAMPLE 3

Synthesis of Compound S-3

Compound S-3 (3.19 g, yield 78%) was obtained from N-Boc-aminoacetic acid (3.20 g, 18.3 mmol) and chloromethyl chlorosulfonate (3.53 g, 21.4 mmol) through 2.5-hour reaction according to the Typical Method for Synthesizing Chloromethyl Ester.

$^1$H NMR (CDCl$_3$, 270 MHz)δ ppm; 5.75 (s, 2H) 5.1 (br s, 1H), 3.99 (d, J=6.9 Hz, 1H), 1.46 (s, 9H)

REFERENCE EXAMPLE 4

Synthesis of Compound S-4

Compound S-4 (1.06 g, yield 33%) was obtained from N-(methoxycarbonyl)aminoacetic acid (2.33 g, 17.5 mmol) and chloromethyl chlorosulfonate (3.50 g, 21.2 mmol) through 2-hour reaction according to the Typical Method for Synthesizing Chloromethyl Ester.

$^1$H NMR (CDCl$_3$, 270 MHz)δ ppm; 5.75 (S, 2H), 5.16 (br s, 1H), 4.06 (d, J=6.4 Hz, 2H), 3.72 (s, 3H)

REFERENCE EXAMPLE 5

Synthesis of Compound S-5

Benzyl aminoacetate p-toluenesulfonate (3.87 g, 11.5 mmol) was dissolved in dichloromethane (23 mL) and triethylamine (1.8 mL). This solution was stirred at 25° C. for 5 minutes. Thereto were successively added 2,3:4,6-di-O-isopropylidene-2-keto-L-gulonic acid monohydrate (3.36 g, 11.5 mmol) and a solution of DCC (5.21 g, 25.3 mmol) in dichloromethane (17 mL). This mixture was stirred at 0 to 25° C. for 17 hours. After insoluble matters contained in the reaction mixture were separated by filtration, the ordinary post-treatment was conducted. The reaction product was purified by column chromatography (silica gel; eluted with ethyl acetate/n-hexane=4/1 to 7/3) to obtain the corresponding condensate (3.08 g, yield 64%). This condensate (2.06 g, 4.89 mmol) was dissolved in ethanol (100 mL), and 10% palladium/carbon (containing 50 wt % water; 430 mg) was added thereto. This mixture was stirred in a hydrogen atmosphere at 25° C. for 1.5 hours. The reaction mixture was filtered, and the filtrate was concentrated to obtain the corresponding carboxylic acid (1.62 g, yield 100%). From this carboxylic acid (1.58 g, 4.77 mmol) and chloromethyl chlorosulfonate (906 mg, 5.49 mmol) was obtained Compound S-5 (1.07 g, yield 59%) through 2.5 hour reaction according to the Typical Method for Synthesizing Chloromethyl Ester.

$^1$H NMR (CDCl$_3$, 270 MHz)δ ppm; 7.58 (m, 1H), 5.76 (d, J=6.3 Hz, 1H), 5.73 (d, J=6.3 Hz, 1H), 4.61 (s, 1H), 4.35 (d, J=1.7 Hz, 1H), 4.2–4.0 (m, 5H), 1.55 (s, 3H), 1.54 (s, 3H), 1.45 (s, 3H), 1.35 (s, 3H)

FABMS m/z 380 (M+H)$^+$ calcd for C$_{15}$H$_{22}$NO$_8$$^{35}$Cl=379

REFERENCE EXAMPLE 6

Synthesis of Compound S-6

Benzyl 3-aminopropionate p-toluenesulfonate (10.51 g, 29.9 mmol) was dissolved in dichloromethane (60 mL) and triethylamine (4.2 mL). This solution was stirred at 25° C. for 5 minutes. Thereto were successively added 2,3:4,6-di-O-isopropylidene-2-keto-L-gulonic acid monohydrate (8.23 g, 28.2 mmol) and a solution of 1-ethyl-3-(3-dimethylaminopropyl)carbodiimide hydro-chloride (8.70 g) in dichloromethane (30 mL). This mixture was stirred at 0 to 25° C. for 1 week. The reaction mixture was subjected to the ordinary post-treatment, and the reaction product was purified by column chromatography (silica gel; ethyl acetate/n-hexane=4/1) to obtain the corresponding condensate (3.57 g, yield 29%). This condensate (3.45 g, 7.92 mmol) was dissolved in ethanol (150 mL), and cyclohexene (75 mL) and 10% palladium/carbon (containing 50 wt % water; 3.56 g) were added thereto. This mixture was stirred at 25° C. for 4 hours. The reaction mixture was filtered, and the filtrate was concentrated. To the residue were added chloroform (30 mL), 2,2-dimethoxy-propane (10 mL), and camphorsulfonic acid (50 mg). This mixture was stirred at 25° C. for 2.5 hours. The reaction mixture was concentrated and then purified again by column chromatography (silica gel; chloroform/methanol=30/1) to obtain the corresponding carboxylic acid (1.12 g, yield 41%). From this carboxylic acid (211 mg, 0.613 mmol) and chloromethyl chlorosulfonate (138 mg, 0.836 mmol) was obtained Compound S-6 (187 mg, yield 78%) through 2.5-hour reaction according to the Typical Method for Synthesizing Chloromethyl Ester.

$^1$H NMR (CDCl$_3$, 270 MHz)δ ppm; 7.50 (br t, J=ca. 6 Hz, 1H), 5.73 (d, J=6.2 Hz, 1H), 5.69 (d, J=6.2 Hz, 1H), 4.56 (s, 1H), 4.33 (d, J=2.0 Hz, 2H), 4.18 (m, 1H), 4.10 (m, 2H), 3.71 (m, 1H), 3.51 (m, 1H), 2.69 (t, J=6.4 Hz, 2H), 1.53 (s, 6H), 1.44 (s, 3H), 1.31 (s, 3H) EIMS m/z 393 M+calcd for C$_{16}$H$_{24}$NO$_8$Cl=393

REFERENCE EXAMPLE 7

Synthesis of Compound S-7

A condensate (1.98 g, yield 38%) was obtained from benzyl 3-aminopropionate p-toluenesulfonate (4.23 g, 12.0 mmol), the carboxylic acid (3.30 g, 12.0 mmol) obtained by oxidizing 1,2:2,4-di-O-isopropylidene-D-galactopyranose with PDC (pyridinium dichlorochromate), triethylamine (1.68 mL), and DCC (2.98 g, 14.4 mmol) in the same manner as in Reference Example 5. All the condensate was dissolved in ethanol (100 mL), and 10% palladium/carbon (containing 50 wt % water; 400 mg) was added thereto. This mixture was stirred in a hydrogen atmosphere at 25° C. for 1.5 hours. The reaction mixture was filtered, and the filtrate was concentrated to obtain carboxylic acid (1.70 g, quantitative). From this carboxylic acid (1.67 g, 4.84 mmol) and chloromethyl chlorosulfonate (915 mg, 5.55 mmol) was obtained Compound S-7 (1.36 g, yield 72%) through 4-hour reaction.

$^1$H NMR (CDCl$_3$, 270 MHz)δ ppm; 6.99 (m, 1H), 5.73 (d, J=6.3 Hz, 1H), 5.69 (d, J=6.3 Hz, 1H), 5.59 (d, J=5.0 Hz, 1H), 4.65 (s, 2H), 4.36 (d, J=5.0 Hz, 1H) 4.28 (s, 1H), 3.8–3.4 (m, 2H), 2.66 (m, 2H), 1.51 (s, 3H), 1.38 (s, 3H), 1.34 (s, 3H), 1.32 (s, 3H)

REFERENCE EXAMPLE 8

Synthesis of Compound S-8

Compound S-8 (1.86 g, yield 91%) was obtained from Boc-L-Glu(OH)-OBu$^t$ (1.76 g, 5.81 mmol) and chloromethyl chlorosulfonate (1.15 g, 6.97 mmol) through 2-hour reaction according to the Typical Method for Synthesizing Chloromethyl Ester.

$^1$H NMR (CDCl$_3$, 270 MHz)δ ppm; 5.71 (s, 2H), 4.21 (m, 1H), 2.48 (m, 2H), 2.19 (m, 1H), 1.93 (m, 1H), 1.47 (s, 9H), 1.44 (s, 9H)

REFERENCE EXAMPLE 9

Synthesis of Compound S-9

Compound S-9 (1.52 g, yield 61%) was obtained from MeOCO-L-Glu(OH)-OMe (2.03 g, 9.28 mmol) and chloromethyl chlorosulfonate (2.75 g, 16.7 mmol) through 4-hour reaction according to the Typical Method for Synthesizing Chloromethyl Ester.

$^1$H NMR (CDCl$_3$, 270 MHz)δ ppm; 5.72 (d, J=5.9 Hz, 1H), 5.68 (d, J=5.9 Hz, 1H), 5.30 (br d, J=ca. 6 Hz, 1H), 4.42 (br q, J=ca. 6 Hz, 1H), 3.77 (s, 3H), 3.69 (s, 3H), 2.50 (m, 2H), 2.24 (m, 1H), 2.02 (m, 1H)

REFERENCE EXAMPLE 10

Synthesis of Compound S-10

A condensate (6.84 g, yield 78%) was obtained from L-Glu(OCH$_2$Ph)-OMe.HCl (5.08 g, 17.4 mmol), 2,3:4,6-di-O-isopropylidene-2-keto-L-gulonic acid monohydrate (5.00 g, 17.1 mmol), triethylamine (2.42 mL), and DCC (8.96 g, 43.4 mmol) in the same manner as for the compound produced in Reference Example 5. All the condensate was dissolved in ethyl acetate (300 mL), and 10% palladium/carbon (containing 50 wt % water; 1.19 g) was added thereto. This mixture was stirred in a hydrogen atmosphere at 25° C. for 1.5 hours. The reaction mixture was filtered, and the filtrate was concentrated to obtain carboxylic acid (5.93 g, quantitative). From this carboxylic acid (5.70 g, 13.7 mmol) and chloromethyl chlorosulfonate (2.60 g, 15.8 mmol) was obtained Compound S-10 (3.41 g, yield 54%) through 2.5-hour reaction according to the Typical Method for Synthesizing Chloromethyl Ester.

$^1$H NMR (CDCl$_3$, 270 MHz)δ ppm; 7.57 (br d, J=8.6 Hz, 1H), 5.72 (d, J=5.9 Hz, 1H), 5.65 (d, J=5.9 Hz, 1H), 4.67 (m, 1H), 4.59 (s, 1H), 4.34 (d, J=2.0 Hz, 1H), 4.18 (m, 1H), 4.14 (d, J=2.0 Hz, 2H), 3.77 (s, 3H), 2.6–1.9 (m, 4H), 1.54 (s, 3H), 1.54 (s, 3H), 1.45 (s, 3H), 1.33 (s, 3H)

FABMS m/z 466 (M+H)$^+$ calcd for $C_{19}H_{28}NO_{10}{}^{35}Cl$=465

REFERENCE EXAMPLE 11

Synthesis of Compound S-11

A condensate (2.43 g, yield 50%) was obtained from L-Glu(OCH$_2$Ph)-OMe.HCl (2.76 g, 9.58 mmol), the carboxylic acid (2.63 g, 9.58 mmol) obtained by oxidizing 1,2:2,4-di-O-isopropylidene-D-galactopyranose with PDC (pyridinium dichlorochromate), triethylamine (1.34 mL), and DCC (2.37 g, 11.5 mmol) in the same manner as for the compound produced in Reference Example 5. The condensate (1.96 g, 3.87 mmol) was dissolved in ethanol (80 mL), and 10% palladium/carbon (containing 50 wt % water; 340 mg) was added thereto. This mixture was stirred in a hydrogen atmosphere at 25° C. for 1.5 hours. The reaction mixture was filtered, and the filtrate was concentrated to obtain carboxylic acid (1.75 g, quantitative). From this carboxylic acid (1.75 g, corresponding to 3.87 mmol) and chloromethyl chlorosulfonate (1.19 g, 7.2 mmol) was obtained Compound S-11 (899 mg, yield 50%) through 3-hour reaction according to the Typical Method for Synthesizing Chloromethyl Ester.

$^1$H NMR (CDCl$_3$, 270 MHz)δ ppm; 7.10 (d, J=8.9 Hz, 1H), 5.73 (d, J=6.2 Hz, 1H), 5.65 (d, J=6.2 Hz, 1H), 5.62 (d, J=5.0 Hz, 1H), 4.75 (m, 1H), 4.66 (m, 2H), 4.37 (d, J=5.0 Hz, 1H), 4.30 (s, 1H), 3.78 (s, H), 1.9–2.6 (m, 4H), 1.51 (s, 3H), 1.42 (s, 3H), 1.34 (s, 3H), 1.33 (s, 3H)

FABMS m/z 466 (M+H)$^+$ calcd for $C_{19}H_{28}NO_{10}{}^{35}Cl$=465

REFERENCE EXAMPLE 12

Synthesis of Compound S-12

A condensate (3.59 g, yield 76%) was obtained from L-Glu(OCH$_2$Ph)-OMe.HCl (3.30 g, 11.5 mmol), p-acetoxybenzoic acid (2.05 g, 11.4 mmol), triethylamine (1.74 mL), and DCC (3.09 g, 15.0 mmol) in the same manner as for the compound produced in Reference Example 5. All the condensate was dissolved in ethanol (200 mL), and 10% palladium/carbon (containing 50 wt % water; 794 mg) was added thereto. This mixture was stirred in a hydrogen atmosphere at 25° C. for 1.5 hours. The reaction mixture was filtered, and the filtrate was concentrated to obtain carboxylic acid (2.98 g, quantitative). From this carboxylic acid (2.57 g, 7.96 mmol) and chloromethyl chlorosulfonate (1.43 g, 8.67 mmol) was obtained Compound S-12 (2.31 g, yield 78%) through 4-hour reaction according to the Typical Method for Synthesizing Chloromethyl Ester.

$^1$H NMR (CDCl$_3$, 270 MHz)δ ppm; 7.84 (m, 2H), 7.19 (m, 2H), 6.85 (br d, J=7.3 Hz, 1H), 5.70 (d, J=6.1 Hz, 1H), 5.66 (d, J=6.1 Hz, 1H), 4.84 (m, 1H), 3.80 (s, 3H), 2.5–2.0 (m, 4H), 2.32 (s, 3H)

FABMS m/z 372 (M+H)$^+$ calcd for $C_{16}H_{18}NO_7{}^{35}Cl$=371

REFERENCE EXAMPLE 13

Synthesis of Compound S-13

A condensate (7.14 g, yield 88%) was obtained from L-Glu(OCH$_2$Ph)-OMe.HCl (5.76 g, 20.0 mmol), 2,2-bis(hydroxymethyl)propionic acid diisopropylidene acetal (3.48 g, 20.0 mmol), triethylamine (3.07 mL), and DCC (7.43 g, 36.0 mmol) in the same manner as for the compound produced in Reference Example 5. All the condensate was dissolved in ethanol (200 mL), and 10% palladium/carbon (containing 50 wt % water; 1.13 g) was added thereto. This mixture was stirred in a hydrogen atmosphere at 25° C. for 3 hours. The reaction mixture was filtered, and the filtrate was concentrated to obtain carboxylic acid (6.26 g, quantitative). From this carboxylic acid (5.24 g, 16.5 mmol) and chloromethyl chlorosulfonate (3.14 g, 19.0 mmol) was obtained Compound S-13 (4.42 g, yield 73%) through 4-hour reaction according to the Typical Method for Synthesizing Chloromethyl Ester.

FABMS m/z 366 (M+H)$^+$ calcd for $C_{15}H_{24}NO_7{}^{35}Cl$=365

REFERENCE EXAMPLE 14

Synthesis of Compound S-14

Compound S-14 (388 mg, yield 44%) was obtained from 3-(maleoylamino)butyric acid (700 mg, 3.83 mmol) and chloromethyl chlorosulfonate (720 mg, 4.36 mmol) through 2.5-hour reaction according to the Typical Method for Synthesizing Chloromethyl Ester.

$^1$H NMR (CDCl$_3$, 270 MHz)δ ppm; 6.71 (s, 2H), 5.70 (s, 2H), 3.61 (t, J=6.8 Hz, 2H), 2.42 (t, J=7.4 Hz, 2H), 1.97 (m, 2H)

REFERENCE EXAMPLE 15

Synthesis of Compound S-15

Compound S-15 (1.53 g, yield 61%) was obtained from 3-(4-acetoxyphenyl)-2-(acetylamino)propionic acid (2.12 g, 8.02 mmol) and chloromethyl chlorosulfonate (1.51 g, 9.15 mmol) through 2.5-hour reaction according to the Typical Method for Synthesizing Chloromethyl Ester.

$^1$H NMR (CDCl$_3$, 270 MHz)δ ppm; 7.16 (m, 2H), 7.03 (m, 2H), 5.89 (br s, 1H), 5.84 (d, J=6.1 Hz, 1H), 5.65 (d, J=6.1 Hz, 1H), 4.93 (m, 1H), 3.16 (m, 2H), 2.30 (s, 3H), 2.00 (s, 3H)

FABMS m/z 314 (M+H)$^+$ calcd for $C_{14}H_{16}NO_5{}^{35}Cl$=313

REFERENCE EXAMPLE 16

Synthesis of Compound S-16

Compound S-16 (2.70 g, yield 59%) was obtained from 4-acetoxybenzoic acid (3.60 g, 20.0 mmol) and chloromethyl chlorosulfonate (3.61 g, 21.9 mmol) through 2-hour reaction according to the Typical Method for Synthesizing Chloromethyl Ester.

$^1$H NMR (CDCl$_3$, 270 MHz)δ ppm; 8.11 (m, 2H), 7.21 (m, 2H), 5.95 (s, 2H), 2.33 (s, 3H)

FABMS m/z 229 (M+H)$^+$ calcd for $C_{10}H_9O_4{}^{35}Cl$=228

REFERENCE EXAMPLE 17

Synthesis of Compound S-17

Compound S-17 (5.15 g, yield 75%) was obtained from 3-acetoxybenzoic acid (5.40 g, 30.0 mmol) and chloromethyl chlorosulfonate (5.42 g, 32.8 mmol) through 2-hour reaction according to the Typical Method for Synthesizing Chloromethyl Ester.

$^1$H NMR (CDCl$_3$, 270 MHz)δ ppm; 7.96 (m, 1H), 7.81 (m, 1H), 7.50 (m, 1H), 7.36 (m, 1H), 5.95 (s, 2H), 2.33 (s, 3H)

FABMS m/z 229 (M+H)$^+$ calcd for $C_{10}H_9O_4{}^{35}Cl$=228

REFERENCE EXAMPLE 18

Synthesis of Compound S-18

Compound S-18 (1.26 g, yield 49%) was obtained from 3-(4-acetoxyphenyl)propionic acid (2.08 g, 10.0 mmol) and chloromethyl chlorosulfonate (1.89 g, 11.5 mmol) through 2-hour reaction according to the Typical Method for Synthesizing Chloromethyl Ester.

$^1$H NMR (CDCl$_3$, 270 MHz)δ ppm; 7.21 (m, 2H), 5.70 (s, 2H), 2.97 (t, J=7.8 Hz, 2H), 2.70 (t, J=7.8 Hz, 2H), 2.29 (s, 3H)

FABMS m/z 257 (M+H)$^+$ calcd for $C_{12}H_{13}O_4{}^{35}Cl$=256

REFERENCE EXAMPLE 19

Synthesis of Compound S-19

Compound S-19 (1.89 g, yield 40%) was obtained from 3-(4-acetoxyphenyl)butyric acid (3.88 g, 17.5 mmol) and chloromethyl chlorosulfonate (3.32 g, 20.1 mmol) through 2-hour reaction according to the Typical Method for Synthesizing Chloromethyl Ester.

$^1$H NMR (CDCl$_3$, 270 MHz)δ ppm; 7.18 (m, 2H), 5.69 (s, 2H), 2.67 (t, J=7.3 Hz, 2H), 2.41 (t, J=7.3 Hz, 2H), 2.29 (s, 3H), 1.98 (m, 2H)

FABMS m/z 271 (M+H)$^+$ calcd for $C_{13}H_{15}O_4{}^{35}Cl$=270

REFERENCE EXAMPLE 20

Synthesis of Compound S-20

Compound S-20 (1.82 g, yield 75%) was obtained from 3-(methoxycarbonylamino)benzoic acid (1.95 g, 10.0 mmol) and chloromethyl chlorosulfonate (1.88 g, 11.4 mmol) through 2-hour reaction according to the Typical Method for Synthesizing Chloromethyl Ester.

$^1$H NMR (CDCl$_3$, 270 MHz)δ ppm; 8.02 (m, 1H), 7.80 (m, 2H), 7.43 (m, 1H), 6.78 (br s, 1H), 5.95 (s, 2H), 3.80 (s, 3H)

REFERENCE EXAMPLE 21

Synthesis of Compound S-21

Compound S-21 (528 mg, yield 23%) was obtained from 3,6,9-trioxadecanoic acid (1.78 g, 10.1 mmol) and chloromethyl chlorosulfonate (1.90 g, 11.5 mmol) through 2-hour reaction according to the Typical Method for Synthesizing Chloromethyl Ester.

$^1$H NMR (CDCl$_3$, 270 MHz)δ ppm; 5.76 (s, 2H), 4.25 (s, 2H), 3.39 (s, 3H)

FABMS m/z 227 (M+H)$^+$ calcd for $C_8H_{15}ClO_5$=226

REFERENCE EXAMPLE 22

Synthesis of Compound S-22

Compound S-22 (439 mg, yield 28%) was obtained from 3,6,9,12,15,18-hexaoxanonadecanoic acid (1.36 g, 4.39 mmol) and chloromethyl chlorosulfonate (834 mg, 5.05 mmol) through 3-hour reaction according to the Typical Method for Synthesizing Chloromethyl Ester.

$^1$H NMR (CDCl$_3$, 270 MHz)δ ppm; 5.76 (s, 2H), 4.25 (s, 2H), 3.8–3.5 (m, 20H), 3.38 (s, 3H)

REFERENCE EXAMPLE 23

Synthesis of Compound S-23

4,5-Dibromomethyl-1,3-dioxolene (4.8 g, 18 mmol) was dissolved in N,N-dimethylformamide (24 mL). Thereto was added potassium formate (1.5 g, 18 mmol). This mixture was stirred at 25° C. for 20 minutes. After the ordinary post-treatment, the residue was dissolved in methanol (63 mL) and this solution was stirred at 70° C. for 30 minutes. The reaction mixture was concentrated and purified by silica gel chromatography (eluted with n-hexane/ethyl acetate=2/1) to obtain Compound S-23 (0.75 g, yield 20%).

$^1$H NMR (CDCl$_3$, 100 MHz)δ ppm; 4.53 (s, 2H), 4.30 (s, 2H)

REFERENCE EXAMPLE 24

Synthesis of Compound S-24

Compound S-23 (1.1 g, 5.4 mmol) obtained in Reference Example 23 was dissolved in N,N-dimethylformamide (23 mL). Thereto were added chlorotriethylsilane (1.8 mL, 11 mmol) and imidazole (1.5 g, 22 mmol). This mixture was stirred at 0° C. for 20 minutes. After the ordinary post-treatment, the reaction product was purified by silica gel chromatography (eluted with n-hexane/ethyl acetate=20/1) to obtain Compound S-24 (1.4 g, yield 79%).

$^1$H NMR (CDCl$_3$, 100 MHz)δ ppm; 4.53 (s, 2H), 4.46 (s, 2H), 0.99 (m, 9H), 0.67 (m, 6H)

REFERENCE EXAMPLE 25

Synthesis of Compound S-25

Compound S-23 (100 mg, 0.48 mmol) obtained in Reference Example 23 was dissolved in chloroform (3.0 mL). Thereto were added dimethoxymethane (6.4 mL, 72 mmol) and phosphorus pentaoxide (27 mg, 0.19 mmol). This mixture was stirred at 40° C. for 1 week. After the ordinary post-treatment, the reaction product was purified by silica gel chromatography (eluted with n-hexane/ethyl acetate=2/1) to obtain Compound S-25 (19 mg, yield 34%).

$^1$H NMR (CDCl$_3$, 100 MHz)δ ppm; 4.69 (s, 2H), 4.41 (s, 2H), 4.26 (s, 2H), 3.41 (s, 3H)

REFERENCE EXAMPLE 26

Synthesis of Compound S-26

4—Chloromethyl-5-methyl-2-oxo-1,3-dioxolene (52 mg, 0.25 mmol) and 3,4-di-O-tert-butyldimethylsilyl-6-deoxy-L-glucal (150 mg, 0.49 mmol) were dissolved in dichloromethane (7.7 mL). Thereto was added camphorsulfonic acid (11 mg, 0.049 mmol). This mixture was stirred at 0° C. for 2 hours. After the ordinary post-treatment, the reaction product was purified by silica gel chromatography (eluted with n-hexane/ethyl acetate=10/1) to obtain Compound S-26 (110 mg, yield 77%). $^1$H NMR revealed that Compound S-26 was an approximately 2:1 mixture of diastereomers.

$^1$H NMR (CDCl$_3$, 400 MHz)δ ppm; 4.85 (dd, J=3.7, 1.7 Hz) and 4.82 (dd, J=3.7, 1.7 Hz) (total 1H), 4.57 (d, J=14.4 Hz, 1H), 4.47 (d, J=14.4 Hz, 1H), 4.43 (d, J=14.4 Hz, 1H), 4.32 (d, J=14.4 Hz, 1H), 4.03–3.13 (m, 3H), 2.37–2.03 (m, 1H), 1.74–1.53 (m, 1H), 1.23 (d, J=6.4 Hz, 3H), 0.90 (s, 18H), 0.10 (d, J=2.0 Hz, 12H)

REFERENCE EXAMPLE 27

Synthesis of Compound S-27

Compound S-23 (0.16 g, 0.75 mmol) obtained in Reference Example 23 and tri-O-triethylsilyl-D-glucal (0.73 g, 1.5 mmol) were dissolved in dichloromethane (24 mL). Thereto was added camphorsulfonic acid (0.035 g, 0.15 mmol). This mixture was stirred at 0° C. for 3.5 hours. After the ordinary post-treatment, the reaction product was purified by silica gel chromatography (eluted with n-hexane/ethyl acetate=15/1) to obtain Compound S-27 (110 mg, yield 77%). $^1$H NMR revealed that Compound S-27 was an approximately 2:1 mixture of diastereomers.

$^1$H NMR (CDCl$_3$, 400 MHz)δ ppm; 4.87 (d, J=2.6 Hz) and 4.84 (d, J=2.6 Hz) (total 1H), 4.42 (d, J=14.2 Hz, 1H), 4.32 (d, J=14.2 Hz, 1H), 4.29 (d, J=11.9 Hz, 1H), 4.28 (d, J=11.9 Hz, 1H), 4.05–3.10 (m, 5H), 2.18–2.03 (m, 1H), 1.70–1.55 (m, 1H), 0.96 (m, 27H), 0.62 (m, 18H)

REFERENCE EXAMPLE 28

Synthesis of Compound S-28

Compound S-23 (100 mg, 0.68 mmol) obtained in Reference Example 23 was dissolved in carbon tetrachloride (5.0 mL). Thereto were added N-bromosuccinimide (120 mg, 0.68 mmol) and α,α'-azobisisobutyronitrile (5.6 mg, 0.034 mmol). This mixture was stirred at 80° C. for 2 hours. After the ordinary post-treatment, the reaction product was purified by silica gel chromatography (eluted with n-hexane/ethyl acetate=10/1) to obtain Compound S-28 (44 mg, yield 29%).

$^1$H NMR (CDCl$_3$, 100 MHz)δ ppm; 4.40 (s, 2H), 4.25 (s, 2H)

REFERENCE EXAMPLE 29

Synthesis of Compound S-29

Compound S-23 (0.15 g, 0.72 mmol) obtained in Reference Example 23 and tri-O-acetyl-D-glucal (0.394 g, 1.5 mmol) were dissolved in dichloromethane (23 mL). Thereto was added camphorsulfonic acid (0.20 g, 0.87 mmol). This mixture was stirred at 40° C. for 13 hours. After the ordinary post-treatment, the reaction product was purified by silica gel chromatography (eluted with n-hexane/ethyl acetate=3/2) to obtain Compound S-29 (300 mg, yield 100%).

$^1$H NMR (CDCl$_3$, 400 MHz)δ ppm; 5.84 (ddd, J=10.3, 2.7, 2.2 Hz, 1H), 5.34 (m, 1H), 5.12 (d, J=1.1 Hz, 1H), 4.58 (d, J=14.0 Hz, 1H), 4.45 (d, J=14.0 Hz, 1H), 4.26 (m, 2H), 4.02–4.33 (m, 4H), 2.03 (m, 6H)

REFERENCE EXAMPLE 30

Synthesis of 4-Bromomethyl-5-formyloxymethyl-2-oxo-1,3-dioxolene (Compound S-30)

4,5-Dibromomethyl-2-oxo-1,3-dioxolene (150 mg, 0.55 mmol) was dissolved in acetonitrile (4.0 mL). Potassium formate (46 mg, 0.55 mmol) was added thereto. This mixture was stirred at 25° C. for 5 hours. Through the ordinary post-treatment, crude Compound S-30 (85 mg, yield 65%) was obtained.

$^1$H NMR (CDCl$_3$, 100 MHz)δ ppm; 8.07 (br s, 1H), 5.00 (br s, 2H), 4.32 (br s, 2H)

REFERENCE EXAMPLE 31

Synthesis of 4-Acetoxymethyl-5-bromomethyl-2-oxo-1,3-dioxolene (Compound S-31)

4-Acetoxymethyl-5-methyl-2-oxo-1,3-dioxolene (159 mg, 0.92 mmol) was dissolved in carbon tetrachloride (5.0 mL). Thereto were added N-bromosuccinimide (164 mg, 0.92 mmol) and benzoyl peroxide (11 mg, 0.046 mmol). This mixture was stirred at 80° C. for 1 hours. Through the ordinary post-treatment, crude Compound S-31 (220 mg, yield 95%) was obtained.

$^1$H NMR (CDCl$_3$, 100 MHz)δ ppm; 4.88 (br s, 2H), 4.29 (br s, 2H), 2.10 (s, 3H)

FABMS m/z (M+H)$^+$ calcd for C$_7$H$_7$O$_5$Br=172

REFERENCE EXAMPLE 32

Synthesis of 4-Bromomethyl-5-(2-methoxyethoxy)acetoxymethyl-2-oxo-1,3-dioxolene (Compound S-32)

4,5-Dibromomethyl-2-oxo-1,3-dioxolene (136 mg, 0.50 mmol) was dissolved in acetonitrile (5.0 mL). Thereto were added 2-methoxyethoxyacetic acid (0.057 mL, 0.50 mmol) and potassium carbonate (69 mg, 0.50 mmol) This mixture was stirred at 25° C. for 30 minutes. After the ordinary post-treatment, the reaction product was purified by thin-layer chromatography (developed with chloroform) to obtain Compound S-32 (45 mg, yield 28%).

REFERENCE EXAMPLE 33

Synthesis of 4-Bromomethyl-5-(N-Boc-aminoisobutyryloxy)methyl-2-oxo-1,3-dioxolene (Compound S-33)

4,5-Dibromomethyl-2-oxo-1,3-dioxolene (188 mg, 0.69 mmol) was dissolved in acetonitrile (5.0 mL). Thereto were added 2-(N-Boc-amino)isobutyric acid (70 mg, 0.35 mmol) and potassium carbonate (48 mg, 0.35 mmol). This mixture was stirred at 25° C. for 18 hours. After the ordinary post-treatment, the reaction product was purified by thin-layer chromatography (developed with chloroform) to obtain Compound S-33 (50 mg, yield 18%).

$^1$H NMR (CDCl$_3$, 100 MHz)δ ppm; 4.92 (br s, 2H), 4.30 (br s, 2H), 1.44 (s, 6H), 1.36 (s, 9H)

REFERENCE EXAMPLE 34

Synthesis of 4-(N-Acetylglycyl)-methyl-4-bromomethyl-2-oxo-1,3-dioxolene (Compound S-34)

4,5-Dibromomethyl-2-oxo-1,3-dioxolene (272 mg, 1.0 mmol) was dissolved in acetonitrile (10 ML). Thereto were added N-acetylglycine (82 mg, 0.70 mmol) and potassium carbonate (138 mg, 1.0 mmol). This mixture was stirred at 25° C. for 20 hours. After the ordinary post-treatment, the reaction product was purified by thin-layer chromatography to obtain Compound S-34 (56 mg, yield 18%).

$^1$H NMR (CDCl$_3$, 100 MHz)δ ppm; 6.02 (m, 1H), 4.94 (br s, 2H), 4.26 (br s, 2H), 4.15 (d, J=6.3 Hz, 2H), 2.02 (s, 3H)

REFERENCE EXAMPLE 35

Synthesis of Compound S-35

Compound S-23 (0.16 g, 0.75 mmol) obtained in Reference Example 23 and 3,4-di-O-acetyl-6-deoxy-L-glucal (0.17 g, 0.80 mmol) were dissolved in dichloromethane (25 mL). Thereto was added camphorsulfonic acid (0.037 g, 0.16 mmol). This mixture was stirred at 25° C. for 2 hours. After the ordinary post-treatment, the reaction product was purified by silica gel chromatography (eluted with n-hexane/ethyl acetate=4/1) to obtain Compound S-35 (93 mg, yield 28%).

$^1$H NMR (CDCl$_3$, 400 MHz)δ ppm; 5.93 (dd, J=10.2, 1.2 Hz, 1H), 5.80 (ddd, J=10.2, 2.7, 2.1 Hz, 1H), 5.04 (m, 1H), 4.55 (d, J=14.0 Hz, 1H), 4.46 (d, J=14.0 Hz, 1H), 4.24 (s, 2H), 3.95 (m, 1H), 2.10 (s, 3H), 2.08 (m, 3H), 1.23 (d, J=6.2 Hz, 3H)

REFERENCE EXAMPLE 36

Synthesis of Compound S-36

3,4-Di-O-acetyl-6-deoxy-L-glucal was treated with sodium methoxide to remove the acetyl group therefrom and with chlorotrimethylsilane and 2,6-lutidine to incorporate a triethylsilyl group thereinto. Thus, 3,4-di-O-triethylsilyl-6-deoxy-L-glucal was obtained. Compound S-23 (0.15 g, 0.72 mmol) obtained in Reference Example 23 and the 3,4-di-O-triethylsilyl-6-deoxy-L-glucal (0.514 g, 1.4 mmol) were dissolved in dichloromethane (23 mL). Thereto was added camphorsulfonic acid (0.033 g, 1.4 mmol). This mixture was stirred at 0° C. for 1 hour. After the ordinary post-treatment, the reaction product was purified by silica gel chromatography (eluted with n-hexane/ethyl acetate=10/1) to obtain Compound S-36 (0.27 g, yield 66%). $^1$H NMR revealed that Compound S-36 was an approximately 2:1 mixture of diastereomers.

$^1$H NMR (CDCl$_3$, 400 MHz)δ ppm; major isomer 4.84 (d, J=2.5 Hz, 1H), 4.41 (d, J=14.3 Hz, 1H), 4.30 (d, J=14.3 Hz, 1H), 4.25 (s, 2H), 3.85 (m, 1H), 3.62 (m, 1H), 3.18 (m, 1H), 1.60 (m, 2H), 1.24 (d, J=6.3 Hz, 3H), 0.97 (m, 18H), 0.70–0.58 (m, 12H); minor isomer 5.25 (br s, 1H), 4.57 (d, J=14.3 Hz, 1H), 4.47 (d, J=14.3 Hz, 1H), 4.26 (s, 2H), 3.96 (m, 1H), 3.57 (m, 1H), 3.26 (m, 1H), 1.60 (m, 2H), 1.22 (d, J=6.3 Hz, 3H), 0.97 (m, 18H), 0.70–0.58 (m, 12H)

REFERENCE EXAMPLE 37

Synthesis of Compound S-37

A condensate (3.59 g, yield 51%) was obtained from benzyl 4-aminobutyrate hydrochloride (4.65 g, 20.2 mmol), 2,2-bis(hydroxymethyl)propionic acid isopropylidene acetal (3.52 g, 20.2 mmol), DCC (7.51 g, 36.4 mmol), and triethylamine (3.1 mL) in the same manner as in the synthesis of Compound S-5 described in Reference Example 5. All the condensate was dissolved in ethanol (200 mL), and 10% palladium carbon (containing 50 wt % water; 1.13 g) was added thereto. This mixture was stirred in a hydrogen atmosphere at 25° C. for 4 hours. The reaction mixture was filtered, and the filtrate was concentrated to obtain the corresponding carboxylic acid (2.67 g, quantitative yield).

From the whole carboxylic acid obtained above and chloromethyl chlorosulfonate (1.96 g, 10.3 mmol) was obtained Compound S-37 (2.05 g, yield 65%) through 5-hour reaction according to the Typical Method for Synthesizing Chloromethyl Ester.

$^1$H NMR (CDCl$_3$, 270 MHz)δ ppm; 7.18 (br s, 1H), 5.71 (s, 2H), 3.90 (d, J=12.4 Hz, 2H), 3.77 (d, J=12.4 Hz, 2H), 3.38 (m, 2H), 2.49 (t, J=7.4 Hz, 2H), 1.92 (m, 2H), 1.48 (s, 3H), 1.43 (s, 3H), 1.00 (s, 3H)

FABMS m/z 308 (M+H)$^+$ calcd for C$_{13}$H$_{22}$$^{35}$ClNO$_5$=307

REFERENCE EXAMPLE 38

Synthesis of Compound S-38

A condensate (1.44 g, yield 11%) was obtained from benzyl 4-aminobutyrate hydrochloride (6.90 g, 30.0 mmol), 2,3:4,6-di-O-isopropylidene-2-keto-L-glonic acid monohydrate (8.74 g, 31.9 mmol), 1-ethyl-3-(3-dimethylaminopropyl) carbodiimide hydrochloride (14.5 g, 75.6 mmol), and triethylamine (4.2 mL) in the same manner as in the synthesis of Compound S-5 described in Reference Example 5. All the condensate was dissolved in ethanol (50 mL), and 10% palladium carbon (containing 50 wt % water; 400 mg) was added thereto. This mixture was stirred in a hydrogen atmosphere at 25° C. for 1 hour.

The reaction mixture was filtered, and the filtrate was concentrated to obtain the corresponding carboxylic acid (1.15 g, yield 100%).

From the whole carboxylic acid obtained above and chloromethyl chlorosulfonate (608 mg, 3.20 mmol) was obtained Compound S-38 (852 mg, yield 65%) through 5-hour reaction according to the Typical Method for Synthesizing Chloromethyl Ester.

$^1$H NMR (CDCl$_3$, 270 MHz)δ ppm; 7.24 (br s, 1H), 5.72 (d, J=5.9 Hz, 1H), 5.68 (d, J=5.9 Hz, 1H), 4.57 (s, 1H), 4.33 (d, J=1.3 Hz, 1H), 4.19 (d, J=1.3 Hz, 1H), 4.12 (br s, 2H), 3.5–3.2 (m, 2H), 2.47 (d, J=7.4 Hz, 2H) 1.93 (m, 2H), 1.55 (s, 3H), 1.54 (s, 3H), 1.45 (s, 3H), 1.31 (s, 3H)

FABMS m/z 408 (M+H)$^+$ calcd for C$_{17}$H$_{26}$$^{35}$ClNO$_8$=407

REFERENCE EXAMPLE 39

Synthesis of Compound S-39

A condensate (2.86 g, yield 36%) was obtained from benzyl 4-aminobutyrate hydrochloride (4.12 g, 18.0 mmol), the carboxylic acid (4.92 g, 18.0 mmol) obtained by oxidizing 1,2:2,4-di-O-isopropylidene-D-galacto-pyranose with PDC, triethylamine (2.5 mL), and 1-ethyl-3-(3-dimethylaminopropyl)carbodiimide hydrochloride (5.16 g, 26.9 mmol) in the same manner as in the synthesis of Compound S-5 described in Reference Example 5. All the condensate was dissolved in ethanol (120 mL), and 10% palladium carbon (containing 50 wt % water; 556 mg) was added thereto. This mixture was stirred in a hydrogen atmosphere at room temperature for 1.5 hours. The reaction mixture was filtered, and the filtrate was concentrated and purified by silica gel chromatography (eluted with chloroform/methanol=50/1 to 4/1) to obtain carboxylic acid (1.24 g, yield 54%). From the whole carboxylic acid obtained above and chloromethyl chlorosulfonate (656 mg, 3.45 mmol) was obtained the target compound (844 mg, yield 60%) through 4.5-hour reaction according to the Typical Method for Synthesizing Chloromethyl Ester.

$^1$H NMR (CDCl$_3$, 270 MHz)δ ppm; 6.61 (br s, 1H), 5.73 (d, J=5.9 Hz, 1H), 5.68 (d, J=5.9 Hz, 1H), 5.59 (d, J=4.8 Hz, 1H), 4.66 (s, 2H), 4.36 (d, J=4.8 Hz, 1H), 4.29 (s, 1H), 3.52 (m, 1H), 3.26 (m, 1H), 2.46 (m, 2H), 1.90 (m, 2H), 1.52 (s, 3H), 1.42 (s, 3H), 1.34 (s, 6H)

FABMS m/z 408 (M+H)$^+$ calcd for C$_{17}$H$_{26}$$^{35}$ClNO$_8$=407

REFERENCE EXAMPLE 40

Synthesis of Compound S-40

A condensate (10.47 g, yield 96%) was obtained from L-Glu(OCH$_2$Ph)-OMe hydrochloride (8.63 g, 30.0 mmol), L-pyroglutamic acid (4.28 g, 33.1 mmol), 1-ethyl-3-(3-dimethylaminopropyl)carbodiimide hydrochloride (0.48 g, 39.0 mmol), and triethylamine (4.2 mL) in the same manner as in the synthesis of Compound S-5 described in Reference Example 5. All the condensate was dissolved in ethanol (300 mL), and 10% palladium carbon (containing 50 wt % water; 2.0 g) was added thereto. This mixture was stirred in a hydrogen atmosphere at 25° C. for 1.5 hours. The reaction mixture was filtered, and the filtrate was concentrated to obtain carboxylic acid (8.34 g, quantitative yield).

The carboxylic acid obtained above (9.02 g) was dissolved in methanol (100 mL) and water (15 mL). Thereto was added an aqueous cesium carbonate solution (20 wt %, approximately 25 mL) to adjust the pH to 7.0. The solvent of the resultant solution was distilled off, and the remaining water was removed by conducting azeotropic distillation twice using DMF. The residue was sufficiently dried and then dissolved in DMF (100 ML). Thereto was added a solution of chloromethyl chlorosulfonate (7.56 g, 40.0 mmol) in DMF (15 mL). This mixture was stirred at 25° C. for 1.5 hours. An brine was added to the reaction mixture, which was then sufficiently extracted with chloroform. The organic layer was washed with saturated brine and then dried with magnesium sulfate. The solvent was distilled off, and the residue was purified by column chromatography (silica gel; chloroform/methanol=20/1) to obtain Compound S-40 (1.54 g, yield 17%).

$^1$H NMR (CDCl$_3$, 270 MHz)δ ppm; 7.46 (br d, J=8.4 Hz, 1H), 7.00 (br s, 1H), 5.72 (d, J=6.4 Hz, 1H), 5.68 (d, J=6.4 Hz, 1H), 4.67 (m, 1H), 4.22 (m, 1H), 3.76 (s, 3H), 2.6–2.0 (m, 8H)

FABMS m/z 321 (M+H)$^+$ calcd for C$_{12}$H$_{17}$$^{35}$ClN$_2$O$_6$=320

REFERENCE EXAMPLE 41

Synthesis of Compound S-41

A condensate was obtained from benzyl 4-aminobutyrate hydrochloride (13.76 g, 59.9 mmol), L-pyroglutamic acid (7.44 g, 57.6 mmol), 1-ethyl-3-(3-dimethylaminopropyl) carbodiimide hydrochloride (17.3 g, 90.3 mmol), and triethylamine (8.4 mL) in the same manner as in the synthesis of Compound S-5 described in Reference Example 5. All the condensate was dissolved in ethanol (500 mL), and 10% palladium carbon (containing 50 wt % water; 4.0 g) was added thereto. This mixture was stirred in a hydrogen atmosphere at 25° C. for 1 hour. The reaction mixture was filtered, and the filtrate was concentrated to obtain the corresponding carboxylic acid (10.2 g, yield 83%).

The carboxylic acid obtained above (5.34 g, 24.9 mmol) was reacted with a solution of chloromethyl chlorosulfonate (7.12 g, 37.5 mmol) in DMF (20 mL) at 25° C. for 1.5 hours in the same manner as in the synthesis of Compound S-40 described in Reference Example 40. As a result, Compound S-41 (278 mg, yield 4.3%) was obtained.

$^1$H NMR (CDCl$_3$, 270 MHz)δ ppm; 7.37 (br s, 1H), 7.18 (m, 1H), 5.72 (d, J=5.9 Hz, 1H), 5.69 (d, J=5.9 Hz, 1H), 4.17 (m, 1H), 3.34 (m, 2H), 2.6–2.1 (m, 6H), 1.90 (m, 2H)

FABMS m/z 263 (M+H)$^+$ calcd for C$_{10}$H$_{15}$$^{35}$ClN$_2$O$_4$=262

REFERENCE EXAMPLE 42

Synthesis of Compound S-42

Compound S-42 (963 mg, yield 15%) was obtained from 4-(2-oxopyrrolidinyl)butyric acid (5.15 g, 30 mmol) and chloromethyl chlorosulfonate (5.70 g, 30 mmol) through 2-hour reaction according to the Typical Method for Synthesizing Chloromethyl Ester.

$^1$H NMR (CDCl$_3$, 270 MHz)δ ppm; 5.70 (s, 2H), 3.40 (t, J=7.1 Hz, 2H), 3.33 (t, J=7.1 Hz, 2H), 2.5–2.3 (m, 4H), 2.1–1.8 (m, 4H)

FABMS m/z 220 (M+H)$^+$ calcd for C$_9$H$_4$$^{35}$ClNO$_3$=219

REFERENCE EXAMPLE 43

Synthesis of Compound S-43

1-(2-Hydroxyethyl)-2-pyrrolidone (3.87 g, 30.0 mmol) was dissolved in dichloromethane (15 mL) and triethylamine (4.2 mL). While this solution was kept being stirred with cooling with ice, a solution of chloromethyl chloroformate (2.8 mL) in dichloromethane (45 mL) was added dropwise thereto over a period of 50 minutes. Subsequently, the reaction mixture was continuously stirred with cooling with ice for 4.5 hours. The salt formed in the resultant reaction mixture was separated by filtration. Thereafter, washing with saturated aqueous sodium bicarbonate solution, washing with saturated brine, drying with sodium sulfate, and distillation for solvent removal were successively conducted. The residue was sufficiently dried under vacuum to obtain Compound S-43 (4.46 g, yield 67%).

$^1$H NMR (CDCl$_3$, 270 MHz) ppm; 5.73 (s, 2H), 4.36 (t, J=5.1 Hz, 2H), 3.60 (t, J=5.1 Hz, 2H), 3.48 (t, J=6.9 Hz, 2H), 2.39 (t, J=8.1 Hz, 2H), 2.05 (m, 2H)

FABMS m/z 222 (M+H)$^+$ calcd for C$_8$H$_{12}$$^{35}$ClNO$_4$=221

REFERENCE EXAMPLE 44

Synthesis of Compound S-44

Compound S-44 (2.12 g, yield 26%) was obtained from 3,6,9,12-tetraoxatridecanoic acid (6.66 g, 30.0 mmol) and chloromethyl chlorosulfonate (5.70 g, 34.5 mmol) through 2.5-hour reaction according to the Typical Method for Synthesizing Chloromethyl Ester.

$^1$H NMR (CDCl$_3$, 270 MHz)δ ppm; 5.76 (s, 2H), 4.25 (s, 2H), 3.8–3.5 (m, 12H), 3.67 (s, 3H)

FABMS m/z 271 (M+H)$^+$ calcd for C$_8$H$_{19}$$^{35}$ ClO$_6$=270

REFERENCE EXAMPLE 45

Synthesis of Compound S-45

Diethylene glycol monomethyl ether (12.0 g, 100 mmol) was dissolved in dichloromethane (50 mL) and triethylamine (15 mL). While this solution was kept being stirred with cooling with ice, a solution of chloromethyl chloroformate (9.25 mL) in dichloromethane (150 mL) was added dropwise thereto over a period of 1.5 hours. Subsequently, the reaction mixture was continuously stirred with cooling with ice for 5 hours. The salt formed in the resultant reaction mixture was separated by filtration. Thereafter, washing with saturated aqueous sodium bicarbonate solution, washing with saturated brine, drying with sodium sulfate, and distillation for solvent removal were successively conducted. The residue was sufficiently dried under vacuum to obtain the target compound (18.9 g, 88.9 mmol, yield 89%) as a colorless, transparent, oily substance.

$^1$H NMR (CDCl$_3$, 270 MHz)δ ppm; 5.74 (s, 2H), 4.38 (m, 2H), 3.75 (m, 2H), 3.66 (m, 2H), 3.38 (s, 3H)

FABMS m/z 213 (M+H)$^+$ calculated for C$_7$H$_{13}$ClO$_5$=212

REFERENCE EXAMPLE 46

Synthesis of Compound S-46

Triethylene glycol monomethyl ether (4.93 g, 30.0 mmol) was dissolved in dichloromethane (15 mL) and triethylamine (4.2 mL). While this solution was kept being stirred with cooling with ice, a solution of chloromethyl chloroformate (2.8 mL) in dichloromethane (45 mL) was added dropwise thereto over a period of 50 minutes. Subsequently, the reaction mixture was continuously stirred with cooling with ice for 3.5 hours. The salt formed in the resultant reaction mixture was separated by filtration. Thereafter, washing with saturated aqueous sodium bicarbonate solution, washing with saturated brine, drying with sodium sulfate, and distillation for solvent removal were successively conducted. The residue was purified by silica gel chromatography (eluted with n-hexane/ethyl acetate=7/3 to 2/1) and sufficiently dried under vacuum to obtain Compound S-46 (5.72 g, yield 74%).

$^1$H NMR (CDCl$_3$, 270 MHz)δ ppm; 5.74 (s, 2H), 4.38 (m, 2H), 3.8–3.5 (m, 10H), 3.39 (s, 3H)

FABMS m/z 257 (M+H)$^+$ calcd for C$_9$H$_{17}$$^{35}$ClO$_6$=256

REFERENCE EXAMPLE 47

Synthesis of Compound S-47

Water (8.0 mL) and sodium hydroxide (8.0 g) were added to ethylene glycol (22.2 g, 209 mmol), and the mixture was stirred at 130° C. for 30 minutes. Thereto was added 4-methoxybenzyl chloride (7.82 g, 49.9 mmol). This mixture was stirred at 130° C. for 11 hours. The reaction mixture was subjected to the ordinary post-treatment, and the resultant residue was purified by silica gel chromatography (eluted with n-hexane/ethyl acetate=2/1 to 1/1) to obtain the corresponding monoether (5.75 g, yield 51%).

Sodium hydride (60% dispersion in oil, 5.3 g) was suspended in THF (50 mL). The monoether (5.75 g, 25.4 mmol) and a solution of chloroacetic acid (5.00 g, 52.9 mmol) in THF (100 mL) were added to the suspension with stirring and cooling with ice. This mixture was stirred under refluxing and heating for 18 hours. Water was added to the reaction mixture, and the aqueous layer was washed with diethyl ether and acidified with concentrated hydrochloric acid. Extraction with chloroform, drying with magnesium sulfate, distillation for solvent removal, and drying under vacuum were successively conducted to obtain the corresponding carboxylic acid (6.36 g, yield 88%).

From this carboxylic acid (6.36 g, 22.4 mmol) and chloromethyl chlorosulfonate (4.32 g, 22.7 mmol) was obtained Compound S-47 (4.36 g, yield 58%) through 3-hour reaction according to the Typical Method for Synthesizing Chloromethyl Ester.

$^1$H NMR (CDCl$_3$, 270 MHz)δ ppm; 7.27 (m, 2H), 6.87 (m, 2H), 5.74 (s, 2H), 4.49 (s, 2H), 4.24 (s, 2H), 3.80 (s, 3H), 3.8–3.5 (m, 8H)

FABMS m/z 333 (M+H)$^+$ calcd for C$_{15}$H$_{21}$$^{35}$ClO$_6$=332

REFERENCE EXAMPLE 48

Synthesis of Compound S-48

A condensate (2.04 g, yield 96%) was obtained from D-Glu(OCH$_2$Ph)-OMe.HCl (1.50 g, 5.21 mmol), 2,2-bis (hydroxymethyl)propionic acid isopropylidene acetal (908 mg, 5.21 mmol), triethylamine (0.73 mL), and 1-ethyl-3-(3-dimethylaminopropyl)carbodiimide hydro-chloride (1.30 g, 6.78 mmol) in the same manner as in the synthesis of Compound 13 described in Reference Example 13.

All the condensate was dissolved in ethanol (80 mL), and 10% palladium/carbon (containing 50 wt % water, 455 mg) was added thereto. This mixture was stirred in a hydrogen atmosphere at 25° C. for 2.5 hours. The reaction mixture was filtered, and the filtrate was concentrated to obtain carboxylic acid (1.66 g, quantitative). From all the carboxylic acid and chloromethyl chlorosulfonate (0.99 g) was obtained Compound S-48 (694 mg, yield 38%) through 2.5-hour reaction according to the Typical Method for Synthesizing Chloromethyl Ester.

$^1$H NMR: (CDCl$_3$, 270 MHz)δ ppm; 7.78 (br d, J=7.6 Hz, 1H), 5.72 (d, J=6.1 Hz, 1H), 5.67 (d, J=6.1 Hz, 1H), 4.75 (m, 1H), 4.0–3.7 (m, 4H), 3.77 (s, 3H), 2.6–2.0 (m, 4H), 1.49 (s, 6H), 1.0 (s, 3H)

FABMS m/z 366 (M+H)$^+$ calcd for C$_{15}$H$_{24}$NO$_7$$^{35}$Cl=365

While the invention has been described in detail and with reference to specific embodiments thereof, it will be apparent to one skill in the art that various changes and modifications can be made therein without departing from the spirit and scope thereof.

What is claimed is:

1. A DC107 derivative represented by formula (I) or a pharmaceutically acceptable salt thereof (I)

[Chemical structure shown]

wherein R$^1$ represents:

hydrogen;

lower alkoxyalkyl;

aralkyloxyalkyl;

lower alkoxyalkoxyalkyl;

lower alkoxyalkoxyalkoxyalkyl;

aralkyl;

tetrahydropyranyl;

[Chemical structure shown]

{wherein Q$^1$ represents CH$_2$, O, S, SO, SO$_2$, or N-Q$^3$ (wherein Q$^3$ represents substituted or unsubstituted aryl, or lower alkoxycarbonyl); and Q$^2$ represents a lower alkyl};

COR$^4$ (wherein R$^4$ represents alkyl, alicyclic alkyl, aralkyl, substituted or unsubstituted aryl, a substituted or unsubstituted heterocyclic group, lower alkoxy, alicyclic alkoxy, 9-fluorenylmethoxy, aralkyloxy, substituted or unsubstituted aryloxy, —(CH$_2$)$_{n1}$R$^{4A}$ <wherein n1 represents an integer of 1 to 3; and R$^{4A}$ represents hydroxy, lower alkoxy, carboxy, lower alkoxycarbonyl, lower dialkylamino, substituted or unsubstituted aryl, a substituted or unsubstituted heterocyclic group, substituted or unsubstituted aralkyloxy, or NR$^{4B}$COR$^{4C}$ {wherein R$^{4B}$ represents hydrogen or lower alkyl; and R$^{4C}$ represents lower alkyl, lower alkoxy, aralkyloxy, aryl, aryloxy, 9-fluorenylmethoxy, —(CH$_2$)$_{n2}$NHCOR$^{4D}$ (wherein n2 represents an integer of 1 to 3; and R$^{4D}$ represents alkyl, lower alkoxy, aralkyloxy, aryl, aryloxy, or 9-fluorenylmethoxy), or —CHR$^{4E}$NHCOR$^{4F}$ (wherein R$^{4E}$ represents lower alkyl or hydroxy(lower alkyl); and R$^{4F}$ has the same meaning as R$^{4D}$)}>, or —CHR$^{4G}$NHCOR 4H (wherein R$^{4G}$ has the same meaning as R$^{4E}$; and R$^{4H}$ has the same meaning as R$^{4C}$)); or —CH$_2$OCOR$^5$ <wherein R$^5$ represents —(CH$_2$)$_{n3}$R$^{5A}$ {wherein n3 represents an integer of 1 to 5; and R$^{5A}$ represents lower alkoxy, lower alkanoyloxy, —OSiR$^{5B}$$_3$ (wherein R$^{5B}$s are the same or different, and represent lower alkyl or aryl), lower alkanoyl, lower alkoxycarbonyl, lower alkoxycarbonylamino, lower alkoxycarbonyloxy, lower dialkylaminocarbonyloxy, halogen, or nitro}, or —CH$_2$(OCH$_2$CH$_2$)$_{n4}$OCH$_3$ (wherein n4 represents an integer of 1 to 10)>;

R$^2$ represents:

hydrogen; or

COR$^6$ (wherein R$^6$ represents lower alkyl, aralkyl, substituted or unsubstituted aryl, or a substituted or unsubstituted heterocyclic group);

R$^3$ represents:

—CH$_2$OCOR$^1$ (wherein R$^7$ represents —(CH$_2$)$_{n5}$R$^{7A}$ (wherein n5 represents an integer of 1 to 5; and R$^{7A}$ represents hydroxy, lower alkoxy, substituted or unsubstituted aralkyloxy, lower alkanoyloxy, —OPO(OH)$_2$, —OSO$_3$H, —OSiR$^{7B}$$_3$ (wherein R$^{7B}$ has the same meaning as R$^{5B}$), lower alkanoyl, carboxy, lower alkoxycarbonyl, lower alkoxycarbonylamino, aralkyloxycarbonylamino, lower alkoxycarbonyloxy, lower dialkylaminocarbonyloxy, halogen, nitro, maleimido, 2-pyrrolidinon-1-yl, or —NHCOR$^{7C}$ <wherein R$^{7C}$ represents substituted or unsubstituted lower alkyl, substituted or unsubstituted alicyclic alkyl, substituted or unsubstituted aryl, substituted or unsubstituted aralkyl, a substituted or unsubstituted heterocyclic group,

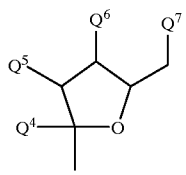

{wherein Q$^4$ to Q$^7$ are the same or different, and each represents hydrogen, hydroxy, lower alkanoyloxy, or —OSiQ$^8$$_3$ (wherein Q$^8$ has the same meaning as R$^{5B}$), or Q$^4$ and Q$^5$, or Q$^6$ and Q$^7$ are combined with each other to represent —OC(CH$_3$)$_2$O—}, or

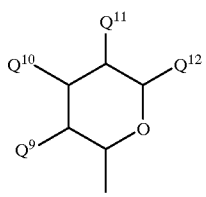

(wherein Q$^9$ to Q$^{12}$ have the same meanings as Q$^4$ to Q$^7$, respectively)>), —C(CH$_3$)$_2$R$^{7D}$ {wherein R$^{7D}$ represents lower alkoxycarbonylamino, aralkyloxycarbonylamino, or —NHCOR$^{7E}$ (wherein R$^{7E}$ has the same meaning as R$^{7C}$)}, —(CH$_2$)$_{n6}$CHR$^{7F}$R$^{7G}$ (wherein n6 represents an integer of 0 to 3; R$^{7F}$ represents lower alkanoyl, carboxy, lower alkoxycarbonyl, substituted or unsubstituted aryl, substituted or unsubstituted lower alkyl, or substituted or unsubstituted aralkyl; and R$^{7G}$ has the same meaning as R$^{7D}$), alicyclic alkyl having a substituent, substituted or unsubstituted aryl, substituted or unsubstituted aralkyl, —CH$_2$(OCH$_2$CH$_2$)$_{n7}$R$^{7H}$ (wherein R$^{7H}$ represents hydrogen, lower alkyl, substituted or unsubstituted aryl, or substituted or unsubstituted aralkyl; and n7 represents an integer of 1 to 10), —(OCH$_2$CH$_2$)$_{n8}$OCH$_3$ (wherein n8 represents an integer of 1 to 10), or —OCH$_2$CH$_2$ (2-pyrrolidinon-1-yl));

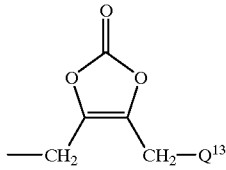

<wherein Q$^{13}$ represents halogen, hydroxy, lower alkoxyalkyl, —OSiR$^{7I}$$_3$ (wherein R$^{7I}$ has the same meaning as R$^{5B}$), —OCOQ$^{14}$ {wherein Q$^{14}$ represents hydrogen, alkyl, alicyclic alkyl, aralkyl, substituted or unsubstituted aryl, a substituted or unsubstituted heterocyclic group, lower alkoxy, alicyclic alkoxy, 9-fluorenylmethoxy, aralkyloxy, substituted or unsubstituted aryloxy, alkylamino, (hydroxyalkyl)amino, —(CH$_2$)$_{n9}$Q$^{14A}$ (wherein n9 represents an integer of 1 to 3; and Q$^{14A}$ represents carboxy or lower dialkylamino), CQ$_{14B2}$NQ$^{14C}$COQ$^{14D}$ (wherein Q$^{14B}$ represents hydrogen or lower alkyl; Q$^{14C}$ represents hydrogen or lower alkyl; and Q$^{14D}$ represents lower alkyl, lower alkoxy, aralkyloxy, aryl, aryloxy, or 9-fluorenylmethoxy), or —CH$_2$(OCH$_2$CH$_2$)$_{n10}$OCH$_3$ (wherein n10 represents an integer of 1 to 10)}, or

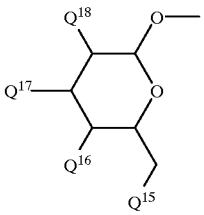

{wherein Q$^{15}$ represents hydrogen, hydroxy, —OSiR$^{7J}$$_3$ (wherein R$^{7J}$ has the same meaning as R$^{5B}$), or lower alkanoyloxy; and Q$^{16}$ to Q$^{18}$ are the same or different, and each represents hydroxy, —OSiR$^{7J}$$_3$ (wherein R$^{7J}$ has the same meaning as R$^{5B}$), or lower alkanoyloxy; and Q$^{17}$ and Q$^{18}$ may be combined with each other to represent a bond}>;

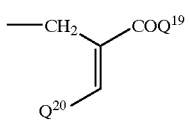

(wherein Q$^{19}$ represents hydroxy, lower alkoxy, or a substituted or unsubstituted heterocyclic group; and Q$^{20}$ represents hydrogen, lower alkyl, or aryl);

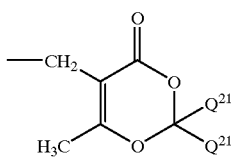

(wherein $Q^2$ represents alkyl);

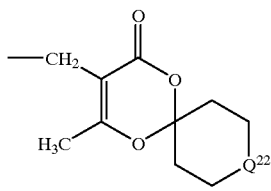

{wherein $Q^{22}$ represents $CH_2$, O, or $N-CO_2Q^{23}$ (wherein $Q^{23}$ represents lower alkyl)};

lower alkoxyalkyl;
aralkyloxyalkyl;
lower alkoxyalkoxyalkyl;
lower alkoxyalkoxyalkoxyalkyl; or phthalimidomethyl; and
W represents:
oxygen; or $NR^8$ (wherein $R^8$ represents hydroxy, lower alkoxy, lower alkenyloxy, aralkyloxy, substituted or unsubstituted arylsulfonylamino, or lower alkoxycarbonylamino).

2. The DC107 derivative or a pharmaceutically acceptable salt thereof according to claim 1, wherein $R^3$ is $-CH_2OCOR^7$ (wherein $R^7$ has the same meaning as defined above).

3. The DC107 derivative or a pharmaceutically acceptable salt thereof according to claim 2, wherein $R^7$ is $-(CH_2)_{n6}CHR^{7F}R^{7G}$ (whereinn n6, $R^{7F}$, and $R^{7G}$ have the same meanings as defined above).

4. A pharmaceutical composition comprising a compound according to claim 1 and a pharmaceutically acceptable carrier.

5. A method for preventing or treating a patient exhibiting symptoms of microbial or tumor activity comprising administering an effective amount of the DC107 derivative or a pharmaceutically acceptable salt thereof according to claim 1.

* * * * *

UNITED STATES PATENT AND TRADEMARK OFFICE
CERTIFICATE OF CORRECTION

PATENT NO. : 5,981,558
DATED : November 9, 1999
INVENTOR(S) : HITOSHI ARAI ET AL.

Page 1 of 7

It is certified that error appears in the above-identified patent and that said Letters Patent is hereby corrected as shown below:

COLUMN 3

Line 34, "7D $R^{7D}$)," should read --$R^{7D}$),--;
Line 63, "$Q^{14}D$" should read --$Q^{14D}$--;
Line 65, "$n_{10}$" should read --n10--;

COLUMN 6

Line 3, "—OPO(OH)$_2$," should read --substituted or unsubstituted aryloxycarbonyl, ---OPO(OH)$_2$,--.

COLUMN 9

Line 28, " 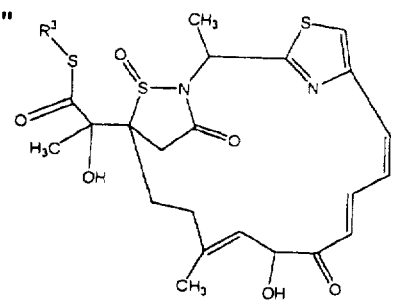 " should read

UNITED STATES PATENT AND TRADEMARK OFFICE
CERTIFICATE OF CORRECTION

PATENT NO. : 5,981,558
DATED : November 9, 1999
INVENTOR(S) : HITOSHI ARAI ET AL.

It is certified that error appears in the above-identified patent and that said Letters Patent is hereby corrected as shown below:

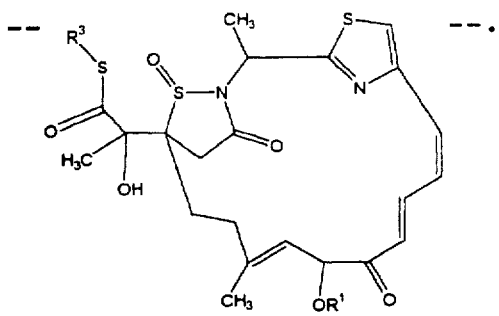

COLUMN 20

Line 63, "COR" should read --$COR^6$--.

COLUMN 22

Line 49, "$R^3$" should read --$R^8$--.

COLUMN 24

Line 41, "17" should be deleted;
Line 52, "Ria" should read --$R^{1a}$--.

COLUMN 31

Line 47, "R" should read --$R^1$--.

UNITED STATES PATENT AND TRADEMARK OFFICE
CERTIFICATE OF CORRECTION

PATENT NO. : 5,981,558
DATED : November 9, 1999
INVENTOR(S) : HITOSHI ARAI ET AL.

It is certified that error appears in the above-identified patent and that said Letters Patent is hereby corrected as shown below:

COLUMN 39

Table 1, "14    H    $CH_2OCCCH_2OH$" should read
--14    H    $CH_2OCOCH_2OH$--.

COLUMN 87

Line 3, "$C_3BH_{43}N_3O_{13}S_3=845$" should read --$C_{38}H_{43}N_3O_{13}S_3=730$--.

COLUMN 89

Line 31, "$C_{34}H_3N_2O_{10}S_3=730$" should read --$C_{34}H_{38}N_2O_{10}S_3=730$--.

COLUMN 93

Line 35, "36-to" should read --36 to--.

COLUMN 98

Line 34, "$C_3BH_{44}N_2O_{12}S_3=816$" should read --$C_{38}H_{44}N_2O_{12}S_3=816$--;
Line 55, "(toral 1H)" should read --(total 1H).

COLUMN 105

Line 52, "4,74" should read --4.74--.

COLUMN 106

Line 14, "(d,-J=1.2 Hz, 3H)," should read
--(d,J=1.2 Hz, 3H),--.

UNITED STATES PATENT AND TRADEMARK OFFICE
CERTIFICATE OF CORRECTION

PATENT NO. : 5,981,558
DATED : November 9, 1999
INVENTOR(S) : HITOSHI ARAI ET AL.

It is certified that error appears in the above-identified patent and that said Letters Patent is hereby corrected as shown below:

COLUMN 110

Line 39, "chloroform/methanol 96/4)" should read --chloroform/methanol = 96/4)--;
Line 50, "-7.40 (s, 1H)" should read --7.40 (s, 1H)--.

COLUMN 118

Line 2, "5.183" should read --5.83--;
Line 4, "5.0 3" should read --5.03--;
Line 7, "1.988" should read --1.88--;
Line 10, "M/z" should read --m/z--.

COLUMN 120

Line 35, "$C_{27}H_{33}N_2OBS_3$" should read --$C_{27}H_{33}N_2O_8S_3$--.

COLUMN 127

Line 49, "¯H NMR" should read --'H NMR--.

COLUMN 132

Line 27, "J 3.6," should read --J = 3.6,--.

COLUMN 138

Line 38, "$C_{31}H_{37}N3O_{11}S_3=723$" should read --$C_{31}H_{37}N_3O_{11}S_3=723$--.

UNITED STATES PATENT AND TRADEMARK OFFICE
CERTIFICATE OF CORRECTION

PATENT NO. : 5,981,558
DATED : November 9, 1999
INVENTOR(S) : HITOSHI ARAI ET AL.

It is certified that error appears in the above-identified patent and that said Letters Patent is hereby corrected as shown below:

COLUMN 141

Table 5, "    S.9    9    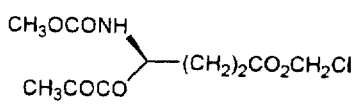    "

should read

--    S.9    9    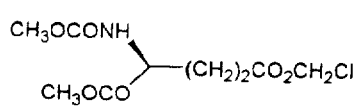    -- .

COLUMN 149

Table 15, "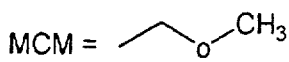" should read

-- 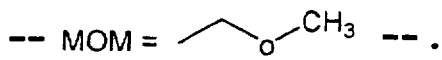 -- .

COLUMN 162

Line 7, "¶The" should read --The--.

UNITED STATES PATENT AND TRADEMARK OFFICE
CERTIFICATE OF CORRECTION

PATENT NO. : 5,981,558
DATED : November 9, 1999
INVENTOR(S) : HITOSHI ARAI ET AL.

It is certified that error appears in the above-identified patent and that said Letters Patent is hereby corrected as shown below:

COLUMN 163

Line 11, "An brine" should read --Brine--;
Line 61, "$C_9H_4{}^{35}ClNO_3=219$" should read --$C_9H_{14}{}^{35}ClNO_3=219$--.

COLUMN 164

Line 1, "kept" should be deleted;
Line 2, "with" (1st occurrence) should read --,--;
Line 5, "with" (1st occurrence) should read --,--;
Line 29, "$C_8H_{19}{}^{35}ClO_6=270$" should read --$C_{10}H_{19}{}^{35}ClO_6=270$--;
Line 35, "dichioromethane" should read --dicloromethane--;
Line 40, "with" should read --,--.

COLUMN 166

Line 65, "--$CHR^{4G}NHCOR\ 4H$" should read ---$CHR^{4G}NHCOR^{4H}$ --.

COLUMN 168

Line 24, "$CQ_{14B2}NQ^{14C}COQ^{14D}$" should read --$CQ^{14B}{}_2NQ^{14C}COQ^{14D}$ --.

COLUMN 169

Line 1, "$Q^2$ should read --$Q^{21}$--.

UNITED STATES PATENT AND TRADEMARK OFFICE
CERTIFICATE OF CORRECTION

PATENT NO. : 5,981,558
DATED : November 9, 1999
INVENTOR(S) : HITOSHI ARAI ET AL.

Page 7 of 7

It is certified that error appears in the above-identified patent and that said Letters Patent is hereby corrected as shown below:

<u>COLUMN 170</u>

Line 10, "(whereinn" should read --(wherein--;

" 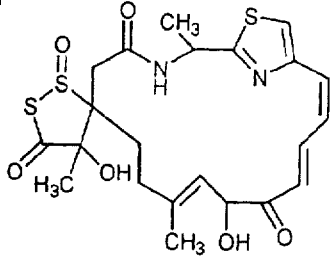 " should read

-- 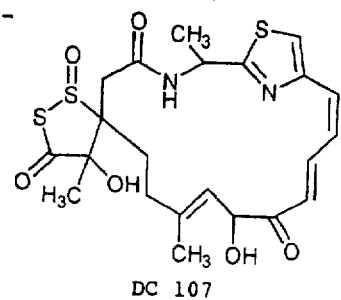  --.

DC 107

Signed and Sealed this

Seventeenth Day of April, 2001

Attest:

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 5,981,558  
DATED : November 9, 1999  
INVENTOR(S) : Hitoshi Arai et al.

Page 1 of 1

It is certified that error appears in the above-identified patent and that said Letters Patent is hereby corrected as shown below:

Column 119,
Line 32, "¶ 'H NMR" should read -- 'H NMR --.

Signed and Sealed this

Twentieth Day of November, 2001

Attest:

*Nicholas P. Godici*

NICHOLAS P. GODICI
*Attesting Officer*  *Acting Director of the United States Patent and Trademark Office*